(12) United States Patent
Barbosa et al.

(10) Patent No.: US 7,557,190 B2
(45) Date of Patent: Jul. 7, 2009

(54) OPTIMIZED PROTEINS THAT TARGET EP-CAM

(75) Inventors: Maria D. Barbosa, San Dimas, CA (US); Aaron K. Chamberlain, Pasadena, CA (US); John R. Desjarlais, Pasadena, CA (US)

(73) Assignee: Xencor, Inc., Monrovia, CA (US)

( * ) Notice: Subject to any disclaimer, the term of this patent is extended or adjusted under 35 U.S.C. 154(b) by 8 days.

(21) Appl. No.: 11/484,183

(22) Filed: Jul. 10, 2006
(Under 37 CFR 1.47)

(65) Prior Publication Data

US 2007/0161783 A1 Jul. 12, 2007

Related U.S. Application Data

(60) Provisional application No. 60/745,078, filed on Apr. 18, 2006, provisional application No. 60/779,961, filed on Mar. 6, 2006, provisional application No. 60/741,966, filed on Dec. 2, 2005, provisional application No. 60/697,768, filed on Jul. 8, 2005.

(51) Int. Cl.
*C12P 21/08* (2006.01)
*C07K 16/00* (2006.01)
*C07K 17/00* (2006.01)

(52) U.S. Cl. ............... 530/387.1; 530/387.3; 530/388.1; 530/389.7

(58) Field of Classification Search ........................ None
See application file for complete search history.

(56) References Cited

U.S. PATENT DOCUMENTS

| | | | |
|---|---|---|---|
| 3,691,016 A | 9/1972 | Patel |
| 3,773,919 A | 11/1973 | Boswell et al. |
| 3,969,287 A | 7/1976 | Jaworek et al. |
| 4,179,337 A | 12/1979 | Davis et al. |
| 4,195,128 A | 3/1980 | Hildebrand et al. |
| 4,229,537 A | 10/1980 | Hodgins et al. |
| 4,247,642 A | 1/1981 | Hirohara et al. |
| 4,301,144 A | 11/1981 | Iwashita et al. |
| 4,330,440 A | 5/1982 | Ayers et al. |
| 4,485,045 A | 11/1984 | Regen |
| 4,496,689 A | 1/1985 | Mitra |
| 4,522,918 A | 6/1985 | Schlom et al. |
| 4,544,545 A | 10/1985 | Ryan et al. |
| 4,612,282 A | 9/1986 | Schlom et al. |
| 4,640,835 A | 2/1987 | Shimizu et al. |
| 4,670,417 A | 6/1987 | Iwasaki et al. |
| 4,791,192 A | 12/1988 | Nakagawa et al. |
| 4,816,567 A | 3/1989 | Cabilly et al. |
| 4,975,278 A | 12/1990 | Senter et al. |
| 4,978,745 A | 12/1990 | Schoemaker et al. |
| 5,013,556 A | 5/1991 | Woodle et al. |
| 5,208,020 A | 5/1993 | Chari et al. |
| 5,225,539 A | 7/1993 | Winter |
| 5,264,586 A | 11/1993 | Nicolaou et al. |
| 5,292,658 A | 3/1994 | Cormier et al. |
| 5,418,155 A | 5/1995 | Cormier et al. |
| 5,530,101 A | 6/1996 | Queen et al. |
| 5,585,089 A | 12/1996 | Queen et al. |
| 5,624,821 A | 4/1997 | Winter et al. |
| 5,658,570 A | 8/1997 | Newman et al. |
| 5,668,002 A | 9/1997 | Linnenbach et al. |
| 5,681,566 A | 10/1997 | Stevenson |
| 5,683,888 A | 11/1997 | Campbell |
| 5,693,761 A | 12/1997 | Queen et al. |
| 5,693,762 A | 12/1997 | Queen et al. |
| 5,712,374 A | 1/1998 | Kuntsmann et al. |
| 5,714,586 A | 2/1998 | Kunstmann et al. |
| 5,741,668 A | 4/1998 | Ward et al. |
| 5,750,105 A | 5/1998 | Newman et al. |
| 5,773,001 A | 6/1998 | Hamann et al. |
| 5,777,079 A | 7/1998 | Tsien et al. |
| 5,804,387 A | 9/1998 | Cormack et al. |
| 5,804,396 A | 9/1998 | Plowman |
| 5,821,337 A | 10/1998 | Carter et al. |
| 5,859,205 A | 1/1999 | Adair et al. |
| 5,874,304 A | 2/1999 | Zolotukhin et al. |
| 5,876,995 A | 3/1999 | Bryan |
| 5,885,573 A | 3/1999 | Bluestone et al. |
| 5,925,558 A | 7/1999 | Tsien et al. |
| 6,054,297 A | 4/2000 | Carter et al. |
| 6,165,745 A | 12/2000 | Ward et al. |
| 6,180,370 B1 | 1/2001 | Queen et al. |
| 6,194,551 B1 | 2/2001 | Idusogie et al. |

(Continued)

FOREIGN PATENT DOCUMENTS

EP  0 252 741 B1  1/1988

(Continued)

OTHER PUBLICATIONS

Winter, et al., "Expression of Ep-CAM Shifts the State of Cadherin-Mediated Adhesions from Strong to Weak" *Experimental Cell Research*, vol. 285, No. 1, (2003), 50-58, Elsevier, Orlando, U.S.A.

(Continued)

*Primary Examiner*—Maher M Haddad
*Assistant Examiner*—Chun Dahle
(74) *Attorney, Agent, or Firm*—Dorsey & Whitney LLP

(57) ABSTRACT

Humanized Ep-CAM-targeting antibodies and methods of making and using the same are provided.

10 Claims, 44 Drawing Sheets

U.S. PATENT DOCUMENTS

Figure 5:
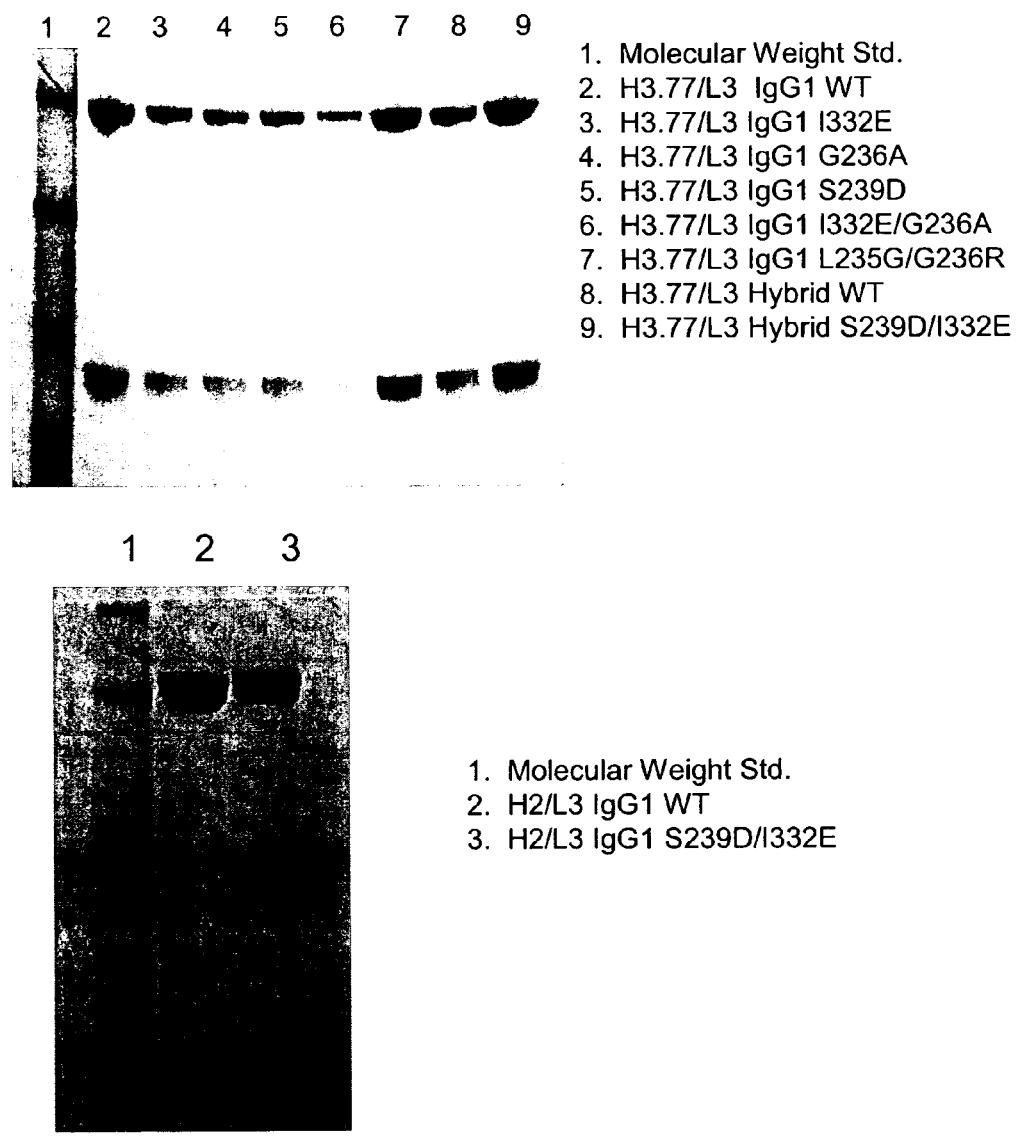

| | | |
|---|---|---|
| 6,277,375 B1 | 8/2001 | Ward |
| 6,403,312 B1 | 6/2002 | Dahiyat et al. |
| 6,407,213 B1 | 6/2002 | Carter et al. |
| 6,444,207 B1 | 9/2002 | Schoemaker et al. |
| 6,602,684 B1 | 8/2003 | Umana et al. |
| 6,963,841 B2 | 11/2003 | Handal et al. |
| 6,737,056 B1 | 5/2004 | Presta |
| 7,129,261 B2 | 10/2006 | Ng et al. |
| 7,276,585 B2 | 10/2007 | Lazar et al. |
| 7,317,091 B2 | 1/2008 | Lazar et al. |
| 2001/0044003 A1 | 11/2001 | Gallucci et al. |
| 2002/0034765 A1 | 3/2002 | Daugherty et al. |
| 2002/0048772 A1 | 4/2002 | Dahiyat et al. |
| 2002/0090648 A1 | 7/2002 | Dahiyat et al. |
| 2002/0098193 A1 | 7/2002 | Ward |
| 2002/0119492 A1 | 8/2002 | Chirino et al. |
| 2002/0137022 A1 | 9/2002 | Li et al. |
| 2002/0156033 A1 | 10/2002 | Bratzler et al. |
| 2002/0168640 A1 | 11/2002 | Li et al. |
| 2002/0172968 A1 | 11/2002 | Liu et al. |
| 2002/0177170 A1 | 11/2002 | Luo et al. |
| 2002/0187153 A1 | 12/2002 | Goldenberg |
| 2003/0003097 A1 | 1/2003 | Reff et al. |
| 2003/0017534 A1 | 1/2003 | Buelow et al. |
| 2003/0022285 A1 | 1/2003 | Chirino et al. |
| 2003/0036643 A1 | 2/2003 | Jin et al. |
| 2003/0049647 A1 | 3/2003 | Dahiyat et al. |
| 2003/0068649 A1 | 4/2003 | Doberstein et al. |
| 2003/0072759 A1 | 4/2003 | Schoemaker et al. |
| 2003/0108555 A1 | 6/2003 | Marinkovich |
| 2003/0124537 A1 | 7/2003 | Liu et al. |
| 2003/0130827 A1 | 7/2003 | Desjarlais et al. |
| 2003/0148463 A1 | 8/2003 | Kufer et al. |
| 2003/0157054 A1 | 8/2003 | Gillies et al. |
| 2003/0157108 A1 | 8/2003 | Presta et al. |
| 2003/0190311 A1 | 10/2003 | Dall'Acqua et al. |
| 2004/0002587 A1 | 1/2004 | Watkins et al. |
| 2004/0110226 A1 | 6/2004 | Lazar et al. |
| 2004/0132101 A1 | 7/2004 | Lazar et al. |
| 2005/0009097 A1 | 1/2005 | Better et al. |
| 2005/0014934 A1 | 1/2005 | Hinton et al. |
| 2005/0032133 A1 | 2/2005 | Barratt et al. |
| 2005/0084913 A1 | 4/2005 | Punnonen et al. |
| 2005/0114037 A1 | 5/2005 | Desjarlais et al. |
| 2005/0136050 A1 | 6/2005 | Kufer et al. |
| 2005/0163785 A1 | 7/2005 | Knick et al. |
| 2005/0244418 A1 | 11/2005 | Gillies et al. |
| 2005/0249723 A1 | 11/2005 | Lazar et al. |
| 2006/0003412 A1 | 1/2006 | Chamberlain et al. |
| 2006/0008883 A1 | 1/2006 | Lazar et al. |
| 2006/0024298 A1 | 2/2006 | Lazar et al. |
| 2006/0121032 A1 | 6/2006 | Dahiyat et al. |
| 2007/0274982 A1 | 11/2007 | Peters et al. |

FOREIGN PATENT DOCUMENTS

| | | |
|---|---|---|
| EP | 0 256 654 B1 | 2/1988 |
| EP | 0 478 146 A1 | 4/1992 |
| EP | 0 614 355 B1 | 9/1994 |
| EP | 0 755 683 A1 | 1/1997 |
| EP | 0 970 126 B1 | 1/2000 |
| EP | 1 140 168 B1 | 10/2001 |
| EP | 1 198 251 B1 | 4/2002 |
| WO | WO 81/01145 | 4/1981 |
| WO | WO 87/05330 | 9/1987 |
| WO | WO 88/07378 | 10/1988 |
| WO | WO 89/04872 | 6/1989 |
| WO | WO 90/03799 | 4/1990 |
| WO | WO 92/11018 | 7/1992 |
| WO | WO 92/15673 | 9/1992 |
| WO | WO 93/10763 | 6/1993 |
| WO | WO 93/11161 | 6/1993 |
| WO | WO 93/21232 | 10/1993 |
| WO | WO 93/22332 | 11/1993 |
| WO | WO 94/11026 | 5/1994 |
| WO | WO 94/13804 | 6/1994 |
| WO | WO 95/07463 | 3/1995 |
| WO | WO 96/30347 | 10/1996 |
| WO | WO 96/33978 | 10/1996 |
| WO | WO 96/33980 | 10/1996 |
| WO | WO 97/00946 | 1/1997 |
| WO | WO 97/34631 | 9/1997 |
| WO | WO 97/38731 | 10/1997 |
| WO | WO 97/38983 | 10/1997 |
| WO | WO 98/14605 | 4/1998 |
| WO | WO 98/23289 | 6/1998 |
| WO | WO 98/26277 | 6/1998 |
| WO | WO 98/43960 | 10/1998 |
| WO | WO 98/52976 | 11/1998 |
| WO | WO 98/59244 | 12/1998 |
| WO | WO 99/06378 | 2/1999 |
| WO | WO 99/06396 | 2/1999 |
| WO | WO 99/09016 | 2/1999 |
| WO | WO 99/49019 | 9/1999 |
| WO | WO 99/58572 | 11/1999 |
| WO | WO 00/06605 | 2/2000 |
| WO | WO 00/42072 | 7/2000 |
| WO | WO 00/61739 | 10/2000 |
| WO | WO 01/07082 | 2/2001 |
| WO | WO 01/14539 | 3/2001 |
| WO | WO 01/29246 A1 | 4/2001 |
| WO | WO 01/30854 A2 | 5/2001 |
| WO | WO 01/59066 | 8/2001 |
| WO | WO 02/05146 | 1/2002 |
| WO | WO 02/22826 | 3/2002 |
| WO | WO 02/30954 A1 | 4/2002 |
| WO | WO 02/31140 A1 | 4/2002 |
| WO | WO 02/060919 | 8/2002 |
| WO | WO 02/066653 | 8/2002 |
| WO | WO 02/068453 | 9/2002 |
| WO | WO 02/068698 | 9/2002 |
| WO | WO 02/069232 | 9/2002 |
| WO | WO 02/077187 | 10/2002 |
| WO | WO 02/079232 | 10/2002 |
| WO | WO 02/088304 | 11/2002 |
| WO | WO 02/090566 | 11/2002 |
| WO | WO 02/098450 | 12/2002 |
| WO | WO 03/000405 | 1/2003 |
| WO | WO 03/006154 | 1/2003 |
| WO | WO 03/014325 | 2/2003 |
| WO | WO 03/025154 | 3/2003 |
| WO | WO 03/030249 | 4/2003 |
| WO | WO 03/033654 | 4/2003 |
| WO | WO 03/040725 A2 | 5/2003 |
| WO | WO 03/097092 A1 | 11/2003 |
| WO | WO 2004/004798 | 1/2004 |
| WO | WO 2004/014421 A1 | 2/2004 |
| WO | WO 2004/035752 | 4/2004 |
| WO | WO 2004/063351 | 7/2004 |
| WO | WO 2004/074455 | 9/2004 |
| WO | WO 2004/091655 | 10/2004 |
| WO | WO 2004/091658 | 10/2004 |
| WO | WO 2004/092219 | 10/2004 |
| WO | WO 2004/096271 | 11/2004 |
| WO | WO 2004/099249 | 11/2004 |
| WO | WO 2004/106379 | 12/2004 |
| WO | WO 2004/106380 | 12/2004 |
| WO | WO 2004/106383 | 12/2004 |
| WO | WO 2005/056606 | 6/2005 |
| WO | WO 2005/056759 | 6/2005 |
| WO | WO 2005/080428 A2 | 9/2005 |
| WO | WO 2006/020114 | 2/2006 |
| WO | WO 2006/031370 | 3/2006 |
| WO | WO 2006/053301 A2 | 5/2006 |

| WO | WO 2006/085967 | 8/2006 |
| WO | WO 2006/105338 | 10/2006 |
| WO | WO 2007/041635 | 4/2007 |

OTHER PUBLICATIONS

Winter, et al., "The Epithelial Cell Adhesion Molecule (Ep-CAM) as a Morphoregulatory Molecule Is a Tool in Surgical Pathology" *Amer. J. of Path.*, vol. 163, No. 6, (2003) 2139-2148, American Society for Investigative Pathology, Bethesda.

Wu, et al., "Humanization of a Murine Monoclonal Antibody by Simultaneous Optimization of Framework and CDR Residues" *J. Mol. Biol.*, vol. 294, No. 1, (1999) 151-162.

Xu, et al., "In Vitro Characterization of Five Humanized OKT3 Effector Function Variant Antibodies" *Cell. Immunol.*, vol. 200, No. 1, (2000) 16-26.

Yekebas, et al., "Strong Prognostic Value of Nodal and Bone Marrow Micro-Involvement in Patients with Pancreatic Ductal Carcinoma Receiving No Adjuvant Chemotherapy" *World J. Gastroenterology*, vol. 12, No. 40, (2006), 6515-6521.

Yoshida, et al., "Human Neonatal Fc Receptor Mediates Transport of IgG into Luminal Secretions for Delivery of Antigens to Mucosal Dendritic Cells" *Immunity*, vol. 20, No. 6, (2004) 769-783, Cell Press, Cambridge.

Zeidler, et al., "Simultaneous Activation of T Cells and Accessory Cells by a New Class of Intact Bispecific Antibody Results in Efficient Tumor Cell Killing" *The J. of Immuno.*, vol. 163, No. 3, (1999), 1246-1252, American Association of Immunologists, Bethesda.

Zellweger, et al., "Expression Patterns of Potential Therapeutic Targets in Prostate Cancer" *Int. J. Cancer*, vol. 113, No. 4, (2005) 619-628, Wiley-Liss, New York, U.S.A.

Zhang, et al., "A New Strategy for the Synthesis of Glycoproteins" *Science*, vol. 303, No. 5656, (2003) 371-373, American Association for the Advancement of Science, Washington, DC.

Zhou, et al., "Generation of Mutated Variants of the Human Form of the MHC Class I-related Receptor, FcRn, with Increased Affinity for Mouse Immunoglobulin G" *J. Mol. Biol.*, vol. 332, No. 4, (2003) 901-913, Elsevier.

Abdullah Nik, et al., "The Role of Monocytes and Natural Killer Cells in Mediating Antibody-Dependent Lysis of Colorectal Tumour Cells," *Cancer Immun Immunotherapy*, vol. 48, No. 9 (Dec. 1999), 517-524.

Abe, Hironori, et al., "Preparation of Recombinant MK-1/Ep-CAM and Establishment of an Elisa System for Determining Solube MK-1/EP-CAM Levels in Sera of Cancer Patients" *Journal of Immuno. Methods*, vol. 270, No. 2, (2002), 227-233, Elsevier, Amsterdam.

Alegre, et al., "A non-activating humanized anti-CD3 monoclonal antibody retains immunosuppressive properties in vivo" *Transplantation*, vol. 57, No. 11, (1994) 1537-1543.

Alliot, "Edrecolomab in the adjuvant treatment of colorectal carcinoma" *The Lancet*, vol. 361, No. 9351, (2003), 82-83, Lancet, London, England.

Amigorena, et al., "Fc receptor signaling and trafficking : a connection for antigen processing" *Immunol. Rev.*, vol. 172, (1999) 279-284, Blackwell, Oxford.

Ammons, et al., "In Vitro and In Vivo Pharmacology and Pharmacokinetics of a Human Engineered™ Monoclonal Antibody to Epithelial Cell Adhesion Molecule" *Neoplasia*, vol. 5, No. 2, (Mar./Apr. 2003), 146-154.

Anderson, et al., "An Expanded Genetic Code with a Functional Quadruplet Codon" *Proc. Natl. Acad. Sci. USA*, vol. 101, No. 20, (2004) 7566-7571, National Academy of Sciences of the United States of America, Washington, DC.

Aplin, et al., "Preparation, Properties, and Applications of Carbohydrate Conjugates of Proteins and Lipids" *CRC Crit. Reve. Biochem.*, vol. 10, No. 4, (1981) 259-306.

Armour, et al., "Recombinant Human IgG Molecules Lacking Fcγ Receptor I Binding and Monocyte Triggering Activities" *Eur. J. Immunol.*, vol. 29, No. 8, (1999) 2613-2624, Wiley-VCH, Weinheim.

Armstrong, et al., "EpCAM: A new therapeutic target for an old cancer antigen" *Cancer Biol. Ther.*, vol. 2, No. 4, (2003) 320-326.

Ashkenazi, et al., "Immunoadhesins as Research Tools and Therapeutic Agents" *Current Opinion In Immunology*, vol. 9, No. 2, (1997) 195-200, Current Biology, London, England.

Atwell, et al., "Stable Heterodimers from Remodeling the Domain Interface of a Homodimer using a Phage Display Library" *J. Mol. Biol.*, vol. 270, No. 1, (1997) 26-35, Elsevier, Oxford.

Baca, et al., "Antibody Humanization Using Monovalent Phage Display" *J. Bio. Chem.*, vol. 272, No. 16, (1997) 10678-10687, American Society for Biochemistry and Molecular Biology, Bethesda.

Baeuerle, et al., "EpCAM (CD326) Finding its Role in Cancer" *British Journal of Cancer*, vol. 96, No. 3 (2007), 417-423.

Balzar, et al., "The Structural Analysis of Adhesions Mediated by Ep-CAM" *Experimental Cell Research*, vol. 246, No. 1 (1999), 108-121.

Balzar, et al., "Epidermal Growth Factor-Like Repeats Mediate Lateral and Reciprocal Interactions of Ep-CAM Molecules in Homophilic Adhesions" *Molecular and Cellular Biology*, vol. 21, No. 7, (2001), 2570-2580.

Beigier-Bompadre, et al., "The formyl peptide N-formyl-methionyl-leucylphenylalanine downregulates the expression of FcγRs in interferon-γ-activated monocytes/macrophages in vitro and in vivo" *Scand. J. of Immunol.*, vol. 57, No. 3, (2003) 221-228.

Bermudez, et al., "Aggregation and Denaturation of Antibodies: a Capillary Electrophoresis, Dynamic Light Scattering, and Aqueous Two-Phase Partitioning Study" *Journal of Chromatography B*, vol. 807, No. 1, (2004), 17-24.

Better, et al., "Recombinant Human Engineered ING-1 Monoclonal Antibody, ING-1(heMAb), Exhibits Minimal Immunogenicity in Patients with Advanced Adenocarcinomas" CG0775 Xoma.com.

Bier, et al., "Anti-(epidermal growth factor) receptor monoclonal antibodies for the induction of antibody-dependent cell-mediated cytotoxicity against squamous cell carcinoma lines of the head and neck" *Cancer immunology and immunotherapy*, vol. 46, No. 3, (1998) 167-173, Springer, Berlin.

Bird, et al., "Single-Chain Antigen-Binding Proteins" *Science*, vol. 242, No. 4877, (1988) 423-426, American Association for the Advancement of Science, Washington, DC.

Bitoni, et al., "Pulmonary Delivery of an Erythropoietin Fc Fusion Protein in Non-Human Primates Through an Immunoglobulin Transport Pathway" *Proc. Natl. Acad. Sci. USA*, vol. 101, No. 26, (2004) 9763-9768, National Academy of Sciences of the United States of America, Washington, DC.

Bleeker, et al, "Dual mode of action of a human anti-epidermal growth factor receptor monoclonal antibody for cancer therapy" *The Journal of Immunology* vol. 173, No. 7, (2004) 4699-4707, American Association of Immunologists, Bethesda.

Bogoevski, et al., "Mode of Spread in the Early Phase of Lymphatic Metastasis in Pancreatic Ductal Adenocarcinoma" *Annals of Surgery*, vol. 240, No. 6, (2004) 993-1001.

Boruchov, et al., "Activating and Inhibitory IgG Fc Receptors on Human DCs Mediate Opposing Functions" *J. Clin. Invest.*, vol. 115, No. 10, (2005) 2914-2923, American Society for Clinical Investigation, Ann Arbor.

Bradbury, "Rational Design of Peptide Drugs: Avoiding Aggregation" *Drug Discovery Today*, vol. 10, No. 18 (2005) 1208-1209.

Bremer, et al., "Target Cell-Restricted and-enhanced apoptosis induction by a scFv:sTRAIL Fusion Protein with Specificity for the Pancarcinoma-associated Antigen EGP2" *Int. J. Cancer*, vol. 109, No. 2, (2004) 281-290.

Brischwein, et al., "MT110: A Novel Bispecific Single-Chain Antibody Construct with High Efficacy in Eradicating Established Tumors" *Mol. Immun.*, vol. 43, No. 8, (2005) 1129-1143.

Bruggeman, et al., "Regulation of the Flavin Redox Potential by Flavin-Binding Antibodies" *Eur. J. Biochem.*, vol. 249, No. 2, (1997) 393-400, Blackwell, Oxford.

Burmeister, et al., "Crystal Structure of the Complex of Rat Neonatal Fc Receptor with Fc" *Nature*, vol. 372, No. 6504, (1994) 378-383, Nature Publishing, London.

Caldas, et al., "Sizing Up miRNAs as Cancer Genes" *Nature Medicine*, vol. 11, No. 7, (2005) 712-714, Nature Publishing Group.

Caron, et al., "Engineered Humanized Dimeric Forms of IgG Are More Effective Antibodies" *J. Exp. Med.*, vol. 176, No., (1992), 1991-1195, Rockefeller University Press, New York.

Carter, et al., "Humanization of Anti-P185^HER2 Antibody for Human Cancer Therapy" *Proc. Natl. Acad. Sci. USA*, vol. 89 No., (1992) 4285-4289, National Academy of Sciences of the United States of America, Washington, DC.

Carter, "Improving the Efficacy of Antibody-Based Cancer Therapies" *Nature*, vol. 1, No. 2, (2001) 118-129, Macmillan Magazines Ltd.

Cartron, et al., "Therapeutic Activity of Humanized Anti-CD20 Monoclonal Antibody and Polymorphism in IgG Fc Receptor Fcγ RIII Gene" *Blood*, vol. 99, No. 3, (2002) 754-758, The Americain Society of Hematology, Washington, DC, U.S.A.

Chalfie, et al., "Green fluorescent protein as a marker for gene expression" *Sci.*, vol. 263, No. 5148, (1994) 802-805.

Chamow, et al., "Immunoadhesins: Principles and Applications" *TiBtech*, vol. 14, No. 2, (1996) 52-60, Elsevier Science, Oxford.

Chappel, et al. "Identification of The FC-Gamma Receptor Class I Binding Site in Human IGG Through the Use of Recominant IGG1-IGG2 Hybrid and Point-Mutated Antibodies," *Proc of the Nat'l Acad of Sci of USA*, vol. 88, No. 20, (Oct. 1991), 9036-9040, National Academy of Science, Washington, D.C., U.S.A.

Chari, et al., "Immunoconjugates Containing Novel Maytansinoids: Promising Anticancer Drugs" *Cancer Research*, vol. 52, No. 1, (1992) 127-131, American Association for Cancer Research, Philadelphia.

Chaudry, et al., "EpCAM an Immunotherapeutic Target for Gastrointestinal Malignancy: Current Experience and Future Challenges" *British Journal of Cancer*, vol. 96, No. 7, (2007) 1013-1019.

Chin, et al., "An Expanded Eukaryotic Genetic Code" *Science*, vol. 301, No. 5635, (2003) 964-967.

Chirino, et al., "Characterizing Biological Products and Assessing Comparability Following Manufacturing Changes" *Nature Biotechnology*, vol. 22, No. 11, (2004) 1383-1391.

Choudhuri, et al., "T-Cell Receptor Triggering is Critically Dependent on the Dimension of its Peptide-MHC Ligand" *Nature*, vol. 436, No. 28, (2005) 578-582.

Clark, "Antibody Humanization: A Case of the 'Emperor's New Clothes'?" *Immuno. Today*, vol. 21, No. 8, (2000) 397-402, Elsevier Scienve.

Clynes, et al., "Fc Receptors are Required in Passive and Active Immunity to Melanoma" *Proc. Natl. Acad. Sci. USA*, vol. 95, No., (1998) 652-656, National Academy of Sciences of the United States of America, Washington, DC, U.S.A.

Clynes, et al., "Inhibitory Fc Receptors Modulate In Vivo Cytoxicity Against Tumor Targets" *Nature Medicine*, vol. 6, No. 4, (2000) 443-446.

Cobleigh, et al., "Multinational Study of the Efficacy and Safety of Humanized Anti-HER2 Monoclonal Antibody in Women Who Have HER2-Overexpressing Metastatic Breast Cancer That Has Progressed After Chemptherapy for Metastatic Disease" *J. Clin. Oncol.*, vol. 17, No. 9, (1999) 2639-2649, Lippincott Williams & Wilkins, Baltimore, U.S.A.

Cragg, et al., "Signaling Antibodies in Cancer Therapy" *Cancer*, vol. 11, No. 5, (1999) 541-547, Current Biology, London, England.

Cropp, et al., "An Expanding Genetic Code" *Trends in Genetics*, vol. 20, No. 12, (2004) 625-630, Elsevier Science, Oxford.

Cutsem, et al., Adjuvant Treatment of Colorectal Cancer (current expert opinion derived from the Third International Conference: Perspectives in Colorectal Cancer, Dublin, 2001) *European J. of Cancer*, vol. 28, No. 11, (2002) 1429-1436, Elsevier, Oxford.

Dall' Acqua, et al., "Increasing the Affinity of a Human IgG1 for the Neonatal Fc Receptor: Biological Consequences," *Journ of Immun*, vol. 169, No. 9, (Nov. 1, 2002), 5171-5180, The Williams and Wilkins Co., Baltimore, U.S.A.

Dall'Ozzo, et al., "Rituximab-dependent cytotoxicity by natural killer cells: Influence of FCGR3A polymorphism on the concentration-effect relationship" *Cancer Research*, vol. 64, No. 13, (2004) 4664-4669.

Davies, et al., "Expression of GnTIII in a Recombinant Anti-CD20 CHO Production Cell Line: Expression of Antibodies with Altered Glycoforms Leads to an Increase in ADCC Through Higher Affinity for FcγRIII" *Biotech. and Bioeng.*, vol. 74, No. 4, (2001) 289-294, Wiley, New York.

Davis, et al., "Fc Receptor Homologs: Newest Members of a Remarkably Diverse Fc Receptor Gene Family" *Immuno. Rev.*, vol. 190, No. (2002) 123-136, Blackwell, Oxford.

de Bono, et al., "ING-1, a Monoclonal Antibody Targeting Ep-CAM in Patients with Advanced Adenocarcinomas" *Clinical Cancer Research*, vol. 10, No. 22, (2004) 7555-7565.

de Bono, et al., "Safety, Tolerability, and Maximum Tolerated Dose of an Intravenously Administered Human-Engineered Monoclonal Antibody, ING-1 (heMab), in Patients with Advanced Adenocarcinomas" CG 0776 Xoma.com, May 18-21, 2002, ASCO Annual Meeting Poster.

Di Paolo, et al., "A Recombinant Immunotoxin Derived from a Humanized Epithelial Cell Adhesion Molecule-specific Single-Chain Antibody Fragment Has Potent and Selective Antitumor Activity[1]" *Clinical Cancer Research*, vol. 9, No. 7, (2003) 2837-2848.

Dickinson, et al., "Bidirectional FcRn-Dependent IgG Transport in a Polarized Human Intestinal Epithelial Cell Line" *J. Clin. Invest.*, vol. 104, No. 7, (1999) 903-911.

Ding, et al., "Lipoxygenase Inhibition Induced Apoptosis Morphological Changes, and Carbonic Anhydrase Expression in Human Pancreatic Cancer Cells" *Biochem. And Biophys. Res. Comm.*, vol. 266, No. 2, (1999) 392-399.

Doronina, et al., "Development of potent monoclonal antibody auristatin conjugates for cancer therapy" *Nat. Biotech.*, vol. 21, No. 7, (2003) 778-784.

Drapkin, et al., "Expression of Candidate Tumor Markers in Ovarian Carcinoma and Benign Ovary: Evidence for a Link Between Epithelial Phenotype and Neoplasia" *Human Pathology*, vol. 35, No. 8, (2004) 1014-1021, Elsevier, New York, U.S.A.

Dubowchik, et al., "Receptor-mediated and enzyme-dependent targeting of cytotoxic anticancer drugs" *Pharmacology & Therapeutics*, vol. 83, No. 2, (1999), 67-123, Elsevier, Amsterdam.

Duksin, et al., "Relationship of the Structure and Biological Activity of the Natural Homolouges of Tunicamycin" *J. Biol. Chem.*, vol. 257, No. 6, (1982) 3105-3109.

Duncan, et al., "Localization of the Binding Site for the Human High-Affinity Fc Receptor on IgG" *Nature*, vol. 332, No. 6164, (1988) 563-564, Nature Publishing, London, UK.

Edge, et al., "Deglycosylation of Glycoproteins by Trifluoromethanesulfonic Acid" *Anal. Biochem.*, vol. 118, No. 3, (1981) 131-137.

Epstein, et al., "Biological activity of liposome-encapsulated murine interferon γ is mediated by a cell membrane receptor" *Proc. Natl. Acad. Sci. USA*, vol. 82, No. 11, (1985) 3688-3692, National Academy of Sciences of the United States of America, Washington, DC.

Erickson, "Idle Computers Get Busy Screening Drug Targets for Cancer" *Nat. Med.*, vol 11, No. 6, (2005), 584.

Fogler, et al., "Enhanced Cytotoxicity Against Colon Carcinoma by Combinations of Noncompeting Monoclonal Antibodies to the 171A Antigen" *Cancer Research*, vol. 48, No. 22, (1988), 6303-6308, American Association for Cancer Research, Philadelphia, U.S.A.

Francisco, et al., "cAC10-VCMMAE, an anti-CD30-monomethyl auristatin E conjugate with potent and selective antitumor activity" *Blood*, vol. 102, No. 4, (2003) 1458-1465, The Americain Society of Hematology, Washington, DC.

Gabizon, et al, "Pharmacokinetics and tissue distribution of doxorubicin encapsulated in stable liposomes with long circulation times" *J. Nat. Cancer.*, vol. 81, No. 19, (1989) 1484-1488, Oxford University Press, Cary.

Gastl, et al., "Ep-CAM Overexpression in Breast Cancer as a Predictor of Survival" *The Lancet*, vol. 356, No. 9246, (2000), 1981-1982, Lancet, London, UK.

Ghetie, et al., "Abnormally short serum half-lives of IgG in β2-microglobulin-deficient mice" *Eur. J. Immunol.*, vol. 26, No. 3, (1996) 690-696.

Ghetie, et al., "Increasing the serum persistence of an IgG fragment by random mutagenesis" *Nat. Biotechnol.*, 15(7), (1997) 637-640.

Ghetie, et al., "Multiple Roles for the Major Histocompatibility Complex Class I-Related Receptor FcRn" *Annu. Rev. Immunol.*, vol. 18, No., (2000) 739-766.

Gillies, et al., "Antibody-IL-12 Fusion Proteins Are Effective in SCID Mouse Models of Prostate and Colon Carinoma Metastases"

*The Journal of Immuno.*, vol. 160, No. 12, (1998), 6195-6203, American Association of Immunologists, Bethesda, MD.

Girardet, et al., "Immunochemical Characterization of Two Antigens Recognized by New Monoclonal Antibodies Against Human Colon Carcinoma" *The Journal of Immuno.*, vol. 136, No. 4, (1986) American Association of Immunologists, Bethesda, MD.

Glenn, et al., "Inhibition of Breast Cancer Invasion by EpCAM Gene Silencing: Inhibition is Wnt-Signaling Pathway-Independent Despite Evidence of Beta-Catenin Redistribution" *Journal of the American College of Surgeons*, vol. 201, No. 3, (2005), 85.

Glennie, et al., "Clinical Trials of Antibody Therapy" *Immunology Today*, vol. 21, No. 8, (2000) 403-410, Elsevier.

Gorman, et al., "Reshaping a Therapeutic CD4 Antibody" *Proc. Natl. Acad. Sci. USA*, vol. 88, No. 10(1991) 4181-4185, National Academy of Sciences of the United States of America, Washington, DC.

Gottlinger, et al., "The epithelial cell surface antigen 17-1A, a target for antibody-mediated tumor therapy: its biochemical nature, tissue distribution and recognition by different monoclonal antibodies" *Int. J. Cancer.*, vol. 38, No. 1, (1986) 47-53.

Griffiths, et al., "Strategies for Selection of Antibodies by Phage Display" *Current Opinion in Biotech.*, vol. 9, No. 1, (1998) 102-108, Current Biology, London.

Hakimuddin, et al., "A Chemical Method For The Deglycosylation Of Proteins" *Arch. Biophys.*, vol. 259, (1987) 52.

Hamada, et al., "MK-1 Expression in Carcinoma of the Ampulla of Vater as a Predictor of Improved Prognosis after Surgical Resection" *Cancer Letters*, vol. 243, No. 2, (2006) 211-216, Elsevier, Shannon, Ireland.

Hammer, et al., "Precise Prediction of Major Histocompatibility Complex Class II-Peptide Interaction Based on Peptide Side Chain Scanning" *J. Exp. Med.*, vol. 180, No. 6 (1994) 2353-2358, The Rockefeller University Press.

Hartung, et al., "Adjuvant Therapy with Edrecolomab Versus Observation in Stage II Colon Cancer: A Multicenter Randomized Phase III Study" *Onkologie*, vol. 28, No. 6-7, (2005), 347-350, Karger, Basel, Suisse.

Hayhurst, et al., "High-Throughput Antibody Isolation" *Current Opinion in Chem. Bio.*, vol. 5, No. 6 (2001) 683-689, Elsevier Science.

He, et al., "Humanization and Pharmacokinetics of a Monoclonal Antibody with Specificity for Both E- and P- Selectin" *J. Immunol.*, vol. 160, No. 2 (1998) 1029-1035, The American Association of Immunologists.

Heim, et al., "Engineering Green Fluorescent for Improved Brightness, Longer Wavelengths and Fluorescence Resonance Energy Transfer" *Current Bio.*, vol. 6, No. 2 (1996) 178-182.

Herlyn, et al., "Colorectal Carcinoma-Specific Antigen: Detection by Means of Monoclonal Antibodies" *Proceedings of the National Academy of Sciences of the United States of America*, vol. 76, No. 3, (1979), 1438-1442.

Herlyn, et al., "IgG2a Monoclonal Antibodies Inhibit Human Tumor Growth Through Interaction with Effector Cells" *Proceedings of the National Academy of Sciences of the United States of America*, vol. 79, No. 15, (1982) 4761-4765.

Hermeling, et al., "Structural Characterization and Immunogenicity in Wild—Type and Immune Tolerant Mice of Degraded Recombinant Human Interferon Alpha2b" *Pharmaceutical Research*, vol. 22, No. 12, (2005), 1997-2006, Springer, New York, U.S.A.

Hingorani, et al., "Preinvasive and Invasive Ductal Pancreatic Cancer and Its Early Detection in the Mouse" *Cancer Cell*, vol. 4, No. 6, (2003) 437-450, Elsevier.

Hinman, et al., "Preparation and characterization of monoclonal antibody conjugates of the calicheamicins : a novel and potent family of antitumor antibiotics" *Cancer Research*, vol. 53, No. 14, (1993) 3336-3342.

Hinton, et al., "Engineered Human IgG Antibodies with Longer Serum Half-Lives in Primates," *Journ of Bio Chem*, vol. 279, No. 8, (Feb. 20, 2004), 6213-6216, American Society of Biochemical Biologists, Birmingham, U.S.A.

Holliger, et al., "Engineering Bispecific Antibodies" *Current Opinion Biotech.*, vol. 4, No. 4 (1993) 446-449.

Holliger, et al., "Diabodies: Small Bivalent and Bispecific Antibody Fragments" *Proc. Natl. Acad. Sci. USA*, vol. 90, No. 14 (1993) 6444-6448, National Academy of Sciences of the United States of America, Washington, DC.

Hu, et al., "Minibody: A Novel Engineered Antio-Carcinoembyronic Antigen Antibody Fragment (Single-Chain Fv-$C_H3$) Which Exhibits Rapid, High-Level Targeting of Xenografts" *Cancer Research*, vol. 56, No. 13, (1996) 3055-3061, American Association for Cancer Research, Philadelphia.

Huls, et al., "A Recombinant, Fully Human Monoclonal Antibody with Antitumor Activity Constructed from Phage-Displayed Antibody Fragments" *Nature Biotechnology*, vol. 17, No. 3, (1999), 276-281, Nature, New York, U.S.A.

Huls, et al., "Antitumor Immune Effector Mechanisms Recruited by Phage Display-derived Fully Human IgG1 and IgA1 Monoclonal Antibodies[1]" *Cancer Research*, vol. 59, No. 22, (1999) 5778-5784.

Hunter, et al., "Inhibition of Fcγ receptor-mediated phagocytosis by a nonphagocytic Fcγ receptor" *Blood*, vol. 91, No. 5, (1998) 1762-1768.

Huston, et al., "Protein Engineering of Antibody Binding Sites: Recovery of Specific Activity in an Anti-Digoxin Single-Chain Fv Analogue Produced in *Escherichia coli*" *Proc. Natl. Acad. Sci. USA*, vol. 85, No. 16, (1988) 5879-5883.

Hutchins, et al., "Improved Biodistribution, Tumor Targeting, and Reduced Immunogenicity in Mice with a γ4 Variant of Campath-1H" *Proc. Natl. Acad. Sci. USA*, vol. 92, No. 26, (1995) 11980-11984, National Academy of Sciences of the United States of America, Washington, DC.

Hwang, et al., "Hepatic uptake and degradation of unilamellar sphingomyelin/cholesterol liposomes: a kinetic study" *Proc. Natl. Acad. Sci. USA*, vol. 77, No. 7, (1980) 4030-4034.

Ichiki, et al., "Regulation of the Expression of Human Cε Germline Transcript" *J. Immuno.*, vol. 150, No. 12, (1993) 5408-5417, The American Association of Immunologists.

Idusogie, et al., "Mapping of the C1q Binding Site on Rituxan, a Chimeric Antibody with a Human IgG1 Fc" *J. Immunol.*, vol. 164, No. 8, (2000) 4178-4184.

Idusogie, et al., "Engineered Antibodies with Increased Activity to Recruit Complement" *J. Immunol.*, vol. 166, No. 4, (2001) 2571-2575.

Israel, et al., "Increased Clearance of IGG in Mice that Lack Beta 2-Microglobulin: Possible Protective Role of FCRN" *Immunol*, vol. 89, No. 4, (1996) 573-578.

Izbicki, et al., "Prognostic Value of Immunohistochemically Identifiable Tumor Cells in Lymph Nodes of Patients with Completely Resected Esophageal Cancer" *The New England Journal of Medicine*, vol. 337, No. 17, (1997), 1118-1194, Massachusetts Medical Society, Boston, U.S.A.

Jefferis, et al., "Recognition Sites on Human IgG for FcγReceptors: The Role of Glycosylation" *Immuno. Ltrs.*, vol. 44, No. 2-3, (1995) 111-117, Elsevier, Amsterdam.

Jefferis, et al., "Modulation of FcγR and Human Complement Activation by IgG3-Core Oligosaccharide Interactions" *Immuno. Ltr.*, vol. 54, No., (1996) 101-104, Elsevier.

Jefferis, et al., "Interaction Sites on Human IgG-Fc for FcγR: Current Models" *Immuno. Ltrs.*, vol. 82, No., (2002) 57-65.

Jones, et al., "Replacing the Complementarity-Determining regions in a Human Antibody with Those from a Mouse" *Nature*, vol. 321, No. 6069, (1986) 522-525.

Junghans, et al., "The Protection Receptor for IgG Catabolism is the $\beta_2$-Microglobulin-Containing Neonatal Intestinal Transport Receptor" *Proc. Natl. Acad. Sci. USA*, vol. 93, No. 11, (1996) 5512-5516, National Academy of Sciences of the United States of America, Washington, DC.

Kabat, et al "Sequences of Proteins of Immunological Interest" vol. 1, Fifth Edition, 1991, Diane Publishing Co.

Kaiser, et al., "Tackling the Cancer Genome" *Science*, vol. 309, No. 5735 (2005) 693.

Kan, et al., "Thioether-Bonded Constructs on Fab'γ and Fcγ Modules Utilizing Differential Reduction of Interchain Disulfide Bonds" *J. Immunol.*, vol. 166, No. 2, (2001) 1320-1326.

Kim, et al., "Mapping the Site on Human IgG for Binding of the MHC Class I-Related Receptor, FcRn" *Eur. J. Immunol*, vol. 29, No. 9, (1999) 2819-2825, Wiley-VCH, Weinheim.

Kim, "Targeted Therapies for the Treatment of Cancer" *The American Journal of Surgery*, vol. 186, No. 3, (2003), 264-268, Elsevier, New York, U.S.A.

Krauss, et al., "Specificity Grafting on Human Antibody Frameworks Selected from a Phage Display Library: Generation of a Highly Stable Humanized Anti-CD22 Single-Chain Fv Fragment" *Protein Engineering*, vol. 16, No. 10, (2003) 753-759.

Laheru, et al., "Immunotherapy For Pancreatic Cancer-Science Driving Clinical Progress" *Nature Review Cancer*, vol. 5, No. 6, (2005), 459-467, Nature Publishing Group.

Leach, "Mouse Models of Pancreatic Cancer: The Fur is Finally Flying!" *Cancer Cell*, vol. 5, No. 1, (2004) 7-11, Cell Press.

Lehrnbecher, et al., "Variant Genotypes of the Low-Affinity Fcγ Receptors in Two Control Populations and a Review of Low-Affinity Fcγ Receptor Polymorphisms in Control and Disease Populations" *Blood*, vol. 94, No. 12, (1999) 4220-4232, The Americain Society of Hematology, Washington, DC, U.S.A.

Liljefors, et al., "Clinical effects of a chimeric anti-EpCAM monoclonal antibody in combination with granutocyte-macrophage colony-stimulating factor in patients with metastatic colorectal carcinoma" *International of Journal of Oncology*, vol. 26, No. 6, (2005), 1581-1589, Editorial Academy of the International Journal of Oncology, Athens, Greece.

Linnenbach, et al., "Sequence investigation of the major gastrointestinal tumor-associated antigen gene family, GA733" *Proc. Natl. Acad. Sci. USA*, vol. 86, No. 1, (1989) 27-31.

Linnenbach, et al., "Retroposition in a family of carcinoma-associated antigen genes" *Mol. Cell. Biol.*, vol. 13, No. 3, (1993) 1507-1515.

Little, et al., "Of Mice and Men: Hybridoma and Recombinant Antibodies" *Immuno. Today*, vol. 21, No. 8, (2000)364-370, Elsevier.

Litvinov, et al., "Ep-CAM: A Human Epithelial Antigen Is a Homophilic Cell-Cell Adhesion Molecule" *The Journal of Cell Biology*, vol. 125, No. 2, (1994) 437-446, Rockefeller University Press, New York, U.S.A.

Lobuglio, et al., "Mouse/Human Chimeric Monoclonal Antibody in Man: Kinetics and Immune Response" *Proc. Natl. Acad. Sci. U.S.A*, vol. 86, No. 11, (1989), 4220-4224, National Academy of Sciences of the United States of America, Washington, DC, U.S.A.

Lockhart, et al., "Treatment for Pancreatic Cancer: Current Therapy and Continued Progress" *Gastroenterology*, vol. 128, No. 6, (2005), 1642-1654, Elsevier, New York, U.S.A.

Lode, et al., "Targeted therapy with a novel enediyne antibiotic calicheamicin $\Theta^1_1$ effectively suppresses growth and dissemination of liver metastases in a syngeneic model of murine neuroblastoma" *Cancer Research*, vol. 58, No. 14, (1998) 2925-2928.

Lowman, et al., "Selecting High-Affinity Binding Proteins by Monovalent Phage Display" *Biochem.*, vol. 30, No. 4, (1991) 10832-10838, American Chemical Society, Washington, DC.

Lund, et al., "Human FcγRI and FcγRIII Interact with Distinct But Overlapping Sites on Human IgG" *The J. of Immuno.*, vol. 147, No. 8, (1991) 2657-2662, American Association of Immunologists, Bethesda, U.S.A.

Lund, et al., "Multiple Binding Sites on the Ch2 Domain of IgG for Mouse FcγR11" *Mol. Immuno.*, vol. 29, No. 1, (1992) 53-59, Elsevier, Oxford.

Lund, et al., "Oligosaccharide-Protein Interactions in IgG Can Modulate Recognition By Fcγ Receptors" *The FASEB Journal*, vol. 9, No. 1, (1995) 115-119, Federation of American Societies for Experimental Biology, Bethesda.

Lund, et al., "Multiple Interactions of IgG with Its Core Oligosaccharide Can Modulate Recognition by Complement and Human Fcγ Receptor I and Influence the Sythesis of Its Oligosaccharide Chains" *The J. of Immunol.*, vol. 157, No. 11, (1996) 4963-4969, American Association of Immunologists, Bethesda.

Lutterbuese, et al., "Exchanging Human Fcγ1 with Murine Fcγ2a Highly Potentiates Anti-Tumor Activity of Anit-EpCAM Anitbody Adecatumumab in a Syngeneic Mouse Lung Metastasis Model" *Cancer Immunol Immunother*, vol. 56., No. 4, (2006) 459-468, Springer-Verlag.

Mallios, "Class II MHC Quantitative Binding Motifs Derived from a Large Molecular Database with a Versatile Iterative Stepwise Discriminant Analysis Meta-Algorithm" *Bioinformatics*, vol. 15, No. 6, (1999) 432-439, Oxford University Press, Oxford.

Mallios, "Predicting Class II MHC/Peptide Multi-Level Binding with an Iterative Stepwise Discriminant Analysis Meta-Algorithm" *Bioinformatics*, vol. 17, No. 10, (2001) 942-948.

Margulies, et al., "Genome Sequencing in Microfabricated High-Density Picolitre Reactors" *Nature*, vol. 437, No. 7057, (2005), 376-380, Nature Publishing, London, England.

Marshall, et al., "Prediction of Peptide Affinity to HLA DRB1* 0401" *J. Immunol.*, vol. 154, No. 11, (1995) 5927-5933, American Association of Immunologists, Bethesda.

Martin, et al., "Expression of the 17-1A Antigen in Gastric and Gastro-Oesophageal Junction Adenocarcinomas: A Potential Immunotherapeutic Target?" *Journal of Clinical Pathology*, vol. 52, No. 9, (1999) 701-704, BMJ, London.

Martin, et al., "Crystal Structure at 2.8 A of an FcRn/Heterodimeric Fc Complex: Mechanish of pH-Dependent Binding" *Mol. Cell*, vol. 7, No. 4, (2001) 867-877.

Massey, "Catalytic Antibodies Catching On" *Nature*, vol. 328, No., (1987) 457-458.

Maynard, et al., "Antibody Engineering" *Annu. Rev. Biomed. Eng.*, vol. 2, No., (2000) 339-376.

McLaughlin, et al., "Rituximab Chimeric Anti-CD20 Monoclonal Antibody Therapy for Relapsed Indolent Lymphoma: Half of Patients Respond to a Four-Dose Treatment Program" *J. Clin. Oncol.*, vol. 16, No. 8, (1998) 2825-2833, Lippincott Williams & Wilkins, Baltimore.

McLaughlin, et al., "The Epithelial Glycoprotein 2 (EGP-2) Promoter-driven Epithelieal-specific Expression of EGP-2 in Transgenic Mice: A New Model to Study Carcinoma-directed Immunotherapy[1]" *Cancer Research*, vol. 61, No. 10, (2001) 4105-4111.

Mechetina, et al., "Identification of CD16-2, a Novel Mouse Receptor Homologous to CD16/FcγRIII" *Immunogenetics*, vol. 54, No. 7, (2002) 463-468, Springer, Heidelberg.

Medesan, et al., "Delineation of the Amino Acid Residues Involved in Transytosis and Catabolism of Mouse IgG1" *J. Immunol.*, vol. 158, No. 5, (1997) 2211-2217, American Association of Immunologists, Bethesda.

Mellstedt, et al., "Ga733/EpCAM as a Target for Passive and Active Specific Immunotherapy in Patients with Colorectal Carcinoma" *Annals of the New York Academy of Sciences*, vol. 910, No. 1, (2000), 254-262.

Meyaard, et al., Retraction of: Meyaard, et al. "The Epithelial Cellular Adhesion Molecule (Ep-CAM) is a Ligand for the Leukocyte-associated Immunoglobulin-like Receptor (LAIR) J.Exp. Med. 194; 107-112" J. Exp. Med, Oct. 6, 2003, 198; (7) :1129.

"Micromet's Human Antibody MT201 Poside to Improve Carcinoma Treatment" Micromet News Release,(Jul. 11, 2002) 1-2.

Morea, et al., "Antibody Structure, Prediction and Redesign" *Biophysical Chemistry*, vol. 68, No. 1-3, (1997) 9-16, Elsevier, Amsterdam.

Morea, et al., "Antibody Modeling: Implications for Engineering and Design" *Methods*, vol. 20, No., (2000) 267-279.

Mosolits, et al., "Vaccination with Ep-CAM Protein or Anti-Idiotypic Antibody Induces Th1-Biased Response against MHC Class I- and II-Restricted Ep-CAM Epitopes in Colorectal Carcinoma Patients" *Clinical Cancer Research*, vol. 10, No. 16, (2004) 5391-5402.

Munz, et al., "The Tumor-Associated Antigen EpCAM Upregulates the Fatty Acid Binding Protein E-FABP" *Cancer Letters*, vol. 225, No., (2005), 151-157.

Naundorf, et al., "In vitro and in vivo activity of MT201, a fully human monoclonal antibody for pancarcinoma treatment" *Int. J. Cancer*, vol. 100, No. 1, (2002), 101-110, Wiley-Liss, New York, U.S.A.

Newman, et al., "Primatization" of Recombinant Antibodies for Immunotherapy of Human Diseases: A Macaque/Human Chimeric Antibody Against Human CD4 *Biotech.*, vol. 10, (1992) 1455-1460.

Nimmerjahn, et al., "Divergent immunoglobulin G subclass activity through selective Fc receptor binding" *Sci.*, vol. 310, No. 5753, (2005) 1510-1512, American Association for the Advancement of Science, Washington, DC.

Nimmerjahn, et al., "Fcγ receptors : Old friends and new family members" *Immunity*, vol. 24, No.1, (2006) 19-28, Cell Press, Cambridge.

Nochi, et al., "Biological role of Ep-CAM in the physical interaction between epithelial cells and lymphocytes in intestinal epithelium" *Clinical Immuno.*, vol. 113, No. 3, (2004) 326-339, Elsevier, San Diego, U.S. A.

Nolan, et al., "Fluorescence-Activated Cell Analysis and Sorting of Viable Mammalian Cells Based on β-D-Galactosidase Activity After Transduction of *Escherichia coli* lacZ" *Proc. Natl. Acad. Sci. USA*, vol. 85, No. 8, (1988) 2603-2607, National Academy of Sciences of the United States of America, Washington, DC.

O'Connor, et al., "Humanization of an Antibody Against Human Protein C and Calcium-Dependence Involving Framework Residues" *Pro. Eng.*, vol. 11, No. 4, (1998) 321-328.

Osta, et al., "EpCAM is Overexpressed in Breast Cancer and Is a Potential Target for Breast Cancer Gene Therapy" *Cancer Research*, vol. 64, No. 16, (2004) 5818-5824, American Association for Cancer Research, Philadelphia, U.S.A.

Penichet, et al., "Antibody-Cytokine Fusion Proteins for the Therapy of Cancer" *J. Immunol. Methods*, vol. 248, No. 1-2, (2001) 91-101, Elsevier, Amsterdam.

Peters, et al., "Phase I Study of the Novel Fully Human Monoclonal Antibody MT201, Directed Against Epithelial Cellular Adhesion Molecule (Ep-CAM), in Patients with Hormone-Refractory Prostate Cancer (HRPC)" *Journal of Clinical Oncology*, vol. 22, No. 14, (2004), 2600, American Society of Clinical Oncology.

Prang, et al., "Cellular and Complement-Dependent Cytotoxicity of EP-CAM-specific Monoclonal Antibody MT201 Against Breast Cancer Cell Lines" *British Journal of Cancer*, vol. 92, No. 2, (2005) 342-349.

Preithner, et al., "High Concentrations of Therapeutic IgG1 Antibodies are Needed to Compensate for Inhibition of Antibody-Dependent Cellular Cytotoxicity by Excess Endogenous Immunoglobulin G" *Mol. Immuno.*, vol. 43, No. 8, (2006), 1183-1193, Elsevier, Oxford.

Presta, et al., "Humanization of an Anti-Vascular Endothelial Growth Factor Monoclonal Antibody for the Therapy of Solid Tumors and Other Disorders" *Cancer Research*, vol. 57, No. 20, (1997) 4593-4599, American Association for Cancer Research, Philadelphia.

Presta, et al., "Engineering Therapeutic Antibodies for Improved Function" *Biochemical Society Transactions*, vol. 30, No. 4, (2002) 487-490, Portland Press, Colchester, UK.

Pricop, et al., "Differential Modulation of Stimulatory and Inhibitory Fcγ Receptors on Human Monocytes by Th1 and Th2 Cytokines" *J. Immunol.*, vol. 166, (2001) 531-537.

Punt, et al., "Edrecolomab Alone or In Combination with Fluorouracil and Folinic Acid in the Adjuvant Treatment of Stage III Colon Cancer: A Randomised Study" *The Lancet*, vol. 360, No. 9334, (2002), 671-677, Lancet, London, England.

Queen, et al., "A Humanized Antibody that Binds to the Interleukin 2 Receptor" *Proc. Natl. Acad. Sci. USA*, vol. 86, No. 24, (1989) 10029-10033.

Rader, et al., "A Phage Display Approach for Rapid Antibody Humanization: Designed Combinatorial V Gene Libraries" *Proc. Natl. Acad. Sci. USA*, vol. 95, No. 15, (1998) 8910-8915.

Raghavan, et al., "Fc Receptors and Their Interactions with Immunoglobulins" *Annu. Rev. Cell Dev. Biol.*, vol. 12, No., (1996) 181-220, Annual Reviews, Palo Alto, U.S.A.

Ragupathi, et al., "Antibodies against tumor cell glycolipids and proteins, but not mucins, mediate complement-dependent cytotoxicity" *The Journal of Immuno.*, vol. 174, No. 9, (2005), 5706-5712, American Association of Immunologists, Bethesda, U.S.A.

Rao, et al., "Expression of epithelial cell adhesion molecule in carcinoma cells present in blood and primary and metastatic tumors" Int. J. Oncol., (2005), 49-57, vol. 27 No. 1.

Raum, et al., "Anti-self Antibodies Selected from a Human IgD Heavy Chain Repertoire: A Novel Approach to Generate Therapeutic Human Antibodies Against Tumor-Associated Differentiation Antigens" *Cancer Immun. Immuno.*, vol. 50, No. 3 , (2001) 141-150.

Ravetch, et al., "IgG Fc Receptors" *Annu. Rev. Immunol.*, vol. 19, No., (2001) 275-290.

"Recombinant Human EpCAM (TROP-1)/Fc Chimera" R&D Systems, Catalog No. 960-EP, Jun. 28, 2004.

Reddy, et al., "Elimination of Fc Receptor-Dependent Effector Functions of a Modified IgG4 Monoclonal Antibody to Human CD4" *J. Immunol.*, vol. 164, No. 4, (2000) 1925-1933.

Reiter, et al., "Engineering Antibody Fv Fragments for Cancer Detection and Therapy: Disulfide-Stabilized Fv Fragments" *Nature*, vol. 14., No. 10, (1996) 1239-1245, Nature, New York.

Ren-Heidenreich, et al., "Redirected T-cell cytotoxicity to epithelieal cell adhesion molecule-overexpressing adenocarcinomas by a novel antibody, E3Bi, in vitro and in an animal model" *Cancer*, vol. 100, No. 5 (2004) 1095-1103.

Riechmann, et al., "Reshaping Human Antibodies for Therapy" *Nature*, vol. 332, (1988), 323-327.

Roguska, et al., "Humanization of Murine Monoclonal Antibodies Through Variable Domain Resurfacing" *Proc. Natl. Acad. Sci. USA*, vol. 91, No. 3, (1994) 969-973, National Academy of Sciences of the United States of America, Washington, DC.

Roque, et al., "Antibodies and Genetically Engineered Related Molecules: Production and Purification" *Biotech.*, vol. 20, No. 3, (2004) 639-654, American Chemical Society, Washington, DC.

Rosok, et al., "A Combinatorial Library Strategy for the Rapid Humanization of Anticarcinoma BR96 Fab" *J. Bio. Chem.*, vol. 271, No. 37, (1996) 22611-22618, American Society for Biochemistry and Molecular Biology.

Ruan, et al. "Inhibition of tumor metastasis by ING-1 (heMab), a human-engineered™ monoclonal antibody targeting the epithelial cell adhesion molecule" Poster Sessions Xoma.com, 503, S151, 2002. vol. 38. Supp17 pp. 151.

Samuelsson, et al., "Anti-inflammatory activity of IVIG mediated through the inhibitory Fc receptor" *Sci.*, vol. 291, No. 5503, (2001) 484-486.

Schmidt, et al., "Trends in Cancer Therapy: Role of Monoclonal Antibodies" *Sem. In Oncology Nursing*, vol. 19, No. 3, (2003), 169-179, Elsevier, Philadelphia, U.S.A.

Schmidt, et al., "CD44 Variant Isoforms Associate with Tetraspanins and EpCAM" *Experimental Cell Research*, vol. 297, No. 2, (2004), 329-347, Elsevier, Orlando, U.S.A.

Schmitt, et al., "Opsonization with Trifunctional Bispecific (alphaCD3 x alphaEpCAM) Antibody Results in Efficient Lysis In Vitro and In Vivo of EpCAM Positive Tumor Cells by Cytotoxic T Lymphocytes" *Int. J. Oncol.*, vol. 25, No. 4, (2004), 841-848, Editorial Academy of the International Journal of Oncology, Athens, Greece.

Schroeder, et al., "Purging of Epithelial Tumor Cells from Peripheral Blood Stem Cells by Means of the Bispecific Antibody BIS-1¹" *Clinical Cancer Research*, vol. 6, No. 6, (2000) 2521-2527.

Schwartzberg, "Clinical Experience with Edrecolomab: A Monoclonal Antibody Therapy for Colorectal Carcinoma" *Critical Reviews in Oncology Hematology*, vol. 40, No. 1, (2001) 17-24, Elsevier Science, Shannon, Ireland.

Shields, et al., "High Resolution Mapping of the Binding Site on Human IgG1 for FcγRI, FcγRII, FcγRIII, and FcRn and Design of IgG1 Variants with Improved Binding to the FcγR," *Journ of Bio Chem*, vol. 276, No. 9, (Mar. 2, 2001), 6591-6604, American Society of Biolochemical Biologists, Birmingham, U.S.A.

Shields, et al., "Lack of Fucose on Human IfG1 N-Linked Oligosaccharide Improves Binding to Human FcγRIII and Antibody-dependent Cellular Toxicity" *J. Bio. Chem.*, vol. 277, No. 30, (2002) 26733-26740, American Society for Biochemistry and Molecular Biology, Bethesda.

Shinkawa, et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity" *J. Bio. Chem.*, vol. 278, No. 5, (2003) 3466-3473, American Society for Biochemistry and Molecular Biology, Bethesda.

Shopes, "A Genetically Engineered Human IgG Mutant with Enhanced Cytolytic Activity" *J. Immunol.*, vol. 148, No. 9, (1992) 2918-2922, American Association, of Immunologists.

Simon, et al., "Epithelial Glycoprotein is a Member of a Family of Epithelial Cell Surface Antigens Homologous to Nidogen, a Matrix Adhesion Protein" *Proc. Natl. Acad. Sci. USA*, vol. 87, No., (1990), 2755-2759, National Academy of Sciences of the United States of America, Washington, DC, U.S.A.

Simon, et al., "Peptoids: A Modular Approach to Drug Discovery" *Proc. Natl. Acad. Sci. USA*, vol. 89, No. 20, (1992) 9367-9371.

Sizmann, et al., "Drug Points: Prolonged Urticaria with 17-1A Antibody" *British Medical Journal*, vol. 317, No. 7173 (1998) 1631, British Medical Association, London, England.

Smith, "Filamentous Fusion Phage: Novel Expression Vectors That Display Cloned Antigens on the Virion Surface" *Science*, vol. 228, No. 4705, (1985) 1315-1317, American Association for the Advancement of Science, Washington, DC.

Spizzo, et al, Correspondence to Author Cornelis Punt, The Lancet, (2003) 83, vol. 361.

Spizzo, et al., "High Ep-CAM Expression is Associated with Poor Prognosis in Node-Positive Breast Cancer" *Breast Cancer Research and Treatment*, vol. 86, No. 3, (2004), 207-213, Springer, Dordrecht.

Stauber, et al., "Development and applications of enhanced green fluorescent protein mutants" *Biotech.*, vol. 24, No. 3, (1998) 462-471.

Stella, et al., "Prodrugs: A Chemical Approach to Targeted Drug Delivery" (1985) The Human Press.

Stemmler, et al., "Combined Treatment of Metastatic Breast Cancer (MBC) by High-Dose Chemotherapy (HDCT) and Bispecific Antibodies: a Pilot Study" *Anticancer Res.*, vol. 25, No. 4, (2005) 3045-3054.

Steplewski, et al., "Biological Activity of Human-Mouse IgG1, IgG2, IgG3, and IgG4 Chimeric Monoclonal Anitbodies with Antitumor Specificity" *Proc. Natl. Acad. Sci. USA*, vol. 85, No., (1988), 4852-4856, National Academy of Sciences of the United States of America, Washington, U.S.A.

Stern, et al., "Overview of Monoclonal Antibodies in Cancer Therapy: Present and Promise" *Crit. Rev. in Oncology/Hematology*, vol. 54, No. 1, (2005), 11-29, Elsevier Science, Shannon, Ireland.

Stevenson, et al., "Engineered Antibody for Treating Lymphoma" *Recent Results Cancer Res.*, vol. 159, (2002) 104-112.

Sturniolo, et al., "Generation of Tissue-Specific and Promiscuous HLA Ligand Databases Using DNA Microarrays and Virtual HLA Class II Matrices" *Nature Biotech.*, vol. 17, No. 6, (1999) 555-561, Nature, New York.

Sun, et al., "Chimeric Antibody with Human Constant Regions and Mouse Variable Regions Directed Against Carcinoma-Associated Antigen 17-1A," *Proceedings of the Nat'l Academy of Sciences of USA*, vol. 84, No. 1, (1987), 214-218, National Academy of Science, Washington, D.C., U.S.A.

Szala, et al., "Molecular Cloning of cDNA for the Carcinoma-Associated Antigen GA733-2" *Proc. Natl. Acad. Sci. USA*, vol. 87, No. 9, (1990), 3542-3546, Wistar Institute of Anatomy and Biology, Philadelphia, U.S.A.

Tan, et al., "CD40-CD40L Interaction in Alzheimer's Disease" *Curr. Opin. Pharm.*, vol. 2, No. 4, (2002) 445-451, Elsevier Science.

Thotakura, et al., "Enzymatic Deglycosylation of Glycoproteins" Methods of Enzymology, vol. 138, No., (1987) 350-359.

Thrush, et al., "Immunotoxins: An Update" *Ann. Rev. Immunol.*, vol. 14, (1996) 49-71, Annual Reviews, Palo Alto, USA.

Tomita, et al., "Molecular Identification of a Human Carcinoma-Associated Glycoprotein Antigen Recognized by Mouse Monoclonal Antibody FU-MK-1" *Jpn. J. Cancer Res.*, vol. 91, No. 2, (2000) 231-238, Japanese Cancer Association, Tokyo, Japan.

Tomlinson, et al., "Methods for Generating Multivalent and Bispecific Antibody Fragments" *Methods in Enzymology*, vol. 326, No., (2000) 461-479.

Trail, et al., "Monoclonal Antibody Drug Conjugates in the Treatment of Cancer" *Curr. Opin. Immunol.*, vol. 11, No. 5, (1999) 584-588, Elsevier Science.

Tridandapani, et al., "Regulated Expression and Inhibitory Function of Fcγ RIIb in Human Monocytic Cells" *J. Biol. Chem.*, vol. 277, No. 7, (2002) 5082-5089.

Tsurshita, et al., "Humanization of Monoclonal Antibodies" (2004) 533-545, Elsevier Science.

Umana, et al., "Engineered Glycoforms of an Antineuro-blastoma IgG1 with Optimized Antibody-Dependent Cellular Cytotoxic Activity" *Nature Biotechnology*, vol. 17, No. 2, (1999) 176-180, Nature, New York.

Van Mirre, et al., "Neutrophil responsiveness to IgG, as determined by fixed ratios of mRNA levels for activating and inhibitory FcγRII (CD32), is stable over time and unaffected by cytokines" *Blood*, vol. 108, No. 2, (2006) 584-590.

Verhoeyen, et al., "Reshaping Human Antibodies: Grafting an Antilysozyme Activity" *Science*, vol. 239, No. 4847, (1988) 1534-1536, American Association for the Advancement of Science, Washington, DC.

Veronese, et al., "Monoclonal Antibodies in the Treatment of Colorectal Cancer" *European J. Cancer*, vol. 40, No. 9, (2004) 1292-1301, Elsevier, Oxford.

Vitetta, et al., "Redesigning Nature's Poisons to Create Anti-Tumor Reagents" *Sci*, vol. 238 (1971) 1098.

Ward, et al., "Binding Activities of a Repertoire of Single Immunoglobulin Variable Domains Secreted from *Escherichia coli*" *Nature*, vol. 341, No. 6242, (1989) 543-545, Nature Publishing, London.

Weitz, et al., "Colorectal Cancer" *The Lancet*, vol. 365, No. 9454, (2005), 153-165, Lancet, London, England.

Weng, et al., "Two immunoglobulin g fragment C receptor polymorphisms independently predict response to rituximab in patients with follicular lymphoma" *J. Clin. Oncol.*, vol. 21, No. 21, (2003) 3940-3947.

Went, et al., "Frequent EpCam Protein Expression in Human Carcinomas" *Human Pathology*, vol. 35, No. 1, (2004), 122-128, Elsevier, New York, U.S.A.

Went, et al., "Frequent High-Level Expression of the Immunotherapeutic Target Ep-CAM in Colon, Stomach, Prostate and Lung Cancers" *British Journal of Cancer*, vol. 94, No. 1, (2006) 128-135.

White, et al., "Design and Expression of Polymeric Immunoglobulin Fusion Proteins: A Strategy for Targeting Low-Affinity Fcγ Receptors" *Protein expression and purification.*, vol. 21, No. 3, (2001) 446-455.

Willuda, et al., "High thermal Stability Is Essential for Tumor Targeting of Antibody Fragments: Engineering of a Humanized Anti-epithelial Glycoprotein-2 (Epithelial Cell Adhesion Molecule) Single-Chain Fv Fragment[1]" *Cancer Research*, vol. 59, No. 22, (1999) 5758-5767.

Wilman, "Prodrugs in Cancer Chemotherapy" *Biochem. Soc. Trans.*, vol. 14, No. 2, (1986) 375-382.

FIGURE 1A

H017-1A   SEQ ID NO:1
QVQLQQSGAELVRPGTSVKVSCKASGYAFTNYLIEWVKQRPGQGLEWIGVIN
PGSGGTNYNEKFKGKATLTADKSSSTAYMQLSSLTSDDSAVYFCARDGPWFAYWG
QGTLVTVSA

H1   SEQ ID NO:2
QVQLVQSGAEVKKPGASVKVSCKASGYAFTNYLIEWVRQAPGQGLEWMGVI
NPGSGGTNYNESLKSRVTISADKSISTAYLQISSLKAEDTAVYFCARDGPWFAYWGQ
GTLVTVSS

H2.0   SEQ ID NO:3
QVQLVQSGHEVKQPGASVKVSCKASGYAFTNYLIEWVRQAPGQGLEWMGVI
NPGSGGTNYNESLKSRVTISADKSISTAYMELSSLRSEDTAVYFCARDGPWFAYWGQ
GTLVTVSS

H2.1   SEQ ID NO:4
QVQLVQSGHEVKQPSQTLSLTCAISGYAFTNYLIEWVRQAPGQGLEWMGVIN
PGSGGTNYNESLKSRVTISADKSISTAYMELSSLRSEDTAVYFCARDGPWFAYWGQG
TLVTVSS

H2.2   SEQ ID NO:5
QVQLVQSGSGLVKPSQTLSLTCAVSGYAFTNYLIEWVRQAPGQGLEWMGVI
NPGSGGTNYNESLKSRVTISADKSISTAYMELSSLRSEDTAVYFCARDGPWFAYWGQ
GTLVTVSS

H2.3   SEQ ID NO:6
QVQLVQSGPGLVKPSQTLSLTCAISGYAFTNYLIEWVRQAPGQGLEWMGVIN
PGSGGTNYNESLKSRVTISADKSISTAYMELSSLRSEDTAVYFCARDGPWFAYWGQG
TLVTVSS

H2.4   SEQ ID NO:7
QVQLQESGPGLVKPPGTLSLTCKASGYAFTNYLIEWVRQAPGQGLEWMGVIN
PGSGGTNYNESLKSRVTISADKSISTAYMELSSLRSEDTAVYFCARDGPWFAYWGQG
TLVTVSS

H2.5   SEQ ID NO:8
QVTLRESGPALVKPTQTLTLTCKASGYAFTNYLIEWVRQAPGQGLEWMGVIN
PGSGGTNYNESLKSRVTISADKSISTAYMELSSLRSEDTAVYFCARDGPWFAYWGQG
TLVTVSS

H2.6   SEQ ID NO:9
QVTLKESGPVLVKPTETLTLTCTVSGYAFTNYLIEWVRQAPGQGLEWMGVIN
PGSGGTNYNESLKSRVTISADKSISTAYMELSSLRSEDTAVYFCARDGPWFAYWGQG
TLVTVSS

H2.7   SEQ ID NO:10
QVQLVQSGPVLVKPTETLTLTCKASGYAFTNYLIEWVRQAPGQGLEWMGVI
NPGSGGTNYNESLKSRVTISADKSISTAYMELSSLRSEDTAVYFCARDGPWFAYWGQ
GTLVTVSS

FIGURE 1A CONTINUED

H2.8  SEQ ID NO:11
QLQLQESGPGLVKPSETLKVSCKASGYAFTNYLIEWVRQAPGQGLEWMGVIN
PGSGGTNYNESLKSRVTISADKSISTAYMELSSLRSEDTAVYFCARDGPWFAYWGQG
TLVTVSS

H2.9  SEQ ID NO:12
QITLKESGPTLVKPTQTVKVSCKASGYAFTNYLIEWVRQAPGQGLEWMGVIN
PGSGGTNYNESLKSRVTISADKSISTAYMELSSLRSEDTAVYFCARDGPWFAYWGQG
TLVTVSS

H2.10 SEQ ID NO:13
QVQLLESGGGLVQPGGSLRLSCKASGYAFTNYLIEWVRQAPGQGLEWMGVI
NPGSGGTNYNESLKSRVTISADKSISTAYMELSSLRSEDTAVYFCARDGPWFAYWGQ
GTLVTVSS

H2.11 SEQ ID NO:14
QVQLVESGGGLVEPGGSLRLSCAASGYAFTNYLIEWVRQAPGQGLEWMGVI
NPGSGGTNYNESLKSRVTISADKSISTAYMELSSLRSEDTAVYFCARDGPWFAYWGQ
GTLVTVSS

H2.12 SEQ ID NO:15
QVQLVQSGHEVKQPGASVKVSCKASGYAFTNYLIEWVRQAPGQGLEWMGVI
NPGSGGTNYNESLKSRVTISADKSISQVVLTMTNMDPVDTAVYFCARDGPWFAYWG
QGTLVTVSS

H2.13 SEQ ID NO:16
QVQLVQSGHEVKQPGASVKVSCKASGYAFTNYLIEWVRQAPGQGLEWMGVI
NPGSGGTNYNESLKSRVTISADKSISTAYLTMTNMDPVDTAVYFCARDGPWFAYWG
QGTLVTVSS

H2.14 SEQ ID NO:17
QVQLVQSGHEVKQPGASVKVSCKASGYAFTNYLIEWVRQAPGQGLEWMGVI
NPGSGGTNYNESLKSRLTITKDTSKNQVVLTMTNMDSEDTAVYFCARDGPWFAYW
GQGTLVTVSS

H2.15 SEQ ID NO:18
QVQLVQSGHEVKQPGASVKVSCKASGYAFTNYLIEWVRQAPGQGLEWMGVI
NPGSGGTNYNESLKSRLTISKDTSKNQVVLTMTNMDPVDTAVYFCARDGPWFAYW
GQGTLVTVSS

H2.16 SEQ ID NO:19
QVQLVQSGHEVKQPGASVKVSCKASGYAFTNYLIEWVRQAPGQGLEWMGVI
NPGSGGTNYNESLKSRVTISADKSINTLYLQMNNLRAEGTAVYFCARDGPWFAYWG
QGTLVTVSS

H2.17 SEQ ID NO:20
QVQLVQSGHEVKQPGASVKVSCKASGYAFTNYLIEWVRQAPGQGLEWMGVI
NPGSGGTNYNESLKSRVTISADKSKNQFSLKLSSVTAADTAVYFCARDGPWFAYWG
QGTLVTVSS

FIGURE 1A CONTINUED

H2.18 SEQ ID NO:21
QVQLVQSGHEVKQPGASVKVSCKASGYAFTNYLIEWVRQAPGQGLEWMGVI
NPGSGGTNYNESLKSRVTISVDRSKNQFSLKLSSVTAADTAVYFCARDGPWFAYWG
QGTLVTVSS

H2.19 SEQ ID NO:22
QVQLVQSGHEVKQPGASVKVSCKASGYAFTNYLIEWVRQAPGQGLEWMGVI
NPGSGGTNYNESLKSRVTINPDTSKNQFSLQLNSVTPEDTAVYFCARDGPWFAYWG
QGTLVTVSS

H2.20 SEQ ID NO:23
QVQLVQSGHEVKQPGASVKVSCKASGYAFTNYLIEWVRQAPGQGLEWMGVI
NPGSGGTNYNESLKSRITINPDTSKNQFSLQLNSVTSEDTAVYFCARDGPWFAYWGQ
GTLVTVSS

H2.21 SEQ ID NO:24
QVQLVQSGPELVKPTETLTLTCKASGYAFTNYLIEWVRQAPGQGLEWMGVIN
PGSGGTNYNESLKSRVTISADKSISTAYMELSSLRSEDTAVYFCARDGPWFAYWGQG
TLVTVSS

H2.22 SEQ ID NO:25
QVQLVQSGHEVKQPGASVKVSCKASGYSFTNYLIEWVRQAPGQGLEWMGVI
NPGSGGTNYNPSLKSRVTISADKSISTAYMELSSLRSEDTAVYFCARDGPWFAYWGQ
GTLVTVSS

H2.23 SEQ ID NO:26
QVQLVQSGHEVKQPGASVKVSCKASGYSFTNYLIEWVRQAPGQGLEWMGVI
NPGSGGTNYNESLKSRVTISADKSISTAYMELSSLRSEDTAVYFCARDGPWFAYWGQ
GTLVTVSS

H3 SEQ ID NO:27
EVQLVESGGGLVQPGGSLRLSCAASGYAFTNYLIEWVRQAPGQGLEWMGVI
NPGSGGTNYNESLKSRVTISADKSISTAYMELSSLRSEDTAVYFCARDGPWFAYWGQ
GTLVTVSS

H3.1 SEQ ID NO:28
QVQLVESGGGLVQPGGSLRLSCAASGYAFTNYLIEWVRQAPGQGLEWMGVI
NPGSGGTNYNESLKSRVTISADKSISTAYMELSSLRSEDTAVYFCARDGPWFAYWGQ
GTLVTVSS

H3.2 SEQ ID NO:29
TVQLVESGGGLVQPGGSLRLSCAASGYAFTNYLIEWVRQAPGQGLEWMGVI
NPGSGGTNYNESLKSRVTISADKSISTAYMELSSLRSEDTAVYFCARDGPWFAYWGQ
GTLVTVSS

H3.3 SEQ ID NO:30
ELQLVESGGGLVQPGGSLRLSCAASGYAFTNYLIEWVRQAPGQGLEWMGVI
NPGSGGTNYNESLKSRVTISADKSISTAYMELSSLRSEDTAVYFCARDGPWFAYWGQ
GTLVTVSS

FIGURE 1A CONTINUED

H3.4 SEQ ID NO:31
EVELVESGGGLVQPGGSLRLSCAASGYAFTNYLIEWVRQAPGQGLEWMGVI
NPGSGGTNYNESLKSRVTISADKSISTAYMELSSLRSEDTAVYFCARDGPWFAYWGQ
GTLVTVSS

H3.5 SEQ ID NO:32
EVQIVESGGGLVQPGGSLRLSCAASGYAFTNYLIEWVRQAPGQGLEWMGVIN
PGSGGTNYNESLKSRVTISADKSISTAYMELSSLRSEDTAVYFCARDGPWFAYWGQG
TLVTVSS

H3.6 SEQ ID NO:33
EVQLQESGGGLVQPGGSLRLSCAASGYAFTNYLIEWVRQAPGQGLEWMGVI
NPGSGGTNYNESLKSRVTISADKSISTAYMELSSLRSEDTAVYFCARDGPWFAYWGQ
GTLVTVSS

H3.7 SEQ ID NO:34
EVQLLESGGGLVQPGGSLRLSCAASGYAFTNYLIEWVRQAPGQGLEWMGVI
NPGSGGTNYNESLKSRVTISADKSISTAYMELSSLRSEDTAVYFCARDGPWFAYWGQ
GTLVTVSS

H3.8 SEQ ID NO:35
EVQLVQSGGGLVQPGGSLRLSCAASGYAFTNYLIEWVRQAPGQGLEWMGVI
NPGSGGTNYNESLKSRVTISADKSISTAYMELSSLRSEDTAVYFCARDGPWFAYWGQ
GTLVTVSS

H3.9 SEQ ID NO:36
EVQLVESGHGLVQPGGSLRLSCAASGYAFTNYLIEWVRQAPGQGLEWMGVI
NPGSGGTNYNESLKSRVTISADKSISTAYMELSSLRSEDTAVYFCARDGPWFAYWGQ
GTLVTVSS

H3.10 SEQ ID NO:37
EVQLVESGAGLVQPGGSLRLSCAASGYAFTNYLIEWVRQAPGQGLEWMGVI
NPGSGGTNYNESLKSRVTISADKSISTAYMELSSLRSEDTAVYFCARDGPWFAYWGQ
GTLVTVSS

H3.11 SEQ ID NO:38
EVQLVESGGELVQPGGSLRLSCAASGYAFTNYLIEWVRQAPGQGLEWMGVI
NPGSGGTNYNESLKSRVTISADKSISTAYMELSSLRSEDTAVYFCARDGPWFAYWGQ
GTLVTVSS

H3.12 SEQ ID NO:39
EVQLVESGGGVVQPGGSLRLSCAASGYAFTNYLIEWVRQAPGQGLEWMGVI
NPGSGGTNYNESLKSRVTISADKSISTAYMELSSLRSEDTAVYFCARDGPWFAYWGQ
GTLVTVSS

H3.13 SEQ ID NO:40
EVQLVESGGGLKQPGGSLRLSCAASGYAFTNYLIEWVRQAPGQGLEWMGVI
NPGSGGTNYNESLKSRVTISADKSISTAYMELSSLRSEDTAVYFCARDGPWFAYWGQ
GTLVTVSS

FIGURE 1A CONTINUED

H3.14 SEQ ID NO:41
EVQLVESGGGLVKPGGSLRLSCAASGYAFTNYLIEWVRQAPGQGLEWMGVI
NPGSGGTNYNESLKSRVTISADKSISTAYMELSSLRSEDTAVYFCARDGPWFAYWGQ
GTLVTVSS

H3.15 SEQ ID NO:42
EVQLVESGGGLVRPGGSLRLSCAASGYAFTNYLIEWVRQAPGQGLEWMGVI
NPGSGGTNYNESLKSRVTISADKSISTAYMELSSLRSEDTAVYFCARDGPWFAYWGQ
GTLVTVSS

H3.16 SEQ ID NO:43
EVQLVESGGGLVQPGASLRLSCAASGYAFTNYLIEWVRQAPGQGLEWMGVI
NPGSGGTNYNESLKSRVTISADKSISTAYMELSSLRSEDTAVYFCARDGPWFAYWGQ
GTLVTVSS

H3.17 SEQ ID NO:44
EVQLVESGGGLVQPGTSLRLSCAASGYAFTNYLIEWVRQAPGQGLEWMGVI
NPGSGGTNYNESLKSRVTISADKSISTAYMELSSLRSEDTAVYFCARDGPWFAYWGQ
GTLVTVSS

H3.18 SEQ ID NO:45
EVQLVESGGGLVQPGRSLRLSCAASGYAFTNYLIEWVRQAPGQGLEWMGVI
NPGSGGTNYNESLKSRVTISADKSISTAYMELSSLRSEDTAVYFCARDGPWFAYWGQ
GTLVTVSS

H3.19 SEQ ID NO:46
EVQLVESGGGLVQPGGSVRLSCAASGYAFTNYLIEWVRQAPGQGLEWMGVI
NPGSGGTNYNESLKSRVTISADKSISTAYMELSSLRSEDTAVYFCARDGPWFAYWGQ
GTLVTVSS

H3.20 SEQ ID NO:47
EVQLVESGGGLVQPGGSLKLSCAASGYAFTNYLIEWVRQAPGQGLEWMGVI
NPGSGGTNYNESLKSRVTISADKSISTAYMELSSLRSEDTAVYFCARDGPWFAYWGQ
GTLVTVSS

H3.21 SEQ ID NO:48
EVQLVESGGGLVQPGGSLRVSCAASGYAFTNYLIEWVRQAPGQGLEWMGVI
NPGSGGTNYNESLKSRVTISADKSISTAYMELSSLRSEDTAVYFCARDGPWFAYWGQ
GTLVTVSS

H3.22 SEQ ID NO:49
EVQLVESGGGLVQPGGSLRLSCKASGYAFTNYLIEWVRQAPGQGLEWMGVI
NPGSGGTNYNESLKSRVTISADKSISTAYMELSSLRSEDTAVYFCARDGPWFAYWGQ
GTLVTVSS

H3.23 SEQ ID NO:50
EVQLVESGGGLVQPGGSLRLSCRASGYAFTNYLIEWVRQAPGQGLEWMGVI
NPGSGGTNYNESLKSRVTISADKSISTAYMELSSLRSEDTAVYFCARDGPWFAYWGQ
GTLVTVSS

FIGURE 1A CONTINUED

H3.24 SEQ ID NO:51
EVQLVESGGGLVQPGGSLRLSCTASGYAFTNYLIEWVRQAPGQGLEWMGVI
NPGSGGTNYNESLKSRVTISADKSISTAYMELSSLRSEDTAVYFCARDGPWFAYWGQ
GTLVTVSS

H3.25 SEQ ID NO:52
EVQLVESGGGLVQPGGSLRLSCAVSGYAFTNYLIEWVRQAPGQGLEWMGVI
NPGSGGTNYNESLKSRVTISADKSISTAYMELSSLRSEDTAVYFCARDGPWFAYWGQ
GTLVTVSS

H3.26 SEQ ID NO:53
EVQLVESGGGLVQPGGSLRLSCAATGYAFTNYLIEWVRQAPGQGLEWMGVI
NPGSGGTNYNESLKSRVTISADKSISTAYMELSSLRSEDTAVYFCARDGPWFAYWGQ
GTLVTVSS

H3.27 SEQ ID NO:54
EVQLVESGGGLVQPGGSLRLSCAASAYAFTNYLIEWVRQAPGQGLEWMGVI
NPGSGGTNYNESLKSRVTISADKSISTAYMELSSLRSEDTAVYFCARDGPWFAYWGQ
GTLVTVSS

H3.28 SEQ ID NO:55
EVQLVESGGGLVQPGGSLRLSCAASGFAFTNYLIEWVRQAPGQGLEWMGVI
NPGSGGTNYNESLKSRVTISADKSISTAYMELSSLRSEDTAVYFCARDGPWFAYWGQ
GTLVTVSS

H3.29 SEQ ID NO:56
EVQLVESGGGLVQPGGSLRLSCAASGYSFTNYLIEWVRQAPGQGLEWMGVI
NPGSGGTNYNESLKSRVTISADKSISTAYMELSSLRSEDTAVYFCARDGPWFAYWGQ
GTLVTVSS

H3.30 SEQ ID NO:57
EVQLVESGGGLVQPGGSLRLSCAASGYAFSNYLIEWVRQAPGQGLEWMGVI
NPGSGGTNYNESLKSRVTISADKSISTAYMELSSLRSEDTAVYFCARDGPWFAYWGQ
GTLVTVSS

H3.31 SEQ ID NO:58
EVQLVESGGGLVQPGGSLRLSCAASGYAFTDYLIEWVRQAPGQGLEWMGVI
NPGSGGTNYNESLKSRVTISADKSISTAYMELSSLRSEDTAVYFCARDGPWFAYWGQ
GTLVTVSS

H3.32 SEQ ID NO:59
EVQLVESGGGLVQPGGSLRLSCAASGYAFTNYLLEWVRQAPGQGLEWMGVI
NPGSGGTNYNESLKSRVTISADKSISTAYMELSSLRSEDTAVYFCARDGPWFAYWGQ
GTLVTVSS

H3.33 SEQ ID NO:60
EVQLVESGGGLVQPGGSLRLSCAASGYAFTNYLMEWVRQAPGQGLEWMGV
INPGSGGTNYNESLKSRVTISADKSISTAYMELSSLRSEDTAVYFCARDGPWFAYWG
QGTLVTVSS

FIGURE 1A CONTINUED

H3.34 SEQ ID NO:61
EVQLVESGGGLVQPGGSLRLSCAASGYAFTNYLISWVRQAPGQGLEWMGVI
NPGSGGTNYNESLKSRVTISADKSISTAYMELSSLRSEDTAVYFCARDGPWFAYWGQ
GTLVTVSS

H3.35 SEQ ID NO:62
EVQLVESGGGLVQPGGSLRLSCAASGYAFTNYLINWVRQAPGQGLEWMGVI
NPGSGGTNYNESLKSRVTISADKSISTAYMELSSLRSEDTAVYFCARDGPWFAYWGQ
GTLVTVSS

H3.36 SEQ ID NO:63
EVQLVESGGGLVQPGGSLRLSCAASGYAFTNYLIDWVRQAPGQGLEWMGVI
NPGSGGTNYNESLKSRVTISADKSISTAYMELSSLRSEDTAVYFCARDGPWFAYWGQ
GTLVTVSS

H3.37 SEQ ID NO:64
EVQLVESGGGLVQPGGSLRLSCAASGYAFTNYLIYWVRQAPGQGLEWMGVI
NPGSGGTNYNESLKSRVTISADKSISTAYMELSSLRSEDTAVYFCARDGPWFAYWGQ
GTLVTVSS

H3.38 SEQ ID NO:65
EVQLVESGGGLVQPGGSLRLSCAASGYAFTNYLIEWIRQAPGQGLEWMGVIN
PGSGGTNYNESLKSRVTISADKSISTAYMELSSLRSEDTAVYFCARDGPWFAYWGQG
TLVTVSS

H3.39 SEQ ID NO:66
EVQLVESGGGLVQPGGSLRLSCAASGYAFTNYLIEWVRQRPGQGLEWMGVI
NPGSGGTNYNESLKSRVTISADKSISTAYMELSSLRSEDTAVYFCARDGPWFAYWGQ
GTLVTVSS

H3.40 SEQ ID NO:67
EVQLVESGGGLVQPGGSLRLSCAASGYAFTNYLIEWVRQAPGQGLEWMGGI
NPGSGGTNYNESLKSRVTISADKSISTAYMELSSLRSEDTAVYFCARDGPWFAYWGQ
GTLVTVSS

H3.41 SEQ ID NO:68
EVQLVESGGGLVQPGGSLRLSCAASGYAFTNYLIEWVRQAPGQGLEWMGWI
NPGSGGTNYNESLKSRVTISADKSISTAYMELSSLRSEDTAVYFCARDGPWFAYWGQ
GTLVTVSS

H3.42 SEQ ID NO:69
EVQLVESGGGLVQPGGSLRLSCAASGYAFTNYLIEWVRQAPGQGLEWMGIIN
PGSGGTNYNESLKSRVTISADKSISTAYMELSSLRSEDTAVYFCARDGPWFAYWGQG
TLVTVSS

H3.43 SEQ ID NO:70
EVQLVESGGGLVQPGGSLRLSCAASGYAFTNYLIEWVRQAPGQGLEWMGVV
NPGSGGTNYNESLKSRVTISADKSISTAYMELSSLRSEDTAVYFCARDGPWFAYWGQ
GTLVTVSS

FIGURE 1A CONTINUED

H3.44 SEQ ID NO:71
EVQLVESGGGLVQPGGSLRLSCAASGYAFTNYLIEWVRQAPGQGLEWMGVI
NPGSGATNYNESLKSRVTISADKSISTAYMELSSLRSEDTAVYFCARDGPWFAYWGQ
GTLVTVSS

H3.45 SEQ ID NO:72
EVQLVESGGGLVQPGGSLRLSCAASGYAFTNYLIEWVRQAPGQGLEWMGVI
NPGSGGSNYNESLKSRVTISADKSISTAYMELSSLRSEDTAVYFCARDGPWFAYWGQ
GTLVTVSS

H3.46 SEQ ID NO:73
EVQLVESGGGLVQPGGSLRLSCAASGYAFTNYLIEWVRQAPGQGLEWMGVI
NPGSGGTYYNESLKSRVTISADKSISTAYMELSSLRSEDTAVYFCARDGPWFAYWGQ
GTLVTVSS

H3.47 SEQ ID NO:74
EVQLVESGGGLVQPGGSLRLSCAASGYAFTNYLIEWVRQAPGQGLEWMGVI
NPGSGGTNYNPSLKSRVTISADKSISTAYMELSSLRSEDTAVYFCARDGPWFAYWGQ
GTLVTVSS

H3.48 SEQ ID NO:75
EVQLVESGGGLVQPGGSLRLSCAASGYAFTNYLIEWVRQAPGQGLEWMGVI
NPGSGGTNYNEKLKSRVTISADKSISTAYMELSSLRSEDTAVYFCARDGPWFAYWG
QGTLVTVSS

H3.49 SEQ ID NO:76
EVQLVESGGGLVQPGGSLRLSCAASGYAFTNYLIEWVRQAPGQGLEWMGVI
NPGSGGTNYNESLKSRVTISRDKSISTAYMELSSLRSEDTAVYFCARDGPWFAYWGQ
GTLVTVSS

H3.50 SEQ ID NO:77
EVQLVESGGGLVQPGGSLRLSCAASGYAFTNYLIEWVRQAPGQGLEWMGVI
NPGSGGTNYNESLKSRVTISADKSKSTAYMELSSLRSEDTAVYFCARDGPWFAYWG
QGTLVTVSS

H3.51 SEQ ID NO:78
EVQLVESGGGLVQPGGSLRLSCAASGYAFTNYLIEWVRQAPGQGLEWMGVI
NPGSGGTNYNESLKSRVTISADKSINTAYMELSSLRSEDTAVYFCARDGPWFAYWG
QGTLVTVSS

H3.52 SEQ ID NO:79
EVQLVESGGGLVQPGGSLRLSCAASGYAFTNYLIEWVRQAPGQGLEWMGVI
NPGSGGTNYNESLKSRVTISADKSITTAYMELSSLRSEDTAVYFCARDGPWFAYWGQ
GTLVTVSS

H3.53 SEQ ID NO:80
EVQLVESGGGLVQPGGSLRLSCAASGYAFTNYLIEWVRQAPGQGLEWMGVI
NPGSGGTNYNESLKSRVTISADKSISSAYMELSSLRSEDTAVYFCARDGPWFAYWGQ
GTLVTVSS

FIGURE 1A CONTINUED

H3.54 SEQ ID NO:81
EVQLVESGGGLVQPGGSLRLSCAASGYAFTNYLIEWVRQAPGQGLEWMGVI
NPGSGGTNYNESLKSRVTISADKSISTLYMELSSLRSEDTAVYFCARDGPWFAYWGQ
GTLVTVSS

H3.55 SEQ ID NO:82
EVQLVESGGGLVQPGGSLRLSCAASGYAFTNYLIEWVRQAPGQGLEWMGVI
NPGSGGTNYNESLKSRVTISADKSISTVYMELSSLRSEDTAVYFCARDGPWFAYWGQ
GTLVTVSS

H3.56 SEQ ID NO:83
EVQLVESGGGLVQPGGSLRLSCAASGYAFTNYLIEWVRQAPGQGLEWMGVI
NPGSGGTNYNESLKSRVTISADKSISTAYLELSSLRSEDTAVYFCARDGPWFAYWGQ
GTLVTVSS

H3.57 SEQ ID NO:84
EVQLVESGGGLVQPGGSLRLSCAASGYAFTNYLIEWVRQAPGQGLEWMGVI
NPGSGGTNYNESLKSRVTISADKSISTAYMQLSSLRSEDTAVYFCARDGPWFAYWGQ
GTLVTVSS

H3.58 SEQ ID NO:85
EVQLVESGGGLVQPGGSLRLSCAASGYAFTNYLIEWVRQAPGQGLEWMGVI
NPGSGGTNYNESLKSRVTISADKSISTAYMEMSSLRSEDTAVYFCARDGPWFAYWG
QGTLVTVSS

H3.59 SEQ ID NO:86
EVQLVESGGGLVQPGGSLRLSCAASGYAFTNYLIEWVRQAPGQGLEWMGVI
NPGSGGTNYNESLKSRVTISADKSISTAYMELNSLRSEDTAVYFCARDGPWFAYWG
QGTLVTVSS

H3.60 SEQ ID NO:87
EVQLVESGGGLVQPGGSLRLSCAASGYAFTNYLIEWVRQAPGQGLEWMGVI
NPGSGGTNYNESLKSRVTISADKSISTAYMELSSLRAEDTAVYFCARDGPWFAYWG
QGTLVTVSS

H3.61 SEQ ID NO:88
EVQLVESGGGLVQPGGSLRLSCAASGYAFTNYLIEWVRQAPGQGLEWMGVI
NPGSGGTNYNESLKSRVTISADKSISTAYMELSSLRSEDTAVYYCARDGPWFAYWG
QGTLVTVSS

H3.62 SEQ ID NO:89
EVQLVESGGGLVQPGGSLRLSCAASGYAFTNYLIEWVRQAPGQGLEWMGVI
NPGSGGTNYNESLKSRVTISADKSISTAYMELSSLRSEDTAVYFCVRDGPWFAYWGQ
GTLVTVSS

H3.63 SEQ ID NO:90
EVQLVESGGGLVQPGGSLRLSCAASGYAFTNYLIEWVRQAPGQGLEWMGVI
NPGSGGTNYNESLKSRVTISADKSISTAYMELSSLRSEDTAVYFCGRDGPWFAYWGQ
GTLVTVSS

FIGURE 1A CONTINUED

H3.64 SEQ ID NO:91
EVQLVESGGGLVQPGGSLRLSCAASGYAFTNYLIEWVRQAPGQGLEWMGVI
NPGSGGTNYNESLKSRVTISADKSISTAYMELSSLRSEDTAVYFCAKDGPWFAYWGQ
GTLVTVSS

H3.65 SEQ ID NO:92
EVQLVESGGGLVQPGGSLRLSCAASGYAFTNYLIEWVRQAPGQGLEWMGVI
NPGSGGTNYNESLKSRVTISADKSISTAYMELSSLRSEDTAVYFCARDGPWYAYWG
QGTLVTVSS

H3.73 SEQ ID NO:93
EVQLVQSGGGLVQPGGSLRLSCAASGYSFTNYLIEWVRQAPGQGLEWMGVI
NPGSGGTNYNESLKSRVTISADKSISTAYMELSSLRSEDTAVYFCARDGPWFAYWGQ
GTLVTVSS

H3.74 SEQ ID NO:94
EVQLVESGGGLVQPGGSLRLSCAASGYSFTNYLIEWVRQAPGQGLEWMGIIN
PGSGGTNYNESLKSRVTISADKSISTAYMELSSLRSEDTAVYFCARDGPWFAYWGQG
TLVTVSS

H3.75 SEQ ID NO:95
EVQLVESGGGLVQPGGSLRLSCAASGYSFTNYLIEWVRQAPGQGLEWMGIIN
PGSGGTNYNPSLKSRVTISADKSISTAYMELSSLRSEDTAVYFCARDGPWFAYWGQG
TLVTVSS

H3.76 SEQ ID NO:96
EVQLVQSGGGLVQPGGSLRLSCAASGYSFTNYLIEWVRQAPGQGLEWMGIIN
PGSGGTNYNPSLKSRVTISADKSISTAYMELSSLRSEDTAVYFCARDGPWFAYWGQG
TLVTVSS

H3.77 SEQ ID NO:97
EVQLVESGGGLVQPGGSLRLSCAASGYSFTNYLIEWVRQAPGQGLEWMGVI
NPGSGGTNYNPSLKSRVTISADKSISTAYMELSSLRSEDTAVYFCARDGPWFAYWGQ
GTLVTVSS

H3.78 SEQ ID NO:98
EVQLVESGGGLVQPGGSLRLSCAASGYSFTNYLIEWVRQAPGQGLEWMGVI
NPGSGGTNYNENLKSRVTISADKSISTAYMELSSLRSEDTAVYFCARDGPWFAYWG
QGTLVTVSS

H3.79 SEQ ID NO:99
EVQLVESGGGLVQPGGSLRLSCAASGYSFTNYLIEWVRQAPGQGLEWMGVI
NPGSGGTNYNEALKSRVTISADKSISTAYMELSSLRSEDTAVYFCARDGPWFAYWG
QGTLVTVSS

H3.80 SEQ ID NO:100
EVQLVESGGGLVQPGGSLRLSCAASGYSFTNYLIEWVRQAPGQGLEWMGVI
NPGSGGTNYAESLKSRVTISADKSISTAYMELSSLRSEDTAVYFCARDGPWFAYWGQ
GTLVTVSS

FIGURE 1A CONTINUED

H3.81 SEQ ID NO:101
EVQLVESGGGLVQPGGSLRLSCAASGYSFTNYLIEWVRQAPGQGLEWMGVI
NPGSGGTNYQESLKSRVTISADKSISTAYMELSSLRSEDTAVYFCARDGPWFAYWGQ
GTLVTVSS

H4 SEQ ID NO:102
QVQLVESGGGLVQPGGSLRLSCAASGYAFTNYLIEWVRQAPGQGLEWMGVI
NPGSGGTNYNEKFQGRVTITRDTSASTAYLQISSLKAEDTAVYFCARDGPWFAYWG
QGTLVTVSS

H5 SEQ ID NO:103
QVQLVESGGGLVQPGGSLRLSCAASGYAFTNYLIEWVRQAPGQGLEWMGVI
NPGSGGTNYAEKFQGRVTITRDTSASTAYLQISSLKAEDTAVYYCARDGPWFAYWG
QGTLVTVSS

H6 SEQ ID NO:104
QVQLVESGGGLVQPGGSLRLSCAASGYAFTNYLIEWVRQAPGQGLEWMGVI
NPGSGGTNYNEKFQGRVTMTTDTSTSTAYLQISSLKAEDTAVYFCARDGPWFAYWG
QGTLVTVSS

FIGURE 1B

CDR1

| | |
|---|---|
| SEQ ID NO:122 | YAFTNYL |
| SEQ ID NO:123 | YSFTNYL |
| SEQ ID NO:124 | FAFTNYL |
| SEQ ID NO:125 | YAFSNYL |
| SEQ ID NO:126 | YAFTDYL |

CDR2

| | |
|---|---|
| SEQ ID NO:127 | NPGSGG |
| SEQ ID NO:128 | NPGSGA |

CDR3

| | |
|---|---|
| SEQ ID NO:129 | DGPWFAY |
| SEQ ID NO:130 | DGPWYAY |

FIGURE 2A

L0 17-1A    SEQ ID NO:105
NIVMTQSPKSMSMSVGERVTLTCKASENVVTYVSWYQQKPEQSPKLLIYGAS
NRYTGVPDRFTGSGSATDFTLTISSVQAEDLADYHCGQGYSYPYTFGGGTKLEIK

L1    SEQ ID NO:106
NIVMTQSPSSLSASVGDRVTITCQASENVVTYVSWYQQKPDQSPKLLIYGASN
RYTGVPDRFTGSGSATEFTLTISSLQSEDFADYHCGQGYSYPYTFGGGTKLEIK

L2    SEQ ID NO:107
NIVMTQSPATLSLSPGERATLSCRASENVVTYVSWYQQKPDQSPKLLIYGASN
RYTGVPDRFTGSGSATDFTLTISSLQAEDVAVYHCGQGYSYPYTFGGGTKLEIK

L3    SEQ ID NO:108
NIVMTQSPDSLAVSLGERATLSCRASENVVTYVSWYQQKPGQSPQLLIYGAS
NRYTGVPDRFTGSGSATDFTLTINSLEAEDAATYYCGQGYSYPYTFGGGTKLEIK

L3.1    SEQ ID NO:109
NIVMTQSPDSLAVSLGERATLSCRASQNVVTYVSWYQQKPGQSPQLLIYGAS
NRYTGVPDRFTGSGSATDFTLTINSLEAEDAATYYCGQGYSYPYTFGGGTKLEIK

L3.2    SEQ ID NO:110
NIVMTQSPDSLAVSLGERATLSCRASENVVTYLSWYQQKPGQSPQLLIYGAS
NRYTGVPDRFTGSGSATDFTLTINSLEAEDAATYYCGQGYSYPYTFGGGTKLEIK

L3.3    SEQ ID NO:111
NIVMTQSPDSLAVSLGERATLSCRASENVVTYVSWYLQKPGQSPQLLIYGAS
NRYTGVPDRFTGSGSATDFTLTINSLEAEDAATYYCGQGYSYPYTFGGGTKLEIK

L3.4    SEQ ID NO:112
NIVMTQSPDSLAVSLGERATLSCRASENVVTYVSWYQQKPGQPPQLLIYGAS
NRYTGVPDRFTGSGSATDFTLTINSLEAEDAATYYCGQGYSYPYTFGGGTKLEIK

L3.5    SEQ ID NO:113
NIVMTQSPDSLAVSLGERATLSCRASENVVTYVSWYQQKPGQSPQLLIYDAS
NRYTGVPDRFTGSGSATDFTLTINSLEAEDAATYYCGQGYSYPYTFGGGTKLEIK

L3.6    SEQ ID NO:114
NIVMTQSPDSLAVSLGERATLSCRASENVVTYVSWYQQKPGQSPQLLIYGAS
NRYTGVPDRFSGSGSATDFTLTINSLEAEDAATYYCGQGYSYPYTFGGGTKLEIK

L3.7    SEQ ID NO:115
NIVMTQSPDSLAVSLGERATLSCRASENVVTYVSWYQQKPGQSPQLLIYGAS
NRYTGVPDRFSGSGSGTDFTLTINSLEAEDAATYYCGQGYSYPYTFGGGTKLEIK

L3.8    SEQ ID NO:116
NIVMTQSPDSLAVSLGERATLSCRASENVVTYVSWYQQKPGQSPQLLIYGAS
NRYTGVPDRFTGSGSGTDFTLTINSLEAEDAATYYCGQGYSYPYTFGGGTKLEIK

FIGURE 2A CONTINUED

L3.9   SEQ ID NO:117
NIVMTQSPDSLAVSLGERATLSCRASENVVTYVSWYQQKPGQSPQLLIYGAS
NRYTGVPDRFTGSGSATDFTLTINSLEAEDAATYYCHQGYSYPYTFGGGTKLEIK

L3.10   SEQ ID NO:118
NIVMTQSPDSLAVSLGERATLSCRASENVVTYVSWYQQKPGQSPQLLIYGAS
NRYTGVPDRFTGSGSATDFTLTINSLEAEDAATYYCQQGYSYPYTFGGGTKLEIK

L3.11   SEQ ID NO:119
NIVMTQSPDSLAVSLGERATLSCRASENVVTYVSWYQQKPGQSPQLLIYGAS
NRYTGVPDRFTGSGSATDFTLTINSLEAEDAATYYCQQYYSYPYTFGGGTKLEIK

L3.12   SEQ ID NO:120
NIVMTQSPDSLAVSLGERATLSCKASQNVVTYVSWYQQKPGQSPQLLIYGAS
NRYTGVPDRFTGSGSATDFTLTINSLEAEDAATYYCGQGYSYPYTFGGGTKLEIK

L4   SEQ ID NO:121
NIVMTQSPDSLAVSLGERATLSCRASENVVTYVSWYQQKPGQPPQLLIYGAS
NRYTGVPDRFTGSGSGTDFTLTINSLEAEDAAVYYCGQGYSYPYTFGGGTKLEIK

FIGURE 2B

CDR1

| SEQ ID NO:131 | ENVVTY |
| SEQ ID NO:132 | QNVVTY |

CDR2

| SEQ ID NO:133 | GASNRYT |
| SEQ ID NO:134 | DASNRYT |

CDR3

| SEQ ID NO:135 | GYSYPYT |
| SEQ ID NO:136 | YYSYPYT |

FIGURE 3

CH IgG1 (Human)    SEQ ID NO:137
    ASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTHTCPP
CPAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKG
QPREPQVYTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPGK CH Hybrid (Human)   SEQ ID NO:138
    ASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTHTCPP
CPAPELLGGPSVFLFPPKPKDTLMISRTPEVTCVVVDVSHEDPEVQFNWYVDGVEVH
NAKTKPREEQFNSTFRVVSVLTVVHQDWLNGKEYKCKVSNKALPAPIEKTISKTKGQ
PREPQVYTLPPSREEMTKNQVSLTCLVKGFYPSDIAVEWESNGQPENNYKTTPPMLD
SDGSFFLYSKLTVDKSRWQQGNVFSCSVMHEALHNHYTQKSLSLSPGK CH Hybrid S239D/I332E (Human)   SEQ ID NO:139
    ASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTHTCPP
CPAPELLGGPDVFLFPPKPKDTLMISRTPEVTCVVVDVSHEDPEVQFNWYVDGVEVH
NAKTKPREEQFNSTFRVVSVLTVVHQDWLNGKEYKCKVSNKALPAPEEKTISKTKG
QPREPQVYTLPPSREEMTKNQVSLTCLVKGFYPSDIAVEWESNGQPENNYKTTPPML
DSDGSFFLYSKLTVDKSRWQQGNVFSCSVMHEALHNHYTQKSLSLSPGK CH mIgG2a (Mouse)   SEQ ID NO:140
    AKTTAPSVYPLAPVCGDTTGSSVTLGCLVKGYFPEPVTLTWNSGSLSSGVHTF
PAVLQSDLYTLSSSVTVTSSTWPSQSITCNVAHPASSTKVDKKIEPRGPTIKPCPPCKC
PAPNLLGGPSVFIFPPKIKDVLMISLSPMVTCVVVDVSEDDPDVQISWFVNNVEVLTA
QTQTHREDYNSTLRVVSALPIQHQDWMSGKEFKCKVNNKALPAPIERTISKPKGSVR
APQVYVLPPPEEEMTKKQVTLTCMVTDFMPEDIYVEWTNNGKTELNYKNTEPVLDS
DGSYFMYSKLRVEKKNWVERNSYSCSVVHEGLHNHHTTKSFSRTPGK CH mIgG1 (Mouse)   SEQ ID NO:141
    AKTTPPSVYPLAPGSAAQTNSMVTLGCLVKGYFPEPVTVTWNSGSLSSGVHT
FPAVLQSDLYTLSSSVTVPSSTWPSQTVTCNVAHPASSTKVDKKIVPRDCGCKPCICT
VPEVSSVFIFPPKPKDVLTITLTPKVTCVVVDISKDDPEVQFSWFVDDVEVHTAQTKP
REEQFNSTFRSVSELPIMHQDWLNGKEFKCRVNSAAFPAPIEKTISKTKGRPKAPQVY
TIPPPKEQMAKDKVSLTCMITDFFPEDITVEWQWNGQPAENYKNTQPIMDTDGSYFV
YSKLNVQKSNWEAGNTFTCSVLHEGLHNHHTEKSLSHSPGK CL Kappa (Human)   SEQ ID NO:142
    RTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSFNRGEC CL mKappa (Mouse)   SEQ ID NO:143
    RADAAPTVSIFPPSSEQLTSGGASVVCFLNNFYPKDINVKWKIDGSERQNGVL
NSWTDQDSKDSTYSMSSTLTLTKDEYERHNSYTCEATHKTSTSPIVKSFNRNEC

Figure 4

| Name | # Plates | Concentration (mg/mL) | Volume (mL) | Total amt. (mg) |
|---|---|---|---|---|
| H3.77/L3 IgG1 WT | 6 | 5.09 | 0.198 | 1.01 |
| H3.77/L3 IgG1 I332E | 6 | 1.50 | 0.13 | 0.20 |
| H3.77/L3 IgG1 G236A | 6 | 1.32 | 0.16 | 0.21 |
| H3.77/L3 IgG1 S239D | 6 | 2.72 | 0.16 | 0.42 |
| H3.77/L3 IgG1 I332E/G236A | 6 | 1.63 | 0.16 | 0.26 |
| H3.77/L3 IgG1 L235G/G236R | 6 | 3.43 | 0.291 | 1.00 |
| H3.77/L3 Hybrid WT | 6 | 4.28 | 0.15 | 0.64 |
| H3.77/L3 Hybrid S239D/I332E | 6 | 3.91 | 0.158 | 0.62 |
| H3.77/L3 Hybrid S239D/H268E | 6 | 2.43 | 0.209 | 0.51 |
| H3.77/L3 Hybrid I332E/H268E | 6 | 1.26 | 0.192 | 0.24 |
| H3.77/L3 Hybrid S239D/I332E/G236A | 6 | 2.14 | 0.14 | 0.30 |
| H3.77/L3 Hybrid S239D/I332E/A330Y | 6 | 5.28 | 0.156 | 0.82 |
| H3.77/L3 Hybrid S239D/H268E/G236A | 6 | 3.12 | 0.226 | 0.71 |
| H3.77/L3 mIgG2aa WT | 10 | 0.77 | 0.175 | 0.14 |
| H3.77/L3 mIgG2aa I332E | 6 | 1.04 | 0.122 | 0.13 |
| H3.77/L3 mIgG2aa S239D/I332E | 6 | 2.49 | 0.132 | 0.33 |
| H3.77/L3 Hybrid I332E/G236A | 10 | 0.51 | 0.175 | 0.09 |
| H3.77/L3 Hybrid I332E/H268E/G236A | 6 | 3.11 | 0.164 | 0.51 |
| H3.77/L3 mIgG1 WT | 6 | 2.70 | 0.146 | 0.39 |
| H3.77/L3 mIgG1 S239D/I332E | 10 | 1.09 | 0.175 | 0.19 |

| Lane | Sample |
|------|--------|
| 1 | MW standard |
| 2 | Anti-Epcam H2.12_L3 Hybrid from lec13 cells |

Figure 8
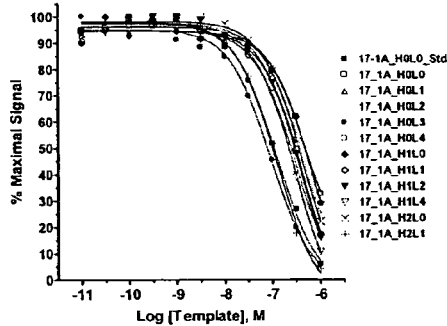
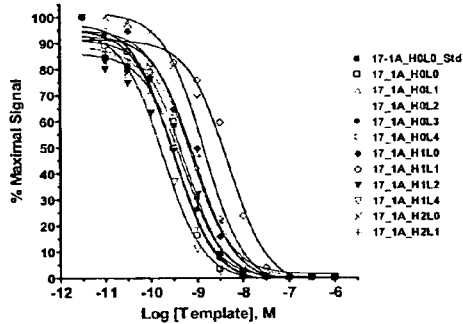
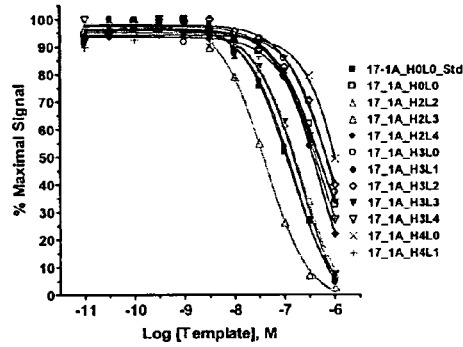
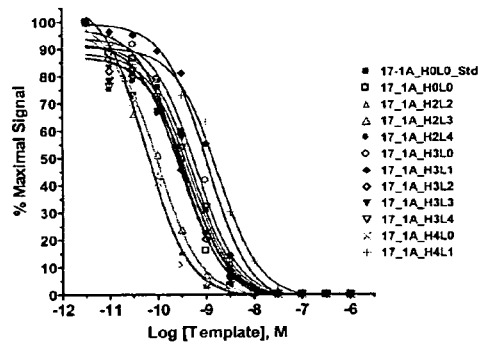
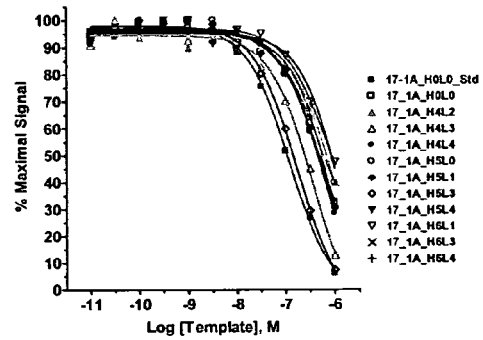
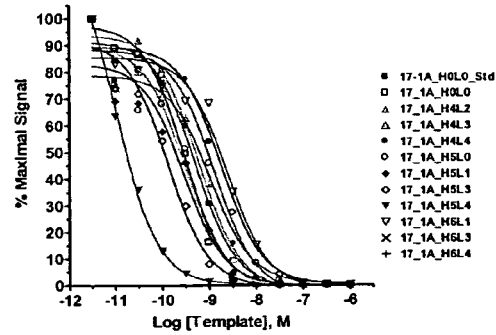

Figure 9

Summary of Antigen and Protein A Binding of 17-1A Humanization Templates

| | DIG-EpCAM Binding | | | | Protein A Binding | | |
|---|---|---|---|---|---|---|---|
| | EC50 | Initial Concentration | Adjusted EC-50 | Fold Increase | EC50 | Adjusted EC-50 | Fold Increase |
| 17-1A_H0L0_Std | 1.2E-07 | 1.58 | 1.9E-07 | 1.00 | 5.2E-10 | 8.3E-10 | 1.00 |
| 17_1A_H0L0 | 5.4E-07 | 0.47 | 2.5E-07 | 0.76 | 3.1E-10 | 1.4E-10 | 5.73 |
| 17_1A_H0L1 | 4.4E-07 | 0.26 | 1.2E-07 | 1.69 | 9.5E-10 | 2.5E-10 | 3.33 |
| 17_1A_H0L2 | 4.8E-07 | 0.53 | 2.5E-07 | 0.77 | 5.1E-10 | 2.7E-10 | 3.07 |
| 17_1A_H0L3 | 9.1E-08 | 0.94 | 8.6E-08 | 2.26 | 3.0E-10 | 2.8E-10 | 2.91 |
| 17_1A_H0L4 | 3.3E-07 | 0.51 | 1.7E-07 | 1.17 | 7.1E-10 | 3.6E-10 | 2.29 |
| 17_1A_H1L0 | 7.3E-07 | 0.28 | 2.1E-07 | 0.95 | 8.6E-10 | 2.4E-10 | 3.42 |
| 17_1A_H1L1 | 4.9E-07 | 0.26 | 1.3E-07 | 1.54 | 4.7E-09 | 1.2E-09 | 0.67 |
| 17_1A_H1L2 | 4.0E-07 | 0.65 | 2.6E-07 | 0.74 | 5.0E-10 | 3.3E-10 | 2.52 |
| 17_1A_H1L4 | 3.1E-07 | 0.81 | 2.5E-07 | 0.77 | 1.8E-10 | 1.5E-10 | 5.56 |
| 17_1A_H2L0 | 4.7E-07 | 0.29 | 1.4E-07 | 1.43 | 1.4E-09 | 4.1E-10 | 2.00 |
| 17_1A_H2L1 | 1.3E-07 | 1.55 | 2.0E-07 | 1.00 | 3.3E-10 | 5.2E-10 | 1.60 |
| 17_1A_H2L2 | 2.1E-07 | 0.69 | 1.4E-07 | 1.36 | 6.3E-11 | 4.4E-11 | 18.83 |
| 17_1A_H2L3 | 4.1E-08 | 2.82 | 1.1E-07 | 1.69 | 1.0E-10 | 2.9E-10 | 2.86 |
| 17_1A_H2L4 | 1.5E-07 | 0.92 | 1.3E-07 | 1.44 | 4.4E-10 | 4.0E-10 | 2.05 |
| 17_1A_H3L0 | 1.4E-06 | 0.29 | 4.0E-07 | 0.49 | 6.3E-10 | 1.8E-10 | 4.51 |
| 17_1A_H3L1 | 5.5E-07 | 0.65 | 3.6E-07 | 0.54 | 1.1E-09 | 7.0E-10 | 1.18 |
| 17_1A_H3L2 | 7.4E-07 | 0.13 | 9.6E-08 | 2.02 | 3.0E-10 | 3.9E-11 | 21.17 |
| 17_1A_H3L3 | 2.0E-07 | 1.60 | 3.2E-07 | 0.61 | 4.2E-10 | 6.7E-10 | 1.24 |
| 17_1A_H3L4 | 5.1E-07 | 0.54 | 2.7E-07 | 0.71 | 4.8E-10 | 2.6E-10 | 3.16 |
| 17_1A_H4L0 | 4.0E-06 | 0.30 | 1.2E-06 | 0.16 | 5.9E-11 | 1.8E-11 | 46.88 |
| 17_1A_H4L1 | 4.7E-07 | 0.57 | 2.7E-07 | 0.73 | 1.8E-09 | 1.0E-09 | 0.82 |
| 17_1A_H4L2 | 9.3E-07 | 0.32 | 3.0E-07 | 0.65 | 6.0E-10 | 1.9E-10 | 4.32 |
| 17_1A_H4L3 | 3.6E-07 | 1.85 | 6.7E-07 | 0.29 | 3.1E-10 | 5.8E-10 | 1.43 |
| 17_1A_H4L4 | 5.9E-07 | 0.69 | 4.1E-07 | 0.47 | 1.3E-09 | 8.9E-10 | 0.93 |
| 17_1A_H5L0 | 4.9E-07 | 0.21 | 1.0E-07 | 1.91 | 1.1E-09 | 2.3E-10 | 3.66 |
| 17_1A_H5L1 | 5.6E-07 | 0.68 | 3.8E-07 | 0.51 | 3.0E-10 | 2.0E-10 | 4.11 |
| 17_1A_H5L3 | 1.7E-07 | 2.64 | 4.6E-07 | 0.42 | 1.3E-10 | 3.5E-10 | 2.34 |
| 17_1A_H5L4 | 1.2E-06 | 0.70 | 8.1E-07 | 0.24 | 1.1E-11 | 7.6E-12 | 108.53 |
| 17_1A_H6L1 | 6.8E-07 | 0.32 | 2.2E-07 | 0.90 | 2.5E-09 | 7.9E-10 | 1.05 |
| 17_1A_H6L3 | 2.7E-07 | 3.15 | 8.7E-07 | 0.22 | 1.0E-10 | 3.3E-10 | 2.50 |
| 17_1A_H6L4 | 1.7E-06 | 0.26 | 4.4E-07 | 0.44 | 1.8E-09 | 4.8E-10 | 1.73 |

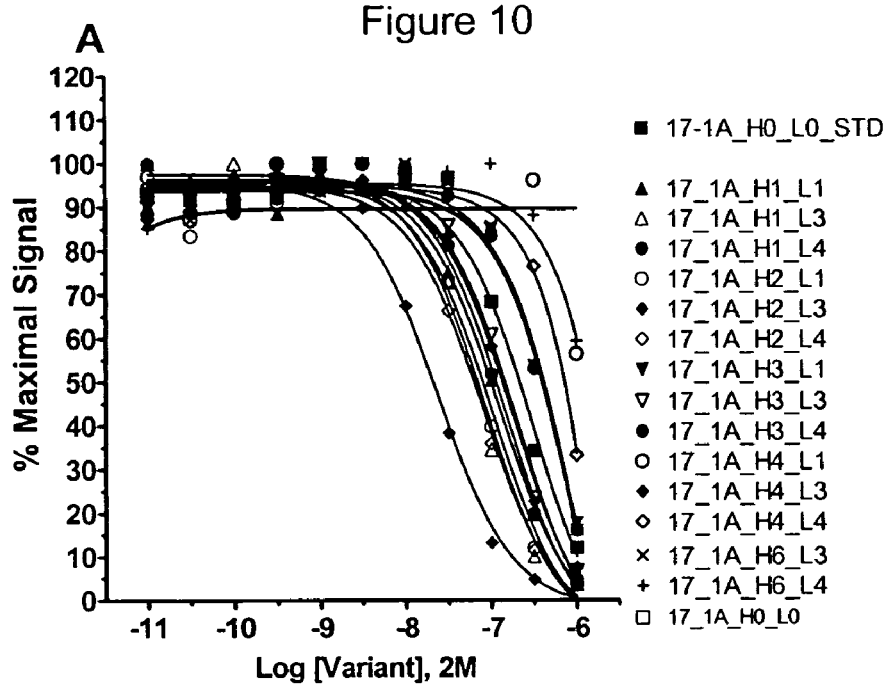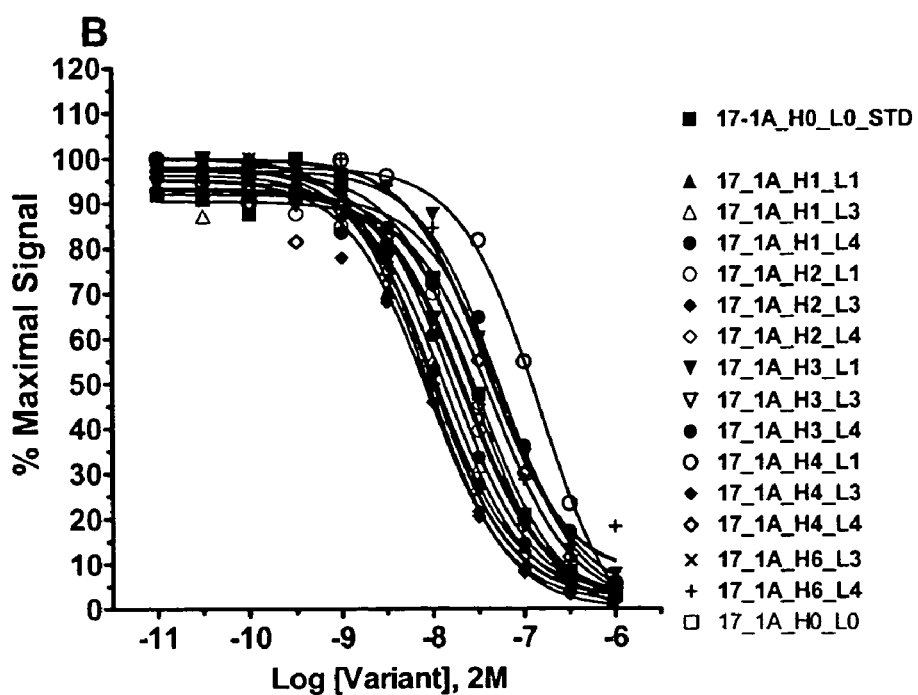
Figure 10

Figure 11

Antigen binding affinity of anti-Ep-CAM humanized antibodies

| Antibody | EC50 | Initial protein Concentration | Adjusted EC-50 | Fold Increase |
|---|---|---|---|---|
| 17-1A_H0L0_Std | 1.2E-07 | 1.58 | 1.9E-07 | 1.00 |
| 17_1A_H0L0 | 5.4E-07 | 0.47 | 2.5E-07 | 0.76 |
| 17_1A_H0L1 | 4.4E-07 | 0.26 | 1.2E-07 | 1.69 |
| 17_1A_H0L2 | 4.8E-07 | 0.53 | 2.5E-07 | 0.77 |
| 17_1A_H0L3 | 9.1E-08 | 0.94 | 8.6E-08 | 2.26 |
| 17_1A_H0L4 | 3.3E-07 | 0.51 | 1.7E-07 | 1.17 |
| 17_1A_H1L0 | 7.3E-07 | 0.28 | 2.1E-07 | 0.95 |
| 17_1A_H1L1 | 4.9E-07 | 0.26 | 1.3E-07 | 1.54 |
| 17_1A_H1L2 | 4.0E-07 | 0.65 | 2.6E-07 | 0.74 |
| 17_1A_H1L4 | 3.1E-07 | 0.81 | 2.5E-07 | 0.77 |
| 17_1A_H2L0 | 4.7E-07 | 0.29 | 1.4E-07 | 1.43 |
| 17_1A_H2L1 | 1.3E-07 | 1.55 | 2.0E-07 | 1.00 |
| 17_1A_H2L2 | 2.1E-07 | 0.69 | 1.4E-07 | 1.36 |
| 17_1A_H2L3 | 4.1E-08 | 2.82 | 1.1E-07 | 1.69 |
| 17_1A_H2L4 | 1.5E-07 | 0.92 | 1.3E-07 | 1.44 |
| 17_1A_H3L0 | 1.4E-06 | 0.29 | 4.0E-07 | 0.49 |
| 17_1A_H3L1 | 5.5E-07 | 0.65 | 3.6E-07 | 0.54 |
| 17_1A_H3L2 | 7.4E-07 | 0.13 | 9.6E-08 | 2.02 |
| 17_1A_H3L3 | 2.0E-07 | 1.60 | 3.2E-07 | 0.61 |
| 17_1A_H3L4 | 5.1E-07 | 0.54 | 2.7E-07 | 0.71 |
| 17_1A_H4L0 | 4.0E-06 | 0.30 | 1.2E-06 | 0.16 |
| 17_1A_H4L1 | 4.7E-07 | 0.57 | 2.7E-07 | 0.73 |
| 17_1A_H4L2 | 9.3E-07 | 0.32 | 3.0E-07 | 0.65 |
| 17_1A_H4L3 | 3.6E-07 | 1.85 | 6.7E-07 | 0.29 |
| 17_1A_H4L4 | 5.9E-07 | 0.69 | 4.1E-07 | 0.47 |
| 17_1A_H5L0 | 4.9E-07 | 0.21 | 1.0E-07 | 1.91 |
| 17_1A_H5L1 | 5.6E-07 | 0.68 | 3.8E-07 | 0.51 |
| 17_1A_H5L3 | 1.7E-07 | 2.64 | 4.6E-07 | 0.42 |
| 17_1A_H5L4 | 1.2E-06 | 0.70 | 8.1E-07 | 0.24 |
| 17_1A_H6L1 | 6.8E-07 | 0.32 | 2.2E-07 | 0.90 |
| 17_1A_H6L3 | 2.7E-07 | 3.15 | 8.7E-07 | 0.22 |

Figure 12

| Anti-Epcam Variant | Conc. (mg/ml) | KD M-1 | Relative ADCC |
|---|---|---|---|
| H2L3 | 3.39 | 2.13E-08 | ++++++ |
| H2L3.6 | 4.27 | 2.26E-08 | +++++++ |
| H2L3.8 | 2.68 | 1.82E-08 | ++++++ |
| H2.14L3 | 2.07 | | ++++ |
| H2.14L3.6 | 2.2 | | ++++ |
| H2.14L3.8 | 1.32 | | +++++ |
| H2.12L3 | 2.42 | 2.46E-08 | ++++++ |
| H2.12L3.6 | 3.02 | 3.70E-08 | ++++ |
| H2.12L3.8 | 2.39 | 2.69E-08 | ++++ |
| H3L3 | 1.95 | 6.20E-08 | ++ |
| H3L3.6 | 2.2 | 8.07E-08 | + |
| H3L3.8 | 1.56 | 7.42E-08 | +++ |
| H3.8L3 | 2.06 | 4.39E-08 | ++++ |
| H3.8L3.6 | 2.52 | | ++++ |
| H3.8L3.8 | 2.06 | | +++ |
| H3.29L3 | 1.76 | 1.68E-08 | + |
| H3.29L3.6 | 2.73 | | + |
| H3.29L3.8 | 1.43 | | +++ |
| IgG1-H0L0 | 0.65 | 4.05E-08 | + |
| IgG2a-H0L0 (mouse) | 0.35 | 1.17E-07 | - |

Figure 13a

| 171A XmAbs Binding to FcgRIIaV and EpCAM Binding, | | | | | | | |
|---|---|---|---|---|---|---|---|
| | | RIIaV Binding | | | DIG-EpCAM Binding Binding | | |
| Mutations: | Conc. (uM) | IC-50s | Adjusted | Fold | IC-50s | Adjusted | Fold |
| 171A_H2L3_global_Std | 10 | 1.24E-08 | 1.24E-07 | 1.00 | 9.25E-08 | 9.25E-07 | 1.00 |
| PBS | N/A | N/A | N/A | N/A | N/A | N/A | N/A |
| 17-1A H0 | 2 | 3.27E-08 | 6.53E-08 | 1.89 | 3.33E-07 | 6.65E-07 | 1.39 |
| ING VH | 1.8 | 4.12E-08 | 7.41E-08 | 1.67 | 2.44E-09 | 4.40E-09 | 210.26 |
| IgG2aa H0 | 3.4 | 8.99E-08 | 3.06E-07 | 0.40 | 5.59E-07 | 1.90E-06 | 0.49 |
| 17-1A_IgG1_H2.12_L3 | 5 | 1.50E-08 | 7.52E-08 | 1.65 | 1.88E-07 | 9.42E-07 | 0.98 |
| H2.12_L3 171A IgG1_S239D | 5 | 2.27E-09 | 1.14E-08 | 10.89 | 2.15E-07 | 1.07E-06 | 0.86 |
| H2.12_L3 171A IgG1_I332D | 26 | 9.41E-10 | 2.45E-08 | 5.06 | 2.85E-08 | 7.40E-07 | 1.25 |
| H2.12_L3 171A IgG1_I332E | 24 | 3.66E-10 | 8.78E-09 | 14.09 | 4.58E-08 | 1.10E-06 | 0.84 |
| H2.12_L3 171A Hyb_S239D/I332E | 21.2 | 1.05E-10 | 2.23E-09 | 55.46 | 4.23E-08 | 8.97E-07 | 1.03 |
| H2.12_L3 171A Hyb_S239D/H268E | 23.6 | 2.28E-10 | 5.39E-09 | 22.95 | 3.11E-08 | 7.33E-07 | 1.26 |
| H2.12_L3 171A Hyb_H268E/I332E | 22.87 | 3.29E-10 | 7.53E-09 | 16.42 | 2.90E-08 | 6.63E-07 | 1.40 |
| H2.12_L3 171A Hyb_S239D/I332E/H268E | 18.53 | 7.78E-11 | 1.44E-09 | 85.81 | 5.60E-08 | 1.04E-06 | 0.89 |
| H2.12_L3 171A Hyb_S239D/I332E/A330Y | 19.87 | 9.30E-11 | 1.85E-09 | 66.93 | 4.52E-08 | 8.97E-07 | 1.03 |
| H2.12_L3 171A Hyb_S239D/I332E/A330L | 11.47 | 3.49E-10 | 4.00E-09 | 30.95 | 1.25E-07 | 1.43E-06 | 0.65 |

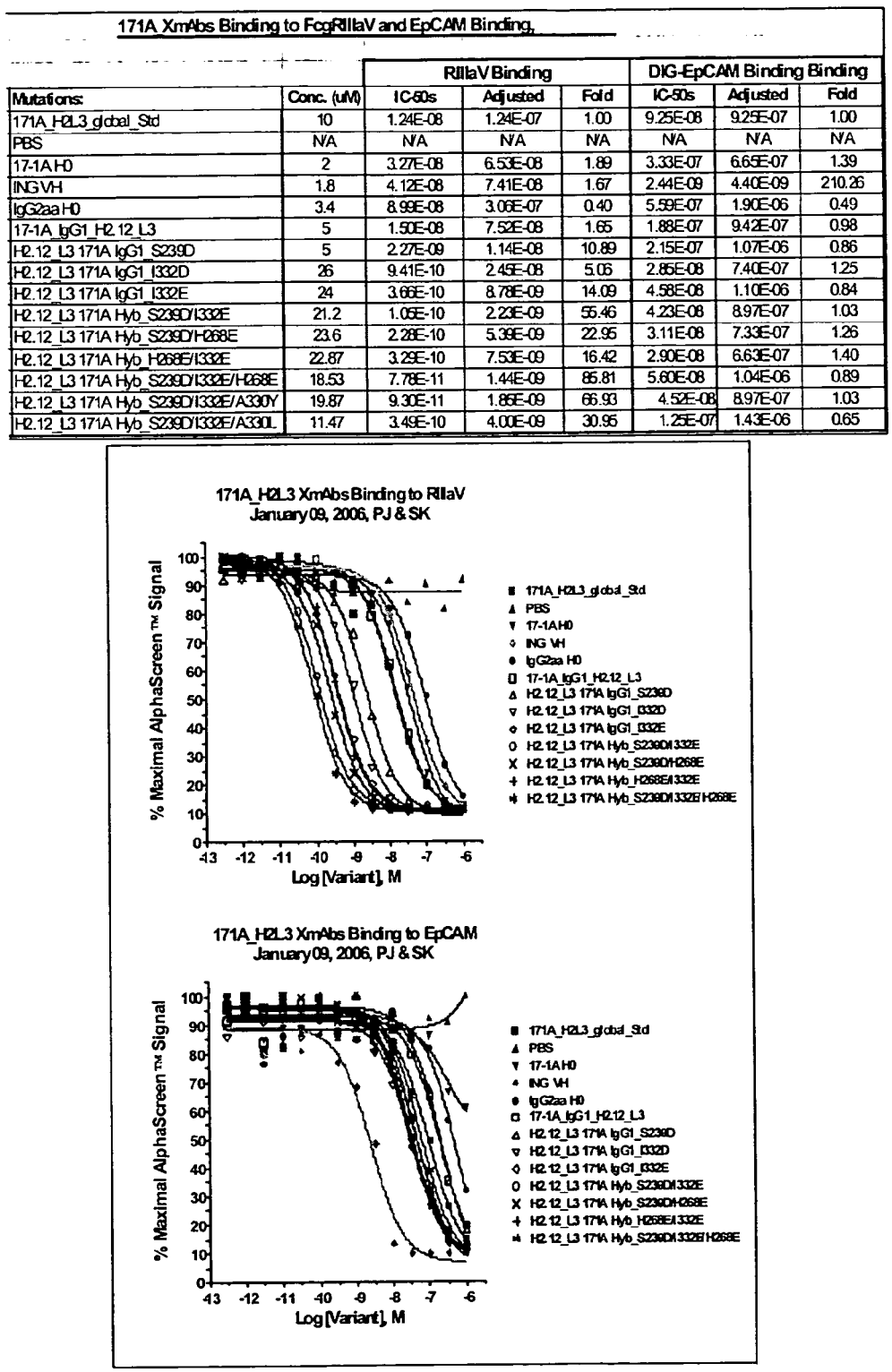

Figure 14

Surface Plasmon Resonance of humaninzed anti-EpCAM anitbodies.

| 17-1A Template | ka (1/Ms) | kd (1/s) | Rmax (RU) | RI (RU) | Conc of analyte | KA (1/M) | KD (M) | KD (nM) | Req (RU) | kobs (1/s) | Chi2 | Fold Increase |
|---|---|---|---|---|---|---|---|---|---|---|---|---|
| H0L0 | 1.70E+05 | 2.68E-02 | 212 | 0 | 1E-07 | 6.34E+06 | 1.58E-07 | 158.00 | 82.5 | 0.044 | 1.61 | 1.0000 |
| H1L1 | 2.80E+05 | 2.18E-02 | 261 | 0 | 1E-07 | 1.29E+07 | 7.78E-08 | 77.80 | 147 | 0.050 | 8.85 | 2.0308 |
| H1L3 | 4.01E+05 | 2.17E-02 | 312 | 0 | 1E-07 | 1.85E+07 | 5.41E-08 | 54.10 | 203 | 0.062 | 20.8 | 2.9205 |
| H1L4 | 3.27E+05 | 1.93E-02 | 290 | 0 | 1E-07 | 1.70E+07 | 5.89E-08 | 58.90 | 182 | 0.052 | 17.5 | 2.6825 |
| H2L1 | 2.92E+05 | 2.20E-02 | 244 | 0 | 1E-07 | 1.33E+07 | 7.54E-08 | 75.40 | 139 | 0.051 | 6.9 | 2.0955 |
| H2L3 | 3.75E+05 | 2.36E-02 | 275 | 0 | 1E-07 | 1.59E+07 | 6.30E-08 | 63.00 | 169 | 0.061 | 14.9 | 2.5079 |
| H2L4 | 3.07E+05 | 2.04E-02 | 264 | 0 | 1E-07 | 1.50E+07 | 6.66E-08 | 66.60 | 159 | 0.051 | 11.4 | 2.3724 |
| H3L1 | 1.29E+05 | 4.98E-02 | 119 | 0 | 1E-07 | 2.60E+06 | 3.85E-07 | 385.00 | 24.5 | 0.063 | 0.292 | 0.4104 |
| H3L3 | 1.50E+05 | 4.38E-02 | 200 | 0 | 1E-07 | 3.42E+06 | 2.92E-07 | 292.00 | 51.1 | 0.059 | 0.607 | 0.5411 |
| H3L4 | 1.18E+05 | 3.94E-02 | 188 | 0 | 1E-07 | 2.99E+06 | 3.35E-07 | 335.00 | 43.3 | 0.051 | 0.606 | 0.4716 |
| H4L1 | 5.62E+04 | 3.71E-01 | 212 | 0 | 1E-07 | 1.51E+05 | 6.60E-06 | 6,600.00 | 3.16 | 0.377 | 0.194 | 0.0239 |
| H4L3 | 6.45E+04 | 8.47E-02 | 212 | 0 | 1E-07 | 7.61E+05 | 1.31E-06 | 1,310.00 | 15 | 0.091 | 0.284 | 0.1206 |
| H4L4 | 3.15E+04 | 9.46E-02 | 212 | 0 | 1E-07 | 3.33E+05 | 3.00E-06 | 3,000.00 | 6.83 | 0.098 | 0.214 | 0.0527 |
| H3L2 | 7.89E+04 | 4.85E-02 | 212 | 0 | 1E-07 | 1.63E+06 | 6.15E-07 | 615.00 | 29.7 | 0.056 | 0.602 | 0.2569 |
| H6L3 | 3.91E+04 | 1.87E-01 | 212 | 0 | 1E-07 | 2.08E+05 | 4.80E-06 | 4,800.00 | 4.33 | 0.191 | 0.215 | 0.0329 |
| H6L4 | 4.94E+04 | 2.57E-01 | 212 | 0 | 1E-07 | 1.92E+05 | 5.20E-06 | 5,200.00 | 4 | 0.262 | 0.195 | 0.0304 |
| H0L0 | 1.75E+05 | 2.79E-02 | 182 | 0 | 1E-07 | 6.28E+06 | 1.59E-07 | 159.00 | 70.2 | 0.046 | 1.09 | 0.9937 |

Figure 16
EpCAM Binding Kinetics
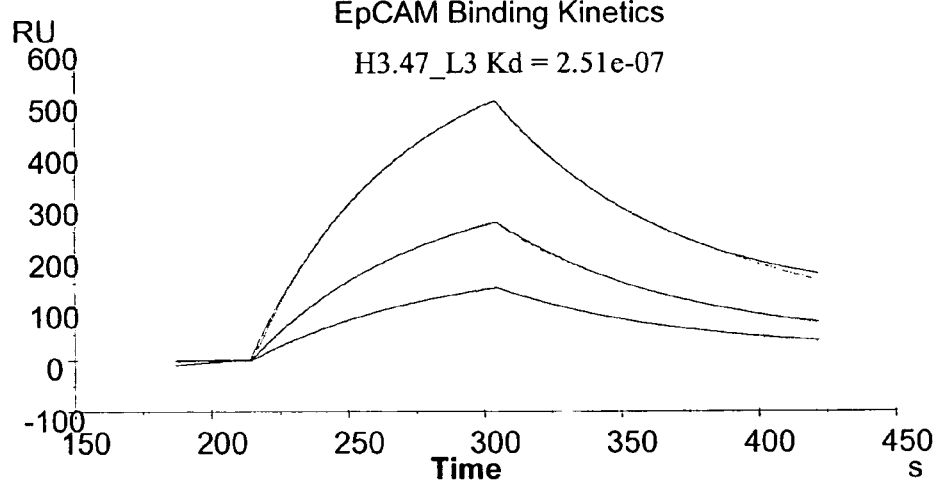
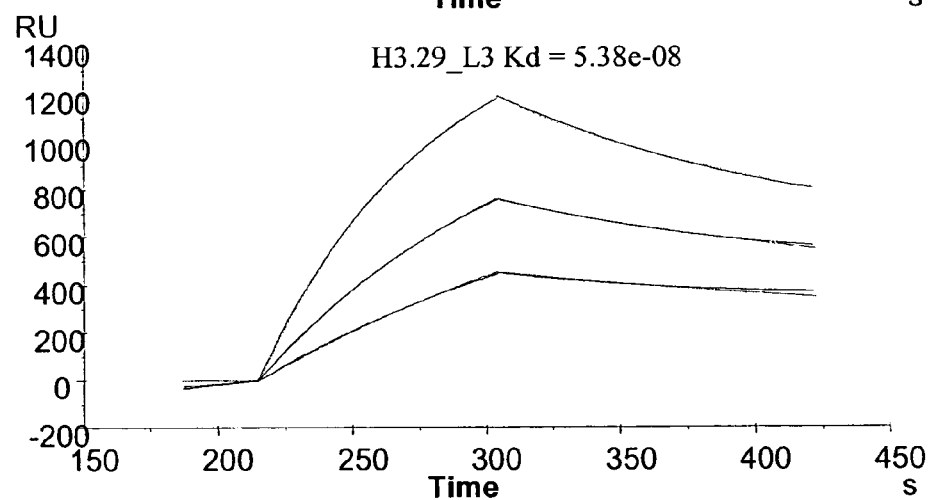
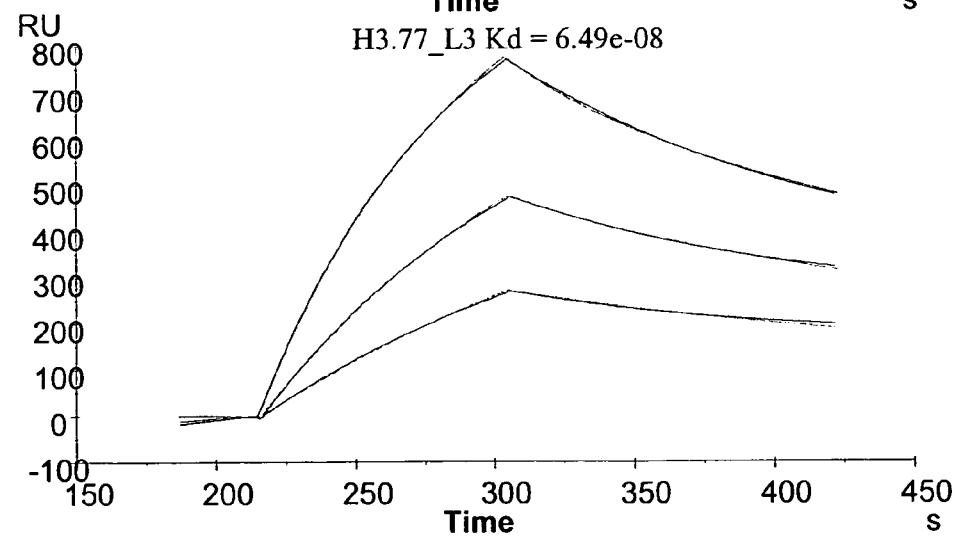

Figure 19
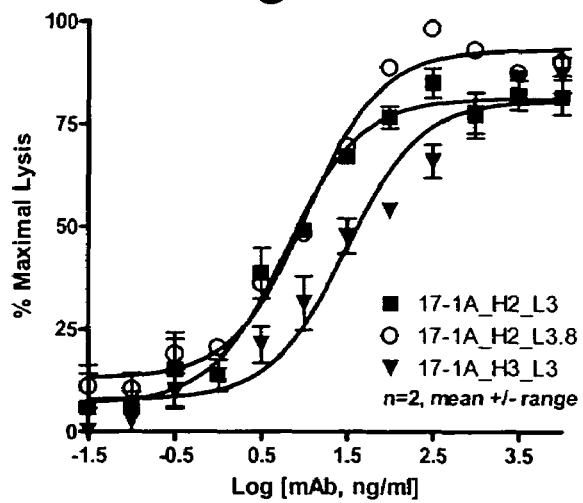
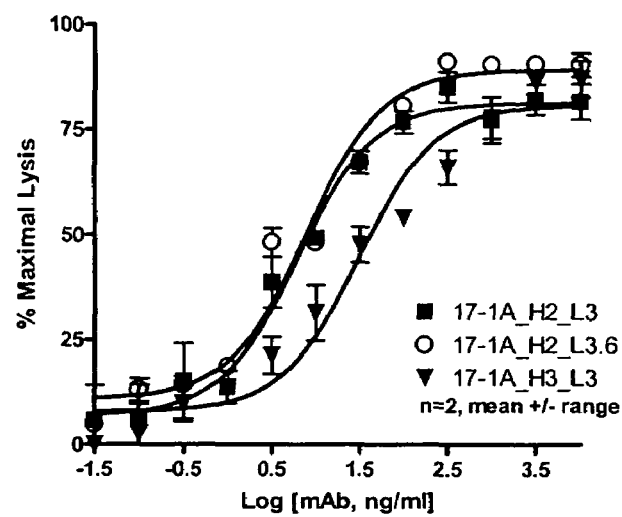
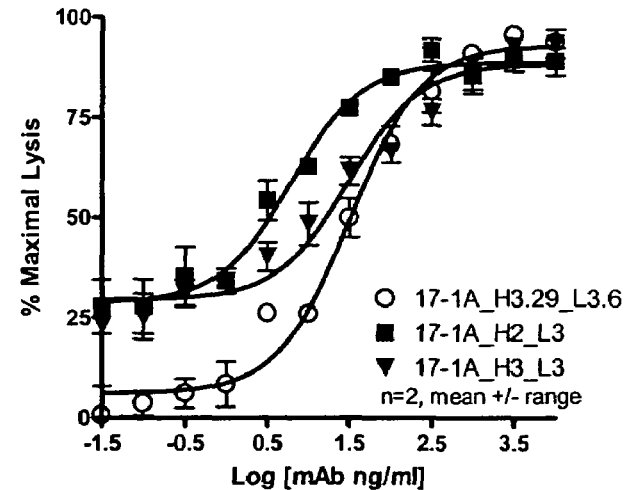

ADCC of EpCAM variants on LS180 Gastric Adenocarcinoma cell line

Figure 20b
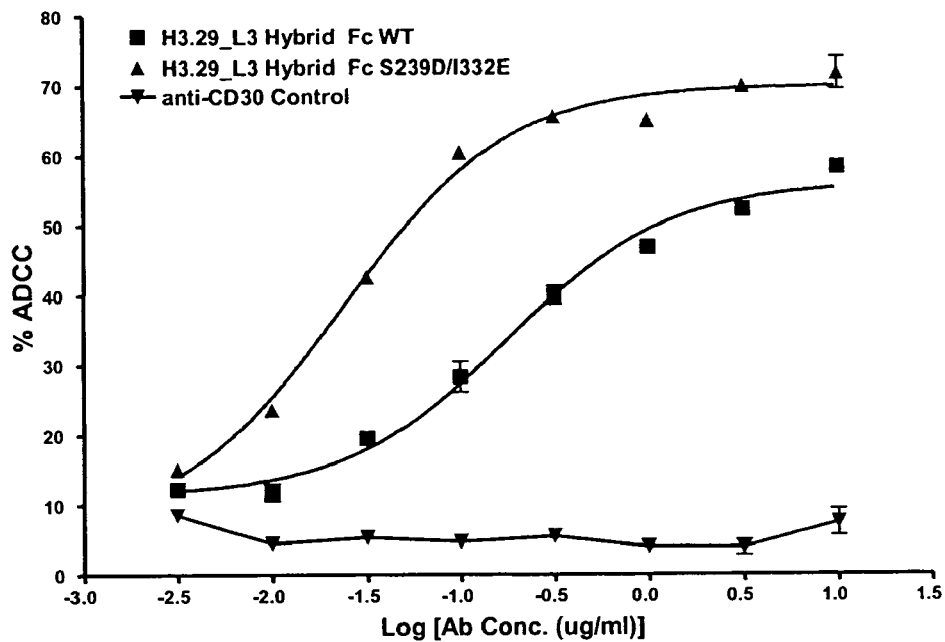
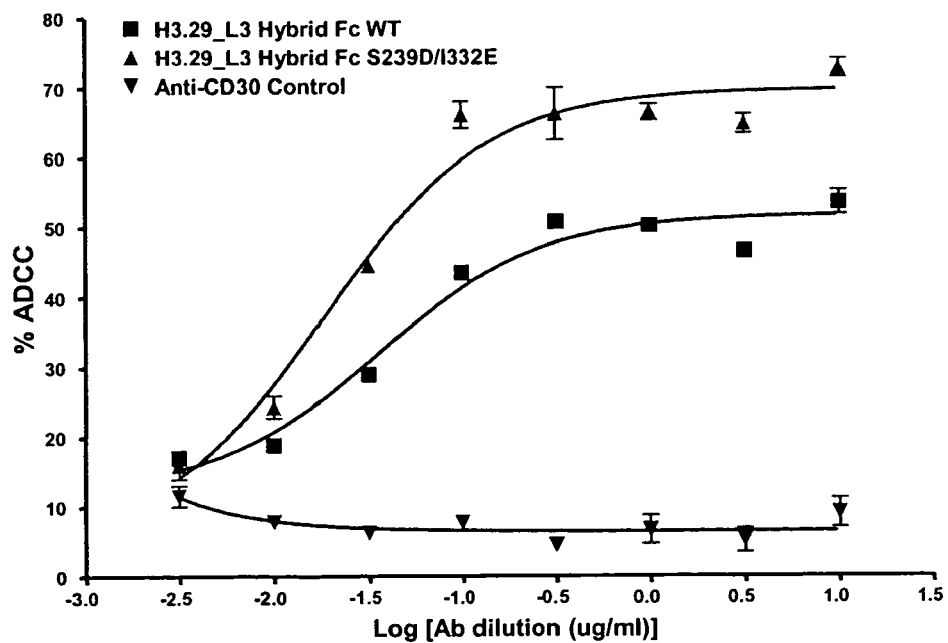

Figure 21
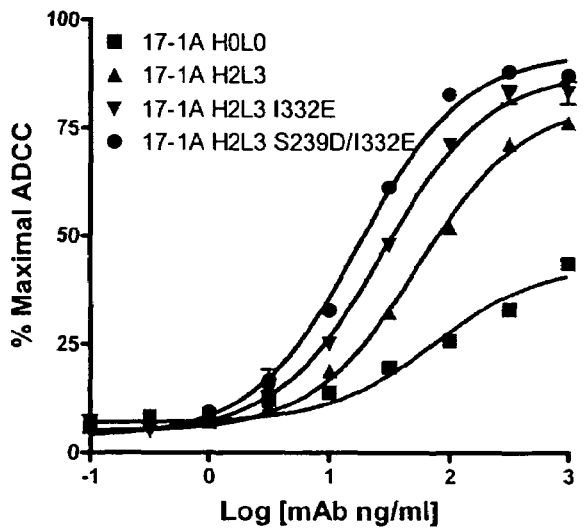
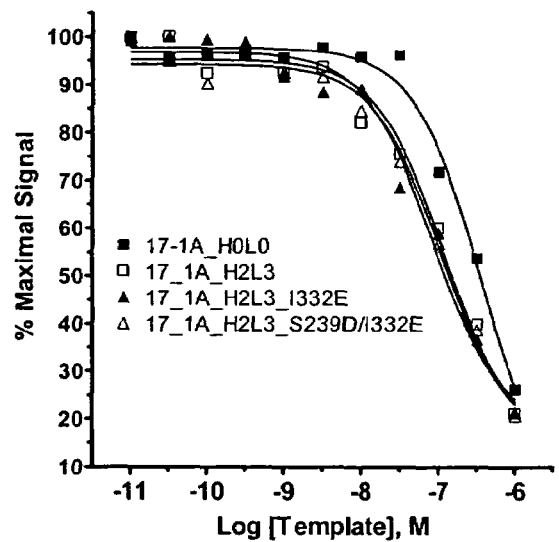
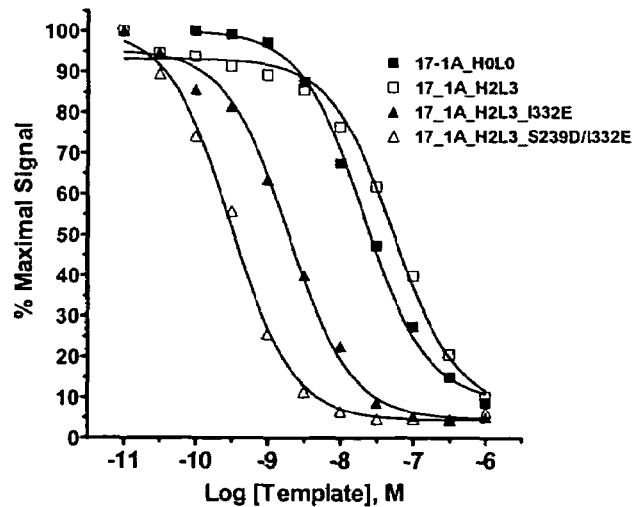

Figure 25
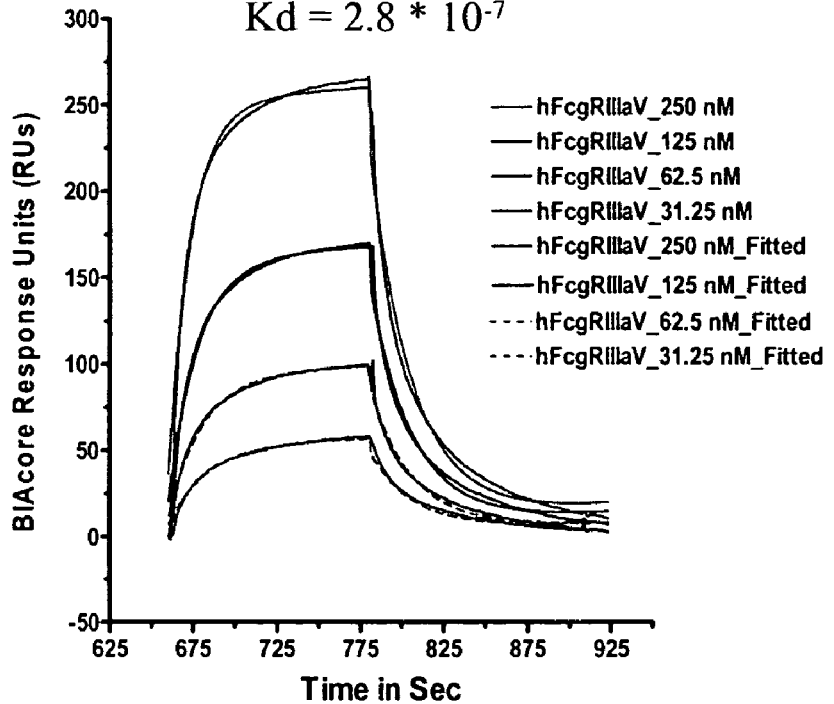
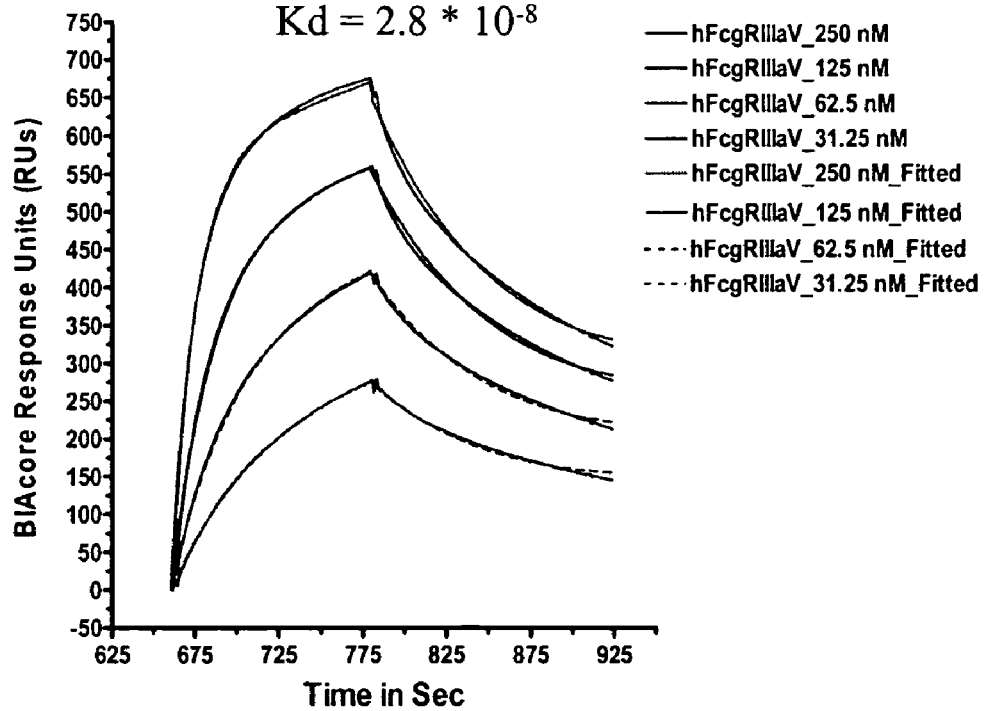

Figure 27

| Antibody | FcgRI KD (M) | FcgRI Fold KD | FcgRI log(1/KD) | R131 FcgRIIa KD (M) | R131 FcgRIIa Fold KD | R131 FcgRIIa log(1/KD) |
|---|---|---|---|---|---|---|
| H3.77_L3 WT IgG1 | 1.00E-09 | 1.0 | 9.0 | 8.86E-07 | 1.0 | 6.1 |
| H3.77_L3 I332E IgG1 | 1.31E-09 | 0.8 | 8.9 | 1.03E-06 | 0.9 | 6.0 |
| H3.77_L3 G236A IgG1 | 1.13E-08 | 0.1 | 7.9 | 2.33E-07 | 3.8 | 6.6 |
| H3.77_L3 S239D IgG1 | 1.37E-09 | 0.7 | 8.9 | 3.76E-07 | 2.4 | 6.4 |
| H3.77_L3 I332E/G236A IgG1 | 1.01E-09 | 1.0 | 9.0 | 1.23E-07 | 7.2 | 6.9 |
| H3.77_L3 L235G/G236R IgG1 | 8.50E-07 | 0.0 | 6.1 | no binding | | |
| H3.77_L3 WT Hybrid | 1.96E-09 | 0.5 | 8.7 | 4.13E-07 | 2.1 | 6.4 |
| H3.77_L3 S239D/I332E Hybrid | 6.46E-10 | 1.5 | 9.2 | 7.89E-08 | 11.2 | 7.1 |
| H3.77_L3 S239D/H268E Hybrid | 1.11E-09 | 0.9 | 9.0 | 4.27E-08 | 20.7 | 7.4 |
| H3.77_L3 I332E/H268E Hybrid | 8.67E-10 | 1.2 | 9.1 | 8.61E-08 | 10.3 | 7.1 |
| H3.77_L3 S239D/I332E/G236A Hybrid | 1.25E-09 | 0.8 | 8.9 | 1.37E-08 | 64.7 | 7.9 |
| H3.77_L3 S239D/I332E/A330Y Hybrid | 1.07E-09 | 0.9 | 9.0 | 8.89E-08 | 10.0 | 7.1 |
| H3.77_L3 S239D/H268E/G236A Hybrid | 9.81E-10 | 1.0 | 9.0 | poor data | | |
| H3.77_L3 I332E/G236A Hybrid | 1.78E-09 | 0.6 | 8.7 | 5.44E-08 | 16.3 | 7.3 |
| H3.77_L3 I332E/H268E/G236A Hybrid | 1.65E-09 | 0.6 | 8.8 | 1.80E-08 | 49.2 | 7.7 |
| H2.12_L3 WT IgG1 | | | | | | |
| H2.12_L3 WT Hybrid Lec13 | | | | | | |

| | FcgRIIb KD (M) | FcgRIIb Fold KD | FcgRIIb log(1/KD) | V158 FcgRIIIa KD (M) | V158 FcgRIIIa Fold KD | V158 FcgRIIIa log(1/KD) | Specificity RIIa/RIIb Fold | Specificity RIIa/RIIb -log (RIIa/RIIb) |
|---|---|---|---|---|---|---|---|---|
| H3.77_L3 WT IgG1 | 2.35E-06 | 1.0 | 5.6 | 2.32E-07 | 1.0 | 6.6 | 2.7 | 0.4 |
| H3.77_L3 I332E IgG1 | 1.47E-06 | 1.6 | 5.8 | 4.54E-08 | 5.1 | 7.3 | 1.4 | 0.2 |
| H3.77_L3 G236A IgG1 | 2.26E-06 | 1.0 | 5.6 | 2.68E-07 | 0.9 | 6.6 | 9.7 | 1.0 |
| H3.77_L3 S239D IgG1 | 2.93E-07 | 8.0 | 6.5 | 4.11E-08 | 5.6 | 7.4 | 0.8 | -0.1 |
| H3.77_L3 I332E/G236A IgG1 | 9.83E-07 | 2.4 | 6.0 | 8.00E-08 | 2.9 | 7.1 | 8.0 | 0.9 |
| H3.77_L3 L235G/G236R IgG1 | no binding | | | no binding | | | | |
| H3.77_L3 WT Hybrid | 6.35E-07 | 3.7 | 6.2 | 1.71E-07 | 1.4 | 6.8 | 1.5 | 0.2 |
| H3.77_L3 S239D/I332E Hybrid | 1.42E-07 | 16.5 | 6.8 | 1.44E-08 | 16.1 | 7.8 | 1.8 | 0.3 |
| H3.77_L3 S239D/H268E Hybrid | 8.15E-08 | 28.8 | 7.1 | 1.61E-08 | 14.4 | 7.8 | 1.9 | 0.3 |
| H3.77_L3 I332E/H268E Hybrid | 1.17E-07 | 20.1 | 6.9 | 2.69E-08 | 8.6 | 7.6 | 1.4 | 0.1 |
| H3.77_L3 S239D/I332E/G236A Hybrid | 1.46E-07 | 16.1 | 6.8 | 2.24E-08 | 10.4 | 7.6 | 10.7 | 1.0 |
| H3.77_L3 S239D/I332E/A330Y Hybrid | 1.44E-07 | 16.3 | 6.8 | 1.10E-08 | 21.1 | 8.0 | 1.6 | 0.2 |
| H3.77_L3 S239D/H268E/G236A Hybrid | poor data | | | poor data | | | | |
| H3.77_L3 I332E/G236A Hybrid | 5.57E-07 | 4.2 | 6.3 | 9.89E-08 | 2.3 | 7.0 | 10.2 | 1.0 |
| H3.77_L3 I332E/H268E/G236A Hybrid | 1.54E-07 | 15.3 | 6.8 | 4.97E-08 | 4.7 | 7.3 | 8.6 | 0.9 |
| H2.12_L3 WT IgG1 | | | | 2.97E-07 | 0.8 | 6.5 | | |
| H2.12_L3 WT Hybrid Lec13 | | | | 2.89E-08 | 8.0 | 7.5 | | |

Figure 28

Figure 28a

| Allotype(s) | Allotype(s) | EU Position | | |
|---|---|---|---|---|
| | | 214 | 356 358 | 431 |
| G1m(1,17) | G1m(a,z) | K | D L | A |
| G1m(1,2,17) | G1m(a,x,z) | K | D L | G |
| G1m(3) | G1m(f) | R | E M | A |
| G1m(1,3) | G1m(a,f) | R | D L | A |
| G1m(17) | G1m(z) | K | E M | A |

Figure 28b

| Substitutions | Fv | IgG | IgG |
|---|---|---|---|
| WT, 214R | H3.77/L3 17-1A | human | IgG1(f) |
| WT, 356D / 358L | H3.77/L3 17-1A | human | IgG1(a,z) |
| 332E, 214R | H3.77/L3 17-1A | human | IgG1(f) |
| 332E, 356D / 358L | H3.77/L3 17-1A | human | IgG1(a,z) |

Figure 29

>H3.77L3 Hybrid WT     SEQ ID NO:144
    EVQLVESGGGLVQPGGSLRLSCAASGYSFTNYLIEWVRQAPGQGLEWMGVI
NPGSGGTNYNPSLKSRVTISADKSISTAYMELSSLRSEDTAVYFCARDGPWFAYWGQ
GTLVTVSSASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEPKSCDKTHT
CPPCPAPELLGGPSVFLFPPKPKDTLMISRTPEVTCVVVDVSHEDPEVQFNWYVDGV
EVHNAKTKPREEQFNSTFRVVSVLTVVHQDWLNGKEYKCKVSNKALPAPIEKTISKT
KGQPREPQVYTLPPSREEMTKNQVSLTCLVKGFYPSDIAVEWESNGQPENNYKTTPP
MLDSDGSFFLYSKLTVDKSRWQQGNVFSCSVMHEALHNHYTQKSLSLSPGK >L3.77L3 Hybrid WT SEQ ID NO:145
    NIVMTQSPDSLAVSLGERATLSCRASENVVTYVSWYQQKPGQSPQLLIYGAS
NRYTGVPDRFTGSGSATDFTLTINSLEAEDAATYYCGQGYSYPYTFGGGTKLEIKRT
VAAPSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC >H3.77L3 Hybrid S239/I332E     SEQ ID NO:146
    EVQLVESGGGLVQPGGSLRLSCAASGYSFTNYLIEWVRQAPGQGLEWMGVI
NPGSGGTNYNPSLKSRVTISADKSISTAYMELSSLRSEDTAVYFCARDGPWFAYWGQ
GTLVTVSSASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEPKSCDKTHT
CPPCPAPELLGGPDVFLFPPKPKDTLMISRTPEVTCVVVDVSHEDPEVQFNWYVDGV
EVHNAKTKPREEQFNSTFRVVSVLTVVHQDWLNGKEYKCKVSNKALPAPEEKTISK
TKGQPREPQVYTLPPSREEMTKNQVSLTCLVKGFYPSDIAVEWESNGQPENNYKTTP
PMLDSDGSFFLYSKLTVDKSRWQQGNVFSCSVMHEALHNHYTQKSLSLSPGK >L3.77L3 Hybrid S239/I332E     SEQ ID NO:147
    NIVMTQSPDSLAVSLGERATLSCRASENVVTYVSWYQQKPGQSPQLLIYGAS
NRYTGVPDRFTGSGSATDFTLTINSLEAEDAATYYCGQGYSYPYTFGGGTKLEIKRT
VAAPSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC >H3.77L3 Hybrid S239D/H268E     SEQ ID NO:148
    EVQLVESGGGLVQPGGSLRLSCAASGYSFTNYLIEWVRQAPGQGLEWMGVI
NPGSGGTNYNPSLKSRVTISADKSISTAYMELSSLRSEDTAVYFCARDGPWFAYWGQ
GTLVTVSSASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEPKSCDKTHT
CPPCPAPELLGGPDVFLFPPKPKDTLMISRTPEVTCVVVDVSEEDPEVQFNWYVDGV
EVHNAKTKPREEQFNSTFRVVSVLTVVHQDWLNGKEYKCKVSNKALPAPIEKTISKT
KGQPREPQVYTLPPSREEMTKNQVSLTCLVKGFYPSDIAVEWESNGQPENNYKTTPP
MLDSDGSFFLYSKLTVDKSRWQQGNVFSCSVMHEALHNHYTQKSLSLSPGK L3.77L3 Hybrid S239D/H268E     SEQ ID NO:149
    NIVMTQSPDSLAVSLGERATLSCRASENVVTYVSWYQQKPGQSPQLLIYGAS
NRYTGVPDRFTGSGSATDFTLTINSLEAEDAATYYCGQGYSYPYTFGGGTKLEIKRT
VAAPSVFIFPPSDEQLKSGTASVVCLLNNFYPREAKVQWKVDNALQSGNSQESVTEQ

Figure 29 continued

DSKDSTYSLSSTLTLSKADYEKHKVYACEVTHQGLSSPVTKSFNRGEC

>H3.77L3 Hybrid H268E/I332E    SEQ ID NO:150
    EVQLVESGGGLVQPGGSLRLSCAASGYSFTNYLIEWVRQAPGQGLEWMGVI
NPGSGGTNYNPSLKSRVTISADKSISTAYMELSSLRSEDTAVYFCARDGPWFAYWGQ
GTLVTVSSASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEPKSCDKTHT
CPPCPAPELLGGPSVFLFPPKPKDTLMISRTPEVTCVVVDVSEEDPEVQFNWYVDGVE
VHNAKTKPREEQFNSTFRVVSVLTVVHQDWLNGKEYKCKVSNKALPAPEEKTISKT
KGQPREPQVYTLPPSREEMTKNQVSLTCLVKGFYPSDIAVEWESNGQPENNYKTTPP
MLDSDGSFFLYSKLTVDKSRWQQGNVFSCSVMHEALHNHYTQKSLSLSPGK >L3.77L3 Hybrid H268E/I332E    SEQ ID NO:151
    NIVMTQSPDSLAVSLGERATLSCRASENVVTYVSWYQQKPGQSPQLLIYGAS
NRYTGVPDRFTGSGSATDFTLTINSLEAEDAATYYCGQGYSYPYTFGGGTKLEIKRT
VAAPSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC >H3.77L3 Hybrid G236A/S239D/I332E    SEQ ID NO:152
    EVQLVESGGGLVQPGGSLRLSCAASGYSFTNYLIEWVRQAPGQGLEWMGVI
NPGSGGTNYNPSLKSRVTISADKSISTAYMELSSLRSEDTAVYFCARDGPWFAYWGQ
GTLVTVSSASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEPKSCDKTHT
CPPCPAPELLAGPDVFLFPPKPKDTLMISRTPEVTCVVVDVSHEDPEVQFNWYVDGV
EVHNAKTKPREEQFNSTFRVVSVLTVVHQDWLNGKEYKCKVSNKALPAPEEKTISK
TKGQPREPQVYTLPPSREEMTKNQVSLTCLVKGFYPSDIAVEWESNGQPENNYKTTP
PMLDSDGSFFLYSKLTVDKSRWQQGNVFSCSVMHEALHNHYTQKSLSLSPGK >L3.77L3 Hybrid G236A/S239D/I332E    SEQ ID NO:153
    NIVMTQSPDSLAVSLGERATLSCRASENVVTYVSWYQQKPGQSPQLLIYGAS
NRYTGVPDRFTGSGSATDFTLTINSLEAEDAATYYCGQGYSYPYTFGGGTKLEIKRT
VAAPSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC >H3.77L3 Hybrid S239D/A330Y/I332E    SEQ ID NO:154
    EVQLVESGGGLVQPGGSLRLSCAASGYSFTNYLIEWVRQAPGQGLEWMGVI
NPGSGGTNYNPSLKSRVTISADKSISTAYMELSSLRSEDTAVYFCARDGPWFAYWGQ
GTLVTVSSASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEPKSCDKTHT
CPPCPAPELLGGPDVFLFPPKPKDTLMISRTPEVTCVVVDVSHEDPEVQFNWYVDGV
EVHNAKTKPREEQFNSTFRVVSVLTVVHQDWLNGKEYKCKVSNKALPYPEEKTISK
TKGQPREPQVYTLPPSREEMTKNQVSLTCLVKGFYPSDIAVEWESNGQPENNYKTTP
PMLDSDGSFFLYSKLTVDKSRWQQGNVFSCSVMHEALHNHYTQKSLSLSPGK >L3.77L3 Hybrid S239D/A330Y/I332E    SEQ ID NO:155
    NIVMTQSPDSLAVSLGERATLSCRASENVVTYVSWYQQKPGQSPQLLIYGAS
NRYTGVPDRFTGSGSATDFTLTINSLEAEDAATYYCGQGYSYPYTFGGGTKLEIKRT
VAAPSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC

Figure 29 continued

>H3.77L3 IgG1 WT   SEQ ID NO:156
    EVQLVESGGGLVQPGGSLRLSCAASGYSFTNYLIEWVRQAPGQGLEWMGVI
NPGSGGTNYNPSLKSRVTISADKSISTAYMELSSLRSEDTAVYFCARDGPWFAYWGQ
GTLVTVSSASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEPKSCDKTHT
CPPCPAPELLGGPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPAPIEKTISK
AKGQPREPQVYTLPPSREEMTKNQVSLTCLVKGFYPSDIAVEWESNGQPENNYKTTP
PVLDSDGSFFLYSKLTVDKSRWQQGNVFSCSVMHEALHNHYTQKSLSLSPGK

>L3.77L3 IgG1 WT   SEQ ID NO:157
    NIVMTQSPDSLAVSLGERATLSCRASENVVTYVSWYQQKPGQSPQLLIYGAS
NRYTGVPDRFTGSGSATDFTLTINSLEAEDAATYYCGQGYSYPYTFGGGTKLEIKRT
VAAPSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC

>H3.77L3 IgG1 I332E      SEQ ID NO:158
    EVQLVESGGGLVQPGGSLRLSCAASGYSFTNYLIEWVRQAPGQGLEWMGVI
NPGSGGTNYNPSLKSRVTISADKSISTAYMELSSLRSEDTAVYFCARDGPWFAYWGQ
GTLVTVSSASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEPKSCDKTHT
CPPCPAPELLGGPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPAPEEKTISK
AKGQPREPQVYTLPPSREEMTKNQVSLTCLVKGFYPSDIAVEWESNGQPENNYKTTP
PVLDSDGSFFLYSKLTVDKSRWQQGNVFSCSVMHEALHNHYTQKSLSLSPGK

>L3.77L3 IgG1 I332E      SEQ ID NO:159
    NIVMTQSPDSLAVSLGERATLSCRASENVVTYVSWYQQKPGQSPQLLIYGAS
NRYTGVPDRFTGSGSATDFTLTINSLEAEDAATYYCGQGYSYPYTFGGGTKLEIKRT
VAAPSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC

OPTIMIZED PROTEINS THAT TARGET EP-CAM

This application claims benefit under 35 U.S.C. §119(e) to U.S. Ser. No. 60/697,768 filed Jul. 8, 2005, U.S. Ser. No. 60/741,966 filed Dec. 2, 2005, U.S. Ser. No. 60/779,961 filed Mar. 6, 2006, and U.S. Ser. No. 60/745,078 filed Apr. 18, 2006, each of which is expressly incorporated by reference in its entirety.

FIELD OF THE INVENTION

The present invention relates to optimized proteins that target the epithelial cell adhesion molecule (Ep-CAM), and their applications, particularly for therapeutic purposes.

BACKGROUND OF THE INVENTION

Epithelial cell adhesion molecule, also known as epithelial glycoprotein 40 [EGP40], epithelial protein 2 [EGP-2], GA733-2, ESA, KSA, 17-1A antigen or other names) is an epithelial transmembrane protein encoded by the GA733-2 gene (Gottlinger, H. G. et al. 1986, Int. J. Cancer. 15:47-53; Linnenbach, A. J. et al. 1989, Proc. Natl. Acad. Sci. USA. 86:27-31; Armstrong, A. and Eck, S. 2003. Cancer Biol. Ther. 2: 320-325, Linnenbach, A. J. et al. 1993. Mol. Cel. Biol. 13:1507-1515; all expressly incorporated by reference). The current model of the tertiary extracellular structure of Ep-CAM indicates the presence of three domains, including an N-terminal EGF-like domain (Armstrong, A. and Eck, S. 2003. Cancer Biol. Ther. 2: 320-325, expressly incorporated by reference). Ep-CAM is present in some normal and most neoplastic ephitelial cells (Armstrong, A. and Eck, S. 2003. Cancer Biol. Ther. 2: 320-325). Most carcinomas express Ep-CAM on their surfaces, including breast cancer, ovarian carcinoma, uterus cervix cancer, prostate cancer, kidney cancer, lung cancer, and colon cancer (Drapkin R. et al. 2004. Hum. Pathology. 35: 1014-1021; Gastl G. et al. 2000. The Lancet. 356: 1981-1982; Osta, W. et al. 2004. Cancer Res. 64: 5818-5824; Went, P. T. H. et al. 2004. Hum. Pathology. 35: 122-128; all expressly incorporated by reference). The GA733-2 gene is expressed on the baso-lateral cell surface in most human normal epithelium (Litvinov et al. 1994. J. Cell Biol. 125: 437-446, expressly incorporated by reference). It has been postulated that the differential localization of Ep-CAM in normal cells (baso-lateral surface) as compared with cancer cells, accounts for limited in vivo accessibility of Ep-CAM in normal tissues (McLaughlin et al. 2001. Cancer Res. 61: 4105-4111, expressly incorporated by reference).

Monoclonal antibodies are a common class of therapeutic proteins. A number of favorable properties of antibodies, including but not limited to specificity for target, ability to mediate immune effector mechanisms, and long half-life in serum, make antibodies powerful therapeutics. A number of antibodies that target Ep-CAM have been evaluated in pre-clinical studies with cell lines and/or xenograft models or in clinical trials for the treatment of cancers. These anti-Ep-CAM antibodies include but are not limited to MT201 (HD69 or adecatumumab; Naundorf, S. 2002. Int. J. Cancer. 100: 101-110; Prang, N. et al. 2005. Br. J. Cancer. 92: 342-349; Raum, T. et al. 2001. Cancer Immunol. Immunother. 50: 141-150), UBS-54 (Huls et al. 1999. Nature Biotech. 17: 276-281), Edrecolomab (Panorex or Mab 17-1A; Punt et al. 2002. The Lancet. 360: 671-677; Veronese, M. L. et al. 2004. Eur. J. Cancer. 40: 1229-1301; Schwartzberg, L. S. 2001. Critical Rev. Oncol./Hematol. 40: 17-24) and chimeric 17-1A mAb (LoBuglio, A. 1989. Proc. Natl. Acad. Sci. USA. 86: 4220-4224); all expressly incorporated by reference.

Antibodies are immunological proteins that bind a specific antigen. In most mammals, including humans and mice, antibodies are constructed from paired heavy and light polypeptide chains. Each chain is made up of individual immunoglobulin (Ig) domains, and thus the generic term immunoglobulin is used for such proteins. Each chain is made up of two distinct regions, referred to as the variable and constant regions. The light and heavy chain variable regions show significant sequence diversity between antibodies, and are responsible for binding the target antigen. The constant regions show less sequence diversity, and are responsible for binding a number of natural proteins to elicit important biochemical events. In humans there are five different classes of antibodies including IgA (which includes subclasses IgA1 and IgA2), IgD, IgE, IgG (which includes subclasses IgG1, IgG2, IgG3, and IgG4), and IgM. The distinguishing features between these antibody classes are their constant regions, although subtler differences may exist in the V region. IgG antibodies are tetrameric proteins composed of two heavy chains and two light chains. The IgG heavy chain is composed of four immunoglobulin domains linked from N- to C-terminus in the order $V_H$-CH1-CH2-CH3, referring to the heavy chain variable domain, heavy chain constant domain 1, heavy chain constant domain 2, and heavy chain constant domain 3 respectively (also referred to as $V_H$-Cγ1-Cγ2-Cγ3, referring to the heavy chain variable domain, constant gamma 1 domain, constant gamma 2 domain, and constant gamma 3 domain respectively). The IgG light chain is composed of two immunoglobulin domains linked from N- to C-terminus in the order $V_L$-$C_L$, referring to the light chain variable domain and the light chain constant domain respectively.

The variable region of an antibody contains the antigen binding determinants of the molecule, and thus determines the specificity of an antibody for its target antigen. The variable region is so named because it is the most distinct in sequence from other antibodies within the same class. The majority of sequence variability occurs in the complementarity determining regions (CDRs). There are 6 CDRs total, three each per heavy and light chain, designated $V_H$ CDR1, $V_H$ CDR2, $V_H$ CDR3, $V_L$ COR1, $V_H$ CDR2, and $V_L$ CDR3. The variable region outside of the CDRs is referred to as the framework (FR) region. Although not as diverse as the CDRs, sequence variability does occur in the FR region between different antibodies. Overall, this characteristic architecture of antibodies provides a stable scaffold (the FR region) upon which substantial antigen binding diversity (the CDRs) can be explored by the immune system to obtain specificity for a broad array of antigens. A number of high-resolution structures are available for a variety of variable region fragments from different organisms, some unbound and some in complex with antigen. The sequence and structural features of antibody variable regions are well characterized (Morea et al., 1997, Biophys Chem 68:9-16; Morea et al, 2000, Methods 20:267-279, expressly incorporated by reference), and the conserved features of antibodies have enabled the development of a wealth of antibody engineering techniques (Maynard et al, 2000, Annu Rev Biomed Eng 2:339-376, expressly incorporated by reference). Fragments comprising the variable region can exist in the absence of other regions of the antibody, including for example the antigen binding fragment (Fab) comprising $V_H$-Cγ1 and $V_H$-$C_L$, the variable fragment (Fv) comprising $V_H$ and $V_L$, the single chain variable fragment (scFv) comprising $V_H$ and $V_L$ linked together in the same chain, as well as a variety of other variable region fragments (Little et al., 2000, *Immunol Today* 21:364-370, expressly incorporated by reference).

The Fc region of an antibody interacts with a number of Fc receptors and ligands, imparting an array of important functional capabilities referred to as effector functions. For IgG the Fc region comprises Ig domains Cγ2 and Cγ3 and the N-terminal hinge leading into Cγ2. An important family of Fc receptors for the IgG class are the Fc gamma receptors (FcγRs). These receptors mediate communication between antibodies and the cellular arm of the immune system (Raghavan et al., 1996, *Annu Rev Cell Dev Biol* 12:181-220; Ravetch et al., 2001, *Annu Rev Immunol* 19:275-290; both expressly incorporated by reference). In humans this protein family includes FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIIb-NA1 and FcγRIIIb-NA2) (Jefferis et al, 2002, *Immunol Lett* 82:57-65, expressly incorporated by reference). These receptors typically have an extracellular domain that mediates binding to Fc, a membrane spanning region, and an intracellular domain that may mediate some signaling event within the cell. These receptors are expressed in a variety of immune cells including monocytes, macrophages, neutrophils, dendritic cells, eosinophils, mast cells, platelets, B cells, large granular lymphocytes, Langerhans' cells, natural killer (NK) cells, and T cells. Formation of the Fc/FcγR complex recruits these effector cells to sites of bound antigen, typically resulting in signaling events within the cells and important subsequent immune responses such as release of inflammation mediators, B cell activation, endocytosis, phagocytosis, and cytotoxic attack. The ability to mediate cytotoxic and phagocytic effector functions is a potential mechanism by which antibodies destroy targeted cells. The cell-mediated reaction wherein nonspecific cytotoxic cells that express FcγRs recognize bound antibody on a target cell and subsequently cause lysis of the target cell is referred to as antibody dependent cell-mediated cytotoxicity (ADCC) (Raghavan et al, 1996, *Annu Rev Cell Dev Biol* 12:181-220; Ghetie et al., 2000, *Annu Rev Immunol* 18:739-766; Ravetch et al., 2001, *Annu Rev Immunol* 19:275-290; all expressly incorporated by reference). The cell-mediated reaction wherein nonspecific cytotoxic cells that express FcγRs recognize bound antibody on a target cell and subsequently cause phagocytosis of the target cell is referred to as antibody dependent cell-mediated phagocytosis (ADCP).

The different IgG subclasses have different affinities for the FcγRs, with IgG1 and IgG3 typically binding substantially better to the receptors than IgG2 and IgG4 (Jefferis et al., 2002, *Immunol Lett* 82:57-65, expressly incorporated by reference). All FcγRs bind the same region on IgG Fc, yet with different affinities: the high affinity binder FcγRI has a Kd for IgG1 of $10^{-8}$ $M^{-1}$, whereas the low affinity receptors FcγRII and FcγRIII generally bind at $10^{-6}$ and $10^{-5}$ respectively. The extracellular domains of FcγRIIIa and FcγRIIIb are 96% identical, however FcγRIIIb does not have an intracellular signaling domain. Furthermore, whereas FcγRI, FcγRIIa/c, and FcγRIIIa are positive regulators of immune complex-triggered activation, characterized by having an intracellular domain that has an immunoreceptor tyrosine-based activation motif (ITAM), FcγRIIb has an immunoreceptor tyrosine-based inhibition motif (ITIM) and is therefore inhibitory. Thus the former are referred to as activation receptors, and FcγRIIb is referred to as an inhibitory receptor. The receptors also differ in expression pattern and levels on different immune cells. Yet another level of complexity is the existence of a number of FcγR polymorphisms in the human proteome. A particularly relevant polymorphism with clinical significance is V158/F158 FcγRIIIa. Human IgG1 binds with greater affinity to the V158 allotype than to the F158 allotype. This difference in affinity, and presumably its effect on ADCC and/or ADCP, has been shown to be a significant determinant of the efficacy of the anti-CD20 antibody rituximab (Rituxan®, a registered trademark of IDEC Pharmaceuticals Corporation). Patients with the V158 allotype respond favorably to rituximab treatment; however, patients with the lower affinity F158 allotype respond poorly (Cartron et al., 2002, *Blood* 99:754-758, expressly incorporated by reference). Approximately 10-20% of humans are V158/V158 homozygous, 45% are V158/F158 heterozygous, and 35-45% of humans are F158/F158 homozygous (Lehrnbecher et al., 1999, *Blood* 94:4220-4232; Cartron et al., 2002, *Blood* 99:754-758; both expressly incorporated by reference). Thus 80-90% of humans are poor responders, that is they have at least one allele of the F158 FcγRIIIa.

An overlapping but separate site on Fc, serves as the interface for the complement protein C1q. In the same way that Fc/FcγR binding mediates ADCC, Fc/C1q binding mediates complement dependent cytotoxicity (CDC). A site on Fc between the Cγ2 and Cγ3 domains, mediates interaction with the neonatal receptor FcRn, the binding of which recycles endocytosed antibody from the endosome back to the bloodstream (Raghavan et al., 1996, *Annu Rev Cell Dev Biol* 12:181-220; Ghetie et al., 2000, *Annu Rev Immunol* 18:739-766; both expressly incorporated by reference). This process, coupled with preclusion of kidney filtration due to the large size of the full length molecule, results in favorable antibody serum half-lives ranging from one to three weeks. Binding of Fc to FcRn also plays a key role in antibody transport. The binding site for FcRn on Fc is also the site at which the bacterial proteins A and G bind. The tight binding by these proteins is typically exploited as a means to purify antibodies by employing protein A or protein G affinity chromatography during protein purification. A key feature of the Fc region is the conserved N-linked glycosylation that occurs at N297. This carbohydrate, or oligosaccharide as it is sometimes referred, plays a critical structural and functional role for the antibody, and is one of the principle reasons that antibodies must be produced using mammalian expression systems.

In addition to antibodies, an antibody-like protein that is finding an expanding role in research and therapy is the Fc fusion (Chamow et al, 1996, *Trends Biotechnol* 14:52-60; Ashkenazi et al., 1997, *Curr Opin Immunol* 9:195-200; both expressly incorporated by reference). An Fc fusion is a protein wherein one or more polypeptides is operably linked to Fc. An Fc fusion combines the Fc region of an antibody, and thus its favorable effector functions and pharmacokinetics, with the target-binding region of a receptor, ligand, or some other protein or protein domain. The role of the latter is to mediate target recognition, and thus it is functionally analogous to the antibody variable region. Because of the structural and functional overlap of Fc fusions with antibodies, the discussion on antibodies in the present invention extends directly to Fc fusions.

There are a number of possible mechanisms by which antibodies destroy tumor cells, including anti-proliferation via blockage of needed growth pathways, intracellular signaling leading to apoptosis, enhanced down regulation and/or turnover of receptors, CDC, ADCC, ADCP, and promotion of an adaptive immune response (Cragg et al., 1999, *Curr Opin Immunol* 11:541-547; Glennie et al., 2000, *Immunol Today* 21:403-410; both expressly incorporated by reference). Antitumor efficacy may be due to a combination of these mechanisms, and their relative importance in clinical therapy appears to be cancer dependent. Despite this arsenal of anti-tumor weapons, the potency of currently available antibodies as anti-cancer agents is unsatisfactory, particularly given their high cost. Patient tumor response data show that monoclonal antibodies provide only a small improvement in therapeutic success over normal single-agent cytotoxic chemotherapeutics. For example, just half of all relapsed low-grade non-Hodgkin's lymphoma patients respond to the anti-CD20 antibody rituximab (McLaughlin et al., 1998, *J Clin Oncol* 16:2825-2833, expressly incorporated by reference). Of 166 clinical patients, 6% showed a complete response and 42% showed a partial response, with median response duration of approximately 12 months. Trastuzumab (Herceptin®, a registered trademark of Genentech), an anti-HER2/neu antibody for treatment of metastatic breast cancer, has less efficacy. The overall response rate using trastuzumab for the 222 patients tested was only 15%, with 8 complete and 26 partial responses and a median response duration and survival of 9 to 13 months (Cobleigh et al., 1999, J Clin Oncol 17:2639-2648, expressly incorporated by reference), Despite the fact that Ep-CAM is expressed on up to 77 percent of colorectat cancer tumors, combination therapy with cetuximab (Erbitux®, Imclone/BMS) had an objective response rate of 22.5% with a median duration of response of 84 days (Saltz et al., 2001, Proc. Am. Soc. Clin. Oncol. 20, 3a); results of the cetuximab single agent treatment group were even worse. Currently for anticancer therapy, any small improvement in mortality rate defines success. Thus there is a significant need to enhance the capacity of antibodies to destroy targeted cancer cells.

A promising means for enhancing the anti-tumor potency of antibodies is via enhancement of their ability to mediate cytotoxic effector functions such as ADCC, ADCP, and CDC. The importance of FcγR-mediated effector functions for the anti-cancer activity of antibodies has been demonstrated in mice (Clynes et al., 1998, *Proc Natl Acad Sci USA* 95:652-656; Clynes et al, 2000, *Nat Med* 6:443-446; both expressly incorporated by reference), and the affinity of interaction between Fc and certain FcγRs correlates with targeted cytotoxicity in cell-based assays (Shields et al, 2001, *J Biol Chem* 276:6591-6604; Presta et al, 2002, *Biochem Soc Trans* 30:487-490; Shields et al., 2002, *J Biol Chem* 277:26733-26740; all expressly incorporated by reference). Additionally, a correlation has been observed between clinical efficacy in humans and their allotype of high (V158) or low (F158) affinity polymorphic forms of FcγRIIIa (Cartron et al., 2002, Blood 99:754-758; Weng & Levy, 2003, Journal of Clinical Oncology, 21:3940-3947; both expressly incorporated by reference). Together these data suggest that an antibody that is optimized for binding to certain FcγRs may better mediate effector functions and thereby destroy cancer cells more effectively in patients. The balance between activating and inhibiting receptors is an important consideration, and optimal effector function may result from an antibody that has enhanced affinity for activation receptors, for example FcγRI, FcγRIIa/c, and FcγRIIIa, yet reduced affinity for the inhibitory receptor FcγRIIb. Furthermore, because FcγRs can mediate antigen uptake and processing by antigen presenting cells, enhanced FcγR affinity may also improve the capacity of antibody therapeutics to elicit an adaptive immune response. With respect to Ep-CAM, ADCC has been implicated as an important effector mechanism for the anti-tumor cytotoxic capacity of some anti-Ep-CAM antibodies (Bleeker et al., 2004, J. Immunol. 173(7):4699-707; Bier et al., 1998, Cancer Immunol Immunother 46:167-173; both expressly incorporated by reference).

Mutagenesis studies have been carried out on Fc towards various goals, with substitutions typically made to alanine (referred to as alanine scanning) or guided by sequence homology substitutions (Duncan et al., 1988, *Nature* 332: 563-564; Lund et al, 1991, *J Immunol* 147:2657-2662; Lund et alt, 1992, *Mol Immunol* 29:53-59; Jefferis et al., 1995, *Immunol Lett* 44:111-117; Lund et alt, 1995, *Faseb J* 9:115-119; Jefferis et al., 1996, *Immunol Lett* 54:101-104; Lund et al., 1996, *J Immunol* 157:4963-4969; Armour et al, 1999, *Eur J Immunol* 29:2613-2624; Shields et al, 2001, *J Biol Chem* 276:6591-6604; Jefferis et al, 2002, *Immunol Lett* 82:57-65; U.S. Pat. No. 5,624,821; U.S. Pat. No. 5,885,573; PCT WO 00/42072; PCT WO 99/58572; all expressly incorporated by reference). Most substitutions reduce or ablate binding with FcγRs. However some success has been achieved at obtaining Fc variants with selectively enhanced binding to FcγRs, and in some cases these Fc variants have been shown to provide enhanced potency and efficacy in cell-based effector function assays. See for example U.S. Pat. No. 5,624,821, PCT WO 00/42072, U.S. Pat. No. 6,737,056, U.S. Ser. No. 10/672,280, PCT US03/30249, and U.S. Ser. No. 10/822,231, and U.S. Ser. No. 60/627,774, filed Nov. 12, 2004 and entitled "Optimized Fc Variants"; all expressly incorporated by reference. Enhanced affinity of Fc for FcγR has also been achieved using engineered glycoforms generated by expression of antibodies in engineered or variant cell lines (Umaña et al., 1999, *Nat Biotechnol* 17:176-180; Davies at al., 2001, *Biotechnol Bioeng* 74:288-294; Shields et al., 2002, *J Biol Chem* 277: 26733-26740; Shinkawa et al, 2003, *J Biol Chem* 278:3466-3473; all expressly incorporated by reference).

The present invention provides variants of Ep-CAM targeting proteins that comprise one or more amino acid modifications that provide enhanced effector function and humanized light and heavy variable regions.

SUMMARY OF THE INVENTION

The present invention is directed to humanized Ep-CAM-targeting antibodies including first and/or second amino acid sequences corresponding to the heavy and light chains of the antibodies, respectively, as well as methods of using the same. In various aspects, the first and second amino acid sequences can include sequences corresponding to CDR3, CDR2, or CDR1 of the humanized Ep-CAM antibody heavy and light chains, Such sequences can be independent, or can be combined.

In a first aspect, the first and second amino acid sequences comprise a sequence corresponding to CDR3 of the humanized Ep-CAM heavy and light chains. In one embodiment, the present invention is directed to a humanized anti-Ep-CAM antibody, wherein said antibody comprises A) a first amino acid sequence comprising i) DGPWX$_1$AY (SEQ ID NO:160), wherein X$_1$ is selected from the group consisting of F and Y; or ii) a sequence selected from the group consisting of SEQ ID NOS:129-130; and/or B) a second amino acid sequence comprising i) X$_1$YSYPYT (SEQ ID NO:161), wherein X$_1$ is selected from the group consisting of G and Y; or ii) a sequence selected from the group consisting of SEQ ID NOS: 135-136. In certain variations, these sequences correspond to CDR3 of the heavy and light chains of the antibody.

In a further aspect, the first amino acid sequence further comprises an amino acid sequence of i) X$_1$X$_2$FX$_3$X$_4$YL (SEQ ID NO:162), wherein X$_1$ is selected from the group consisting of Y and F; X$_2$ is selected from the group consisting of A and S; X$_3$ is selected from the group consisting of T and S; and X$_4$ is selected from the group consisting of N and D; and ii) a sequence selected from the group consisting of SEQ ID NOS:122-126; iii) NPGSGX$_1$ (SEQ ID NO:163), wherein X$_1$ is selected from the group consisting of G and A; iv) the sequence of SEQ ID NOS:131-132. The second amino acid sequence further comprises i) X$_1$NVVTY (SEQ ID NO:164), wherein X$_1$ is selected from the group consisting of E and Q; ii) a sequence selected from the group consisting of SEQ ID NOS: 127-128; iii) X$_1$ASNRYT (SEQ ID NO:165), wherein X$_1$ is selected from the group consisting of G and D; or iv) an amino acid sequence selected from the group consisting of SEQ ID NOS: 133-134. In certain variations, these sequences correspond to CDR1 and CDR2 of the heavy and light chains of the antibody.

In a further aspect, the first and second amino acid sequences part of the same amino acid sequence. In a still further aspect, the first amino acid sequence does not comprise a sequence selected from the group consisting of SEQ ID NOS: 122, 127, and 129, and said second amino acid sequence does not comprise a sequence selected from the group consisting of SEQ ID NOS: 131, 133, and 135.

In certain variations, the first amino acid sequence does not comprise SEQ ID NO:1, and the second amino acid sequence does not comprise SEQ ID NO:105.

In another embodiment, the humanized, the heavy chain variable region comprises a heavy chain framework region selected from the framework regions found in the group consisting of SEQ ID NOS:2-104. The second amino acid comprises a light chain framework region selected from the framework regions found in the group consisting of SEQ ID NOS:106-121.

In another aspect the antibody comprises a heavy chain variable region selected from the group consisting of: SEQ ID NOS: 3, 15, 27, 56 and 97, and/or the light chain variable region of SEQ ID NO:108.

In a further aspect, the first amino acid sequence is selected from the group consisting of SEQ ID NOS: 2-104, and the second amino acid sequence is selected from the group consisting of SEQ ID NOS: 106-121.

In a further aspect, the antibody has an IgG1 Fc domain, or a hybrid IgG1, IgG2 Fc domain.

In another aspect, the present invention is directed to a variant anti-Ep-CAM antibody comprising a variant human Fc domain, the variant human Fc domain comprising at least one modification that alters binding of the antibody to an Fc receptor compared to a parent human Fc domain. In one aspect, the one modification alters binding to an Fcgamma receptor. In certain variations, the modification comprises at least one substitution selected from the group consisting of: 236A, 239D, 268E, 298A, 298D, 326D, 326E, 330L, 330Y, 332E, 333A, 334A, and 396L, wherein the numbering is according to the EU index in Kabat et al.

In certain variations, the modification includes an altered glycoform, such as defucosylation or lacking a fucose moiety.

In certain additional variations, the modifications can alter binding to FcRn.

In certain aspects, the variant anti-Ep-CAM antibody comprise at least one modification that alters an effector function of the variant antibody compared to an unmodified anti-Ep-CAM antibody. In certain variations, the effector function is antibody-dependent cellular cytotoxicity (ADCC) or complement-dependent cytoxicity (CDC).

In certain aspects, the Fc substitution comprises a substitution selected from the group consisting of: 239D and 332E, wherein the numbering is that of the EU index in Kabat et al. In certain other aspects, the anti-Ep-CAM antibody comprises an Fc domain comprising at least one substitution selected from the group consisting of: K326W, K326Y, and E333S, wherein the numbering is according to the EU index in Kabat et al.

In further aspects, the modification increases the affinity of the antibody for FcγRIIIa compared to a parent antibody. In some variations, the modification increases the affinity of the antibody for FcγRIIIa at least 2-fold compared to a parent antibody. In other variations, the modification increases the affinity of the antibody for FcγRIIIa at least 5-fold compared to a parent antibody.

In further aspects, the Fc modification decreases the affinity of the antibody for FcγRIIIa compared to a parent antibody. In some embodiments, the modification decreases the affinity of the antibody for FcγRIIIa by at least 10-fold compared to a parent antibody. The modification can also comprise a substitution selected from the group consisting of: 235G and 236R, wherein the numbering is that of the EU index in Kabat et al.

In further aspects, the Fc modification increases the FcγRIIa:FcγRIIb specificity for the antibody. In some embodiments, the modification increases the FcγRIIa:FcγRIIb specificity for the antibody by at least 2. In further embodiments, the modification increases the FcγRIIa:FcγRIIb specificity for the antibody by at least 8. In still further embodiments, the modification increases the FcγRIIa:FcγRIIb specificity between 7 to 11.

In other aspects, the Fc modification specifically increases maturation or activation of monocytes, macrophages, neutrophils, or dendritic cells by the antibody compared to activation of natural killer (NK) cells by the antibody. In some variations, the modification specifically increases activation of neutrophils by the antibody compared to activation of natural killer (NK) cells by the antibody.

In other aspects, the Fc modification not substantially increase activation of natural killer cells or specifically increases activation by the antibody of dendritic cells.

In further aspects, the modification increases binding to an activating Fc receptor and does not increase binding to FcγRIIb. In certain aspects, the modification specifically increases monocyte or macrophage phagocytosis.

The present invention provides variant Ep-CAM targeting proteins that are optimized for a number of therapeutically relevant properties. A variant Ep-CAM targeting protein comprises one or more amino acid modifications relative to a parent Ep-CAM targeting protein, wherein the amino acid modification(s) provide one or more optimized properties.

BRIEF DESCRIPTION OF THE DRAWINGS AND TABLES

FIGS. 1A and 1B. Sequences of the heavy chain variable region of the original 17-1A antibody and select antibodies of the present invention with reduced potential for immunogenicity (SEQ ID NOS:1-104 and SEQ ID NOS:122-130).

FIGS. 2A and 2B. Sequences of the light chain variable region of the original 17-1A antibody and select antibodies of the present invention with reduced potential for immunogenicity (SEQ ID NOS:105-121 and SEQ ID NOS:131-136).

FIG. 3. Sequences of the constant regions of the original 17-1A antibody and select antibodies of the present invention (SEQ ID NOS:137-143).

FIG. 4. Expression yields of select anti-Ep-CAM antibodies of the present invention.

Figure 6:

FIG. 5. SDS gels of some anti-Ep-CAM antibodies of the present invention,

FIG. 6. An SDS gel of an anti-Ep-CAM antibody purified after expression in lec13 cells. The resulting antibody has an engineered glycoform, that is, it is defucosylated.

Figure 7:
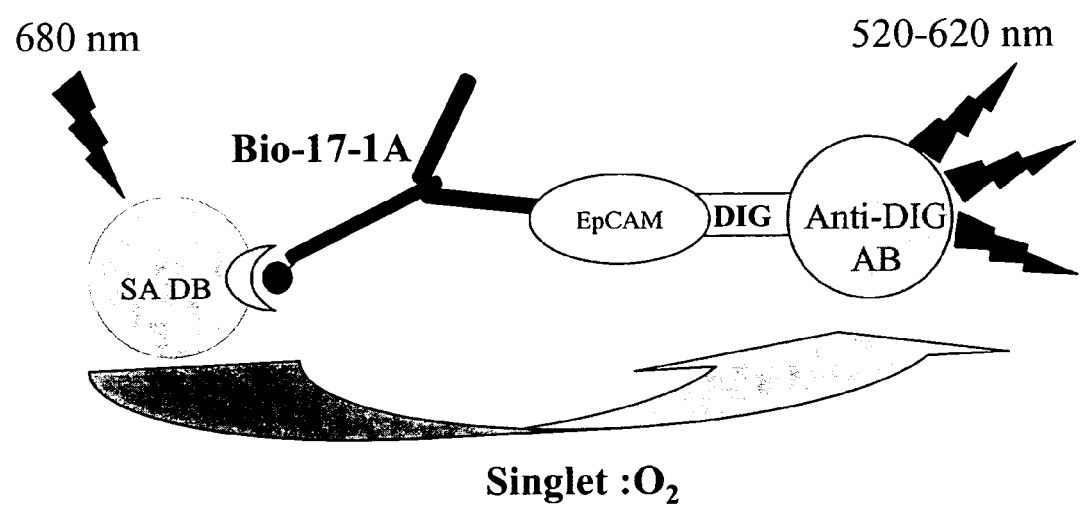

FIG. 7. Schematic representation of the AlphaScreen™ methods used to measure relative binding affinity in the present study.

FIG. 8. AlphaScreen™ data showing the relative binding affinity of antibodies of the present invention to the antigen, Ep-CAM, and to protein A.

FIG. 9. Summary of AlphaScreen™ data showing the relative binding properties of antibodies of the present invention to the antigen, Ep-CAM, and to protein A.

FIG. 10. AlphaScreen™ data showing the relative binding affinity of antibodies of the present invention to (7A) the antigen, Ep-CAM or (7B) the Fc gamma receptor IIIa (FcgRIIIaV).

FIG. 11. Summary of AlphaScreen™ data showing the relative binding properties of antibodies of the present invention to the antigen, Ep-CAM.

FIG. 12. Physicochemical properties of some humanized anti-Ep-CAM antibodies and controls. Humanized variable regions were expressed with human IgG1. H0L0 represent the variable regions of murine 17-1A. IgG1-H0L0 is a chimeric human IgG1 with mouse variable regions. IgG2a-H0L0 contains H0L0 variable domains and mouse kappa/IgG2a constant domains.

Figure 13B:
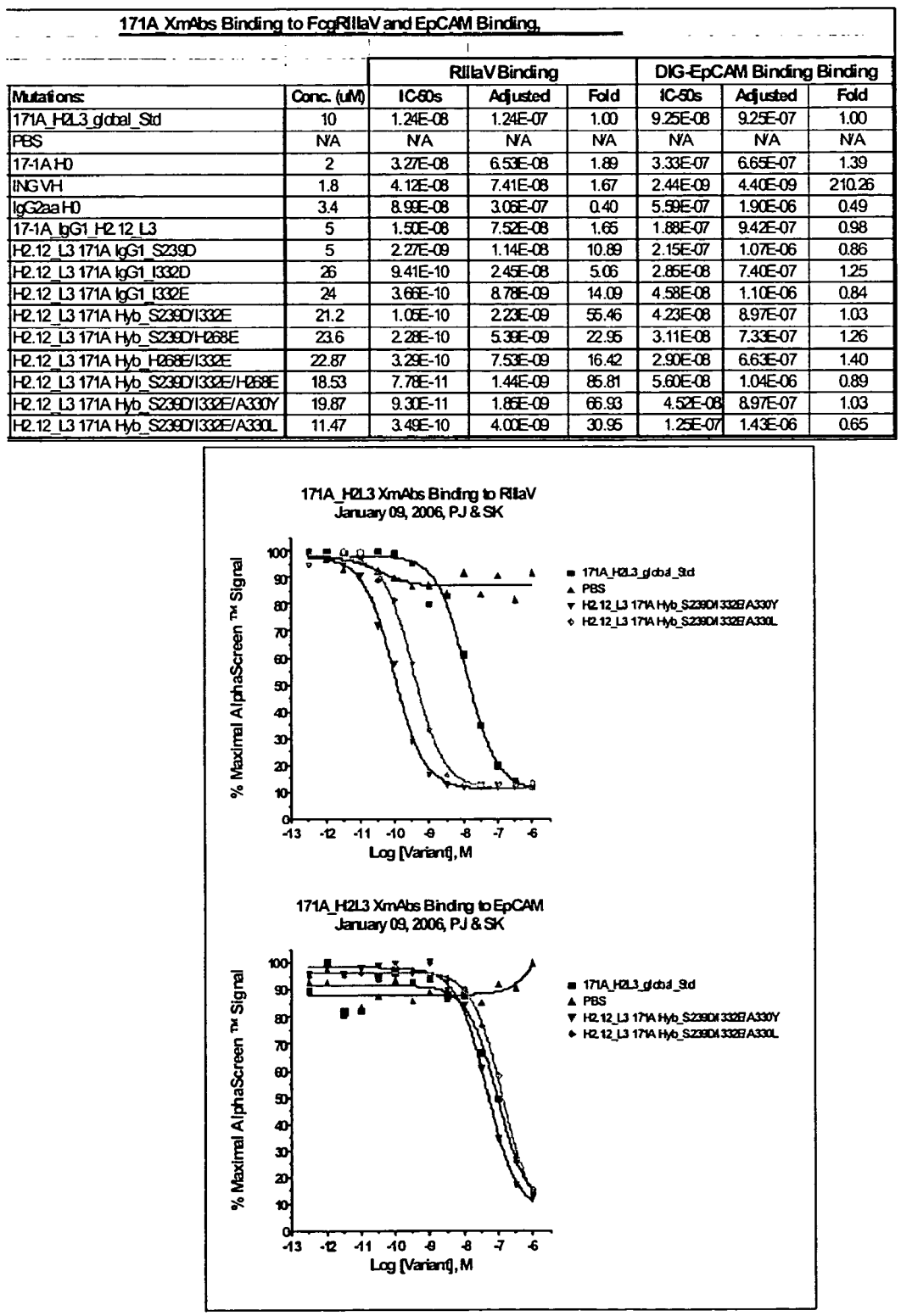

FIG. 13. Binding measurements of anti-Ep-CAM proteins to Ep-CAM and to FcgammaRIIIa.

FIG. 14. Binding data for anti-Ep-CAM antibodies measured by surface plasmon resonance (SPR).

Figure 15:
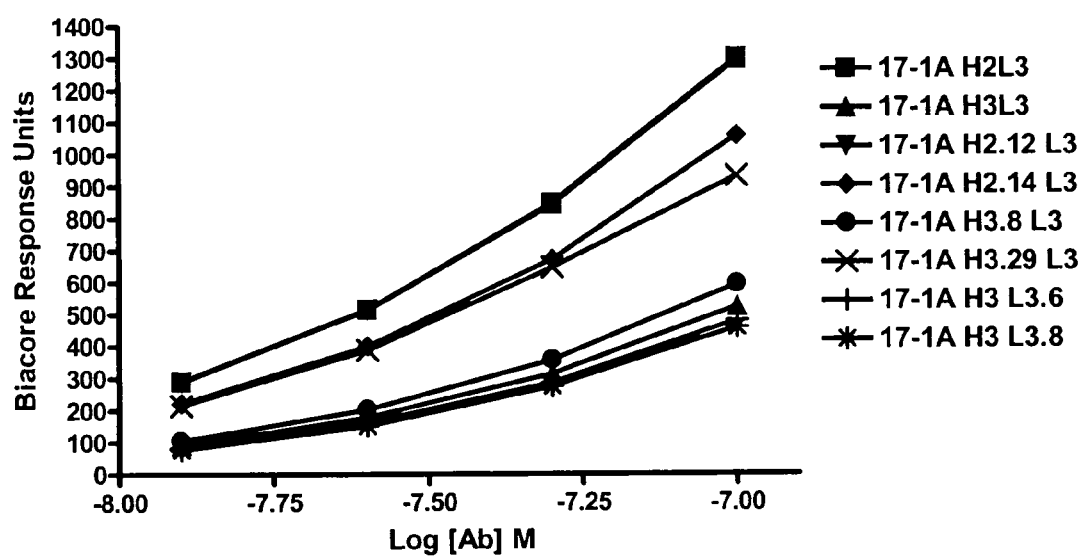

FIG. 15. Binding data for anti-Ep-CAM antibodies measured by surface plasmon resonance (SPR).

FIG. 16. Binding data for anti-Ep-CAM antibodies measured by surface plasmon resonance (SPR).

Figure 17:
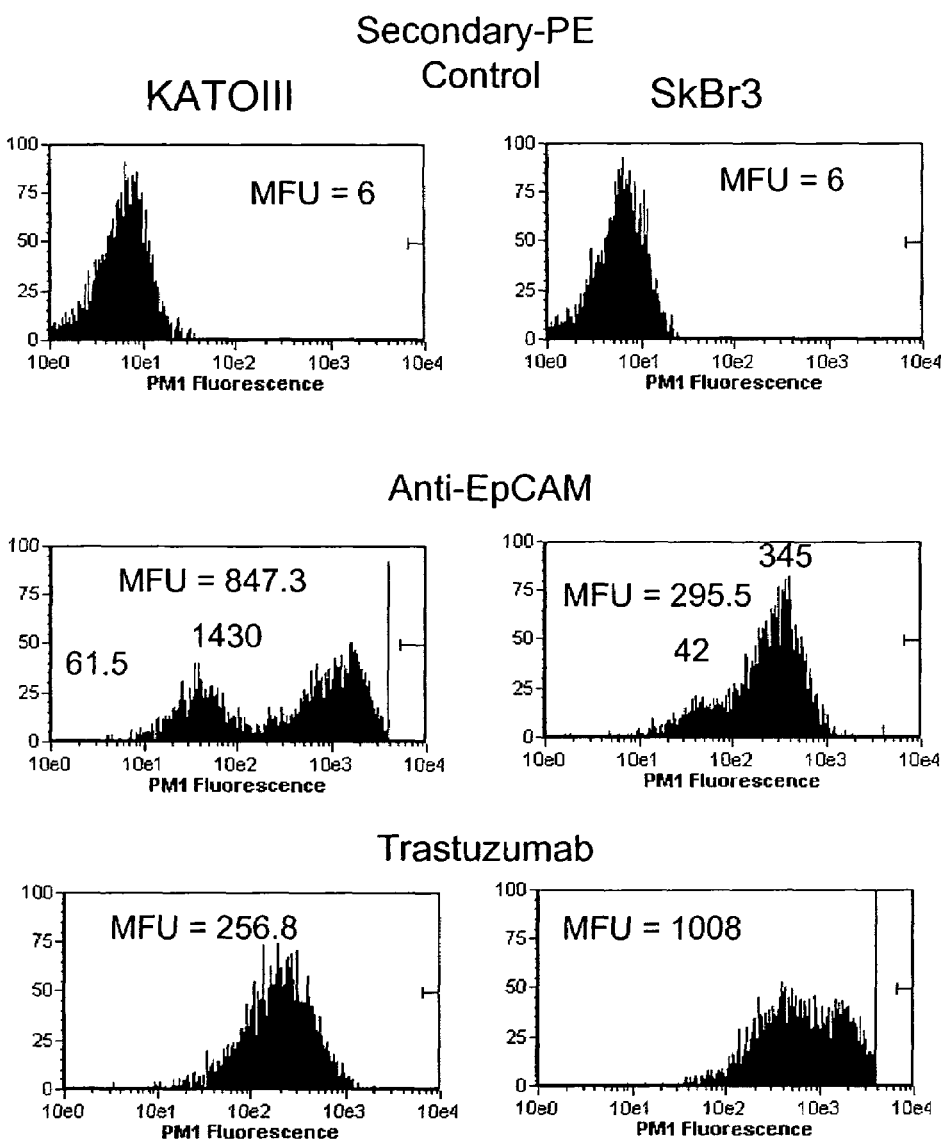

FIG. 17. Relative expression levels of Ep-CAM and Her2 on the cell lines KATO III and SkBr3.

Figure 18:
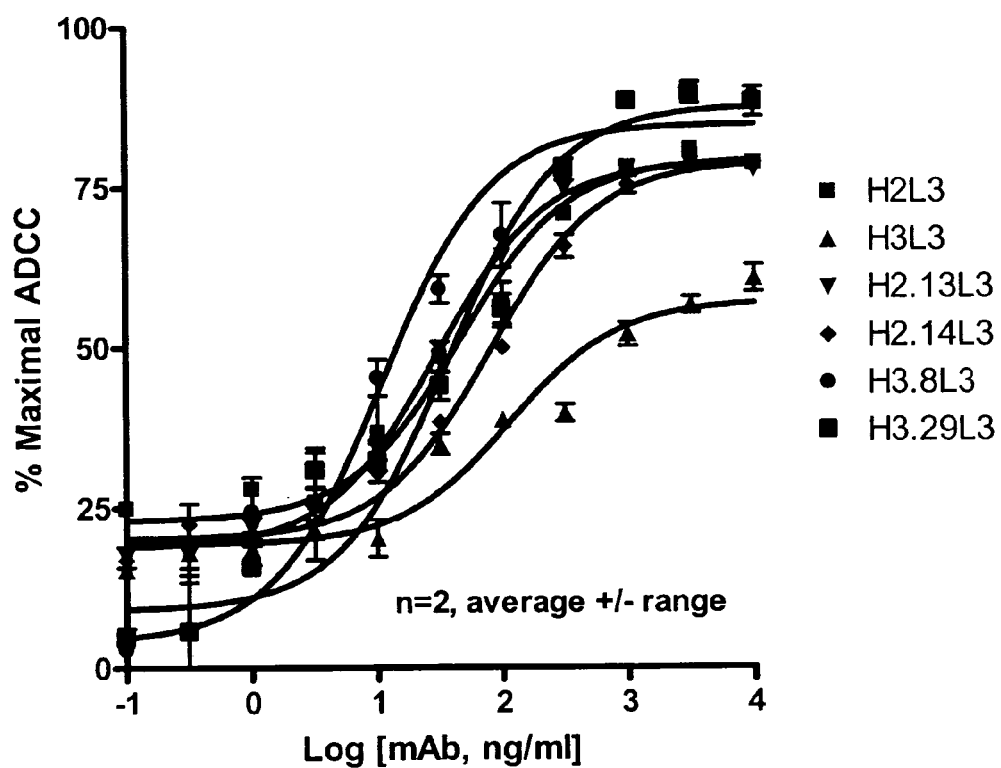

FIG. 18. ADCC activities of anti-Ep-CAM antibodies with the KATO III cell line. Variable regions were expressed with human IgG1.

FIG. 19. ADCC activities of anti-Ep-CAM antibodies with the KATO III cell line. Variable regions were expressed with human IgG1. (A) to (C) represent variants in direct comparison with 17-1A H3L3 and 17-1A H2L3.

FIG. 20. ADCC activities of anti-Ep-CAM antibodies with (a) the LS180 cell line and (b) the LS180 and HT29 cell line.

FIG. 21. Potency and binding affinity of anti-Ep-CAM monoclonal antibodies. (A) ADCC activity with the KATO III cell fine; (B) Binding to Ep-CAM; (C) Binding to FcγRIIaV, ADCC activity was determined with the Europium method. Binding was determined with AlphaScreen. 17-1A H2L3 I332E and 17-1A H2L3 S239D/I332E are shown.

Figure 22:
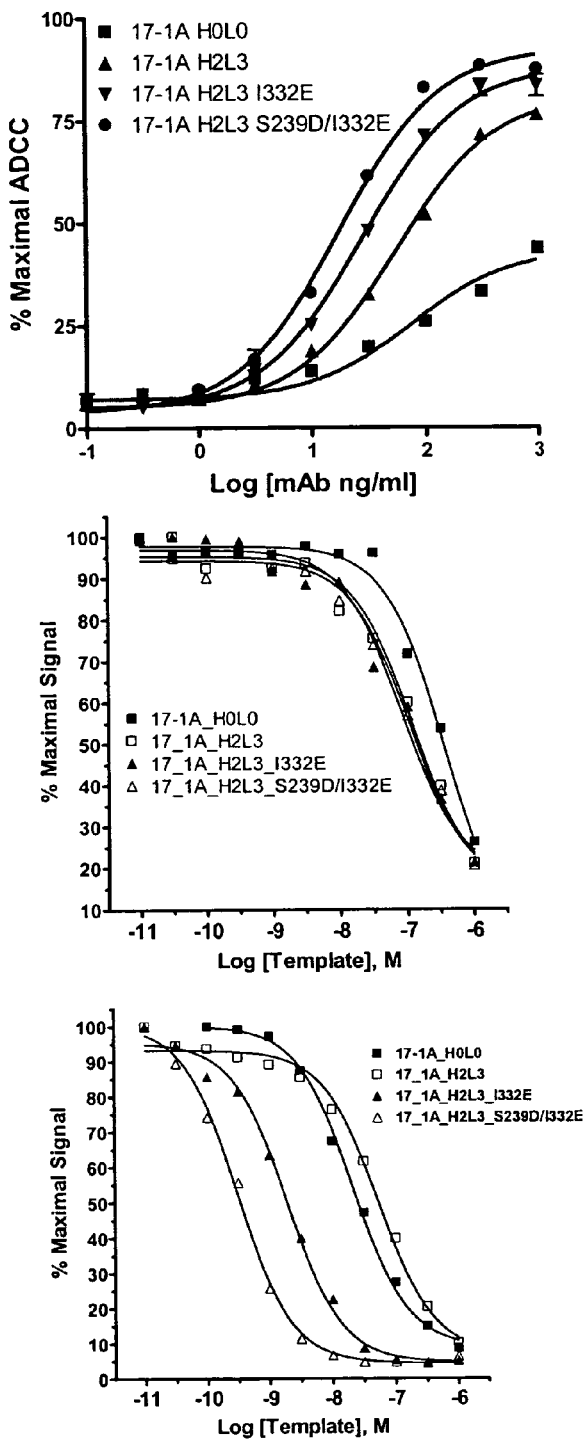

FIG. 22. Potency and binding affinity of anti-Ep-CAM monoclonal antibodies. (A) ADCC activity with the KATO III cell line; (B) Binding to Ep-CAM; (C) Binding to FcγRIIaV. ADCC activity was determined with the Europium method. Binding was determined with AlphaScreen. 17-1A H3L3 I332E and 17-1A H3L3 S239D/I332E are shown.

Figure 23:
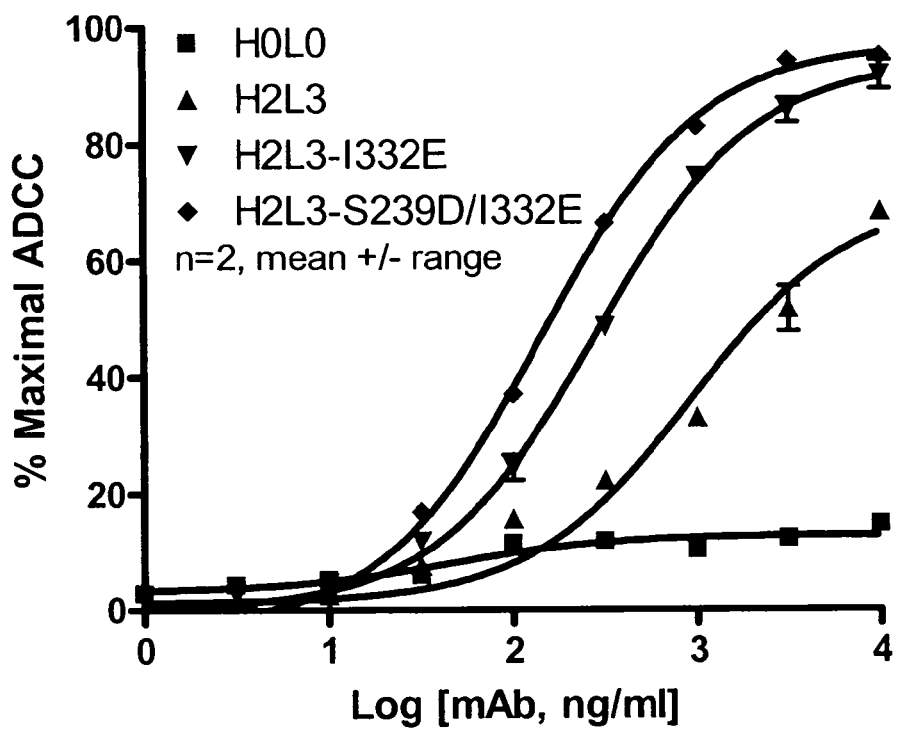

FIG. 23. ADCC activity of anti-Ep-CAM antibodies with the SkBr3 cell line. Variable regions were expressed with human IgG1.

Figure 24:
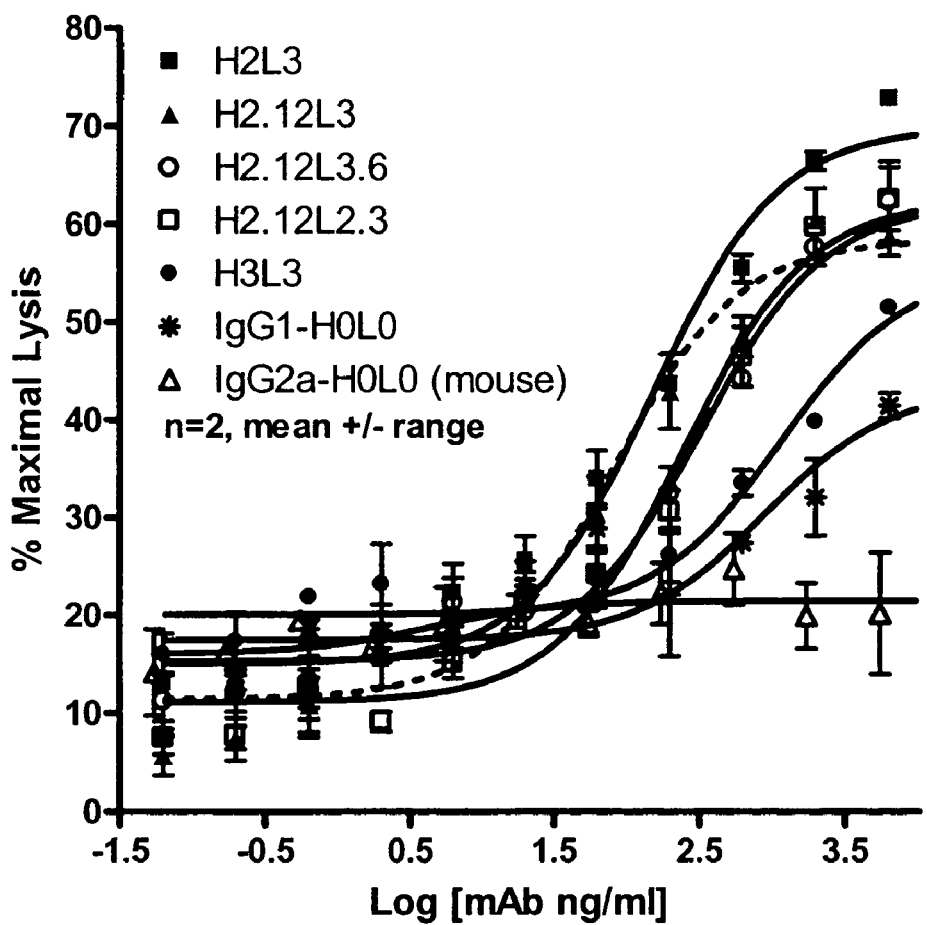

FIG. 24. ADCC activity of anti-Ep-CAM antibodies with the KATO III cell line. Variable regions were of variants expressed with human IgG1.

FIG. 25. FcgammaRIIIa binding to an anti-Ep-CAM protein with a typical carbohydrate attached to an Fc domain and to an anti-Ep-CAM protein with a defucosylated Fc domain. The glycoform variant (lower panel) has stronger binding to the Fc receptor than the protein containing the typical carbohydrate.

Figure 26:
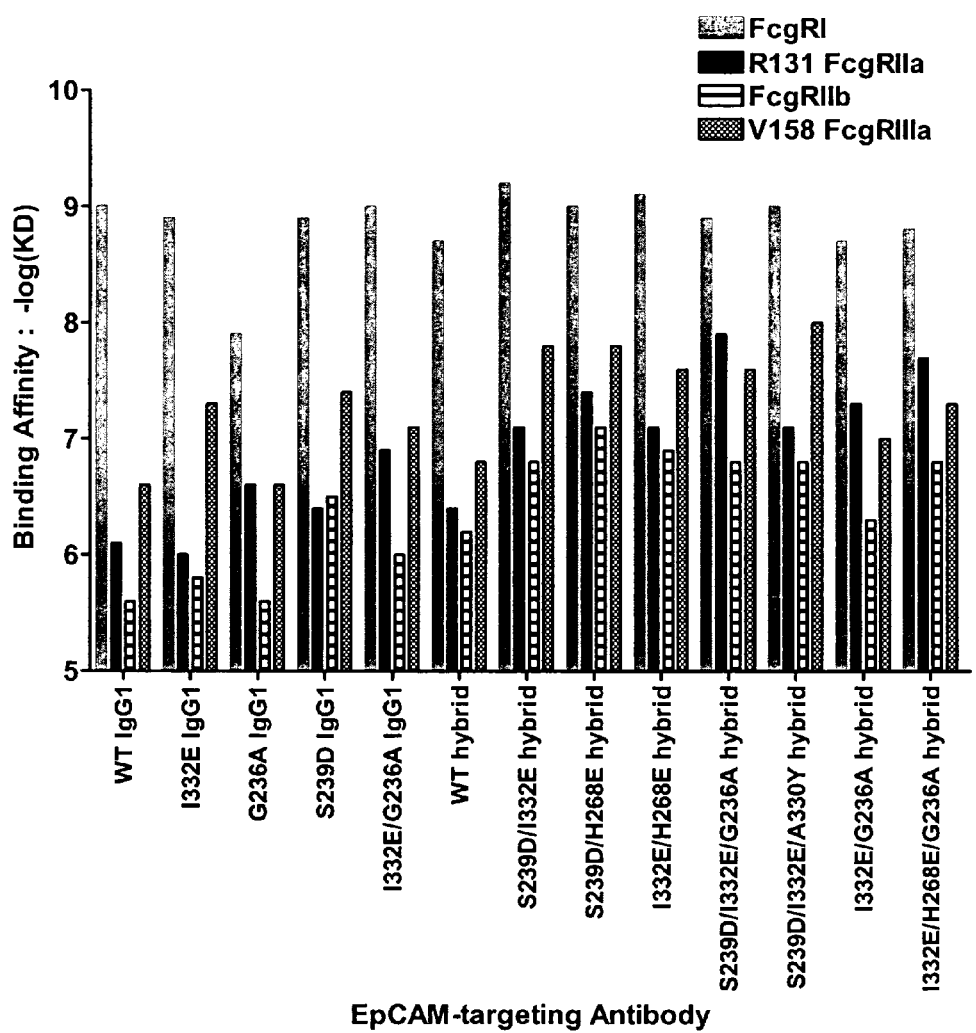

FIG. 26. Binding affinity of wild-type and variant Ep-CAM-targeting antibodies to various FcγR's, Fc gamma receptors. Data shown are collected with H3.77 and L3 variable domains. Constant regions were based on either human IgG1 or a hybrid of human IgG1 and IgG2 sequences. The binding affinity is plotted as $-\log(K_D)$ in molar units, Larger numbers demonstrate tighter binding and a change of 1 unit on the ordinate demonstrates a 10-fold change in binding affinity.

FIG. 27. Binding affinities of modified Ep-CAM-targeting antibodies to Fc receptors. Surface plasmon resonance measurements were used to test the strength of binding, which is reported as $K_D$ values in molar units. Also shown are the fold-change in binding of each antibody relative to the WT IgG1 binding affinity and the $\log(1/K_D)$ values, or $-\log(K_D)$, which are also plotted in FIG. 26. The relative binding of each variant to FcγRIIa compared to FcγRIIB are shown in the last column. A value of zero shows equal binding of the antibody to FcγRIIa and FcγRIIIb, whereas a value of one shows 10-fold tighter binding of the antibody to FcγRIIa than to FcγRIIb.

FIG. 28. (a) Common allotypes of human IgGs. (b) Alternative allotypic versions of anti-Ep-CAM IgG antibodies.

FIG. 29. Sequences of Ep-CAM-targeting antibodies, including both heavy and light chain sequences (SEQ ID NO:144-159),

DETAILED DESCRIPTION OF THE INVENTION

The present invention is directed to humanized Ep-CAM-targeting antibodies including first and/or second amino acid sequences corresponding to the heavy and light chains of the antibodies, respectively, as well as methods of using the same. In various aspects, the first and second amino acid sequences can include sequences corresponding to CDR3, CDR2, or CDR1 of the humanized Ep-CAM antibody heavy and light chains. Such sequences can be independent, or can be combined. Additionally, the Ep-CAM targeting antibodies can be combined with variant Fc regions designed to alter effector function, including those of U.S. patent application Ser. Nos. 11/124,620 filed May 5, 2005, Ser. No. 10/822,231 filed Mar. 26, 2004, and Ser. No. 10/379,392, filed Mar. 3, 2003, each of which is incorporated herein by reference in its entirety.

In order that the invention may be more completely understood, several definitions are set forth below. Such definitions are meant to encompass grammatical equivalents.

By "ADCC" or "antibody dependent cell-mediated cytotoxicity" as used herein is meant the cell-mediated reaction wherein nonspecific cytotoxic cells that express FcγRs recognize bound antibody on a target cell and subsequently cause lysis of the target cell.

By "ADCP" or antibody dependent cell-mediated phagocytosis as used herein is meant the cell-mediated reaction wherein nonspecific cytotoxic cells that express FcγRs recognize bound antibody on a target cell and subsequently cause phagocytosis of the target cell.

By "amino acid modification" herein is meant an amino acid substitution, insertion, and/or deletion in a polypeptide sequence. The preferred amino acid modification herein is a substitution. By "amino acid substitution" or "substitution" herein is meant the replacement of an amino acid at a particular position in a parent polypeptide sequence with another amino acid. For example, the substitution I332E refers to a variant polypeptide, in this case an Fc variant, in which the isoleucine at position 332 is replaced with a glutamic acid.

By "amino acid" and "amino acid identity" as used herein is meant one of the 20 naturally occurring amino acids or any non-natural analogues that may be present at a specific, defined position. By "protein" herein is meant at least two covalently attached amino acids, which includes proteins, polypeptides, oligopeptides and peptides. The protein may be made up of naturally occurring amino acids and peptide bonds, or synthetic peptidomimetic structures, i.e. "analogs", such as peptoids (see Simon et al., 1992, *Proc Natl Acad Sci USA* 89(20):9367) particularly when LC peptides are to be administered to a patient. Thus "amino acid", or "peptide residue", as used herein means both naturally occurring and synthetic amino acids, For example, homophenylalanine, citrulline and norleucine are considered amino acids for the purposes of the invention. "Amino acid" also includes imino acid residues such as proline and hydroxyproline. The side chain may be in either the (R) or the (S) configuration. In the preferred embodiment, the amino acids are in the (S) or L-configuration. If non-naturally occurring side chains are used, non-amino acid substituents may be used, for example to prevent or retard in vivo degradation.

By "affinity" or "binding affinity" as used herein is meant the strength of interaction between two molecules. The strength of affinity is often reported with a dissociation constant, Kd or KD, such as $1*10^{-7}$ M, or a log(Kd), such as –7.0, or –log(Kd), such as 7.0. As is known in the art, lower values of Kd correspond to tighter binding and higher affinity. Higher values of Kd correspond to weaker binding and lower affinity.

The binding "specificity" may be defined as the relative strength of binding of a first molecule to a second molecule compared to the strength of the first molecule to a third molecule. Specificity may be reported as a ratio or quotient of binding constants for the two binding reactions. For example, a FcγRIIa:FcγRIIb specificity of 10 for Antibody A, means that Antibody A binds to FcγRIIa ten-fold more strongly than it binds to FcγRIIb. An additional way to express the same FcγRIIa:FcγRIIb specificity for Antibody A is that the Kd of FcγRIIb is 10-fold higher than the Kd of FcγRIIa.

By "effector function" as used herein is meant a biochemical event that results from the interaction of an antibody Fc region with an Fc receptor or ligand. Effector functions include but are not limited to ADCC, ADCP, and CDC. By "effector cell" as used herein is meant a cell of the immune system that expresses one or more Fc receptors and mediates one or more effector functions. Effector cells include but are not limited to monocytes, macrophages, neutrophils, dendritic cells, eosinophils, mast cells, platelets, B cells, large granular lymphocytes, Langerhans' cells, natural killer (NK) cells, and γγ T cells, and may be from any organism including but not limited to humans, mice, rats, rabbits, and monkeys. By "library" herein is meant a set of Fc variants in any form, including but not limited to a list of nucleic acid or amino acid sequences, a list of nucleic acid or amino acid substitutions at variable positions a physical library comprising nucleic acids that encode the library sequences, or a physical library comprising the Fc variant proteins, either in purified or unpurified form.

By "Ep-CAM targeting protein" as used herein is meant a protein that binds to Ep-CAM, also known as epithelial glycoprotein 40 [EGP40], epithelial protein 2 [EGP-2], GA733-2, ESA, KSA, 17-1A antigen and other names. The Ep-CAM targeting protein of the present invention may be an antibody, Fc fusion, or any other protein that binds Ep-CAM. An Ep-CAM targeting protein of the present invention may bind any epitope or region on Ep-CAM, and may be specific for fragments, splice forms, or aberrent forms of Ep-CAM. Preferred proteins are antibodies, including the antibodies described herein.

By "Fc" or "Fc region", as used herein is meant the polypeptide comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, Fc comprises immunoglobulin domains Cgamma2 and Cgamma3 (Cγ2 and Cγ3) and the hinge between Cgamma1 (Cγ1) and Cgamma2 (Cγ2). Although the boundaries of the Fc region may vary, the human IgG heavy chain Fc region is usually defined to comprise residues C226 or P230 to its carboxyl-terminus, wherein the numbering is according to the EU index as in Kabat. Fc may refer to this region in isolation, or this region in the context of an Fc polypeptide, as described below. By "Fc polypeptide" as used herein is meant a polypeptide that comprises all or part of an Fc region. Fc polypeptides include antibodies, Fc fusions, isolated Fcs, and Fc fragments.

By "Fc fusion" as used herein is meant a protein wherein one or more polypeptides or small molecules is operably linked to an Fc region or a derivative thereof. Fc fusion is herein meant to be synonymous with the terms "immunoadhesin", "Ig fusion", "Ig chimera", and "receptor globulin" (sometimes with dashes) as used in the prior art (Chamow et al, 1996, *Trends Biotechnol* 14:52-60; Ashkenazi et al., 1997, *Curr Opin Immunol* 9:195-200; both expressly incorporated by reference). An Fc fusion combines the Fc region of an immunoglobulin with a fusion partner, which in general can be any protein or small molecule. The role of the non-Fc part of an Fc fusion, i.e. the fusion partner, is often but not always to mediate target binding, and thus it is functionally analogous to the variable regions of an antibody. A variety of linkers, defined and described below, may be used to covalently link Fc to a fusion partner to generate an Fc fusion.

By "Fc gamma receptor" or "FcγR" as used herein is meant any member of the family of proteins that bind the IgG antibody Fc region and are substantially encoded by the FcγR genes. In humans this family includes but is not limited to FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIIb-NA1 and FcγRIIIb-NA2) (Jefferis et al, 2002, *Immunol Lett* 82:57-65, expressly incorporated by reference), as well as any undiscovered human FcγRs or FcγR isoforms or allotypes. An FcγR may be from any organism, including but not limited to humans, mice, rats, rabbits, and monkeys. Mouse FcγRs include but are not limited to FcγRI (CD64), FcγRII (CD32), FcγRIII (CD16), and FcγRIII-2 (CD16-2), as well as any undiscovered mouse FcγRs or FcγR isoforms or allotypes.

By "Fc ligand" as used herein is meant a molecule, preferably a polypeptide, from any organism that binds to the Fc region of an antibody to form an Fc-ligand complex. Fc ligands include but are not limited to FcγRs, FcγRs, FcγRs, FcRn, C1q, C3, mannan binding lectin, mannose receptor, *staphylococcal* protein A, *streptococcal* protein G, and viral FcγR. Fc ligands also include Fc receptor homologs (FcRH), which are a family of Fc receptors that are homologous to the FcγRs (Davis et al., 2002, *Immunological Reviews* 190:123-

136, expressly incorporated by reference). Fc ligands may include undiscovered molecules that bind Fc.

By "IgG" as used herein is meant a polypeptide belonging to the class of antibodies that are substantially encoded by a recognized immunoglobulin gamma gene. In humans this class comprises IgG1, IgG2, IgG3, and IgG4. In mice this class comprises IgG1, IgG2a, IgG2b, IgG3. Also included are hybrids of IgG proteins in which amino acids for one IgG protein substituted for amino acids of a different IgG protein (e.g. IgG1/IgG2 hybrids. By "immunoglobulin (Ig)" herein is meant a protein consisting of one or more polypeptides substantially encoded by immunoglobulin genes. Immunoglobulins include but are not limited to antibodies. Immunoglobulins may have a number of structural forms, including but not limited to full length antibodies, antibody fragments, and individual immunoglobulin domains. By "immunoglobulin (Ig) domain" herein is meant a region of an immunoglobulin that exists as a distinct structural entity as ascertained by one skilled in the art of protein structure. Ig domains typically have a characteristic β-sandwich folding topology. The known Ig domains in the IgG class of antibodies are $V_H$, Cγ1, Cγ2, Cγ3, $V_L$, and $C_L$.

By "parent polypeptide" or "precursor polypeptide" (including Fc parent or precursors) as used herein is meant a polypeptide that is subsequently modified to generate a variant. The parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it. Accordingly, by "parent Fc polypeptide" as used herein is meant a Fc polypeptide that is modified to generate a variant, and by "parent antibody" as used herein is meant an antibody that is modified to generate a variant antibody.

As outlined above, certain positions of the Fc molecule can be altered. By "position" as used herein is meant a location in the sequence of a protein. Positions may be numbered sequentially, or according to an established format, for example the EU index as in Kabat. For example, position 297 is a position in the human antibody IgG1. Corresponding positions are determined as outlined above, generally through alignment with other parent sequences, By "residue" as used herein is meant a position in a protein and its associated amino acid identity. For example, Asparagine 297 (also referred to as Asn297, also referred to as N297) is a residue in the human antibody IgG1.

By "target antigen" as used herein is meant the molecule that is bound specifically by the variable region of a given antibody. A target antigen may be a protein, carbohydrate, lipid, or other chemical compound.

By "target cell" as used herein is meant a cell that expresses a target antigen.

By "variable region" as used herein is meant the region of an immunoglobulin that comprises one or more Ig domains substantially encoded by any of the Vκ, Vλ, and/or $V_H$ genes that make up the kappa, lambda, and heavy chain immunoglobulin genetic loci respectively.

By "variant protein", "protein variant", "variant polypeptide", or "polypeptide variant" as used herein is meant a polypeptide sequence that differs from that of a parent polypeptide sequence by virtue of at least one amino acid modification. Variant polypeptide may refer to the polypeptide itself a composition comprising the polypeptide, or the amino sequence that encodes it. Preferably, the variant polypeptide has at least one amino acid modification compared to the parent polypeptide, e.g. from about one to about ten amino acid modifications, and preferably from about one to about five amino acid modifications compared to the parent. The variant polypeptide sequence herein will preferably possess at least about 80% homology with a parent polypeptide sequence, and most preferably at least about 90% homology, more preferably at least about 95% homology. Accordingly, by "variant Fc" or "Fc variant" as used herein is meant an Fc sequence that differs from that of a parent Fc sequence by virtue of at least one amino acid modification. An Fc variant may only encompass an Fc region, or may exist in the context of an antibody, Fc fusion, or other polypeptide that is substantially encoded by Fc. Fc variant may refer to the Fc polypeptide itself, compositions comprising the Fc variant polypeptide, or the amino acid sequence that encodes it. Also included are Fc variants disclosed in U.S. patent application Ser. Nos. 11/124,620 filed May 5, 2005, Ser. No. 10/822,231 filed Mar. 26, 2004, and Ser. No. 10/379,392, filed Mar. 3, 2003, each of which is incorporated herein by reference in its entirety. Accordingly, by "variant Ep-CAM targeting protein" or "Ep-CAM targeting protein variant" as used herein is meant an Ep-CAM targeting protein, as defined above, that differs in sequence from that of a parent Ep-CAM targeting protein sequence by virtue of at least one amino acid modification. Variant Ep-CAM targeting protein may refer to the protein itself, compositions comprising the protein, or the amino acid sequence that encodes it.

For all immunoglobulin heavy chain constant region positions discussed in the present invention numbering is according to the EU index as in Kabat (Kabat et al., 1991, Sequences of Proteins of Immunological Interest, 5th Ed., United States Public Health Svice, National Institutes of Health, Bethesda). The "EU index as in Kabat" refers to the residue numbering of the human IgG1 EU antibody.

Antibodies

Accordingly, the present invention provides variant antibodies.

Traditional antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. Thus, "isotype" as used herein is meant any of the subclasses of immunoglobulins defined by the chemical and antigenic characteristics of their constant regions. The known human immunoglobulin isotypes are IgG1, IgG2, IgG3, IgG4, IgA1, IgA2, IgM1, IgM2, IgD, and IgE.

The amino-terminal portion of each chain includes a variable region of about 100 to 110 or more amino acids primarily responsible for antigen recognition. In the variable region, three loops are gathered for each of the V domains of the heavy chain and light chain to form an antigen-binding site. Each of the loops is referred to as a complementarity-determining region (hereinafter referred to as a "CDR"), in which the variation in the amino acid sequence is most significant.

The carboxy-terminal portion of each chain defines a constant region primarily responsible for effector function. Kabat et al. collected numerous primary sequences of the variable regions of heavy chains and light chains. Based on the degree of conservation of the sequences, they classified individual primary sequences into the CDR and the framework and made a list thereof (see SEQUENCES OF IMMUNOLOGICAL INTEREST, 5th edition, NIH publication, No. 91-3242, E. A. Kabat et al.).

In the IgG subclass of immunoglobulins, there are several immunoglobulin domains in the heavy chain. By "immunoglobulin (Ig) domain" herein is meant a region of an immunoglobulin having a distinct tertiary structure. Of interest in the present invention are the heavy chain domains, including, the constant heavy (CH) domains and the hinge domains. In the context of IgG antibodies, the IgG isotypes each have three CH regions. Accordingly, "CH" domains in the context of IgG are as follows: "CH1" refers to positions 118-220 according to the EU index as in Kabat. "CH2" refers to positions 237-340 according to the EU index as in Kabat, and "CH3" refers to positions 341-447 according to the EU index as in Kabat, Another type of Ig domain of the heavy chain is the hinge region. By "hinge" or "hinge region" or "antibody hinge region" or "immunoglobulin hinge region" herein is meant the flexible polypeptide comprising the amino acids between the first and second constant domains of an antibody. Structurally, the IgG CH1 domain ends at EU position 220, and the IgG CH2 domain begins at residue EU position 237. Thus for IgG the antibody hinge is herein defined to include positions 221 (D221 in IgG1) to 236 (G236 in IgG1), wherein the numbering is according to the EU index as in Kabat. In some embodiments, for example in the context of an Fc region, the lower hinge is included, with the "lower hinge" generally referring to positions 226 or 230.

Of particular interest in the present invention are the Fc regions. By "Fc" or "Fc region", as used herein is meant the polypeptide comprising the constant region of an antibody excluding the first constant region immunoglobulin domain and in some cases, part of the hinge. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, as illustrated in FIG. 1, Fc comprises immunoglobulin domains Cgamma2 and Cgamma3 (Cg2 and Cg3) and the lower hinge region between Cgamma1 (Cg1) and Cgamma2 (Cg2). Although the boundaries of the Fc region may vary, the human IgG heavy chain Fc region is usually defined to include residues C226 or P230 to its carboxyl-terminus, wherein the numbering is according to the EU index as in Kabat. Fc may refer to this region in isolation, or this region in the context of an Fc polypeptide, as described below. By "Fc polypeptide" as used herein is meant a polypeptide that comprises all or part of an Fc region. Fc polypeptides include antibodies, Fc fusions, isolated Fcs, and Fc fragments.

In some embodiments, the antibodies are full length. By "full length antibody" herein is meant the structure that constitutes the natural biological form of an antibody, including variable and constant regions, including one or more modifications as outlined herein.

Alternatively, the antibodies can be a variety of structures, including, but not limited to, antibody fragments, monoclonal antibodies, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and fragments of each, respectively.

Antibody Fragments

In one embodiment, the antibody is an antibody fragment. Of particular interest are antibodies that comprise Fc regions, Fc fusions, and the constant region of the heavy chain (CH1-hinge-CH2-CH3), again also including constant heavy region fusions.

Specific antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment (Ward et al., 1989, Nature 341:544-546) which consists of a single variable, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988, Science 242:423-426, Huston et al., 1988, Proc. Natl. Acad. Sci. U.S.A. 85:5879-5883), (viii) bispecific single chain Fv dimers (PCT/US92/09965) and (ix) "diabodies" or "triabodies", multivalent or multispecific fragments constructed by gene fusion (Tomlinson et. al., 2000, Methods Enzymol. 326:461-479; WO94/13804; Holliger et al., 1993, Proc. Natl. Acad. Sci. U.S.A. 90:6444-6448, each of which is incorporated herein by reference in its entirety). The antibody fragments may be modified. For example, the molecules may be stabilized by the incorporation of disulphide bridges linking the VH and VL domains (Reiter et al., 1996, Nature Biotech. 14:1239-1245).

Chimeric and Humanized Antibodies

In some embodiments, the scaffold components can be a mixture from different species, For example, if the antibody is a mixture of a human antibody and a mouse antibody, such an antibody may be a chimeric antibody and/or a humanized antibody. In general, both "chimeric antibodies" and "humanized antibodies" refer to antibodies that combine regions from more than one species. For example, "chimeric antibodies" traditionally comprise variable region(s) from a mouse (or rat, in some cases) and the constant region(s) from a human. "Humanized antibodies" generally refer to non-human antibodies that have had the variable-domain framework regions swapped for sequences found in human antibodies. Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, Nature 321:522-525, Verhoeyen et al., 1988, Science 239: 1534-1536. "Backmutation" of selected acceptor framework residues to the corresponding donor residues is often required to regain affinity that is lost in the initial grafted construct (U.S. Pat. No. 5,530,101; U.S. Pat. No. 5,585,089; U.S. Pat. No. 5,693,761; U.S. Pat. No. 5,693,762; U.S. Pat. No. 6,180,370; U.S. Pat. No. 5,859,205; U.S. Pat. No. 5,821,337; U.S. Pat. No. 6,054,297; U.S. Pat. No. 6,407,213). The humanized antibody optimally also will comprise at least a portion of an immunoglobulin constant region, typically that of a human immunoglobulin, and thus will typically comprise a human Fc region. Humanized antibodies can also be generated using mice with a genetically engineered immune system. Roque et al., 2004, Biotechnol. Prog. 20:639-654. A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein). Humanization methods include but are not limited to methods described in Jones et al., 1986, *Nature* 321:522-525; Riechmann et al., 1988; *Nature* 332:323-329; Verhoeyen et al., 1988, *Science*, 239: 1534-1536; Queen et alt, 1989, *Proc Natl Acad Sci, USA* 86:10029-33; He et al., 1998, J. Immunol. 160: 1029-1035; Carter et al., 1992, *Proc Natl Acad Sci USA* 89:4285-9, Presta et al., 1997, Cancer Res. 57(20):4593-9; Gorman et al., 1991, Proc. Natl. Acad. Sci. USA 88:4181-4185; O'Connor et al., 1998, *Protein Eng* 11:321-8. Humanization or other methods of reducing the immunogenicity of nonhuman antibody variable regions may include resurfacing methods, as described for example in Roguska et al., 1994, Proc. Natl. Acad. Sci. USA 91:969-973. In one embodiment, the parent antibody has been affinity matured, as is known in the art. Structure-based methods may be employed for humanization and affinity maturation, for example as described in U.S. Ser. No. 11/004,590. Selection based methods may be employed to humanize and/or affinity mature antibody variable regions, including but not limited to methods described in Wu et al., 1999, J. Mol. Biol. 294:151-162; Baca et al., 1997, J. Biol. Chem. 272(16):10678-10684; Rosok et al., 1996, J. Biol. Chem. 271(37): 22611-22618; Rader et al., 1998, Proc. Natl. Acad. Sci. USA 95: 8910-8915; Krauss et al., 2003, Protein Engineering 16(10):753-759. Other humanization methods may involve changing both CDR and non-CDR regions, including but not limited to methods described in U.S. Ser. No. 09/810,502; Tan et al., 2002, J. Immunol. 169:1119-1125; De Pascalis et al., 2002, J. Immunol. 169:3076-3084.

Bispecific Antibodies

In one embodiment, the antibodies of the invention multispecific antibody, and notably a bispecific antibody, also sometimes referred to as "diabodies". These are antibodies that bind to two (or more) different antigens, Diabodies can be manufactured in a variety of ways known in the art (Holliger and Winter, 1993, Current Opinion Biotechnol. 4:446-449), e.g., prepared chemically or from hybrid hybridomas.

Minibodies

In one embodiment, the antibody is a minibody. Minibodies are minimized antibody-like proteins comprising a scFv joined to a CH3 domain. Hu et al., 1996, Cancer Res. 56:3055-3061. In some cases, the scFv can be joined to the Fc region, and may include some or all of the hinge region.

Human Antibodies

In one embodiment, the antibody is a fully human antibody with at least one modification as outlined herein. "Fully human antibody" or "complete human antibody" refers to a human antibody having the gene sequence of an antibody derived from a human chromosome with the modifications outlined herein.

Antibody Fusions

In one embodiment, the antibodies of the invention are antibody fusion proteins (sometimes referred to herein as an "antibody conjugate"). One type of antibody fusions are Fc fusions, which join the Fc region with a conjugate partner. By "Fc fusion" as used herein is meant a protein wherein one or more polypeptides is operably linked to an Fc region. Fc fusion is herein meant to be synonymous with the terms "immunoadhesin", "Ig fusion", "Ig chimera", and "receptor globulin" (sometimes with dashes) as used in the prior art (Chamow et al., 1996, Trends Biotechnol 14:52-60; Ashkenazi et al., 1997, Curr Opin Immunol 9:195-200). An Fc fusion combines the Fc region of an immunoglobulin with a fusion partner, which in general can be any protein or small molecule. Virtually any protein or small molecule may be linked to Fc to generate an Fc fusion. Protein fusion partners may include, but are not limited to, the variable region of any antibody, the target-binding region of a receptor, an adhesion molecule, a ligand, an enzyme, a cytokine, a chemokine, or some other protein or protein domain. Small molecule fusion partners may include any therapeutic agent that directs the Fc fusion to a therapeutic target. Such targets may be any molecule, preferably an extracellular receptor, that is implicated in disease.

In addition to Fc fusions, antibody fusions include the fusion of the constant region of the heavy chain with one or more fusion partners (again including the variable region of any antibody), while other antibody fusions are substantially or completely full length antibodies with fusion partners. In one embodiment, a role of the fusion partner is to mediate target binding, and thus it is functionally analogous to the variable regions of an antibody (and in fact can be). Virtually any protein or small molecule may be linked to Fc to generate an Fc fusion (or antibody fusion). Protein fusion partners may include, but are not limited to, the target-binding region of a receptor, an adhesion molecule, a ligand, an enzyme, a cytokine, a chemokine, or some other protein or protein domain. Small molecule fusion partners may include any therapeutic agent that directs the Fc fusion to a therapeutic target. Such targets may be any molecule, preferably an extracellular receptor, that is implicated in disease.

The conjugate partner can be proteinaceous or non-proteinaceous; the latter generally being generated using functional groups on the antibody and on the conjugate partner. For example linkers are known in the art; for example, homo- or hetero-bifunctional linkers as are well known (see, 1994 Pierce Chemical Company catalog, technical section on cross-linkers, pages 155-200, incorporated herein by reference).

Suitable conjugates include, but are not limited to, labels as described below, drugs and cytotoxic agents including, but not limited to, cytotoxic drugs (e.g., chemotherapeutic agents) or toxins or active fragments of such toxins. Suitable toxins and their corresponding fragments include diptheria A chain, exotoxin A chain, ricin A chain, abrin A chain, curcin, crotin, phenomycin, enomycin and the like. Cytotoxic agents also include radiochemicals made by conjugating radioisotopes to antibodies, or binding of a radionuclide to a chelating agent that has been covalently attached to the antibody. Additional embodiments utilize calicheamicin, auristatins, geldanamycin, maytansine, and duocarmycins and analogs; for the latter, see U.S. 2003/0050331, hereby incorporated by reference in its entirety.

Covalent modifications of Antibodies

Covalent modifications of (e.g. attachments to) antibodies are included within the scope of this invention, and are generally, but not always, done post-translationally. For example, several types of covalent attachments to the antibody are introduced into the molecule by reacting specific amino acid residues of the antibody with an organic derivatizing agent that is capable of reacting with selected side chains or the N- or C-terminal residues Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate: pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using 125I or 131I to prepare labeled proteins for use in radioimmunoassay, the chloramine T method described above being suitable.

Carboxyl side groups (aspartyl or glutamyl) are selectively modified by reaction with carbodiimides (R'—N=C=N—R'), where R and R' are optionally different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking antibodies to a water-insoluble support matrix or surface for use in a variety of methods, in addition to methods described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W.H. Freeman & Co., San Francisco, pp. 79-86 (19831), acetylation of the N-terminal amine, and amidation of any C-terminal carboxyl group.

Glycosylation

Another type of covalent modification is glycosylation. In another embodiment, the IgG variants disclosed herein can be modified to include one or more engineered glycoforms. By "engineered glycoform" as used herein is meant a carbohydrate composition that is covalently attached to an IgG, wherein said carbohydrate composition differs chemically from that of a parent IgG. Engineered glycoforms may be useful for a variety of purposes, including but not limited to enhancing or reducing effector function. Engineered glycoforms may be generated by a variety of methods known in the art (Umaña et al., 1999, Nat Biotechnol 17:176-180; Davies et al., 2001, Biotechnol Bioeng 74:288-294; Shields et al., 2002, J Biol Chem 277:26733-26740; Shinkawa et al., 2003, J Biol Chem 278:3466-3473); (U.S. Pat. No. 6,602,684; U.S. Ser. No. 10/277,370; U.S. Ser. No. 10/113,929; PCT WO 00/61739A1; PCT WO 01/29246A1; PCT WO 02/31140A1; PCT WO 02/30954A1); (Potelligent™ technology [Biowa, Inc., Princeton, N.J.]; GlycoMAb™ glycosylation engineering technology [GLYCART biotechnology AG, Zürich, Switzerland]). Many of these techniques are based on controlling the level of fucosylated and/or bisecting oligosaccharides that are covalently attached to the Fc region, for example by expressing an IgG in various organisms or cell lines, engineered or otherwise (for example Lec-13 CHO cells or rat hybridoma YB2/0 cells), by regulating enzymes involved in the glycosylation pathway (for example FUT8 [α1,6-fucosyltransferase] and/or β1-4-N-acetylglucosaminyltransferase III [GnTIII]), or by modifying carbohydrate(s) after the IgG has been expressed. Engineered glycoform typically refers to the different carbohydrate or oligosaccharide; thus an IgG variant, for example an antibody or Fc fusion, can include an engineered glycoform. Alternatively, engineered glycoform may refer to the IgS variant that comprises the different carbohydrate or oligosaccharide. As is known in the art, glycosylation patterns can depend on both the sequence of the protein (e.g., the presence or absence of particular glycosylation amino acid residues, discussed below), or the host cell or organism in which the protein is produced. Particular expression systems are discussed below.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are frequently the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the antibody amino acid sequence is preferably altered through changes at the DNA level, particularly by mutating the DNA encoding the target polypeptide at preselected bases such that codons are generated that will translate into the desired amino acids.

Another means of increasing the number of carbohydrate moieties on the antibody is by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published Sep. 11, 1987, and in Aplin and Wriston, 1981, CRC Crit. Rev. Biochem., pp. 259-306.

Removal of carbohydrate moieties present on the starting antibody may be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., 1987, Arch. Biochem. Biophys. 259:52 and by Edge et al., 1981, Anal. Biochem. 118:131. Enzymatic cleavage of carbohydrate moieties on polypeptides can be achieved by the use of a variety of endo- and exo-glycosidases as described by Thotakura et al., 1987, Meth. Enzymol. 138:350. Glycosylation at potential glycosylation sites may be prevented by the use of the compound tunicamycin as described by Duskin et al., 1982, J. Biol. Chem. 257:3105. Tunicamycin blocks the formation of protein-N-glycoside linkages. Additionally, modification of an amino acid in the glycosylation motif may be used to prevent glycosylation.

Another type of covalent modification of the antibody comprises linking the antibody to various nonproteinaceous polymers, including, but not limited to, various polyols such as polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337. In addition, as is known in the art, amino acid substitutions may be made in various positions within the antibody to facilitate the addition of polymers such as PEG. See for example, U.S. Publication No. 2005/0114037, incorporated herein by reference in its entirety.

Labeled Antibodies

In some embodiments, the covalent modification of the antibodies of the invention comprises the addition of one or more labels. In some cases, these are considered antibody fusions.

The term "labelling group" means any detectable label. In some embodiments, the labelling group is coupled to the antibody via spacer arms of various lengths to reduce potential steric hindrance. Various methods for labelling proteins are known in the art and may be used in performing the present invention, In general, labels fall into a variety of classes, depending on the assay in which they are to be detected: a) isotopic labels, which may be radioactive or heavy isotopes; b) magnetic labels (e.g., magnetic particles); c) redox active moieties; d) optical dyes; enzymatic groups (e.g. horseradish peroxidase, β-galactosidase, luciferase, alkaline phosphatase); e) biotinylated groups; and f) predetermined polypeptide epitopes recognized by a secondary reporter (e.g., leucine zipper pair sequences, binding sites for secondary antibodies, metal binding domains, epitope tags, etc.). In some embodiments, the labelling group is coupled to the antibody via spacer arms of various lengths to reduce potential steric hindrance. Various methods for labelling proteins are known in the art and may be used in performing the present invention.

Specific labels include optical dyes, including, but not limited to, chromophores, phosphors and fluorophores, with the latter being specific in many instances. Fluorophores can be either "small molecule" fluores, or proteinaceous fluores.

By "fluorescent label" is meant any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade BlueJ, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Atexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE) (Molecular Probes, Eugene, Oreg.), FITC, Rhodamine, and Texas Red (Pierce, Rockford, Ill.), Cy5, Cy5.5, Cy7 (Amersham Life Science, Pittsburgh, Pa.). Suitable optical dyes, including fluorophores, are described in Molecular Probes Handbook by Richard P. Haugland, hereby expressly incorporated by reference.

Suitable proteinaceous fluorescent labels also include, but are not limited to, green fluorescent protein, including a *Renilla*, *Ptilosarcus*, or *Aequorea* species of GFP (Chalfie et al., 1994, Science 263:802-805), EGFP (Clontech Laboratories, Inc., Genbank Accession Number U55762), blue fluorescent protein (BFP, Quantum Biotechnologies, Inc. 1801 de Maisonneuve Blvd. West, 8th Floor, Montreal, Quebec, Canada H3H 1J9; Stauber, 1998, Biotechniques 24:462-471; Heim et al., 1996, Curr. Biol. 6:178-182), enhanced yellow fluorescent protein (EYFP, Clontech Laboratories, Inc.), luciferase (Ichiki et al., 1993, J. Immunol. 150:5408-5417), β galactosidase (Nolan et al., 1988, Proc. Natl. Acad. Sci. U.S.A. 85:2603-2607) and *Renilla* (WO92/15673, WO95/07463, WO98/14605, WO98/26277, WO99/49019, U.S. Pat. Nos. 5,292,658, 5,418,155, 5,683,888, 5,741,668, 5,777,079, 5,804,387, 5,874,304, 5,876,995, 5,925,558). All of the above-cited references are expressly incorporated herein by reference.

In certain variations, antibody may mean a protein consisting of one or more polypeptides substantially encoded by all or part of the recognized immunoglobulin genes. The recognized immunoglobulin genes, for example in humans, include the kappa (κ), lambda (λ), and heavy chain genetic loci, which together comprise the myriad variable region genes, and the constant region genes mu (υ), delta (δ), gamma (γ), sigma (ε), and alpha (α) which encode the IgM, IgD, IgG (IgG1, IgG2, IgG3, and IgG4), IgE, and IgA (IgA1 and IgA2) isotypes respectively. Antibody herein is meant to include full length antibodies and antibody fragments, and may refer to a natural antibody from any organism, an engineered antibody, or an antibody generated recombinantly for experimental, therapeutic, or other purposes.

Ep-CAM Targeting Proteins

The Ep-CAM targeting proteins of the present invention may be an antibody, referred to herein as "anti-Ep-CAM antibodies". Anti-Ep-CAM antibodies of the present invention may comprise immunoglobulin sequences that are substantially encoded by immunoglobulin genes belonging to any of the antibody classes, including but not limited to IgG (including human subclasses IgG1, IgG2, IgG3, or IgG4 and hybrids thereof), IgA (including human subclasses IgA1 and IgA2), IgD, IgE, IgG, and IgM classes of antibodies. Most preferably the antibodies of the present invention comprise sequences belonging to the human IgG class of antibodies. Anti-Ep-CAM antibodies of the present invention may be nonhuman, chimeric, humanized, or fully human. As will be appreciated by one skilled in the art, these different types of antibodies reflect the degree of "humaness" or potential level of immunogenicity in a human. For a description of these concepts see Clark et al., 2000 and references cited therein (Clark, 2000, *Immunol Today* 21:397-402, expressly incorporated by reference). Chimeric antibodies comprise the variable region of a nonhuman antibody, for example VH and VL domains of mouse or rat origin, operably linked to the constant region of a human antibody (see for example U.S. Pat. No. 4,816,567, expressly incorporated by reference). The nonhuman variable region may be derived from any organism as described above, preferably mammals and most preferably rodents or primates. In one embodiment, the antibody of the present invention comprises monkey variable domains, for example as described in Newman et al., 1992, Biotechnology 10:1455-1460, U.S. Pat. No. 5,658,570, and U.S. Pat. No. 5,750,105; all expressly incorporated by reference. In a preferred embodiment, the variable region is derived from a nonhuman source, but its immunogenicity has been reduced using protein engineering. In a preferred embodiment, the antibodies of the present invention are humanized (Tsurushita & Vasquez, 2004, Humanization of Monoclonal Antibodies, Molecular Biology of B Cells, 533-545, Elsevier Science (USA), expressly incorporated by reference). By "humanized" antibody as used herein is meant an antibody comprising framework regions (FRs) derived from one or more human sequences and one or more complementarity determining regions (CDR's) from a non-human (usually mouse or rat) antibody, One common method used in the art is called "CDR grafting" in which a non-human antibody (the "donor") provides the CDR's and a human antibody (the "acceptor") provides the frameworks (Winter U.S. Pat. No. 5,225,539). In CDR grafting "backmutation" of selected acceptor framework residues to the corresponding donor residues is often required to regain affinity that is lost in the initial grafted construct (U.S. Pat. No. 5,530,101; U.S. Pat. No. 5,585,089; U.S. Pat. No. 5,693,761; U.S. Pat. No. 5,693,762; U.S. Pat. No. 6,180,370; U.S. Pat. No. 5,859,205; U.S. Pat. No. 5,821,337; U.S. Pat. No. 6,054,297; and U.S. Pat. No. 6,407,213; all expressly incorporated by reference). Optimally the humanized antibody also will comprise at least a portion of an immunoglobulin constant region, typically that of a human immunoglobulin, and thus will typically comprise a human Fc region. Alternatively, in a most preferred embodiment, and as described more fully in Example 1, the immunogenicity of the antibody may be reduced using a method described in U.S. Ser. No. 60/619,483, filed Oct. 14, 2004 and U.S. Ser. No. 11/004,590, entitled "Methods of Generating Variant Proteins with Increased Host String Content and Compositions Thereof", filed on Dec. 6, 2004; both expressly incorporated by reference. In an alternate embodiment, the antibodies of the present invention may be fully human, that is the sequences of the antibodies are completely or substantially human. A number of methods are known in the art for generating fully human antibodies, including the use of transgenic mice (Bruggemann et al., 1997, *Curr Opin Biotechnol* 8:455-458, expressly incorporated by reference) or human antibody libraries coupled with selection methods (Griffiths et al., 1998, *Curr Opin Biotechnol* 9:102-108, expressly incorporated by reference).

Of particular interest are techniques that allow optimization of human and non-human components of the antibodies, as described in U.S. Ser. No. 11/149,943 filed Jun. 9, 2005, which are expressly incorporated by reference in their entirety. Specifically, techniques are used that rely on the incorporation of different human non-CDR regions to form a non-CDR region that is composed of sequences from different human sequences (e.g. different human germine sequences); thus, these regions comprise sequences that are "human" to the extent that all the components come from human sequences. These sequences can be additionally optimized with Fc variants, CDR variants, etc.

The Ep-CAM targeting proteins of the present invention may be an Fc fusion, referred to herein as "ant-Ep-CAM Fc fusions", Anti-Ep-CAM Fc fusions of the present invention comprise an Fc polypeptide operably linked to one or more fusion partners. The role of the fusion partner typically, but not always, is to mediate binding of the Fc fusion to a target antigen (Chamow et al., 1996, *Trends Biotechnol* 14:52-60; Ashkenazi et al, 1997, *Curr Opin Immunol* 9:195-200; both expressly incorporated by reference). For the present invention, one of the fusion partners must bind Ep-CAM. Fusion partners may be a protein, polypeptide, or small molecule. Virtually any polypeptide or molecule that targets Ep-CAM may serve as a fusion partner. Undiscovered Ep-CAM ligands may serve as fusion partners for the Ep-CAM targeting proteins of the present invention. Anti-Ep-CAM Fc fusions of the invention may comprise immunoglobutin sequences that are substantially encoded by immunoglobulin genes belonging to any of the antibody classes, including but not limited to IgG (including human subclasses IgG1, IgG2, IgG3, or IgG4), IgA (including human subclasses IgA1 and IgA2), IgD, IgE, IgG, and IgM classes of antibodies. Most preferably the anti-Ep-CAM Fc fusions of the present invention comprise sequences belonging to the human IgG class of antibodies.

Ep-CAM targeting proteins of the present invention, including antibodies and Fc fusions, may comprise Fc fragments. An Fc fragment of the present invention may comprise from 1-90% of the Fc region, with 10-90% being preferred, and 30-90% being most preferred. Thus for example, an Fc fragment of the present invention may comprise an IgG1 Cγ2 domain, an IgG1 Cγ2 domain and hinge region, an IgG1 Cγ3 domain, and so forth. In one embodiment, an Fc fragment of the present invention additionally comprises a fusion partner, effectively making it an Fc fragment fusion. Fc fragments may or may not contain extra polypeptide sequence.

Ep-CAM targeting proteins of the present invention may be substantially encoded by genes from any organism, preferably mammals, including but not limited to humans, rodents including but not limited to mice and rats, lagomorpha including but not limited to rabbits and hares, camelidae including but not limited to camels, llamas, and dromedaries, and non-human primates, including but not limited to Prosimians, Platyrrhini (New World monkeys), Cercopithecoidea (Old World monkeys), and Hominoidea including the Gibbons and Lesser and Great Apes. In a most preferred embodiment, the Ep-CAM targeting proteins of the present invention are substantially human. The Ep-CAM targeting proteins of the present invention may be substantially encoded by immunoglobulin genes belonging to any of the antibody classes. In a most preferred embodiment, the Ep-CAM targeting proteins of the present invention comprise sequences belonging to the IgG class of antibodies, including human subclasses IgG1, IgG2, IgG3, and IgG4. In an alternate embodiment, the Ep-CAM targeting proteins of the present invention comprise sequences belonging to the IgA (including human subclasses IgA1 and IgA2), IgD, IgE, IgG, or IgM classes of antibodies.

The EP-CAM targeting proteins of the present invention may comprise more than one protein chain. That is, the present invention may find use in an Ep-CAM targeting protein that is a monomer or an oligomer, including a homo- or hetero-oligomer.

In the most preferred embodiment, the anti-Ep-CAM antibodies and Fc fusions of the invention are based on human IgG sequences, and thus human IgG sequences are used as the "base" sequences against which other sequences are compared, including but not limited to sequences from other organisms, for example rodent and primate sequences, as well as sequences from other immunoglobulin classes such as IgA, IgE, IgGD, IgGM, and the like. It is contemplated that, although the Ep-CAM targeting proteins of the present invention are engineered in the context of one parent Ep-CAM targeting protein, the variants may be engineered in or "transferred" to the context of another, second parent Ep-CAM targeting protein. This is done by determining the "equivalent" or "corresponding" residues and substitutions between the first and second Ep-CAM targeting proteins, typically based on sequence or structural homology between the sequences of the two Ep-CAM targeting proteins. In order to establish homology, the amino acid sequence of a first Ep-CAM targeting protein outlined herein is directly compared to the sequence of a second Ep-CAM targeting protein. After aligning the sequences, using one or more of the homology alignment programs known in the art (for example using conserved residues as between species), allowing for necessary insertions and deletions in order to maintain alignment (i.e., avoiding the elimination of conserved residues through arbitrary deletion and insertion), the residues equivalent to particular amino acids in the primary sequence of the first EP-CAM targeting protein are defined. Alignment of conserved residues preferably should conserve 100% of such residues. However, alignment of greater than 75% or as little as 50% of conserved residues is also adequate to define equivalent residues. Equivalent residues may also be defined by determining structural homology between a first and second Ep-CAM targeting protein that is at the level of tertiary structure for Ep-CAM targeting proteins whose structures have been determined. In this case, equivalent residues are defined as those for which the atomic coordinates of two or more of the main chain atoms of a particular amino acid residue of the parent or precursor (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the proteins. Regardless of how equivalent or corresponding residues are determined, and regardless of the identity of the parent Ep-CAM targeting protein in which the Ep-CAM targeting proteins are made, what is meant to be conveyed is that the Ep-CAM targeting proteins discovered by the present invention may be engineered into any second parent Ep-CAM targeting protein that has significant sequence or structural homology with the Ep-CAM targeting protein. Thus for example, if a variant anti-Ep-CAM antibody is generated wherein the parent anti-Ep-CAM antibody is human IgG1, by using the methods described above or other methods for determining equivalent residues, the variant anti-Ep-CAM antibody may be engineered in a human IgG2 parent anti-Ep-CAM antibody, a human IgA parent anti-Ep-CAM antibody, a mouse IgG2a or IgG2b parent anti-Ep-CAM antibody, and the like. Again, as described above, the context of the parent Ep-CAM targeting protein does not affect the ability to transfer the Ep-CAM targeting proteins of the present invention to other parent Ep-CAM targeting proteins. For example, the variant anti-Ep-CAM antibodies that are engineered in a human IgG1 antibody that targets one Ep-CAM epitope may be transferred into a human IgG2 antibody that targets a different Ep-CAM epitope, into an Fc fusion that comprises a human IgG1 Fc region that targets yet a different Ep-CAM epitope, and so forth.

The Ep-CAM targeting protein of the present invention may be virtually any antibody, Fc fusion, or other protein that binds Ep-CAM. Ep-CAM targeting proteins of the invention may display selectivity for Ep-CAM versus alternative targets, for example other RTKs, or selectivity for a specific form of the Ep-CAM target versus alternative forms. Examples include full-length versus splice variants, cell-surface vs. soluble forms, selectivity for various polymorphic variants, or selectivity for specific conformational forms of a target. An Ep-CAM targeting protein of the present invention may bind any epitope or region on Ep-CAM, and may be specific for fragments, mutant forms, splice forms, or aberrant forms of Ep-CAM.

The Ep-CAM targeting proteins of the present invention may find use in a wide range of products. In one embodiment the Ep-CAM targeting protein of the invention is a therapeutic, a diagnostic or a research reagent. Alternatively, the Ep-CAM targeting protein of the present invention may be used for agricultural or industrial uses. An anti-Ep-CAM antibody of the present invention may find use in an antibody composition that is monoclonal or polyclonal. The Ep-CAM targeting proteins of the present invention may include agonists, antagonists, neutralizing, inhibitory, or stimulatory. In a preferred embodiment, the Ep-CAM targeting proteins of the present invention are used to kill target cells that bear the Ep-CAM target antigen, for example cancer cells. In an alternate embodiment, the Ep-CAM targeting proteins of the present invention are used to block, antagonize, or agonize the Ep-CAM target antigen. In an alternately preferred embodiment, the Ep-CAM targeting proteins of the present invention are used to block, antagonize, or agonize the target antigen and kill the target cells that bear the target antigen.

Modifications

The present invention provides variant Ep-CAM targeting proteins that are optimized for a number of therapeutically relevant properties. A variant Ep-CAM targeting protein comprises one or more amino acid modifications relative to a parent Ep-CAM targeting protein, wherein the amino acid modification(s) provide one or more optimized properties. Thus the Ep-CAM targeting proteins of the present invention are variants Ep-CAM targeting proteins. An Ep-CAM targeting protein of the present invention differs in amino acid sequence from its parent Ep-CAM targeting protein by virtue of at least one amino acid modification. Thus variant Ep-CAM targeting proteins of the present invention have at least one amino acid modification compared to the parent. Alternatively, the variant Ep-CAM targeting proteins of the present invention may have more than one amino acid modification as compared to the parent, for example from about one to fifty amino acid modifications, preferably from about one to ten amino acid modifications, and most preferably from about one to about five amino acid modifications compared to the parent. Thus the sequences of the variant Ep-CAM targeting proteins and those of the parent Ep-CAM targeting proteins are substantially homologous. For example, the variant Ep-CAM targeting protein sequences herein will possess about 80% homology with the parent Ep-CAM targeting protein sequence, preferably at least about 90% homology, and most preferably at least about 95% homology.

In a most preferred embodiment, the Ep-CAM targeting proteins of the present invention comprise amino acid modifications that provide optimized effector function properties relative to the parent. Most preferred substitutions and optimized effector function properties are described in U.S. Ser. No. 10/672,280, PCT US03/30249, and U.S. Ser. No. 10/822,231, and U.S. Ser. No. 60/627,774, filed Nov. 12, 2004 and entitled "Optimized Fc Variants". Properties that may be optimized include but are not limited to enhanced or reduced affinity for an FcγR. In a preferred embodiment, the Ep-CAM targeting proteins of the present invention are optimized to possess enhanced affinity for a human activating FcγR, preferably FcγRI, FcγRIIa, FcγRIIc, FcγRIIIa, and FcγRIIIb, most preferably FcγRIIIa. In an alternately preferred embodiment, the Ep-CAM targeting proteins are optimized to possess reduced affinity for the human inhibitory receptor FcγRIIb. These preferred embodiments are anticipated to provide Ep-CAM targeting proteins with enhanced therapeutic properties in humans, for example enhanced effector function and greater anti-cancer potency. In an alternate embodiment, the Ep-CAM targeting proteins of the present invention are optimized to have reduced or ablated affinity for a human FcγR, including but not limited to FcγRI, FcγRIIa, FcγRIIb, FcγRIIc, FcγRIIIa, and FcγRIIIb. These embodiments are anticipated to provide Ep-CAM targeting proteins with enhanced therapeutic properties in humans for example reduced effector function and reduced toxicity. In other embodiments, Ep-CAM targeting proteins of the present invention provide enhanced affinity for one or more FcγRs, yet reduced affinity for one or more other FcγRs. For example, an Ep-CAM targeting protein of the present invention may have enhanced binding to FcγRIIIa, yet reduced binding to FcγRIIb. Alternately, an Ep-CAM targeting protein of the present invention may have enhanced binding to FcγRIIa and FcγRI, yet reduced binding to FcγRIIb. In yet another embodiment, an Ep-CAM targeting protein of the present invention may have enhanced affinity for FcγRIIb, yet reduced affinity to one or more activating FcγRs.

In certain embodiments, the Ep-CAM targeting proteins are anti-EpCAM antibodies that comprise an Fc variant of a human Fc polypeptide as defined in U.S. patent application Ser. No. 11/124,620, or variations thereof as derived in U.S. patent application Ser. No. 11/149,943. The Fc variants exhibit altered binding to an Fc ligand as compared to human Fc polypeptide. In one embodiment, the Fc variant has the formula comprising:

Vb(221)-Vb(222)-Vb(223)-Vb(224)-Vb(225)-Fx(226)-Vb(227)-Vb(228)-Fx(229)-Vb(230) -Vb(231)-Vb(232)-Vb(233)-Vb(234)-Vb(235)-Vb(236)-Vb(237)-Vb(238)-Vb(239) -Vb(240)-Vb(241)-Fx(242)-Vb(243)-Vb(244)-Vb(245)-Vb(246)-Vb(247)-Fx(248)-Vb(249)-Fx(250-254)-Vb(255)-Fx(256-257)-Vb(258)-Fx(259)-Vb(260)-Fx(261) -Vb(262)-Vb(263)-Vb(264)-Vb(265)-Vb(266)-Vb(267)-Vb(268)-Vb(269)-Vb(270) -Vb(271)-Vb(272)-Vb(273)-Vb(274)-Vb(275)-Vb(276)-Fx(277)-Vb(278)-Fx(279) -Vb(280)-Vb(281)-Vb(282)-Vb(283)-Vb(284)-Vb(285)-Vb(286)-Fx(287)-Vb(288) -Fx(289)-Vb(290)-Vb(291)-Vb(292)-Vb(293)-Vb(294)-Vb(295)-Vb(296)-Vb(297) -Vb(298)-Vb(299)-Vb(300)-Vb(301)-Vb(302)-Vb(303)-Vb(304)-Vb(305)-Fx(306-312)-Vb(313)-Fx(314-316)-Vb(317)-Vb(318)-Fx(319)-Vb(320)-Fx(321)-Vb(322) -Vb(323)-Vb(324)-Vb(325)-Vb(326)-Vb(327)-Vb(328)-Vb(329)-Vb(330)-Vb(331)-Vb(332)-Vb(333)-Vb(334)-Vb(335)-Vb(336)-Vb(337);

wherein Vb(221) is selected from the group consisting of D, K and Y;

Vb(222) is selected from the group consisting of K, E and Y;

Vb(223) is selected from the group consisting of T, E and K,

Vb(224) is selected from the group consisting of H, E and Y,

Vb(225) is selected from the group consisting of T, E, K and W; Fx(226) is C;

Vb(227) is selected from the group consisting of P, E, G, K, Y

Vb(228) is selected from the group consisting of P, E, G, K, Y Fx(229) is C;

Vb(230) is selected from the group consisting of P, A, E, G AND Y;

Vb(231) is selected from the group consisting of A, E, G, K, P AND Y;

Vb(232) is selected from the group consisting of P, E, G, K AND Y;

Vb(233) is selected from the group consisting of A, D, F, G, H, I, K, L, M, N, Q, R, S, T, V, W, Y;

Vb(234) is selected from the group consisting of L, A, D, E, F, G, H, I, K, M, N, P, Q, R, S, T, V, W, Y Vb(235) is selected from the group consisting of L, A, D, E, F, G, H, I, K, M, N, P, Q, R, S, T, V, W, Y;

Vb(236) is selected from the group consisting of G, A, D, E, F, H, I, K, L, M, N P, Q, R, S, T, V, W, Y;

Vb(237) is selected from the group consisting of G, D, E, F, H, I, K, L, M, N, P, Q, R, S, T, V, W, Y;

Vb(238) is selected from the group consisting of P, D, E, F, G, H, I, K, L, M, N, Q, R, S, T, V, W, Y;

Vb(239) is selected from the group consisting of S, D, E, F, C, H, I, K, L, M, N, P, Q, R, T, V, W, Y Vb(240) is selected from the group consisting of V, A, I, M, T;

Vb(241) is selected from the group consisting of F, D, E, L, R, S, W, Y

Fx(242) is L;

Vb(243) is selected from the group consisting of F, E, H, L, Q, R, W, Y;

Vb(244) is selected from the group consisting of P, H;

Vb(245) is selected from the group consisting of P, A;

Vb(246) is selected from the group consisting of K, D, E, H, Y;

Vb(247) is selected from the group consisting of P, G, V

Fx(248) is K;

Vb(249) is selected from the group consisting of D, H, Q, Y;

Fx(250-254) is the sequence -(T-L-M-I-S)- (SEQ ID NO:166)

Vb(255) is selected from the group consisting of R, E, Y;

Fx(256-257) is the sequence -(T-P)-;

Vb(258) is selected from the group consisting of E, H, S, Y;

Fx(259) is V;

Vb(260) is selected from the group consisting of T, D, E, H, Y;

Fx(261) is C;

Vb(262) is selected from the group consisting of V, A, E, F, I, T;

Vb(263) is selected from the group consisting of V, A, I, M, T;

Vb(264) is selected from the group consisting of V, A, D, E, F, G, H, I, K, L, M, N, P, Q, R, S, T, W and Y;

Vb(265) is selected from the group consisting of D, F, G, H, I, K, L, M, N, P, Q, R, S, T, V, W, Y;

Vb(266) is selected from the group consisting of V, A, I, M, T;
Vb(267) is selected from the group consisting of S, D, E, F, H, I, K, L, M, N, P, Q, R, T, V, W, Y;
Vb(268) is selected from the group consisting of H, D, E, F, G, I, K, L, M, N, P, Q, R, T, V, W, Y;
Vb(269) is selected from the group consisting of E, F, G, H, I, K, L, M, N, P, R, S, T, V, W, Y;
Vb(270) is selected from the group consisting of D, F, G, H, I, L, M, P, Q, R, S, T, W, Y;
Vb(271) is selected from the group consisting of A, D, E, F, G, H, I, K, L, M, N, Q, R, S, T, V, W, Y;
Vb(272) is selected from the group consisting of E, D, F, G, H, I, K, L, M, P, R, S, T, V, W, Y;
Vb(273) is selected from the group consisting of V, I;
Vb(274) is selected from the group consisting of K, D, E, F, G, H, L, M, N, P, R, T, V, W, Y;
Vb(275) is selected from the group consisting of F, L, W;
Vb(276) is selected from the group consisting of N, D, E, F, G, H, I, L, M, P, R, S, T, V, W, Y;
Fx(277) is W;
Vb(278) is selected from the group consisting of Y, D, E, G, H, I, K, L, M, N, P, Q, R, S, T, V, W;
Fx(279) is V;
Vb(280) is selected from the group consisting of D, G, K, L, P, W;
Vb(281) is selected from the group consisting of G, D, E, K, N, P, Q, Y;
Vb(282) is selected from the group consisting of V, E, G, K, P, Y;
Vb(283) is selected from the group consisting of E, G, H, K, L, P, R, Y;
Vb(284) is selected from the group consisting of V, D, E, L, N, Q, T, Y;
Vb(285) is selected from the group consisting of H, D, E, K, Q, W, Y;
Vb(286) is selected from the group consisting of N, E, G, P, Y;
Fx(287) is selected from the group consisting of A;
Vb(288) is selected from the group consisting of K, D, E, Y;
Fx(289) is T;
Vb(290) is selected from the group consisting of K, D, H, L, N, W;
Vb(291) is selected from the group consisting of P, D, E, G, H, I, Q, T;
Vb(292) is selected from the group consisting of R, D, E, T, Y;
Vb(293) is selected from the group consisting of E, F, G, H, I, L, M, N, P, R, S, T, V, W, Y;
Vb(294) is selected from the group consisting of E, F, G, H, I, K, L, M, P, R, S, T, V, W, Y;
Vb(295) is selected from the group consisting of Q, D, E, F, G, H, I, M, N, P, R, S, T, V, W, Y;
Vb(296) is selected from the group consisting of Y, A, D, E, G, H, I, K, L, M, N, Q, R, S, T, V;
Vb(297) is selected from the group consisting of N, D, E, F, G, H, I, K, L, M, P, Q, R, S, T, V, W, Y;
Vb(298) is selected from the group consisting of S, D, E, F, H, I, K, M, N, Q, R, T, W, Y;
Vb(299) is selected from the group consisting of T, A, D, E, F, G, H, I, K, L, M, N, P, Q, R, S, V, W, Y;
Vb(300) is selected from the group consisting of Y, A, D, E, G, H, K, M, N, P, Q, R, S, T, V, W;
Vb(301) is selected from the group consisting of R, D, E, H, Y;
Vb(302) is selected from the group consisting of V, I;
Vb(303) is selected from the group consisting of V, D, E, Y;
Vb(304) is selected from the group consisting of S, D, H, L, N, T;
Vb(305) is selected from the group consisting of V, E, T, Y;
Fx(306-312) is -(L-T-V-L-H-Q-D)- (SEQ ID NO:167);
Vb(313) is selected from the group consisting of W, F;
Fx(314-316) is -(L-N-G)-;
Vb(317) is selected from the group consisting of K, E, Q;
Vb(318) is selected from the group consisting of E, H, L, Q, R, Y;
Fx(319) is Y;
Vb(320) is selected from the group consisting of K, D, F, G, H, I, L, N, P, S, T, V, W, Y;
Fx(321) is C;
Vb(322) is selected from the group consisting of K, D, F, G, H, I, P, S, T, V, W, Y;
Vb(323) is selected from the group consisting of V, I;
Vb(324) is selected from the group consisting of S, D, F, G, H, I, L, M, P, R, T, V, W, Y;
Vb(325) is selected from the group consisting of N, A, D, E, F, G, H, I, K, L, M, P, Q, R, S, T, V, W, Y;
Vb(326) is selected from the group consisting of K, I, L, P, T;
Vb(327) is selected from the group consisting of A, D, E, F, H, I, K, L, M, N, P, R, S, T, V, W, Y;
Vb(328) is selected from the group consisting of L, A, D, E, F, G, H, I, K, M, N, P, Q, R, S, T, V, W, Y;
Vb(329) is selected from the group consisting of P, D, E, F, G, H, I, K, L, M, N, Q, R, S, T, V, W, Y;
Vb(330) is selected from the group consisting of A, E, F, G, H, I, L, M, N, P, R, S, T, V, W, Y;
Vb(331) is selected from the group consisting of P, D, F, H, I, L, M, Q, R, T, V, W, Y;
Vb(332) is selected from the group consisting of I, A, D, E, F, H, K, L, M, N, P, Q, R, S, T, V, W, Y;
Vb(333) is selected from the group consisting of E, F, H, I, L, M, N, P, T, Y;
Vb(334) is selected from the group consisting of K, F, I, L, P, T;
Vb(335) is selected from the group consisting of T, D, F, G, H, I, L, M, N, P, R, S, V, W, Y;
Vb(336) is selected from the group consisting of I, E, K, Y;
Vb(337) is selected from the group consisting of S, E, H, N.

In another embodiment, the Fc region comprises is a variant selected from the group consisting of: S239D/I332E, S239D/G236A, S239D/G236S, S239D/V264I, S239D/H268D, S239D/H268E, S239D/S298A, S239D/K326E, S239D/A330L, S239D/A330Y, S239D/A330I, I332E/A264I, I332E/H268D, I332E/H268E, I332E/S298A, I332E/K326E, I332D/A330L, I332E/A330Y, I332E/A330I, I332E/G236A, I332E/G236S, I332D/V264I, I332D/H268D, I332D/H268E, I332D/S298A, I332D/K326E, I332D/A330L, I332D/A330Y, I332D/A330I, I332D/G236A, I332D/G236S, S239D/K246H/I332E, S239D/V264I/I332E, S239D/S267E/I332E, S239D/H268D/I332E, S239D/H268E/I332E, S239D/S298A/I332E, S239D/S324G/I332E, S239D/S324I/I332E, S239D/K326T/I332E, S239D/K326E/I332E, S239D/K326D/I332E, S239D/A327D/I332E, S239D/A330L/I332E, S239D/A330Y/I332E, S239D/A330I/I332E, S239D/K334T/I332E, S239D/K246H/T260H/I332E, S239D/K246H/H268D/I332E, S239D/K246H/H268E/I332E, S239D/H268D/S324G/I332E, S239D/H268E/S324G/I332E, S239D/H268D/K326T/I332E, S239D/H268E/K326T/I332E, S239D/H268D/A330L/I332E, S239D/H268E/A330L/I332E, S239D/H268D/A330Y/I332E, S239D/H268E/A330Y/I332E, S239D/S298A/S267E/I332E, S239D/S298A/H268D/I332E, S239D/S298A/H268E/I332E, S239D/S298A/S324G/I332E, S239D/S298A/S324I/I332E, S239D/S298A/K326T/I332E, S239D/S298A/K326E/I332E, S239D/S298A/A327D/I332E, S239D/S298A/A330L/I332E, S239D/S298A/A330Y/I332E, S239D/K326T/A330Y/I332E, S239D/K326E/A330Y/I332E, S239D/K326T/A330L/I332E, and S239D/K326E/A330L/I332E, wherein numbering is according to the EU index.

In a further variation, the Fc variant is selected from the group consisting of: G236S, G236A, S239D, S239E, S239N, S239Q, S239T, K246H, T260H, K246Y, D249Y, R255Y, E258Y, V264I, S267E, H268D, H268E, E272Y, E272I, E272H, K274E, G281D, E283L, E283H, S304T, S324G, S324I, K326T, A327D, A330Y, A330L, A330I, I332D, I332E, I332N, I332Q, E333Y, K334T, and K334F, wherein numbering is according to the EU index.

In another variation, the Fc variant further comprising a substitution selected from the group consisting of S298A, K326E, K326D, K326A, E333A, and K334A, wherein numbering is according to the EU index. In still other variations, the Fc variant comprising at least one amino acid modification in the Fc region of said parent Fc polypeptide, wherein said variant protein selectively enhances binding to one or more Fc ligands relative to one or more other Fc ligands, and wherein said Fc variant comprises a substitution at a position selected from the group consisting of: 234, 235, 236, 267, 268, 292, 293, 295, 300, 324, 327, 328, 330, and 335, wherein numbering is according to the EU index.

Preferred embodiments comprise optimization of Fc binding to a human FcγR, however in alternate embodiments the Ep-CAM targeting proteins of the present invention possess enhanced or reduced affinity for FcγRs from nonhuman organisms, including but not limited to rodents and nonhuman primates, Ep-CAM targeting proteins that are optimized for binding to a nonhuman FcγR may find use in experimentation. For example, mouse models are available for a variety of diseases that enable testing of properties such as efficacy, toxicity, and pharmacokinetics for a given drug candidate. As is known in the art, cancer cells can be grafted or injected into mice to mimic a human cancer, a process referred to as xenografting. Testing of Ep-CAM targeting proteins that comprise Ep-CAM targeting proteins that are optimized for one or more mouse FcγRs, may provide valuable information with regard to the efficacy of the protein, its mechanism of action, and the like. The Ep-CAM targeting proteins of the present invention may also be optimized for enhanced functionality and/or solution properties in aglycosylated form. In a preferred embodiment, the aglycosylated Ep-CAM targeting proteins of the present invention bind an Fc ligand with greater affinity than the aglycosylated form of the parent Ep-CAM targeting protein. The Fc ligands include but are not limited to FcγRs, C1q FcRn, and proteins A and G, and may be from any source including but not limited to human, mouse, rat, rabbit, or monkey, preferably human. In an alternately preferred embodiment, the Ep-CAM targeting proteins are optimized to be more stable and/or more soluble than the aglycosylated form of the parent Ep-CAM targeting protein.

Ep-CAM targeting proteins of the invention may comprise modifications that modulate interaction with Fc ligands other than FcγRs, including but not limited to complement proteins, FcRn, and Fc receptor homologs (FcRHs). FcRHs include but are not limited to FcRH1, FcRH2, FcRH3, FcRH4, FcRH5, and FcRH6 (Davis et al., 2002, Immunol. Reviews 190:123-136, expressly incorporated by reference). The modifications that modulate FcRn binding may be used to increase or decrease the in vivo half-life of the Ep-CAM targeting protein. Decreasing the in vivo half-life is useful in decreasing the toxicity of a therapeutic Ep-CAM targeting protein or in in vivo imaging procedures. More preferably, increasing the in vivo half-life is useful to increase the potency of a therapeutic Ep-CAM targeting protein and may be done by increasing the FcRn binding of the Ep-CAM targeting protein at slightly acidic pH (typically about pH 6.0). (See Burmeister et al. 1994 Nature 372:336-343; Israel et al. 1996 Immunology 89(4):573-578; Junghans and Anderson 1996 Proc. Natl. Acad. Sci. USA 93:5512-5516; Ghetie et al. 1996 Eur J. Immunol. 26:690-696. Hinton et al. 2004 J. Biol. Chem. 279(8). 6213-6216; U.S. Pat. No. 6,277,375; and U.S. Ser. No. 10/822,300; all expressly incorporated by reference).

Preferably, the Fc ligand specificity of the Ep-CAM targeting protein of the present invention will determine its therapeutic utility. The utility of a given Ep-CAM targeting protein for therapeutic purposes will depend on the epitope or form of the Ep-CAM target antigen and the disease or indication being treated. For some targets and indications, enhanced FcγR-mediated effector functions may be preferable. This may be particularly favorable for anti-cancer Ep-CAM targeting proteins. Thus Ep-CAM targeting proteins may be used that comprise Ep-CAM targeting proteins that provide enhanced affinity for activating FcγRs and/or reduced affinity for inhibitory FcγRs. For some targets and indications, it may be further beneficial to utilize Ep-CAM targeting proteins that provide differential selectivity for different activating FcγRs; for example, in some cases enhanced binding to FcγRIIa and FcγRIIa may be desired, but not FcγRI, whereas in other cases, enhanced binding only to FcγRIIa may be preferred. For certain targets and indications, it may be preferable to utilize Ep-CAM targeting proteins that enhance both FcγR-mediated and complement-mediated effector functions, whereas for other cases it may be advantageous to utilize Ep-CAM targeting proteins that enhance either FcγR-mediated or complement-mediated effector functions. For some Ep-CAM targets or cancer indications, it may be advantageous to reduce or ablate one or more effector functions, for example by knocking out binding to C1q, one or more FcγR's. FcRn, or one or more other Fc ligands. For other targets and indications, it may be preferable to utilize Ep-CAM targeting proteins that provide enhanced binding to the inhibitory FcγRIIb, yet WT level, reduced, or ablated binding to activating FcγRs. This may be particularly useful, for example, when the goal of an Ep-CAM targeting protein is to inhibit inflammation or auto-immune disease, or modulate the immune system in some way.

Clearly an important parameter that determines the most beneficial selectivity of a given Ep-CAM targeting protein to treat a given disease is the context of the Ep-CAM targeting protein, that is, what type of Ep-CAM targeting protein is being used. Thus the Fc ligand selectivity or specifity of a given Ep-CAM targeting protein will provide different properties depending on whether it composes an antibody, Fc fusion, or an Ep-CAM targeting protein with a coupled fusion or conjugate partner. For example, toxin, radionucleotide, or other conjugates may be less toxic to normal cells if the Ep-CAM targeting protein that comprises them has reduced or ablated binding to one or more Fc ligands. As another example, in order to inhibit inflammation or auto-immune disease, it may be preferable to utilize an Ep-CAM targeting protein with enhanced affinity for activating FcγRs, such as to bind these FcγRs and prevent their activation. Conversely, an Ep-CAM targeting protein that comprises two or more Fc regions with enhanced FcγRIIb affinity may co-engage this receptor on the surface of immune cells, thereby inhibiting proliferation of these cells. Whereas in some cases an Ep-CAM targeting protein may engage its target antigen on one cell type yet engage FcγRs on separate cells from the target antigen, in other cases it may be advantageous to engage FcγRs on the surface of the same cells as the target antigen. For example, if an antibody targets an antigen on a cell that also expresses one or more FcγRs, it may be beneficial to utilize an Ep-CAM targeting protein that enhances or reduces binding to the FcγRs on the surface of that cell. This may be the case, for example when the Ep-CAM targeting protein is being used as an anti-cancer agent, and co-engagement of target antigen and FcγR on the surface of the same cell promote signalling events within the cell that result in growth inhibition, apoptosis, or other anti-proliferative effect. Alternatively, antigen and FcγR co-engagement on the same cell may be advantageous when the Ep-CAM targeting protein is being used to modulate the immune system in some way, wherein co-engagement of target antigen and FcγR provides some proliferative or anti-proliferative effect. Likewise, Ep-CAM targeting proteins that comprise two or more Fc regions may benefit from Ep-CAM targeting proteins that modulate FcγR selectivity or specifity to co-engage FcγRs on the surface of the same cell.

The Fc ligand specificity of the Ep-CAM targeting proteins of the present invention can be modulated to create different effector function profiles that may be suited for particular Ep-CAM epitopes, indications or patient populations. Table 1 describes several preferred embodiments of receptor binding profiles that include improvements to, reductions to or no effect to the binding to various receptors, where such changes may be beneficial in certain contexts. The receptor binding profiles in the table could be varied by degree of increase or decrease to the specified receptors. Additionally, the binding changes specified could be in the context of additional binding changes to other receptors such as C1q or FcRn, for example by combining with ablation of binding to C1q to shut off complement activation, or by combining with enhanced binding to C1q to increase complement activation. Other embodiments with other receptor binding profiles are possible, the listed receptor binding profiles are exemplary.

TABLE 1

| Receptor binding improvement | Receptor binding reduction | Cell activity | Therapeutic activity |
|---|---|---|---|
| Solely I | — | enhance dendritic cell activity and uptake, and subsequence presentation of antigens; enhance monocyte and macrophage response to antibody | Enhancement cell-based immune response against target |
| IIIa | | Enhance ADCC and phagocytosis of broad range of cell types | Increased target cell lysis |
| IIIa | IIb | Enhance ADCC and phagocytosis of broad range of cell types | Increased target cell lysis |
| IIb, Iic | | Reduction of activity of all FcR bearing cell types except NK cells and possible activation of NK cells via IIc receptor signaling | Enhancement of target cell lysis selective for NK cell accessible target cells |
| IIb, IIIa | — | Possible NK cell specific activation and enhancement of NK cell mediated ADCC | Enhancement of target cell lysis selective for NK cell accessible target cells |
| IIIb | | Neutrophil mediated phagocytosis enhancement | Enhanced target cell destruction for neutrophil accessible cells |
| FcαR | | Neutrophil mediated phagocytosis enhancement | Enhanced target cell destruction for neutrophil accessible cells |
| I, IIa, IIIa | IIb | enhance dendritic cell activity and uptake, and subsequence presentation of antigens to T cells; enhance monocyte and macrophage response to antibody | enhance cell-based immune response against target |
| IIb | IIIa, IIa, I | Reduction in activity of monocytes, macrophages, neutrophils, NK, dendritic and other gamma receptor bearing cells | Eliminate or reduce cell-mediated cytotoxicity against target bearing cells |

The presence of different polymorphic forms of FcγRs provides yet another parameter that impacts the therapeutic utility of the Ep-CAM targeting proteins of the present invention. Whereas the specificity and selectivity of a given Ep-CAM targeting protein for the different classes of FcγRs significantly affects the capacity of an Ep-CAM targeting protein to target a given antigen for treatment of a given disease, the specificity or selectivity of an Ep-CAM targeting protein for different polymorphic forms of these receptors may in part determine which research or pre-clinical experiments may be appropriate for testing, and ultimately which patient populations may or may not respond to treatment. Thus the specificity or selectivity of Ep-CAM targeting proteins of the present invention to Fc ligand polymorphisms, including but not limited to FcγR, C1q, FcRn, and FcRH polymorphisms, may be used to guide the selection of valid research and pre-clinical experiments, clinical trial design, patient selection, dosing dependence, and/or other aspects concerning clinical trials.

The Ep-CAM targeting proteins of the present invention may be combined with other amino acid modifications in the Fc region that provide altered or optimized interaction with one or more Fc ligands, including but not limited to FcγRs, C1q, FcRn, FcR homologues, and/or as yet undiscovered Fc ligands. Additional modifications may provide altered or optimized affinity and/or specificity to the Fc ligands. Additional modifications may provide altered or optimized effector functions, including but not limited to ADCC, ADCP, CDC, and/or serum half-life. Such combination may provide additive, synergistic, or novel properties in antibodies or Fc fusions. In one embodiment, the Ep-CAM targeting proteins of the present invention may be combined with known Fc variants (Duncan et al., 1988, Nature 332:563-564; Lund et al., 1991, J Immunol 147:2657-2662; Lund et al, 1992, Mol Immunol 29:53-59; Alegre et al., 1994, Transplantation 57:1537-1543; Hutchins et al., 1995, Proc Natl Acad Sci USA 92:11980-11984; Jefferis et al., 1995, Immunol Lett 44:111-117: Lund et al., 1995, Faseb J 9:115-119; Jefferis et al., 1996, Immunol Lett 54:101-104; Lund et al., 1996, J Immunol 157:4963-4969; Armour et al., 1999, Eur J Immunol 29:2613-2624; Idusogie et al., 2000, J Immunol 164:4178-4184; Reddy et al., 2000, J Immunol 164:1925-1933; Xu et al., 2000, Cell Immunol 200:16-26; Idusogie et al., 2001, J Immunol 166:2571-2575; Shields et al., 2001, J Biol Chem 276: 6591-6604; Jefferis et al., 2002, Immunol Lett 82:57-65; Presta et al., 2002, Biochem Soc Trans 30:487-490; Hinton et al., 2004, J Biol Chem 279:6213-6216; U.S. Pat. No. 5,624, 821; U.S. Pat. No. 5,885,573; U.S. Pat. No. 6,194,551; PCT WO 00/42072; PCT WO 99/58572; US 2004/0002587 A1), U.S. Pat. No. 6,737,056, PCT US2004/000643, U.S. Ser. No. 10/370,749, and PCT/US2004/005112; all expressly incorporated by reference). For example, as described in U.S. Pat. No. 6,737,056, PCT US2004/000643, U.S. Ser. No. 10/370, 749, and PCT/US2004/005112, the substitutions S298A, S298D, K326E, K326D, E333A, K334A, and P396L provide optimized FcγR binding and/or enhanced ADCC. Furthermore, as disclosed in Idusogie et al., 2001, J. Immunology 166:2571-2572, substitutions K326W, K326Y, and E333S provide enhanced binding to the complement protein C1q and enhanced CDC. Finally, as described in Hinton et al., 2004, J. Biol. Chem. 279(8): 6213-6216, substitutions T250Q, T250E, M428L, and M428F provide enhanced binding to FcRn and improved pharmacokinetics.

Because the binding sites for FcγRs, C1q, and FcRn reside in the Fc region, the differences between the IgGs in the Fc region are likely to contribute to differences in FcγR- and C1q-mediated effector functions. It is also possible that the modifications can be made in other non-Fc regions of an EP-CAM targeting protein, including for example the Fab and hinge regions of an antibody, or the Fc fusion partner of an Fc fusion. For example, as disclosed in U.S. Ser. No. 60/614,944; U.S. Ser. No. 60/585,328; U.S. Ser. No. 60/573, 302; entitled "Immunoglobulin Variants Outside the Fc Region with Optimized Effector Function", the Fab and hinge regions of an antibody may impact effector functions such as antibody dependent cell-mediated cytotoxicity (ADCC), antibody dependent cell-mediated phagocytosis (ADCP), and complement dependent cytotoxicity (CDC). Thus modifications outside the Fc region of an Ep-CAM targeting protein of the present invention are contemplated. For example, anti-Ep-CAM antibodies of the present invention may comprise one or more amino acid modifications in the VL, CL, VH, CH1, and/or hinge regions of an antibody.

Other modifications may provide additional or novel binding determinants into an Ep-CAM targeting protein, for example additional or novel Fc receptor binding sites, for example as described in U.S. Ser. No. 60/531,752, filed Dec. 22, 2003, entitled "Ep-CAM targeting proteins with novel Fc receptor binding sites". In one embodiment, an Ep-CAM targeting protein of one antibody isotype may be engineered such that it binds to an Fc receptor of a different isotype. This may be particularly applicable when the Fc binding sites for the respective Fc receptors do not significantly overlap. For example, the structural determinants of IgA binding to FcγRI may be engineered into an IgG Ep-CAM targeting protein.

The Ep-CAM targeting proteins of the present invention may comprise modifications that modulate the in vivo pharmacokinetic properties of an Ep-CAM targeting protein. These include, but are not limited to, modifications that enhance affinity for the neonatal Fc receptor FcRn (U.S. Ser. No. 10/020354; WO2001US0048432; EP 2001000997063; U.S. Pat. No. 6,277,375; U.S. Ser. No. 09/933,497; WO1997US0003321; U.S. Pat. No. 6,737,056; WO2000US0000973; Shields et al. J. Biol. Chem. 276(9), 6591-6604 (2001); Zhou et al. J. Mot. Biol 332, 901-913 (2003), all expressly incorporated by reference). These further include modifications that modify FcRn affinity in a pH-specific manner. In some embodiments, where enhanced in vivo half-life is desired, modifications that specifically enhance FcRn affinity at lower pH (5.5-6) relative to higher pH (7-8) are preferred (Hinton et al. J. Biol. Chem. 279(8), 6213-6216 (2004); Dall' Acqua et al. J. Immuno. 169, 5171-5180 (2002); Ghetie et al. Nat. Biotechnol., 15(7), 637-640 (1997); WO2003US0033037; WO2004US0011213, all expressly incorporated by reference). For example, as described in Hinton et al., 2004, "Engineered Human IgG Antibodies with Longer Serum Half-lives in Primates" J. Biol. Chem. 279(8). 6213-6216, substitutions T250Q, T250E, M428L, and M428F provide enhanced binding to FcRn and improved pharmacokinetics. Additionally preferred modifications are those that maintain the wild-type Fc's improved binding at lower pH relative to the higher pH. In alternative embodiments, where rapid in vivo clearance is desired, modifications that reduce affinity for FcRn are preferred. (U.S. Pat. No. 6,165,745; WO1993US0003895; EP1993000910800; WO1997US0021437; Medesan et al., J. Immunol., 158(5), 2211-2217 (1997); Ghetie and Ward, Annu. Rev. Immunol., 18, 739-766 (2000); Martin et al. Molecular Cell, 7, 867-877 (2001); Kim et al. Eur. J. Immunol. 29, 2819-2825 (1999), all expressly incorporated by reference).

Ep-CAM targeting proteins of the present invention may comprise one or more modifications that provide optimized properties that are not specifically related to effector function per se. The modifications may be amino acid modifications, or may be modifications that are made enzymatically or chemically. Such modification(s) likely provide some improvement in the Ep-CAM targeting protein, for example an enhancement in its stability, solubility, function, or clinical use. The present invention contemplates a variety of improvements that made be made by coupling the Ep-CAM targeting proteins of the present invention with additional modifications.

In a preferred embodiment, the Ep-CAM targeting proteins of the present invention may comprise modifications to reduce immunogenicity in humans. In a most preferred embodiment, the immunogenicity of an Ep-CAM targeting protein of the present invention is reduced using a method described in U.S. Ser. No. 60/619,483, filed Oct. 14, 2004 and U.S. Ser. No. 11/004,590, entitled "Methods of Generating Variant Proteins with Increased Host String Content and Compositions Thereof", filed on Dec. 6, 2004. In alternate embodiments, the antibodies of the present invention are humanized (Clark, 2000, *Immunol Today* 21:397-402, expressly incorporated by reference). In CDR grafting, humanization relies principally on the grafting of donor CDRs onto acceptor (human) VL and VH frameworks (Winter U.S. Pat. No. 5,225,539, expressly incorporated by reference). "Backmutation" of selected acceptor framework residues to the corresponding donor residues is often required to regain affinity that is lost in the initial grafted construct (U.S. Pat. No. 5,530,101; U.S. Pat. No. 5,585,089; U.S. Pat. No. 5,693,761; U.S. Pat. No. 5,693,762; U.S. Pat. No. 6,180,370, U.S. Pat. No. 5,859,205; U.S. Pat. No. 5,821,337; U.S. Pat. No. 6,054,297; U.S. Pat. No. 6,407,213, all expressly incorporated by reference). The humanized antibody optimally also will comprise at least a portion of an immunoglobulin constant region, typically that of a human immunoglobulin, and thus will typically comprise a human Fc region. A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), expressly incorporated by reference). Humanization methods include but are not limited to methods described in Jones et al, 1986, *Nature* 321:522-525; Riechmann et al., 1988; *Nature* 332:323-329; Verhoeyen et al., 1988, *Science*, 239:1534-1536; Queen et al., 1989, *Proc Natl Acad Sci, USA* 86:10029-33; He et al., 1998, J. Immunol. 160:1029-1035; Carter et al, 1992, *Proc Natl Acad Sci USA* 89:4285-9, Presta et al., 1997, Cancer Res.57(20):4593-9; Gorman et al., 1991, Proc. Natl. Acad, Sci. USA 88:4181-4185; O'Connor et al., 1998, *Protein Eng* 11:321-8; all expressly incorporated by reference. Humanization or other methods of reducing the immunogenicity of nonhuman antibody variable regions may include resurfacing methods, as described for example in Roguska et al., 1994, Proc. Natl. Acad. Sci. USA 91:969-973. In one embodiment, selection based methods may be employed to humanize and/or affinity mature antibody variable regions, including but not limited to methods described in Wu et al., 1999, J. Mol. Biol. 294.151-162; Baca et al., 1997, J. Biol. Chem. 272(16):10678-10684; Rosok et al., 1996, J. Biol. Chem. 271(37): 22611-22618; Rader et al., 1998, Proc. Nat. Acad. Sci. USA 95: 8910-8915; Krauss et al., 2003, Protein Engineering 16(10):753-759; all expressly incorporated by reference. Other humanization methods may involve the grafting of only parts of the CDRs, including but not limited to methods described in U.S. Ser. No. 09/810,502; Tan et al., 2002, J. Immunol. 169:1119-1125; De Pascalis et al., 2002, J. Immunol. 169:3076-3084; all expressly incorporated by reference. Structure-based methods may be employed for humanization and affinity maturation, for example as described in U.S. Ser. No. 10/153,159, expressly incorporated by reference, and related applications.

Modifications to reduce immunogenicity may include modifications that reduce binding of processed peptides derived from the parent sequence to MHC proteins. For example, amino acid modifications would be engineered such that there are no or a minimal number of immune epitopes that are predicted to bind, with high affinity, to any prevalent MHC alleles. Several methods of identifying MHC-binding epitopes in protein sequences are known in the art and may be used to score epitopes in an Ep-CAM targeting protein of the present invention. See for example WO 98/52976; WO 02/079232; WO 00/3317; U.S. Ser. No. 09/903,378; U.S. Ser. No. 10/039,170; U.S. Ser. No. 60/222,697; U.S. Ser. No. 10/339,788; PCT WO 01/21823; and PCT WO 02/00165; Mallios, 1999, *Bioinformatics* 15: 432-439; Mallios, 2001, *Bioinformatics* 17: 942-948; Sturniolo et al., 1999, *Nature Biotech.* 17: 555-561; WO 98/59244; WO 02/069232; WO 02/77187; Marshall et al., 1995, *J. Immunol.* 154: 5927-5933; and Hammer et al., 1994, *J. Exp. Med.* 180: 2353-2358; all expressly incorporated by reference. Sequence-based information can be used to determine a binding score for a given peptide—MHC interaction (see for example Mallios, 1999, *Bioinformatics* 15: 432-439; Mallios, 2001, *Bioinformatics* 17: p942-948; Sturniolo et. al., 1999, *Nature Biotech.* 17: 555-561, all expressly incorporated by reference). It is possible to use structure-based methods in which a given peptide is computationally placed in the peptide-binding groove of a given MHC molecule and the interaction energy is determined (for example, see WO 98/59244 and WO 02/069232, both expressly incorporated by reference). Such methods may be referred to as "threading" methods. Alternatively, purely experimental methods can be used; for example a set of overlapping peptides derived from the protein of interest can be experimentally tested for the ability to induce T-cell activation and/or other aspects of an immune response. (see for example WO 02/77187, expressly incorporated by reference). In a preferred embodiment, MHC-binding propensity scores are calculated for each 9-residue frame along the protein sequence using a matrix method (see Sturniolo et. al., supra; Marshall et al., 1995, *J. Immunol.* 154: 5927-5933, and Hammer et al., 1994, *J. Exp. Med.* 180: 2353-2358; all expressly incorporated by reference). It is also possible to consider scores for only a subset of these residues, or to consider also the identities of the peptide residues before and after the 9-residue frame of interest. The matrix comprises binding scores for specific amino acids interacting with the peptide binding pockets in different human class II MHC molecule. In the most preferred embodiment, the scores in the matrix are obtained from experimental peptide binding studies. In an alternate preferred embodiment, scores for a given amino acid binding to a given pocket are extrapolated from experimentally characterized alleles to additional alleles with identical or similar residues lining that pocket. Matrices that are produced by extrapolation are referred to as "virtual matrices". In an alternate embodiment, additional amino acid modifications may be engineered to reduce the propensity of the intact molecule to interact with B cell receptors and circulating antibodies.

Anti-Ep-CAM antibodies and Fc fusions of the present invention may comprise amino acid modifications in one or more regions outside the Fc region, for example the antibody Fab region or the Fc fusion partner, that provide optimal properties. In one embodiment, the variable region of an antibody of the present invention may be affinity matured, that is to say that amino acid modifications have been made in the VH and/or VL domains of the antibody to enhance binding of the antibody to its target antigen. Likewise, modifications may be made in the Fc fusion partner to enhance affinity of the Fc fusion for its target antigen. Such types of modifications may improve the association and/or the dissociation kinetics for binding to the target antigen. Other modifications include those that improve selectivity for target antigen vs. alternative targets. These include modifications that improve selectivity for antigen expressed on target vs. non-target cells. Other improvements to the target recognition properties may be provided by additional modifications. Such properties may include, but are not limited to, specific kinetic properties (i.e. association and dissociation kinetics), selectivity for the particular target versus alternative targets, and selectivity for a specific form of target versus alternative forms. Examples include full-length versus splice variants, cell-surface vs. soluble forms, selectivity for various polymorphic variants, or selectivity for specific conformational forms of the Ep-CAM target.

Ep-CAM targeting proteins of the invention may comprise one or more modifications that provide reduced or enhanced internalization of an Ep-CAM targeting protein. In one embodiment, Ep-CAM targeting proteins of the present invention can be utilized or combined with additional modifications in order to reduce the cellular internalization of an Ep-CAM targeting protein that occurs via interaction with one or more Fc ligands. This property might be expected to enhance effector function, and potentially reduce immunogenicity of the Ep-CAM targeting proteins of the invention. Alternatively, Ep-CAM targeting proteins of the present invention can be utilized directly or combined with additional modifications in order to enhance the cellular internalization of an Ep-CAM targeting protein that occurs via interaction with one or more Fc ligands. For example, in a preferred embodiment, an Ep-CAM targeting protein is used that provides enhanced binding to FcγRI, which is expressed on dendritic cells and active early in immune response. This strategy could be further enhanced by combination with additional modifications, either within the Ep-CAM targeting protein or in an attached fusion or conjugate partner, that promote recognition and presentation of Fc peptide fragments by MHC molecules. These strategies are expected to enhance target antigen processing and thereby improve antigenicity of the target antigen (Bonnerot and Amigorena, 1999, Immunol Rev. 172:279-84, expressly incorporated by reference), promoting an adaptive immune response and greater target cell killing by the human immune system. These strategies may be particularly advantageous when the targeted antigen is shed from the cellular surface. An additional application of these concepts arises with idiotype vaccine immunotherapies, in which clone-specific antibodies produced by a patient's lymphoma cells are used to vaccinate the patient.

In a preferred embodiment, modifications are made to improve biophysical properties of the Ep-CAM targeting proteins of the present invention, including but not limited to stability, solubility, and oligomeric state. Modifications can include, for example, substitutions that provide more favorable intramolecular interactions in the Ep-CAM targeting protein such as to provide greater stability, or substitution of exposed nonpolar amino acids with polar amino acids for higher solubility. A number of optimization goals and methods are described in U.S. Ser. No. 10/379,392, expressly incorporated by reference, that may find use for engineering additional modifications to further optimize the Ep-CAM targeting proteins of the present invention. The Ep-CAM targeting proteins of the present invention can also be combined with additional modifications that reduce oligomeric state or size, such that tumor penetration is enhanced, or in vivo clearance rates are increased as desired.

Other modifications to the Ep-CAM targeting proteins of the present invention include those that enable the specific formation or homodimeric or homomultimeric molecules. Such modifications include but are not limited to engineered disulfides, as well as chemical modifications or aggregation methods, which may provide a mechanism for generating covalent homodimeric or homomultimers. For example, methods of engineering and compositions of such molecules are described in Kan et al., 2001, J. Immunol., 2001, 166: 1320-1326; Stevenson et al., 2002, Recent Results Cancer Res. 159:104-12; U.S. Pat. No. 5,681,566; Caron et al., 1992, J. Exp. Med. 176:1191-1195, and Shopes, 1992, J. Immunol. 148(9):2918-22; all expressly incorporated by reference. Additional modifications to the variants of the present invention include those that enable the specific formation or heterodimeric, heteromultimeric, bifunctional, and/or multifunctional molecules. Such modifications include, but are not limited to, one or more amino acid substitutions in the CH3 domain, in which the substitutions reduce homodimer formation and increase heterodimer formation. For example, methods of engineering and compositions of such molecules are described in Atwell et al., 1997, J. Mol. Biol. 270(1):26-35, and Carter et al., 2001, J. Immunol. Methods 248:7-15; both expressly incorporated by reference. Additional modifications include modifications in the hinge and CH3 domains, in which the modifications reduce the propensity to form dimers.

In further embodiments, the Ep-CAM targeting proteins of the present invention comprise modifications that remove proteolytic degradation sites. These may include, for example, protease sites that reduce production yields, as well as protease sites that degrade the administered protein in vivo. In a preferred embodiment, additional modifications are made to remove covalent degradation sites such as deamidation (i.e. deamidation of glutaminyl and asparaginyl residues to the corresponding glutamyl and aspartyl residues), oxidation, and proteolytic degradation sites. Deamidation sites that are particular useful to remove are those that have enhance propensity for deamidation, including, but not limited to asparaginyl and gltuamyl residues followed by glycines (NG and QG motifs, respectively). In such cases, substitution of either residue can significantly reduce the tendency for deamidation. Common oxidation sites include methionine and cysteine residues. Other covalent modifications, that can either be introduced or removed, include hydroxylation of proline and lysine, phosphorylation of hydroxyl groups of seryl or threonyl residues, methylation of the amino groups of lysine, arginine, and histidine side chains [T. E. Creighton, Proteins: Structure and Molecular Properties, W.H. Freeman & Co., San Francisco, pp. 79-86 (1983), expressly incorporated by reference], acetylation of the N-terminal amine, and amidation of any C-terminal carboxyl group. Additional modifications also may include but are not limited to post-translational modifications such as N-linked or O-linked glycosylation and phosphorylation.

Modifications may include those that improve expression and/or purification yields from hosts or host cells commonly used for production of biologics. These include, but are not limited to various mammalian cell lines (e.g. CHO), yeast cell lines, bacterial cell lines, and plants. Additional modifications include modifications that remove or reduce the ability of heavy chains to form inter-chain disulfide linkages. Additional modifications include modifications that remove or reduce the ability of heavy chains to form intra-chain disulfide linkages.

The Ep-CAM targeting proteins of the present invention may comprise modifications that include the use of unnatural amino acids incorporated using, for example, the technologies developed by Schultz and colleagues, including but not limited to methods described by Cropp & Shultz, 2004, Trends Genet. 20(12):625-30, Anderson et al., 2004, Proc. Natl. Acad. Sci. U.S.A. 101 (2):7566-71, Zhang et al., 2003, 303(5656):371-3, and Chin et al., 2003, Science 301(5635): 964-7; expressly incorporated by reference. In some embodiments, these modifications enable manipulation of various functional, biophysical, immunological, or manufacturing properties discussed above. In additional embodiments, these modifications enable additional chemical modification for other purposes. Other modifications are contemplated herein. For example, the Ep-CAM targeting protein may be linked to one of a variety of nonproteinaceous polymers, e.g., polyethylene glycol (PEG), polypropylene glycol, polyoxyalkylenes, or copolymers of polyethylene glycol and polypropylene glycol. Additional amino acid modifications may be made to enable specific or non-specific chemical or posttranslational modification of the Ep-CAM targeting proteins. Such modifications, include, but are not limited to PEGylation and glycosylation. Specific substitutions that can be utilized to enable PEGylation include, but are not limited to, introduction of novel cysteine residues or unnatural amino acids such that efficient and specific coupling chemistries can be used to attach a PEG or otherwise polymeric moiety. Introduction of specific glycosylation sites can be achieved by introducing novel N-X-T/S sequences into the Ep-CAM targeting proteins of the present invention.

In one embodiment, the Ep-CAM targeting proteins of the present invention comprise one or more engineered glycoforms. By "engineered glycoform" as used herein is meant a carbohydrate composition that is covalently attached to an Ep-CAM targeting protein, wherein the carbohydrate composition differs chemically from that of a parent Ep-CAM targeting protein. An engineered protein comprising a position that lacks an attached oligosaccharide or carbohydrate may be referred to as comprising an engineered glycoform, if its parent molecule comprises an oligosaccharide, or carbohydrate at that position. Engineered glycoforms may be useful for a variety of purposes, including but not limited to enhancing or reducing effector function. Engineered glycoforms may be generated by a variety of methods known in the art (Umaña et al., 1999, *Nat Biotechnol* 17:176-180; Davies et al., 2001, *Biotechnol Bioeng* 74:288-294; Shields et al., 2002, *J Biol Chem* 277:26733-26740; Shinkawa et al., 2003, *J Biol Chem* 278:3466-3473; U.S. Pat. No. 6,602,684; U.S. Ser. No. 10/277,370; U.S. Ser. No. 10/113,929; PCT WO 00/61739A1; PCT WO 01/29246A1; PCT WO 02/31140A1; PCT WO 02/30954A1; all expressly incorporated by reference; Potelligent™ technology [Biowa, Inc., Princeton, N.J.]; GlycoMAb™ glycosylation engineering technology [GLYCART biotechnology AG, Zürich, Switzerland]). Many of these techniques are based on controlling the level of fucosylated and/or bisecting oligosaccharides that are covalently attached to the Fc region, for example by expressing an Ep-CAM targeting protein in various organisms or cell lines, engineered or otherwise (for example Lec-13 CHO cells or rat hybridoma YB2/0 cells), by regulating enzymes involved in the glycosylation pathway (for example FUT8 [α1,6-fucosyltransferase] and/or β1-4-N-acetylglucosaminyltransferase III [GnTIII]), or by modifying carbohydrate(s) after the Ep-CAM targeting protein has been expressed. Engineered glycoform typically refers to the different carbohydrate or oligosaccharide; thus an Ep-CAM targeting protein, for example an anti-Ep-CAM antibody or Fc fusion, may comprise an engineered glycoform. Alternatively, engineered glycoform may refer to the Ep-CAM targeting protein that comprises the different carbohydrate or oligosaccharide.

The EP-CAM targeting proteins of the present invention may be fused or conjugated to one or more other molecules or polypeptides. Conjugate and fusion partners may be any molecule, including small molecule chemical compounds and polypeptides. For example, a variety of antibody conjugates and methods are described in Trail et al., 1999, Curr. Opin. Immunol. 11:584-588, expressly incorporated by reference.

Possible conjugate partners include but are not limited to cytokines, cytotoxic agents, toxins, radioisotopes, chemotherapeutic agent anti-angiogenic agents, a tyrosine kinase inhibitors, and other therapeutically active agents. In some embodiments, conjugate partners may be thought of more as payloads, that is to say that the goal of a conjugate is targeted delivery of the conjugate partner to a targeted cell for example a cancer cell or immune cell, by the Ep-CAM targeting protein. Thus, for example, the conjugation of a toxin to an anti-Ep-CAM antibody or Fc fusion targets the delivery of the toxin to cells expressing the Ep-CAM antigen. As will be appreciated by one skilled in the art, in reality the concepts and definitions of fusion and conjugate are overlapping. The designation of an Ep-CAM targeting protein as a fusion or conjugate is not meant to constrain it to any particular embodiment of the present invention. Rather, these terms are used loosely to convey the broad concept that any Ep-CAM targeting protein of the present invention may be linked genetically, chemically, or otherwise, to one or more polypeptides or molecules to provide some desirable property.

In one embodiment, the Ep-CAM targeting proteins of the present invention are fused or conjugated to a cytokine. By "cytokine" as used herein is meant a generic term for proteins released by one cell population that act on another cell as intercellular mediators. For example, as described in Penichet et al., 2001, J. Immunol. Methods 248;91-101, expressly incorporated by reference, cytokines may be fused to antibody to provide an array of desirable properties. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor, integrin; thrombopoietin (TPO); nerve growth factors such as NGF-beta; platelet-growth factor; transforming growth factors (TOEs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interteukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; C5a; and other polypeptide factors including LIF and kit ligand (KL). As used herein, the term cytokine includes proteins from natural sources or from recombinant cell culture, and biologically active equivalents of the native sequence cytokines.

In an alternate embodiment, the Ep-CAM targeting proteins of the present invention are fused, conjugated, or operably linked to a toxin, including but not limited to small molecule toxins and enzymatically active toxins of bacterial, fungal, plant or animal origin, including fragments and/or variants thereof. For example, a variety of immunotoxins and immunotoxin methods are described in Thrush et al., 1996, Ann. Rev. Immunol. 14.49-71, expressly incorporated by reference. Small molecule toxins include but are not limited to calicheamicin, maytansine (U.S. Pat. No. 5,208,020, expressly incorporated by reference>, trichothene, and CC1065. In one embodiment of the invention, the anti-Ep- CAM antibody or Fc fusion is conjugated to one or more maytansine molecules (e.g. about 1 to about 10 maytansine molecules per antibody molecule). Maytansine may, for example, be converted to May-SS-Me which may be reduced to May-SH3 and reacted with modified antibody or Fc fusion (Chari et al., 1992, *Cancer Research* 52: 127-131, expressly incorporated by reference) to generate a maytansinoid-antibody or maytansinoid-Fc fusion conjugate. Another conjugate of interest comprises an anti-Ep-CAM antibody or Fc fusion conjugated to one or more calicheamicin molecules. The calicheamicin family of antibiotics are capable of producing double-stranded DNA breaks at sub-picomolar concentrations. Structural analogues of calicheamicin that may be used include but are not limited to $\gamma_1^1$, $\alpha_2^1$, $\alpha_3$, N-acetyl-$\gamma_1^1$, PSAG, and $\theta^1{}_1$, (Hinman et al., 1993, Cancer Research 53:3336-3342; Lode et al., 1998, Cancer Research 58:2925-2928; U.S. Pat. No. 5,714,586; U.S. Pat. No. 5,712,374; U.S. Pat. No. 5,264,586; U.S. Pat. No. 5,773,001; all expressly incorporated by reference). Dolastatin 10 analogs such as auristatin E (AE) and monomethylauristatin E (MMAE) may find use as conjugates for the Ep-CAM targeting proteins of the present invention (Doronina et al., 2003, Nat Biotechnol 21(7):778-84; Francisco et al., 2003 Blood 102(4):1458-65; expressly incorporated by reference). Useful enyzmatically active toxins include but are not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, PCT WO 93/21232, expressly incorporated by reference. The present invention further contemplates a conjugate between an Ep-CAM targeting protein of the present invention and a compound with nucleolytic activity, for example a ribonuclease or DNA endonuclease such as a deoxyribonuclease (Dnase).

In an alternate embodiment, an Ep-CAM targeting protein of the present invention may be fused, conjugated, or operably linked to a radioisotope to form a radioconjugate. A variety of radioactive isotopes are available for the production of radioconjugate antibodies and Fc fusions. Examples include, but are not limited to, At211, I131, I125, Y90, Re186, Re188, Sm153, Bi212, P32, and radioactive isotopes of Lu. See for example, reference.

In yet another embodiment, an targeti Ep-CAM ng protein of the present invention may be conjugated to a "receptor" (such streptavidin) for utilization in tumor pretargeting wherein the Ep-CAM targeting protein-receptor conjugate is administered to the patient, followed by removal of unbound conjugate from the circulation using a clearing agent and then administration of a "ligand" (e.g. avidin) which is conjugated to a cytotoxic agent (e.g. a radionucleotide). In an alternate embodiment, the Ep-CAM targeting protein is conjugated or operably linked to an enzyme in order to employ Antibody Dependent Enzyme Mediated Prodrug Therapy (ADEPT). ADEPT may be used by conjugating or operably linking the Ep-CAM targeting protein to a prodrug-activating enzyme that converts a prodrug (e.g. a peptidyl chemotherapeutic agent, see PCT WO 81/01145) to an active anti-cancer drug. See, for example, PCT WO 88/07378 and U.S. Pat. No. 4,975,278; both expressly incorporated by reference, The enzyme component of the immunoconjugate useful for ADEPT includes any enzyme capable of acting on a prodrug in such a way so as to covert it into its more active, cytotoxic form. Enzymes that are useful in the method of this invention include but are not limited to alkaline phosphatase useful for converting: phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as .beta.-galactosidase and neuramimidase useful for converting glycosylated prodrugs into free drugs; beta-lactamase useful for converting drugs derivatized with .alpha.-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, for example, Massey, 1987, *Nature* 328: 457-458, expressly incorporated by reference). Ep-CAM targeting protein-abzyme conjugates can be prepared for delivery of the abzyme to a tumor cell population. A variety of additional conjugates are contemplated for the Ep-CAM targeting proteins of the present invention. A variety of chemotherapeutic agents, anti-angiogenic agents, tyrosine kinase inhibitors, and other therapeutic agents are described below, which may find use as Ep-CAM targeting protein conjugates.

Also contemplated as fusion and conjugate partners are Fc polypeptides. Thus an Ep-CAM targeting protein may be a multimeric Fc polypeptide, comprising two or more Fc regions. The advantage of such a molecule is that it provides multiple binding sites for Fc receptors with a single protein molecule. In one embodiment Pc regions may be linked using a chemical engineering approach. For example, Fab's and Fc's may be linked by thioether bonds originating at cysteine residues in the hinges, generating molecules such as FabFc$_2$ (Kan et al., 2001, *J. Immunol.*, 2001, 166: 1320-1326; Stevenson et al, 2002, *Recent Results Cancer Res.* 159: 104-12; U.S. Pat. No. 5,681,566; expressly incorporated by reference). Fc regions may be linked using disulfide engineering and/or chemical cross-linking, for example as described in Caron et al., 1992, J. Exp. Med. 176:1191-1195, and Shopes, 1992, J. Immunol. 148(9):2918-22; both expressly incorporated by reference. In a preferred embodiment, Fc regions may be linked genetically. For example multiple C$\gamma$2 domains have been fused between the Fab and Fc regions of an antibody (White et al., 2001, *Protein Expression and Purification* 21: 446-455, expressly incorporated by reference). In a preferred embodiment, Fc regions in an Ep-CAM targeting protein are linked genetically to generated tandemly linked Fc regions as described in U.S. Ser. No. 60/531,752, filed Dec. 22, 2003, entitled "Fc polypeptides with novel Fc receptor binding sites", expressly incorporated by reference. Tandemly linked Fc polypeptides may comprise two or more Fc regions, preferably one to three, most preferably two Fc regions. It may be advantageous to explore a number of engineering constructs in order to obtain homo- or hetero-tandemly linked Ep-CAM targeting proteins with the most favorable structural and functional properties. Tandemly linked Ep-CAM targeting proteins may be homo-tandemly linked Ep-CAM targeting proteins, that is an Ep-CAM targeting protein of one isotype is fused genetically to another Ep-CAM targeting protein of the same isotype. It is anticipated that because there are multiple Fc-$\gamma$R, C1q, and/or FcRn binding sites on tandemly linked Fc polypeptides, effector functions and/or pharmacokinetics may be enhanced. In an alternate embodiment, Ep-CAM targeting proteins from different isotypes may be tandemly linked, referred to as hetero-tandemly linked Ep-CAM targeting proteins. For example, because of the capacity to target FcγR and FcαRI receptors, an Ep-CAM targeting protein that binds both FcγRs and FcαRI may provide a significant clinical improvement.

Fusion and conjugate partners may be linked to any region of an Ep-CAM targeting protein of the present invention, including at the N- or C-termini, or at some residue in-between the termini, In a preferred embodiment, a fusion or conjugate partner is linked at the N- or C-terminus of the Ep-CAM targeting protein, most preferably the N-terminus. A variety of linkers may find use in the present invention to covalently link Ep-CAM targeting proteins to a fusion or conjugate partner or generate an Fc fusion. By "linker", "linker sequence", "spacer", "tethering sequence" or grammatical equivalents thereof, herein is meant a molecule or group of molecules (such as a monomer or polymer) that connects two molecules and often serves to place the two molecules in a preferred configuration. A number of strategies may be used to covalently link molecules together. These include, but are not limited to polypeptide linkages between N- and C-termini of proteins or protein domains, linkage via disulfide bonds, and linkage via chemical cross-linking reagents. In one aspect of this embodiment, the linker is a peptide bond, generated by recombinant techniques or peptide synthesis. Choosing a suitable linker for a specific case where two polypeptide chains are to be connected depends on various parameters, including but not limited to the nature of the two polypeptide chains (e.g., whether they naturally oligomerize), the distance between the N- and the C-termini to be connected if known, and/or the stability of the linker towards proteolysis and oxidation. Furthermore, the linker may contain amino acid residues that provide flexibility. Thus, the linker peptide may predominantly include the following amino acid residues: Gly, Ser, Ala, or Thr. The linker peptide should have a length that is adequate to link two molecules in such a way that they assume the correct conformation relative to one another so that they retain the desired activity. Suitable lengths for this purpose include at least one and not more than 50 amino acid residues. Preferably, the linker is from about 1 to 30 amino acids in length, with linkers of 1 to 20 amino acids in length being most preferred. In addition, the amino acid residues selected for inclusion in the linker peptide should exhibit properties that do not interfere significantly with the activity of the polypeptide. Thus, the linker peptide on the whole should not exhibit a charge that would be inconsistent with the activity of the polypeptide, or interfere with internal folding, or form bonds or other interactions with amino acid residues in one or more of the monomers that would seriously impede the binding of receptor monomer domains. Useful linkers include glycine-serine polymers (including, for example, (GS)n, (GSGGS)n (SEQ ID NO:168), (GGGGS)n (SEQ ID NO:169), and (GGGS)n (SEQ ID NO:170), where n is an integer of at least one), glycine-alanine polymers, alanine-serine polymers, and other flexible linkers such as the tether for the shaker potassium channel, and a large variety of other flexible linkers, as will be appreciated by those in the art. Glycine-serine polymers are preferred since both of these amino acids are relatively unstructured, and therefore may be able to serve as a neutral tether between components. Secondly, serine is hydrophilic and therefore able to solubilize what could be a globular glycine chain. Third, similar chains have been shown to be effective in joining subunits of recombinant proteins such as single chain antibodies. Suitable linkers may also be identified by screening databases of known three-dimensional structures for naturally occurring motifs that can bridge the gap between two polypeptide chains. In a preferred embodiment, the linker is not immunogenic when administered in a human patient. Thus linkers may be chosen such that they have low immunogenicity or are thought to have low immunogenicity. For example, a linker may be chosen that exists naturally in a human. In a most preferred embodiment, the linker has the sequence of the hinge region of an antibody, that is the sequence that links the antibody Fab and Fc regions; alternatively the linker has a sequence that comprises part of the hinge region, or a sequence that is substantially similar to the hinge region of an antibody. Another way of obtaining a suitable linker is by optimizing a simple linker, e.g., (Gly4Ser)n, through random mutagenesis. Alternatively, once a suitable polypeptide linker is defined, additional linker polypeptides can be created to select amino acids that more optimally interact with the domains being linked. Other types of linkers that may be used in the present invention include artificial polypeptide linkers and inteins. In another embodiment, disulfide bonds are designed to link the two molecules. In another embodiment, linkers are chemical cross-linking agents. For example, a variety of bifunctional protein coupling agents may be used, including but not limited to N-succinimidyl-3-(2-pyridyldithiol) propionate (SPDP), succinimidyl-4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., 1971, Science 238:1098, expressly incorporated by reference. Chemical linkers may enable chelation of an isotope. For example, Carbon-14-labeled 1-isothiocyanato-benzyl-3-methyldiethylene triaminepentaacetic acid (MX-DTPA) is an exemplary chelating agent for conjugation of radionucleotide to the antibody (see PCT WO 94/11026). The linker may be cleavable, facilitating release of the cytotoxic drug in the cell. For example, an acid-labile linker, peptidase-sensitive linker, dimethyl linker or disulfide-containing linker (Chari et al., 1992, Cancer Research 52: 127-131, expressly incorporated by reference) may be used. Alternatively, a variety of nonproteinaceous polymers, including but not limited to polyethylene glycol (PEG), polypropylene glycol, polyoxyalkylenes, or copolymers of polyethylene glycol and polypropylene glycol, may find use as linkers, that is may find use to link the Ep-CAM targeting proteins of the present invention to a fusion or conjugate partner to generate an anti-Ep-CAM Fc fusion, or to link the Ep-CAM targeting proteins of the present invention to a conjugate.

Experimental Production of Ep-CAM Targeting Proteins

The present invention provides methods for producing and experimentally testing Ep-CAM targeting proteins. The described methods are not meant to constrain the present invention to any particular application or theory of operation. Rather, the provided methods are meant to illustrate generally that one or more Ep-CAM targeting proteins may be produced and experimentally tested to obtain variant Ep-CAM targeting proteins, General methods for antibody molecular biology, expression, purification, and screening are described in Antibody Engineering, edited by Duebel & Kontermann, Springer-Verlag, Heidelberg, 2001; and Hayhurst & Georgiou, 2001, *Curr Opin Chem Biol* 5:683-689; Maynard & Georgiou, 2000, *Annu Rev Biomed Eng* 2:339-76; Antibodies: A Laboratory Manual by Harlow & Lane, New York: Cold Spring Harbor Laboratory Press, 1988; all expressly incorporated by reference, In one embodiment of the present invention, nucleic acids are created that encode the Ep-CAM targeting proteins, and that may then be cloned into host cells, expressed and assayed, if desired. Thus, nucleic acids, and particularly DNA, may be made that encode each protein sequence. These practices are carried out using well-known procedures. For example, a variety of methods that may find use in the present invention are described in Molecular Cloning—A Laboratory Manual, $3^{rd}$ Ed. (Maniatis, Cold Spring Harbor Laboratory Press, New York, 2001), and Current Protocols in Molecular Biology (John Wiley & Sons); both expressly incorporated by reference. As will be appreciated by those skilled in the art, the generation of exact sequences for a library comprising a large number of sequences is potentially expensive and time consuming, Accordingly, there are a variety of techniques that may be used to efficiently generate libraries of the present invention. Such methods that may find use in the present invention are described or referenced in U.S. Pat. No. 6,403,312; U.S. Ser. No. 09/782,004; U.S. Ser. No. 09/927,790; U.S. Ser. No. 10/218,102; PCT WO 01/40091; and PCT WO 02/25588; all expressly incorporated by reference. Such methods include but are not limited to gene assembly methods, PCR-based method and methods which use variations of PCR, ligase chain reaction-based methods, pooled oligo methods such as those used in synthetic shuffling, error-prone amplification methods and methods which use oligos with random mutations, classical site-directed mutagenesis methods, cassette mutagenesis, and other amplification and gene synthesis methods. As is known in the art, there are a variety of commercially available kits and methods for gene assembly, mutagenesis, vector subcloning, and the like, and such commercial products find use in the present invention for generating nucleic acids that encode Ep-CAM targeting proteins.

The Ep-CAM targeting proteins of the present invention may be produced by culturing a host cell transformed with nucleic acid, preferably an expression vector, containing nucleic acid encoding the Ep-CAM targeting proteins, under the appropriate conditions to induce or cause expression of the protein. The conditions appropriate for expression will vary with the choice of the expression vector and the host cell, and will be easily ascertained by one skilled in the art through routine experimentation. A wide variety of appropriate host cells may be used, including but not limited to mammalian cells, bacteria, insect cells, and yeast. For example, a variety of cell lines that may find use in the present invention are described in the ATCC® cell line catalog, available from the American Type Culture Collection.

In a preferred embodiment, the Ep-CAM targeting proteins are expressed in mammalian expression systems, including systems in which the expression constructs are introduced into the mammalian cells using virus such as retrovirus or adenovirus. Any mammalian cells may be used, with human, mouse, rat, hamster, and primate cells being particularly preferred. Suitable cells also include known research cells, including but not limited to Jurkat T cells, NIH3T3, CHO, BHK, COS, HEK293, PER C.6, HeLa, Sp2/0, NS0 cells and variants thereof. In an alternately preferred embodiment, library proteins are expressed in bacterial cells. Bacterial expression systems are well known in the art, and include *Escherichia coli* (*E. coli*), *Bacillus subtilis*, *Streptococcus cremoris*, and *Streptococcus lividans*. In alternate embodiments, Ep-CAM targeting proteins are produced in insect cells (e.g. Sf21/Sf9, *Trichoplusia ni* Bti-Tn5b1-4) or yeast cells (e.g. *S. cerevisiae, Pichia*, etc). In an alternate embodiment, Ep-CAM targeting proteins are expressed in vitro using cell free translation systems. In vitro translation systems derived from both prokaryotic (e.g. *E. coli*) and eukaryotic (e.g. wheat germ, rabbit reticulocytes) cells are available and may be chosen based on the expression levels and functional properties of the protein of interest. For example, as appreciated by those skilled in the art, in vitro translation is required for some display technologies, for example ribosome display. In addition, the Ep-CAM targeting proteins may be produced by chemical synthesis methods. Also transgenic expression systems both animal (e.g. cow, sheep or goat milk, embryonated hen's eggs, whole insect larvae, etc.) and plant (e.g. corn, tobacco, duckweed, etc.)

The nucleic acids that encode the Ep-CAM targeting proteins of the present invention may be incorporated into an expression vector in order to express the protein. A variety of expression vectors may be utilized for protein expression. Expression vectors may comprise self-replicating extra-chromosomal vectors or vectors which integrate into a host genome. Expression vectors are constructed to be compatible with the host cell type. Thus expression vectors which find use in the present invention include but are not limited to those which enable protein expression in mammalian cells, bacteria, insect cells, yeast, and in in vitro systems. As is known in the art, a variety of expression vectors are available, commercially or otherwise that may find use in the present invention for expressing Ep-CAM targeting proteins.

Expression vectors typically comprise a protein operably linked with control or regulatory sequences selectable markers, any fusion partners, and/or additional elements. By "operably linked" herein is meant that the nucleic acid is placed into a functional relationship with another nucleic acid sequence, Generally, these expression vectors include transcriptional and translational regulatory nucleic acid operably linked to the nucleic acid encoding the Ep-CAM targeting protein, and are typically appropriate to the host cell used to express the protein. In general, the transcriptional and translational regulatory sequences may include promoter sequences, ribosomal binding sites, transcriptional start and stop sequences, translational start and stop sequences, and enhancer or activator sequences. As is also known in the art, expression vectors typically contain a selection gene or marker to allow the selection of transformed host cells containing the expression vector. Selection genes are well known in the art and will vary with the host cell used.

Ep-CAM targeting proteins may be operably linked to a fusion partner to enable targeting of the expressed protein, purification, screening, display, and the like. Fusion partners may be linked to the Ep-CAM targeting protein sequence via a linker sequences. The linker sequence will generally comprise a small number of amino acids, typically less than ten, although longer linkers may also be used. Typically, linker sequences are selected to be flexible and resistant to degradation. As will be appreciated by those skilled in the art, any of a wide variety of sequences may be used as linkers. For example, a common linker sequence comprises the amino acid sequence GGGGS (SEQ ID NO:169). A fusion partner may be a targeting or signal sequence that directs Ep-CAM targeting protein and any associated fusion partners to a desired cellular location or to the extracellular media. As is known in the art, certain signaling sequences may target a protein to be either secreted into the growth media, or into the periplasmic space, located between the inner and outer membrane of the cell. A fusion partner may also be a sequence that encodes a peptide or protein that enables purification and/or screening. Such fusion partners include but are not limited to polyhistidine tags (His-tags) (for example $H_6$ and $H_{10}$ or other tags for use with Immobilized Metal Affinity Chromatography (IMAC) systems (e.g. $Ni^{+2}$ affinity columns)), GST fusions, MBP fusions, Strep-tag, the BSP biotinylation target sequence of the bacterial enzyme BirA, and epitope tags which are targeted by antibodies (for example c-myc tags, flag-tags, and the like). As will be appreciated by those skilled in the art, such tags may be useful for purification, for screening, or both. For example, an Ep-CAM targeting protein may be purified using a His-tag by immobilizing it to a $Ni^{+2}$ affinity column, and then after purification the same His-tag may be used to immobilize the antibody to a $Ni^{+2}$ coated plate to perform an ELISA or other binding assay (as described below). A fusion partner may enable the use of a selection method to screen Ep-CAM targeting proteins (see below). Fusion partners that enable a variety of selection methods are well-known in the art, and all of these find use in the present invention. For example, by fusing the members of an Ep-CAM targeting protein library to the gene III protein, phage display can be employed (Kay et al., Phage display of peptides and proteins: a laboratory manual, Academic Press, San Diego, Calif., 1996; Lowman et al., 1991, *Biochemistry* 30, 10832-10838; Smith, 1985, *Science* 228:1315-1317; all expressly incorporated by reference), Fusion partners may enable Ep-CAM targeting proteins to be labeled. Alternatively, a fusion partner may bind to a specific sequence on the expression vector, enabling the fusion partner and associated Ep-CAM targeting protein to be linked covalently or noncovalently with the nucleic acid that encodes them. For example, U.S. Ser. No. 09/642,574; U.S. Ser. No. 10/080,376; U.S. Ser. No. 09/792,630; U.S. Ser. No. 10/023,208; U.S. Ser. No 09/792,626; U.S. Ser. No. 10/082,671; U.S. Ser. No. 09/953,351; U.S. Ser. No. 10/097,100; U.S. Ser. No. 60/366,658; PCT WO 00/22906; PCT WO 01/49058; PCT WO 02/04852; PCT WO 02/04853; PCT WO 02/08023; PCT WO 01/28702; and PCT WO 02/07466, all expressly incorporated by reference, describe such a fusion partner and technique that may find use in the present invention.

The methods of introducing exogenous nucleic acid into host cells are well known in the art, and will vary with the host cell used. Techniques include but are not limited to dextran-mediated transfection, calcium phosphate precipitation, calcium chloride treatment, polybrene mediated transfection, protoplast fusion, electroporation, viral or phage infection, encapsulation of the polynucleotide(s) in liposomes, and direct microinjection of the DNA into nuclei. In the case of mammalian cells, transfection may be either transient or stable.

In a preferred embodiment, Ep-CAM targeting proteins are purified or isolated after expression. Proteins may be isolated or purified in a variety of ways known to those skilled in the art. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, immunological, precipitation, dialysis, and chromatofocusing techniques. Ultrafiltration and diafiltration techniques, in conjunction with protein concentration, are also useful. As is well known in the art, a variety of natural proteins bind Fc and antibodies, and these proteins can find use in the present invention for purification of Ep-CAM targeting proteins. For example, the bacterial proteins A and G bind to the Fc region, Likewise, the bacterial protein L binds to the Fab region of some antibodies, as of course does the antibody's target antigen. Purification can often be enabled by a particular fusion partner. For example, Ep-CAM targeting proteins may be purified using glutathione resin if a GST fusion is employed, $Ni^{+2}$ affinity chromatography if a His-tag is employed, or immobilized anti-flag antibody if a flag-tag is used. For general guidance in suitable purification techniques, see Protein Purification: Principles and Practice, $3^{rd}$ Ed., Scopes, Springer-Verlag, NY, 1994. The degree of purification necessary will vary depending on the screen or use of the Ep-CAM targeting proteins. In some instances no purification is necessary. For example in one embodiment, if the Ep-CAM targeting proteins are secreted, screening may take place directly from the media. As is well known in the art, some methods of selection do not involve purification of proteins. Thus, for example, if a library of EpCAM targeting proteins is made into a phage display library, protein purification may not be performed.

Experimental Testing of Ep-CAM Targeting Proteins

Assays

Ep-CAM targeting proteins may be screened using a variety of methods, including but not limited to those that use in vitro assays, in vivo and cell-based assays, and selection technologies. Automation and high-throughput screening technologies may be utilized in the screening procedures. Screening may employ the use of a fusion partner or label. The use of fusion partners has been discussed above. By "labeled" herein is meant that the Ep-CAM targeting proteins of the invention have one or more elements, isotopes, or chemical compounds attached to enable the detection in a screen. In general, labels fall into three classes: a) immune labels, which may be an epitope incorporated as a fusion partner that is recognized by an antibody, b) isotopic labels, which may be radioactive or heavy isotopes, and c) small molecule labels, which may include fluorescent and colorimetric dyes, or molecules such as biotin that enable other labeling methods. Labels may be incorporated into the compound at any position and may be incorporated in vitro or in vivo during protein expression.

In a preferred embodiment, the functional and/or biophysical properties of Ep-CAM targeting proteins are screened in an in vitro assay, In vitro assays may allow a broad dynamic range for screening properties of interest. Properties of Ep-CAM targeting proteins that may be screened include but are not limited to stability, solubility, and affinity for Fc ligands, for example FcγRs. Multiple properties may be screened simultaneously or individually. Proteins may be purified or unpurified, depending on the requirements of the assay. In one embodiment, the screen is a qualitative or quantitative binding assay for binding of Ep-CAM targeting proteins to a protein or nonprotein molecule that is known or thought to bind the Ep-CAM targeting protein. In a preferred embodiment, the screen is a binding assay for measuring binding to the Ep-CAM target antigen. In an alternately preferred embodiment, the screen is an assay for binding of Ep-CAM targeting proteins to an Fc ligand, including but are not limited to the family of FcγRs, the neonatal receptor FcRn, the complement protein C1q, and the bacterial proteins A and G. The Fc ligands may be from any organism, with humans, mice, rats, rabbits, and monkeys preferred. Binding assays can be carried out using a variety of methods known in the art, including but not limited to FRET (Fluorescence Resonance Energy Transfer) and BRET (Bioluminescence Resonance Energy Transfer)-based assays, AlphaScreen™ (Amplified Luminescent Proximity Homogeneous Assay), Scintillation Proximity Assay, ELISA (Enzyme-Linked Immunosorbent Assay), SPR (Surface Plasmon Resonance, also known as BIACORE®), isothermal titration calorimetry, differential scanning calorimetry, gel electrophoresis, and chromatography including gel filtration. These and other methods may take advantage of some fusion partner or label of the Ep-CAM targeting protein. Assays may employ a variety of detection methods including but not limited to chromogenic, fluorescent, luminescent, or isotopic labels.

The biophysical properties of Ep-CAM targeting proteins, for example stability and solubility, may be screened using a variety of methods known in the art. Protein stability may be determined by measuring the thermodynamic equilibrium between folded and unfolded states. For example, Ep-CAM targeting proteins of the present invention may be unfolded using chemical denaturant, heat, or pH, and this transition may be monitored using methods including but not limited to circular dichroism spectroscopy, fluorescence spectroscopy, absorbance spectroscopy, NMR spectroscopy, calorimetry, and proteolysis. As will be appreciated by those skilled in the art, the kinetic parameters of the folding and unfolding transitions may also be monitored using these and other techniques. The solubility and overall structural integrity of an Ep-CAM targeting protein may be quantitatively or qualitatively determined using a wide range of methods that are known in the art. Methods which may find use in the present invention for characterizing the biophysical properties of Ep-CAM targeting proteins include gel electrophoresis, isoelectric focusing, capillary electrophoresis, chromatography such as size exclusion chromatography, ion-exchange chromatography, and reversed-phase high performance liquid chromatography, peptide mapping, oligosaccharide mapping, mass spectrometry, ultraviolet absorbance spectroscopy, fluorescence spectroscopy, circular dichroism spectroscopy, isothermal titration calorimetry, differential scanning calorimetry, analytical ultra-centrifugation, dynamic light scattering, proteolysis, and cross-linking, turbidity measurement, filter retardation assays, immunological assays, fluorescent dye binding assays, protein-staining assays, microscopy, and detection of aggregates via ELISA or other binding assay. Structural analysis employing X-ray crystallographic techniques and NMR spectroscopy may also find use. In one embodiment, stability and/or solubility may be measured by determining the amount of protein solution after some defined period of time. In this assay, the protein may or may not be exposed to some extreme condition, for example elevated temperature, low pH, or the presence of denaturant. Because function typically requires a stable, soluble, and/or well-folded/structured protein, the aforementioned functional and binding assays also provide ways to perform such a measurement. For example, a solution comprising an Ep-CAM targeting protein could be assayed for its ability to bind target antigen, then exposed to elevated temperature for one or more defined periods of time, then assayed for antigen binding again. Because unfolded and aggregated protein is not expected to be capable of binding antigen, the amount of activity remaining provides a measure of the Ep-CAM targeting protein's stability and solubility.

In a preferred embodiment, the library is screened using one or more cell-based or in vitro assays. For such assays, Ep-CAM targeting proteins, purified or unpurified, are typically added exogenously such that cells are exposed to individual variants or groups of variants belonging to a library. These assays are typically, but not always, based on the biology of the ability of the anti-Ep-CAM antibody or Fc fusion to bind to Ep-CAM and mediate some biochemical event, for example effector functions like cellular lysis, phagocytosis, ligand/receptor binding inhibition, inhibition of growth and/or proliferation, and the like. Such assays often involve monitoring the response of cells to Ep-CAM targeting protein, for example cell survival, cell death, cellular phagocytosis, cell lysis, change in cellular morphology, or transcriptional activation such as cellular expression of a natural gene or reporter gene, For example, such assays may measure the ability of Ep-CAM targeting proteins to elicit ADCC, ADCP, or CDC. For some assays additional cells or components, that is in addition to the target cells, may need to be added, for example serum complement, or effector cells such as peripheral blood monocytes (PBMCs), NK cells, macrophages, and the like. Such additional cells may be from any organism, preferably humans, mice, rat, rabbit, and monkey. Crosslinked or monomeric antibodies and Fc fusions may cause apoptosis of certain cell lines expressing the antibody's target antigen, or they may mediate attack on target cells by immune cells which have been added to the assay. Methods for monitoring cell death or viability are known in the art, and include the use of dyes, fluorophores, immunochemical, cytochemical, and radioactive reagents. For example, caspase assays or annexin-flour conjugates may enable apoptosis to be measured, and uptake or release of radioactive substrates (e.g. Chromium-51 release assays) or the metabolic reduction of fluorescent dyes such as alamar blue may enable cell growth, proliferation or activation to be monitored. In a preferred embodiment, the DELFIA® EuTDA-based cytotoxicity assay (Perkin Elmer, Mass.) is used. Alternatively, dead or damaged target cells may be monitored by measuring the release of one or more natural intracellular proteins, for example lactate dehydrogenase. Transcriptional activation may also serve as a method for assaying function in cell-based assays. In this case, response may be monitored by assaying for natural genes or proteins which may be upregulated or down-regulated, for example the release of certain interleukins may be measured, or alternatively readout may be via a luciferase or GFP-reporter construct. Cell-based assays may also involve the measure of morphological changes of cells as a response to the presence of an Ep-CAM targeting protein. Cell types for such assays may be prokaryotic or eukaryotic, and a variety of cell lines that are known in the art may be employed. Alternatively, cell-based screens are performed using cells that have been transformed or transfected with nucleic acids encoding the Ep-CAM targeting proteins.

In vitro assays include but are not limited to binding assays, ADCC, CDC, cytotoxicity, proliferation, peroxide/ozone release, chemotaxis of effector cells, inhibition of such assays by reduced effector function antibodies; ranges of activities such as >100× improvement or >100× reduction, blends of receptor activation and the assay outcomes that are expected from such receptor profiles.

Animal Models

The biological properties of the Ep-CAM targeting proteins of the present invention may be characterized in cell, tissue, and whole organism experiments. As is know in the art, drugs are often tested in animals, including but not limited to mice, rats, rabbits, dogs, cats, pigs, and monkeys, in order to measure a drug's efficacy for treatment against a disease or disease model, or to measure a drug's pharmacokinetics, toxicity, and other properties. The animals may be referred to as disease models. With respect to the Ep-CAM targeting proteins of the present invention, a particular challenge arises when using animal models to evaluate the potential for in-human efficacy of candidate polypeptides—this is due, at least in part, to the fact that Ep-CAM targeting proteins that have a specific effect on the affinity for a human Fc receptor may not have a similar affinity effect with the orthologous animal receptor. These problems can be further exacerbated by the inevitable ambiguities associated with correct assignment of true orthologues (Mechetina et al., *Immunogenetics*, 2002 54:463-468, expressly incorporated by reference), and the fact that some orthologues simply do not exist in the animal (e.g. humans possess an FcRIIa whereas mice do not). Therapeutics are often tested in mice, including but not limited to nude mice, SCID mice, xenograft mice, and transgenic mice (including knockins and knockouts). For example, an anti-Ep-CAM antibody or Fc fusion of the present invention that is intended as an anti-cancer therapeutic may be tested in a mouse cancer model, for example a xenograft mouse. In this method, a tumor or tumor cell line is grafted onto or injected into a mouse, and subsequently the mouse is treated with the therapeutic to determine the ability of the anti-Ep-CAM antibody or Fc fusion to reduce or inhibit cancer growth and metastasis. An alternative approach is the use of a SCID murine model in which immune-deficient mice are injected with human PBLs, conferring a semi-functional and human immune system—with an appropriate array of human FcRs—to the mice that have subsequently been injected with antibodies or Fc-polypeptides that target injected human tumor cells. In such a model, the Fc-polypeptides that target the desired antigen (such as her2/neu on SkOV3 ovarian cancer cells) interact with human PBLs within the mice to engage tumoricidal effector functions Such experimentation may provide meaningful data for determination of the potential of the Ep-CAM targeting protein to be used as a therapeutic. Any organism, preferably mammals, may be used for testing. For example because of their genetic similarity to humans, monkeys can be suitable therapeutic models, and thus may be used to test the efficacy, toxicity, pharmacokinetics, or other property of the anti-Ep-CAM antibodies and Fc fusions of the present invention. Tests of the Ep-CAM targeting proteins of the present invention in humans are ultimately required for approval as drugs, and thus of course these experiments are contemplated. Thus the Ep-CAM targeting proteins of the present invention may be tested in humans to determine their therapeutic efficacy, toxicity, pharmacokinetics, and/or other clinical properties.

The Ep-CAM targeting proteins of the present invention may confer superior performance on Fc-containing therapeutics in animal models or in humans. The receptor binding profiles of such Ep-CAM targeting proteins, as described in this specification, may, for example, be selected to increase the potency of cytotoxic drugs or to target specific effector functions or effector cells to improve the selectivity of the drug's action. Further, receptor binding profiles can be selected that may reduce some or all effector functions thereby reducing the side-effects or toxicity of such Fc-containing drug. For example, an Ep-CAM targeting protein with reduced binding to FcγRIIa, FcγRI and FcγRIIa can be selected to eliminate most cell-mediated effector function, or an Ep-CAM targeting protein with reduced binding to C1q may be selected to limit complement-mediated effector functions. In some contexts, such effector functions are known to have potential toxic effects, therefore eliminating them may increase the safety of the Fc-bearing drug and such improved safety may be characterized in animal models. In some contexts, such effector functions are known to mediate the desirable therapeutic activity, therefore enhancing them may increase the activity or potency of the Fc-bearing drug and such improved activity or potency may be characterized in animal models.

Optimized Ep-CAM targeting proteins can be tested in a variety of orthotopic tumor models. These clinically relevant animal models are important in the study of pathophysiology and therapy of aggressive cancers like pancreatic, prostate and breast cancer. Immune deprived mice including, but not limited to athymic nude or SCID mice are frequently used in scoring of local and systemic tumor spread from the site of intraorgan (e.g. pancreas, prostate or mammary gland) injection of human tumor cells or fragments of donor patients.

In preferred embodiments, Ep-CAM targeting proteins of the present invention may be assessed for efficacy in clinically relevant animal models of various human diseases. In many cases, relevant models include various transgenic animals for specific tumor antigens, Relevant transgenic models such as those that express human Fc receptors (e.g., CD16 including the gamma chain, FCγR1, RIIa/b, and others) could be used to evaluate and test Ep-CAM targeting protein antibodies and Fc-fusions in their efficacy. The evaluation of Ep-CAM targeting proteins by the introduction of human genes that directly or indirectly mediate effector function in mice or other rodents that may enable physiological studies of efficacy in tumor toxicity or other diseases such as autoimmune disorders and RA. Human Fc receptors such as FCγRIIIa may possess polymorphisms such as that in position 158 V or F which would further enable the introduction of specific and combinations of human polymorphisms into rodents. The various studies involving polymorphism-specific FcRs is not limited to this section, however encompasses all discussions and applications of FcRs in general as specified in throughout this application. Ep-CAM targeting proteins of the present invention may confer superior activity on Fc-containing drugs in such transgenic models, in particular variants with binding profiles optimized for human FcγRIIIa mediated activity may show superior activity-in transgenic CD16 mice. Similar improvements in efficacy in mice transgenic for the other human Fc receptors, e.g. FcγRIIa, FcγRI, etc., may be observed for EP-CAM targeting proteins with binding profiles optimized for the respective receptors. Mice transgenic for multiple human receptors would show improved activity for Ep-CAM targeting proteins with binding profiles optimized for the corresponding multiple receptors, for example as outlined in Table 1.

Because of the difficulties and ambiguities associated with using animal models to characterize the potential efficacy of candidate therapeutic antibodies in a human patient, some variant polypeptides of the present invention may find utility as proxies for assessing potential in-human efficacy. Such proxy molecules would preferably mimic—in the animal system—the FcR and/or complement biology of a corresponding candidate human Ep-CAM targeting protein. This mimicry is most likely to be manifested by relative association affinities between specific Ep-CAM targeting proteins and animal vs. human receptors. For example, if one were using a mouse model to assess the potential in-human efficacy of an Ep-CAM targeting protein that has enhanced affinity for human FcRIIIa, an appropriate proxy variant would have enhanced affinity for mouse FcRIII-2 (mouse CD16-2), Alternatively if one were using a mouse model to assess the potential in-human efficacy of an Ep-CAM targeting protein that has reduced affinity for the inhibitory human FcRIIb, an appropriate proxy variant would have reduced affinity for mouse FcRII. It should also be noted that the proxy Ep-CAM targeting proteins could be created in the context of a human Ep-CAM targeting protein, an animal Ep-CAM targeting protein, or both.

In a preferred embodiment, the testing of Ep-CAM targeting proteins may include study of efficacy in primates (e.g. cynomolgus monkey model) to facilitate the evaluation of depletion of specific target cells harboring Ep-CAM antigen. Additional primate models include but not limited to that of the rhesus monkey and Fc polypeptides in therapeutic studies of autoimmune, transplantation and cancer, Toxicity studies are performed to determine the antibody or Fc-fusion related-effects that cannot be evaluated in standard pharmacology profile or occur only after repeated administration of the agent. Most toxicity tests are performed in two species—a rodent and a non-rodent—to ensure that any unexpected adverse effects are not overlooked before new therapeutic entities are introduced into man. In general, these models may measure a variety of toxicities including genotoxicity, chronic toxicity, immunogenicity, reproductive/developmental toxicity and carcinogenicity. Included within the aforementioned parameters are standard measurement of food consumption, bodyweight, antibody formation, clinical chemistry, and macro- and microscopic examination of standard organs/tissues (e.g. cardiotoxicity). Additional parameters of measurement are injection site trauma and the measurement of neutralizing antibodies, if any. Traditionally, monoclonal antibody therapeutics, naked or conjugated are evaluated for cross-reactivity with normal tissues, immunogenicity/antibody production, conjugate or linker toxicity and "bystander" toxicity of radiolabeled species. Nonetheless, such studies may have to be individualized to address specific concerns and following the guidance set by ICH S6 (Safety studies for biotechnological products also noted above). As such, the general principles are that the products are sufficiently well characterized and for which impurities/contaminants have been removed, that the test material is comparable throughout development, and GLP compliance.

The pharmacokinetics (PK) of the Ep-CAM targeting proteins of the invention can be studied in a variety of animal systems, with the most relevant being non-human primates such as the cynomolgus, rhesus monkeys. Single or repeated i.v. or s.c. administrations over a dose range of 6000-fold (0.05-300 mg/kg) can be evaluated for the half-life (days to weeks) using plasma concentration and clearance as well as volume of distribution at a steady state and level of systemic absorbance can be measured. Examples of such parameters of measurement generally include maximum observed plasma concentration (Cmax), the time to reach Cmax (Tmax) the area under the plasma concentration-time curve from time 0 to infinity [AUC(0-inf] and apparent elimination half-life (T1/2). Additional measured prameters could include compartmental analysis of concentration-time data obtained following i.v. administration and bioavailability. Examples of pharmacological/toxicological studies using cynomolgus have been established for Rituxan and Zevalin in which monoclonal antibodies to CD20 are cross-reactive. Biodistribution, dosimetry (for radiolabled antibodies or Fc fusions), and PK studies can also be done in rodent models. Such studies would evaluate tolerance at all doses administered, toxicity to local tissues, preferential localization to rodent xenograft animal models, depletion of target cells (e.g. CD20 positive cells).

The Ep-CAM targeting proteins of the present invention may confer superior pharmacokinetics on Fc-containing therapeutics in animal systems or in humans. For example, increased binding to FcRn may increase the half-life and exposure of the Fc-containing drug. Alternatively, decreased binding to FcRn may decrease the half-life and exposure of the Fc-containing drug in cases where reduced exposure is favorable such as when such drug has side-effects.

It is known in the art that the array of Fc receptors is differentially expressed on various immune cell types, as well as in different tissues. Differential tissue distribution of Fc receptors may ultimately have an impact on the pharmacodynamic (PD) and pharmacokinetic (PK) properties of Ep-CAM targeting proteins of the present invention. Because Ep-CAM targeting proteins of the presentation have varying affinities for the array of Fc receptors, further screening of the polypeptides for PD and/or PK properties may be extremely useful for defining the optimal balance of PD, PK, and therapeutic efficacy conferred by each candidate polypeptide.

Pharmacodynamic studies may include, but are not limited to, targeting specific tumor cells or blocking signaling mechanisms, measuring depletion of target antigen expressing cells or signals, etc. The Ep-CAM targeting proteins of the present invention may target particular effector cell populations and thereby direct Fc-containing drugs to recruit certain activities to improve potency or to increase penetration into a particularly favorable physiological compartment. For example, neutrophil activity and localization can be targeted by an Ep-CAM targeting protein that preferentially targets FcγRIIIb. Such pharmacodynamic effects may be demonstrated in animal models or in humans.

Clinical Use of Ep-CAM Targeting Proteins

The Ep-CAM targeting proteins of the present invention may be used for various therapeutic purposes. As will be appreciated by those skilled in the art, the Ep-CAM targeting proteins of the present invention may be used for any therapeutic purpose that antibodies Fc fusions, and the like may be used for. In a preferred embodiment, the Ep-CAM targeting proteins are administered to a patient to treat disorders including but not limited to cancer.

A "patient" for the purposes of the present invention includes both humans and other animals, preferably mammals and most preferably humans. Thus the Ep-CAM targeting proteins of the present invention have both human therapy and veterinary applications. The term "treatment" in the present invention is meant to include therapeutic treatment, as well as prophylactic, or suppressive measures for a disease or disorder. Thus, for example, successful administration of an Ep-CAM targeting protein prior to onset of the disease results in treatment of the disease. As another example, successful administration of an optimized Ep-CAM targeting protein after clinical manifestation of the disease to combat the symptoms of the disease comprises treatment of the disease. "Treatment" also encompasses administration of an optimized Ep-CAM targeting protein after the appearance of the disease in order to eradicate the disease. Successful administration of an agent after onset and after clinical symptoms have developed, with possible abatement of clinical symptoms and perhaps amelioration of the disease, comprises treatment of the disease. Those "in need of treatment" include mammals already having the disease or disorder, as well: as those prone to having the disease or disorder, including those in which the disease or disorder is to be prevented.

Diseases

In one embodiment, an Ep-CAM targeting protein of the present invention is administered to a patient having a disease involving inappropriate expression of a protein or other molecule. Within the scope of the present invention this is meant to include diseases and disorders characterized by aberrant proteins, due for example to alterations in the amount of a protein present, protein localization, posttranslational modification, conformational state, the presence of a mutant or pathogen protein, etc. Similarly, the disease or disorder may be characterized by alterations molecules including but not limited to polysaccharides and gangliosides. An overabundance may be due to any cause, including but not limited to overexpression at the molecular level, prolonged or accumulated appearance at the site of action, or increased activity of a protein relative to normal, Included within this definition are diseases and disorders characterized by a reduction of a protein. This reduction may be due to any cause, including but not limited to reduced expression at the molecular level, shortened or reduced appearance at the site of action, mutant forms of a protein, or decreased activity of a protein relative to normal. Such an overabundance or reduction of a protein can be measured relative to normal expression, appearance, or activity of a protein, and the measurement may play an important role in the development and/or clinical testing of the Ep-CAM targeting proteins of the present invention.

By "cancer" and "cancerous" herein refer to or describe the physiological condition in mammals that is typically characterized by unregulated cell growth. Examples of cancer include but are not limited to carcinoma, lymphoma, blastoma, sarcoma (including liposarcoma), neuroendocrine tumors, mesothelioma, schwanoma, meningioma, adenocarcinoma, melanoma, and leukemia or lymphoid malignancies.

More particular examples of such cancers include hematologic malignancies, such as Hodgkin's lymphoma; non-Hodgkin's lymphomas (Burkitt's lymphoma, small lymphocytic lymphoma/chronic lymphocytic leukemia, mycosis fungoides, mantle cell lymphoma, follicular lymphoma, diffuse large B-cell lymphoma, marginal zone lymphoma, hairy cell leukemia and lymphoplasmacytic leukemia), tumors of lymphocyte precursor cells, including B-cell acute lymphoblastic leukemia/lymphoma, and T-cell acute lymphoblastic leukemia/lymphoma, thymoma, tumors of the mature T and NK cells, including peripheral T-cell leukemias, adult T-cell leukemia/T-cell lymphomas and large granular lymphocytic leukemia, Langerhans cell histocytosis, myeloid neoplasias such as acute myelogenous leukemias, including AML with maturation, AML without differentiation, acute promyelocytic leukemia, acute myelomonocytic leukemia, and acute monocytic leukemias, myelodysplastic syndromes, and chronic myeloproliferative disorders, including chronic myelogenous leukemia; tumors of the central nervous system such as glioma, glioblastoma, neuroblastoma, astrocytoma, medulloblastoma, ependymoma, and retinoblastoma; solid tumors of the head and neck (eg. nasopharyngeal cancer, salivary gland carcinoma, and esophageal cancer), lung (eg. small-cell lung cancer, non-small cell lung cancer, adenocarcinoma of the lung and squamous carcinoma of the lung), digestive system (eg. gastric or stomach cancer including gastrointestinal cancer, cancer of the bile duct or biliary tract, colon cancer, rectal cancer, colorectal cancer, and anal carcinoma), reproductive system (eg. testicular, penile, or prostate cancer, uterine, vaginal, vulval, cervical, ovarian, and endometrial cancer), skin (eg. melanoma, basal cell carcinoma, squamous cell cancer, actinic keratosis), liver (eg. liver cancer, hepatic carcinoma, hepatocellular cancer, and hepatoma), bone (eg. osteoclastoma, and osteolytic bone cancers) additional tissues and organs (eg. pancreatic cancer, bladder cancer, kidney or renal cancer, thyroid cancer, breast cancer, cancer of the peritoneum, and Kaposi's sarcoma), and tumors of the vascular system (eg. angiosarcoma and hemagiopericytoma).

By "autoimmune diseases" herein include allogenic islet graft rejection, alopecia greata, ankylosing spondylitis, antiphospholipid syndrome, autoimmune Addison's disease, antineutrophil cytoplasmic autoantibodies (ANCA), autoimmune diseases of the adrenal gland, autoimmune hemolytic anemia, autoimmune hepatitis, autoimmune myocarditis, autoimmune neutropenia, autoimmune oophoritis and orchitis, autoimmune thrombocytopenia, autoimmune urticaria, Behcet's disease, bullous pemphigoid, cardiomyopathy, Castleman's syndrome, celiac spruce-dermatitis, chronic fatigue immune disfunction syndrome, chronic inflammatory demyelinating polyneuropathy, Churg-Strauss syndrome, cicatrical pemphigoid, CREST syndrome, cold agglutinin disease, Crohn's disease, dermatomyositis, discoid lupus, essential mixed cryoglobulinemia, factor VIII deficiency, fibromyalgia-fibromyositis, glomerulonephritis, Grave's disease, Guillain-Barre, Goodpasture's syndrome, graft-versus-host disease (GVHD), Hashimoto's thyroiditis, hemophilia A, idiopathic pulmonary fibrosis, idiopathic thrombocytopenia purpura (ITP), IgA neuropathy, IgM polyneuropathies, immune mediated thrombocytopenia, juvenile arthritis, Kawasaki's disease, lichen plantus, lupus erthematosis, Meniere's disease, mixed connective tissue disease, multiple sclerosis, type 1 diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobinulinemia, primary biliary cirrhosis, psoriasis, psoriatic arthritis, Reynauld's phenomenon, Reiter's syndrome, rheumatoid arthritis, sarcoidosis, scleroderma, Sjorgen's syndrome, solid organ transplant rejection, stiff-man syndrome, systemic lupus erythematosus, takayasu arteritis, temporal arteristis/giant cell arteritis, thrombotic thrombocytopenia purpura, ulcerative colitis, uveitis, vasculitides such as dermatitis herpetiformis vasculitis, vitiligo, and Wegner's granulomatosis.

By "inflammatory disorders" herein include acute respiratory distress syndrome (ARDS), acute septic arthritis, allergic encephalomyelitis, allergic rhinitis, allergic vasculitis, allergy, asthma, atherosclerosis, chronic inflammation due to chronic bacterial or viral infectionis, chronic obstructive pulmonary disease (COPD), coronary artery disease, encephalitis, inflammatory bowel disease, inflammatory osteolysis, inflammation associated with acute and delayed hypersensitivity reactions, inflammation associated with tumors, peripheral nerve injury or demyelinating diseases, inflammation associated with tissue trauma such as burns and ischemia, inflammation due to meningitis, multiple organ injury syndrome, pulmonary fibrosis, sepsis and septic shock, Stevens-Johnson syndrome, undifferentiated arthropy, and undifferentiated spondyloarthropathy.

By "infectious diseases" herein include diseases caused by pathogens such as viruses, bacteria, fungi, protozoa, and parasites. Infectious diseases may be caused by viruses including adenovirus, cytomegalovirus, dengue, Epstein-Barr, hanta, hepatitis A, hepatitis B, hepatitis C, herpes simplex type I, herpes simplex type II, human immunodeficiency virus, (HIV), human papilloma virus (HPV), influenza, measles, mumps, papova virus, polio, respiratory syncytial virus, rinderpest, rhinovirus, rotavirus, rubella, SARS virus, smallpox, viral meningitis, and the like. Infections diseases may also be caused by bacteria including *Bacillus antracis, Borrelia burgdorferi, Campylobacter jejuni, Chlamydia trachomatis, Clostridium botulinum, Clostridium tetani, Diptheria, E. coli, Legionella, Helicobacter pylori, Mycobacterium rickettsia, Mycoplasma nesisseria, Pertussis, Pseudomonas aeruginosa*, S. *pneumonia, Streptococcus, Staphylococcus, Vibria cholerae, Yersinia pestis*, and the like. Infectious diseases may also be caused by fungi such as *Aspergillus fumigatus, Blastomyces dermatitidis, Candida albicans, Coccidioides immitis, Cryptococcus neoformans, Histoplasma capsulatum, Penicillium marneffei*, and the like. Infectious diseases may also be caused by protozoa and parasites such as chlamydia, kokzidioa, *leishmania*, malaria, *rickettsia, trypanosoma*, and the like.

Furthermore, Ep-CAM targeting proteins of the present invention may be used to prevent or treat additional conditions including but not limited to heart conditions such as congestive heart failure (CHF), myocarditis and other conditions of the myocardium; skin conditions such as rosecea, acne, and eczema; bone and tooth conditions such as bone loss, osteoporosis, Paget's disease, Langerhans' cell histiocytosis, periodontal disease, disuse osteopenia, osteomalacia, monostotic fibrous dysplasia, polyostotic fibrous dysplasia, bone metastasis, bone pain management, humoral malignant hypercalcemia, periodontal reconstruction, spinal cord injury, and bone fractures; metabolic conditions such as Gaucher's disease; endocrine conditions such as Cushing's syndrome; and neurological conditions.

Formulation

Pharmaceutical compositions are contemplated wherein an Ep-CAM targeting protein of the present invention and one or more therapeutically active agents are formulated. Formulations of the Ep-CAM targeting proteins of the present invention are prepared for storage by mixing the Ep-CAM targeting protein having the desired degree of purity with optional pharmaceutically acceptable carriers, excipients or stabilizers (Remington's Pharmaceutical Sciences 16th edition, Osol, A. Ed., 1980, expressly incorporated by reference), in the form of lyophilized formulations or aqueous solutions. Acceptable carriers, excipients, or stabilizers are nontoxic to recipients at the dosages and concentrations employed, and include buffers such as phosphate, citrate, acetate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl orbenzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; sweeteners and other flavoring agents; fillers such as microcrystalline cellulose, lactose, corn and other starches: binding agents; additives; coloring agents; salt-forming counter-ions such as sodium; metal complexes (e.g. Zn-protein complexes); and/or non-ionic surfactants such as TWEEN™, PLURONICS™ or polyethylene glycol (PEG). In a preferred embodiment, the pharmaceutical composition that comprises the Ep-CAM targeting protein of the present invention may be in a water-soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine. The formulations to be used for in vivo administration are preferably sterile. This is readily accomplished by filtration through sterile filtration membranes or other methods.

The Ep-CAM targeting proteins disclosed herein may also be formulated as immunoliposomes. A liposome is a small vesicle comprising various types of lipids, phospholipids and/or surfactant that is useful for delivery of a therapeutic agent to a mammal. Liposomes containing the Ep-CAM targeting protein are prepared by methods known in the art, such as described in Epstein et al., 1985, *Proc Natl Acad Sci USA*, 82:3688; Hwang et al., 1980, *Proc Natl Acad Sci USA*, 77:4030; U.S. Pat. No. 4,485,045; U.S. Pat. No. 4,544,545; and PCT WO 97/38731, all expressly incorporated by reference. Liposomes with enhanced circulation time are disclosed in U.S. Pat. No. 5,013,556, expressly incorporated by reference. The components of the liposome are commonly arranged in a bilayer formation, similar to the lipid arrangement of biological membranes. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. A chemotherapeutic agent or other therapeutically active agent is optionally contained within the liposome (Gabizon et al., 1989, *J National Cancer Inst* 81:1484, expressly incorporated by reference).

The Ep-CAM targeting protein and other therapeutically active agents may also be entrapped in microcapsules prepared by methods including but not limited to coacervation techniques, interfacial polymerization (for example using hydroxymethylcellulose or gelatin-microcapsules, or poly-(methylmethacylate) microcapsules), colloidal drug delivery systems (for example, liposomes, albumin microspheres, microemulsions, nano-particles and nanocapsules), and macroemulsions. Such techniques are disclosed in Remington's Pharmaceutical Sciences 16th edition, Osol, A. Ed., 1980. Sustained-release preparations may be prepared. Suitable examples of sustained-release preparations include semipermeable matrices of solid hydrophobic polymer, which matrices are in the form of shaped articles, e.g. films, or microcapsules. Examples of sustained-release matrices include polyesters, hydrogels (for example poly(2-hydroxyethyl-methacrylate), or poly(vinylalcohol)), polylactides (U.S. Pat. No. 3,773,919), copolymers of L-glutamic acid and gamma ethyl-L-glutamate, non-degradable ethylene-vinyl acetate, degradable lactic acid-glycolic acid copolymers such as the Lupron Depot® (which are injectable microspheres composed of lactic acid-glycolic acid copolymer or lactic acid polymer and leuprolide acetate), poly-D-(−)-3-hydroxybutyric acid, and ProLease® (commercially available from Alkermes, which is a microsphere-based delivery system composed of the desired bioactive molecule incorporated into a matrix of poly-DL-lactide-co-glycolide (PLG)).

Administration

Administration of the pharmaceutical composition comprising an Ep-CAM targeting protein of the present invention, preferably in the form of a sterile aqueous solution, may be done in a variety of ways, including, but not limited to orally, subcutaneously, intravenously, intranasally, intraotically, transdermally, topically (e.g., gels, salves, lotions, creams, etc.), intraperitoneally, intramuscularly, intrapulmonary, vaginally, parenterally, rectally, or intraocularly. In some instances, for example for the treatment of wounds, inflammation, etc., the EP-CAM targeting protein may be directly applied as a solution or spray. As is known in the art, the pharmaceutical composition may be formulated accordingly depending upon the manner of introduction.

Subcutaneous administration may be preferable in some circumstances because the patient may self-administer the pharmaceutical composition. Many protein therapeutics are not sufficiently potent to allow for formulation of a therapeutically effective dose in the maximum acceptable volume for subcutaneous administration. This problem may be addressed in part by the use of protein formulations comprising arginine-HCl, histidine, and polysorbate (see WO 04091658). Anti-Ep-CAM antibodies or Fc fusions of the present invention may be more amenable to subcutaneous administration due to, for example, increased potency, improved serum half-life, or enhanced solubility.

As is known in the art, protein therapeutics are often delivered by IV infusion or bolus. The Ep-CAM targeting proteins of the present invention may also be delivered using such methods. For example, administration may venious be by intravenous infusion with 0.9% sodium chloride as an infusion vehicle.

Pulmonary delivery may be accomplished using an inhaler or nebulizer and a formulation comprising an aerosolizing agent. For example, AERx® inhalable technology commercially available from Aradigm, or Inhance™ pulmonary delivery system commercially available from Nektar Therapeutics may be used. Ep-CAM targeting proteins of the present invention may be more amenable to intrapulmonary delivery. FcRn is present in the lung, and may promote transport from the lung to the bloodstream (e.g. Syntonix WO 04004798, Bitonti et. al. (2004) Proc. Nat. Acad. Sci. 101: 9763-8, both expressly incorporated by reference). Accordingly, anti-Ep-CAM antibodies or Fc fusions that bind FcRn more effectively in the lung or that are released more efficiently in the bloodstream may have improved bioavailability following intrapulmonary administration. Ep-CAM targeting proteins of the present invention may also be more amenable to intrapulmonary administration due to, for example, improved solubility or altered isoelectric point.

Furthermore, Ep-CAM targeting proteins of the present invention may be more amenable to oral delivery due to, for example, improved stability at gastric pH and increased resistance to proteolysis. Furthermore, FcRn appears to be expressed in the intestinal epithelia of adults (Dickinson et. al. (1999) J. Clin. Invest. 104:903-11), so anti-Ep-CAM antibodies or Fc fusions of the present invention with improved FcRn interaction profiles may show enhanced bioavailability following oral administration. FcRn mediated transport of Ep-CAM targeting proteins may also occur at other mucus membranes such as those in the gastrointestinal, respiratory, and genital tracts (Yoshida et. al. (2004) Immunity 20:769-83).

In addition, any of a number of delivery systems are known in the art and may be used to administer the Ep-CAM targeting proteins of the present invention. Examples include, but are not limited to, encapsulation in liposomes, microparticles, microspheres (eg. PLA/PGA microspheres), and the like. Alternatively, an implant of a porous, non-porous, or gelatinous material, including membranes or fibers, may be used. Sustained release systems may comprise a polymeric material or matrix such as polyesters, hydrogels, poly(vinylalcohol), polylactides, copolymers of L-glutamic acid and ethyl-L-gutamate, ethylene-vinyl acetate, lactic acid-glycolic acid copolymers such as the Lupron Depot®, and poly-D-(-)-3-hydroxyburyric acid. It is also possible to administer a nucleic acid encoding the Ep-CAM targeting protein of the current invention, for example by retroviral infection, direct injection, or coating with lipids, cell surface receptors, or other transfection agents. In all cases, controlled release systems may be used to release the Ep-CAM targeting protein at or close to the desired location of action.

Dosing

The dosing amounts and frequencies of administration are, in a preferred embodiment, selected to be therapeutically or prophylactically effective. As is known in the art, adjustments for protein degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

The concentration of the therapeutically active Ep-CAM targeting protein in the formulation may vary from about 0.1 to 100 weight %. In a preferred embodiment, the concentration of the Ep-CAM targeting protein is in the range of 0.003 to 1.0 molar. In order to treat a patient, a therapeutically effective dose of the Ep-CAM targeting protein of the present invention may be administered. By "therapeutically effective dose" herein is meant a dose that produces the effects for which it is administered. The exact dose will depend on the purpose of the treatment, and will be ascertainable by one skilled in the art using known techniques. Dosages may range from 0.0001 to 100 mg/kg of body weight or greater, for example 0.1, 1, 10, or 50 mg/kg of body weight, with 1 to 10 mg/kg being preferred.

In some embodiments, only a single dose of the Ep-CAM targeting protein is used. In other embodiments, multiple doses of the Ep-CAM targeting protein are administered. The elapsed time between administrations may be less than 1 hour, about 1 hour, about 1-2 hours, about 2-3 hours, about 3-4 hours, about 6 hours, about 12 hours, about 24 hours, about 48 hours, about 2-4 days, about 4-6 days, about 1 week, about 2 weeks, or more than 2 weeks.

In other embodiments the Ep-CAM targeting proteins of the present invention are administered in metronomic dosing regimes, either by continuous infusion or frequent administration without extended rest periods. Such metronomic administration may involve dosing at constant intervals without rest periods, Typically such regimens encompass chronic low-dose or continuous infusion for an extended period of time, for example 1-2 days, 1-2 weeks, 1-2 months, or up to 6 months or more. The use of lower doses may minimize side effects and the need for rest periods.

In certain embodiments the Ep-CAM targeting protein of the present invention and one or more other prophylactic or therapeutic agents are cyclically administered to the patient. Cycling therapy involves administration of a first agent at one time, a second agent at a second time, optionally additional agents at additional times, optionally a rest period, and then repeating this sequence of administration one or more times. The number of cycles is typically from 2-10. Cycling therapy may reduce the development of resistance to one or more agents, may minimize side effects, or may improve treatment efficacy.

Combination Therapies

The Ep-CAM targeting proteins of the present invention may be administered concomitantly with one or more other therapeutic regimens or agents. The additional therapeutic regimes or agents may be used to improve the efficacy or safety of the Ep-CAM targeting protein. Also, the additional therapeutic regimes or agents may be used to treat the same disease or a comorbidity rather than to alter the action of the Ep-CAM targeting protein. For example, an EP-CAM targeting protein of the present invention may be administered to the patient along with chemotherapy, radiation therapy, or both chemotherapy and radiation therapy. The Ep-CAM targeting protein of the present invention may be administered in combination with one or more other prophylactic or therapeutic agents, including but not limited to cytotoxic agents, chemotherapeutic agents, cytokines, growth inhibitory agents, anti-hormonal agents, kinase inhibitors, anti-angiogenic agents, cardioprotectants, immunostimulatory agents, immunosuppressive agents, agents that promote proliferation of hematological cells, angiogenesis inhibitors, protein tyrosine kinase (PTK) inhibitors, additional Ep-CAM targeting proteins, FcγRIIb or other Fc receptor inhibitors, or other therapeutic agents.

The terms "in combination with" and "co-administration" are not limited to the administration of the prophylactic or therapeutic agents at exactly the same time. Instead, it is meant that the Ep-CAM targeting protein of the present invention and the other agent or agents are administered in a sequence and within a time interval such that they may act together to provide a benefit that is increased versus treatment with only either the Ep-CAM targeting protein of the present invention or the other agent or agents. It is preferred that the Ep-CAM targeting protein and the other agent or agents act additively, and especially preferred that they act synergistically. Such molecules are suitably present in combination in amounts that are effective for the purpose intended. The skilled medical practitioner can determine empirically, or by considering the pharmacokinetics and modes of action of the agents, the appropriate dose or doses of each therapeutic agent, as well as the appropriate timings and methods of administration.

In one embodiment, the Ep-CAM targeting proteins of the present invention are administered with one or more additional molecules comprising antibodies or Fc. The Ep-CAM targeting proteins of the present invention may be co-administered with one or more other antibodies that have efficacy in treating the same disease or an additional comorbidity; for example two antibodies may be administered that recognize two antigens that are overexpressed in a given type of cancer, or two antigens that mediate pathogenesis of an autoimmune or infectious disease.

Examples of anti-cancer antibodies that may be co-administered include, but are not limited to, anti 17-IA cell surface antigen antibodies such as Panorex™ (edrecolomab); anti-4-1BB antibodies; anti-4Dc antibodies; anti-A33 antibodies such as A33 and CDP-833; anti-α4β1 integrin antibodies such as natalizumab; anti-α4β7 integrin antibodies such as LDP-02; anti-αVβ1 integrin antibodies such as F-200, M-200, and SJ-749; anti-αVβ3 integrin antibodies such as abciximab, CNTO-95, Mab-17E6, and Vitaxin™; anti-complement factor 5 (C5) antibodies such as 5G1.1; anti-CA125 antibodies such as OvaRex® (oregovomab); anti-CD3 antibodies such as Nuvion® (visilizumab) and Rexomab; anti-CD4 antibodies such as IDEC-151, MDX-CD4, OKT4A; anti-CD6 antibodies such as Oncolysin B and Oncolysin CD6; anti-CD7 antibodies such as HB2; anti-CD19 antibodies such as B43, MT-103, and Oncolysin B; anti-CD20 antibodies such as 2H7, 2H7.v16, 2H7.v114, 2H7.v115, Bexxar® (tositumomab), Rituxan® (rituximab), and Zevalin® (Ibritumomab tiuxetan); anti-CG22 antibodies such as Lymphocide™ (epratuzumab); anti-CD23 antibodies such as IDEC-152; anti-CD25 antibodies such as basiliximab and Zenapax® (daclizumab); anti-CD30 antibodies such as AC10, MIDX-060, and SGN-30; anti-CD33 antibodies such as Mylotarg® (gemtuzumab ozogamicin), Oncolysin M, and Smart M195; anti-CD38 antibodies; anti-CD40 antibodies such as SGN40 and toralizumab; anti-CD40L antibodies such as 5c8, Antova™, and IDEC-131; anti-CD44 antibodies such as bivatuzumab; anti-CD46 antibodies; anti-CD52 antibodies such as Campath® (alemtuzumab); anti-CD55 antibodies such as SC-1; anti-CD56 antibodies such as huN901-DM1; anti-CD64 antibodies such as MDX-33; anti-CD66e antibodies such as XR-303; anti-CD74 antibodies such as IMMU-110; anti-CD80 antibodies such as galiximab and IDEC-114; anti-CGD9 antibodies such as MDX-214; anti-CD123 antibodies; anti-CD113B antibodies such as B-B4-DM1; anti-CD146 antibodies such as AA-98; anti-CD148 antibodies; anti-CEA antibodies such as cT84.66, labetuzumab, and Pentacea™; anti-CTLA-4 antibodies such as MDX-101; anti-CXCR4 antibodies; anti-Ep-CAM antibodies such as ABX-EGF, Erbitux® (cetuximab), IMC-C225, and Merck Mab 425; anti-Ep-CAM antibodies such as Crucell's anti-Ep-CAM, ING-1, and IS-IL-2; anti-ephrin B2/EphB4 antibodies; anti-Her2 antibodies such as Herceptin®, MDX-210; anti-FAP (fibroblast activation protein) antibodies such as sibrotuzumab; anti-ferritin antibodies such as NXT-211; anti-FGF-1 antibodies; anti-FGF-3 antibodies, anti-FGF-8 antibodies; anti-FGFR antibodies, anti-fibrin antibodies; anti-G250 antibodies such as WX-G250 and Rencarex®; anti-GD2 ganglioside antibodies such as EMD-273063 and TriGem; anti-GD3 ganglioside antibodies such as BEC2, KW-2871, and mitumomab; anti-gpIIb/IIIa antibodies such as ReoPro; anti-heparinase antibodies; anti-Her2/ErbB2 antibodies such as Herceptin® (trastuzumab), MDX-210, and pertuzumab; anti-HLA antibodies such as Oncolym®, Smart 1D10; anti-HM1.24 antibodies; anti-ICAM antibodies such as ICM3; anti-IgA receptor antibodies; anti-IGF-1 antibodies such as CP-751871 and EM-164; anti-IGF-1R antibodies such as IMC-A12; anti-IL-6 antibodies such as CNTO-328 and elsilimomab; anti-IL-15 antibodies such as HuMax™-IL15; anti-KDR antibodies; anti-laminin 5 antibodies; anti-Lewis Y antigen antibodies such as Hu3S193 and IGN-311; anti-MCAM antibodies; anti-Muc1 antibodies such as BravaRex and TriAb; anti-NCAM antibodies such as ERIC-1 and ICRT; anti-PEM antigen antibodies such as Theragyn and Therex; anti-PSA antibodies; anti-PSCA antibodies such as IG8; anti-Ptk antibodies; anti-PTN antibodies; anti-RANKL antibodies such as AMG-162; anti-RLIP76 antibodies; anti-SK-1 antigen antibodies such as Monopharm C; anti-STEAP antibodies; anti-TAG72 antibodies such as CC49-SCA and MDX-220; anti-TGF-β antibodies such as CAT-152; anti-TNF-α antibodies such as CDP571, CDP870, D2E7, Humira® (adalimumab), and Remicade® (infliximab); anti-TRAIL-R1 and TRAIL-R2 antibodies, anti-VE-cadherin-2 antibodies, and anti-VLA-4 antibodies such as Antegren™. Furthermore, anti-idiotype antibodies including but not limited to the GD3 epitope antibody BEC2 and the gp72 epitope antibody 105AD7, may be used. In addition, bispecific antibodies including but not limited to the anti-CD3/CD20 antibody Bi20 may be used.

Examples of antibodies that may be co-administered to treat autoimmune or inflammatory disease, transplant rejection, GVHD, and the like include, but are not limited to, anti-α4β7 integrin antibodies such as LDP-02, anti-beta2 integrin antibodies such as LDP-01, anti-complement (C5) antibodies such as 5G1.1, anti-CD2 antibodies such as BTI-322, MEDI-507, anti-CD3 antibodies such as OKT3, SMART anti-CD3, anti-CD4 antibodies such as IDEC-151, MDX-CD4, OKT4A, anti-CD11a antibodies, anti-CD14 antibodies such as IC14, anti-CD18 antibodies, anti-CD23 antibodies such as IDEC 152, anti-CD25 antibodies such as Zenapax, anti-CD40L antibodies such as 5c8, Antova, IDEC-131, anti-CD64 antibodies such as MDX-33, anti-CD80 antibodies such as IDEC-114, anti-CD147 antibodies such as ABX-CBL, anti-E-selectin antibodies such as CDP850, anti-gpIIb/IIIa antibodies such as ReoPro/Abcixima, anti-ICAM-3 antibodies such as ICM3, anti-CE antibodies such as VX-740, anti-FcR1 antibodies such as MDX-33, anti-IgE antibodies such as rhuMab-E25, anti-IL-4 antibodies such as S8-240683, anti-IL-5 antibodies such as SB-240563, SCH55700, anti-IL-8 antibodies such as ABX-IL8, anti-interferon gamma antibodies, and anti-TNFa antibodies such as CDP571, CDP870, D2E7, Infliximab, MAK-195F, anti-VLA-4 antibodies such as Antegren. Examples of other Fc-containing molecules that may be co-administered to treat autoimmune or inflammatory disease, transplant rejection, GVHD, and the like include, but are not limited to, the p75 TNF receptor/Fc fusion Enbrel® (etanercept) and Regeneron's IL-1 trap.

Examples of antibodies that may be co-administered to treat infectious diseases include, but are not limited to, anti-anthrax antibodies such as ABthrax, anti-CMV antibodies such as CytoGam and sevirumab, anti-cryptosporidium antibodies such as CryptoGAM, Sporidin-G, anti-helicobacter antibodies such as Pyloran, anti-hepatitis B antibodies such as HepeX-B, Nabi-HB, anti-HIV antibodies such as HRG-214, anti-RSV antibodies such as felvizumab, HNK-20, palivizumab, RespiGam, and anti-staphylococcus antibodies such as Aurexis, Aurograb, BSYX-A110, and SE-Mab.

Alternatively, the Ep-CAM targeting proteins of the present invention may be co-administered with one or more other molecules that compete for binding to one or more Fc receptors. For example, co-administering inhibitors of the inhibitory receptor FcγRIIb may result in increased effector function. Similarly, co-administering inhibitors of the activating receptors such as FcγRIIIa may minimize unwanted effector function-Fc receptor inhibitors include, but are not limited to, Fc molecules that are engineered to act as competitive inhibitors for binding to FcγRIIb FcγRIIIa, or other Fc receptors, as well as other immunoglobulins and specifically the treatment called IVIg (intravenous immunoglobulin). In one embodiment, the inhibitor is administered and allowed to act before the Ep-CAM targeting protein is administered. An alternative way of achieving the effect of sequential dosing would be to provide an immediate release dosage form of the Fc receptor inhibitor and then a sustained release formulation of the Ep-CAM targeting protein of the invention. The immediate release and controlled release formulations could be administered separately or be combined into one unit dosage form. Administration of an FcγRIIb inhibitor may also be used to limit unwanted immune responses, for example anti-Factor VIII antibody response following Factor VIII administration to hemophiliacs.

In one embodiment, the Ep-CAM targeting proteins of the present invention are administered with a chemotherapeutic agent. By "chemotherapeutic agent" as used herein is meant a chemical compound useful in the treatment of cancer. Examples of chemotherapeutic agents include but are not limited to alkylating agents such as thiotepa and cyclosphosphamide (CYTOXAN™); alkyl sulfonates such as busulfan, improsulfan and piposulfan; androgens such as calusterone, dromostanolone propionate, epitiostanol, mepitiostane, testolactone; anti-adrenals such as aminoglutethimide, mitotane, trilostane; anti-androgens such as flutamide, nilutamide, bicalutamide, leuprolide, and goserelin; antibiotics such as aclacinomysins, actinomycin, authramycin, azaserine, bleomycins, cactinomycin, caticheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti estrogens including for example tamoxifen, raloxifene, aromatase inhibiting 4(5)-imidazoles, 4-hydroxytamoxifen, trioxifene, keoxifene, LY 117018, onapristone, and toremifene (Fareston); anti-metabolites such as methotrexate and 5-fluorouracil (5-FU); folic acid analogues such as denopterin, methotrexate, pteropterin, trimetrexate; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; folic acid replenisher such as frolinic acid; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; platinum analogs such as cisplatin and carboplatin; vinblastine; platinum; proteins such as arginine deiminase and asparaginase; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; taxanes, e.g. paclitaxel (TAXOL®, Bristol-Myers Squibb Oncology, Princeton, N.J.) and docetaxel (TAXOTERE®, Rhne-Poulenc Rorer, Antony, France); topoisomerase inhibitor RFS 2000, thymidylate synthase inhibitor (such as Tomudex); additional chemotherapeutics including aceglatone; aldophosphamide glycoside; aminolevulinic acid; amsacrine; bestrabucil; bisantrene; edatraxate; defofamine; demecolcine; diaziquone; difluoromethylornithine (DMFO); elformithine; elliptinium acetate; etoglucid; gallium nitrate; hydroxyurea, lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; chlorambucil; gemcitabine; 6-thioguanine; mercaptopurine; methotrexate; etoposide (VP-16); ifosfamide; mitomycin C; mitoxantrone; vincristine; vinorelbine; navelbine; novantrone; teniposide; daunomycin; aminopterin; xeloda; ibandronate; CPT-11; retinoic acid; esperamicins; capecitabine. Pharmaceutically acceptable salts, acids or derivatives of any of the above may also be used.

A chemotherapeutic or other cytotoxic agent may be administered as a prodrug. By "prodrug" as used herein is meant a precursor or derivative form of a pharmaceutically active substance that is less cytotoxic to tumor cells compared to the parent drug and is capable of being enzymatically activated or converted into the more active parent form. See, for example Wilman, 1986, Biochemical Society Transactions, 615th Meeting Belfast, 14:375-382; and Stella et al., "Prodrugs: A Chemical Approach to Targeted Drug Delivery," Directed Drug Delivery, Borchardt et al., (ed.): 247-267, Humana Press, 1985; both expressly incorporated by reference. The prodrugs that may find use with the present invention include but are not limited to phosphate-containing prodrugs, thiophosphate-containing prodrugs, sulfate-containing prodrugs, peptide-containing prodrugs, D-amino acid-modified prodrugs, glycosylated prodrugs, beta-lactam-containing prod rugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use with the Ep-CAM targeting proteins of the present invention include but are not limited to any of the aforementioned chemotherapeutic agents.

A variety of other therapeutic agents may find use for administration with the Ep-CAM targeting proteins of the present invention. In one embodiment, the Ep-CAM targeting protein is administered with an anti-angiogenic agent. By "anti-angiogenic agent" as used herein is meant a compound that blocks, or interferes to some degree, the development of blood vessels. The anti-angiogenic factor may, for instance, be a small molecule or a protein, for example an antibody, Fc fusion, or cytokine, which binds to a growth factor or growth factor receptor involved in promoting angiogenesis. The preferred anti-angiogenic factor herein is an antibody that binds to Vascular Endothelial Growth Factor (VEGF). Other agents that inhibit signaling through VEGF may also be used, for example RNA-based therapeutics that reduce levels of VEGF or VEGF-R expression, VEGF-toxin fusions, Regeneron's VEGF-trap, and antibodies that bind VEGF-R. In an alternate embodiment, the Ep-CAM targeting protein is administered with a therapeutic agent that induces or enhances adaptive immune response, for example an antibody that targets CTLA-4. Additional anti-angiogenesis agents include, but are not limited to, angiostatin (plasminogen fragment), antithrombin III, angiozyme, ABT-627, Bay 12-9566, benefin, bevacizumab, bisphosphonates, BMS-275291, cartilage-derived inhibitor (CDI), CAI, CD59 complement fragment, CEP-7055, Col 3, combretastatin A-4, endostatin (collagen XVIII fragment), farnesyl transferase inhibitors, fibronectin fragment, gro-beta, halofuginone, heparinases, heparin hexasaccharide fragment, HMV833, human chorionic gonadotropin (hCG), IM-862, interferon alpha, interferon beta, interferon gamma, interferon inducible protein 10 (IP-10), interleukin-12, kringle 5 (plasminogen fragment), marimastat, metalloproteinase inhibitors (eg. TIMPs), 2-methodyestradiol, MMI 270 (CGS 27023A), plasminogen activiator inhibitor (PAI), platelet factor-4 (PF4), prinomastat, prolactin 16 kDa fragment, proliferin-related protein (PRP), PTK 787/ZK 222594, retinoids, solimastat, squalamine, SS3304, SU5416, SU6668, SU11248, tetrahydrocortisol-S, tetrathiomolybdate, thalidomide, thrombospondin-1 (TSP-1), TNP-470, transforming growth factor beta (TGF-β), vasculostatin, vasostatin (calreticulin fragment), ZS6126, and ZD6474.

In a preferred embodiment, the Ep-CAM targeting protein is administered with a tyrosine kinase inhibitor. By "tyrosine kinase inhibitor" as used herein is meant a molecule that inhibits to some extent tyrosine kinase activity of a tyrosine kinase. Examples of such inhibitors include but are not limited to quinazolines, such as PD 153035, 4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo (2,3-d) pyrimidines; curcumin (diferuloyl methane, 4,5-bis (4-fluoroanilino)phthalimide); tyrphostines containing nitrothiophene moieties; PD-0183805 (Warner-Lambert); antisense molecules (e.g. those that bind to ErbB-encoding nucleic acid); quinoxalines (U.S. Pat. No. 5,804,396); tryphostins (U.S. Pat. No. 5,804,396); ZD6474 (Astra Zeneca); PTK-787 (Novartis/Schering A G); pan-ErbB inhibitors such as C1-1033 (Pfizer); Affinitac (ISIS 3521; Isis/Lilly); Imatinib mesylate (STI571, Gleevec®; Novartis); PKI 166 (Novartis); GW2016 (Glaxo SmithKline); C1-1033 (Pfizer); EKB-569 (Wyeth); Semaxinib (Sugen); ZD6474 (AstraZeneca); PTK-787 (Novartis/Schering AG); INC-1C11 (Imclone); or as described in any of the following patent publications: U.S. Pat. No. 5,804,396; PCT WO 99(09016 (American Cyanimid); PCT WO 98/43960 (American Cyanamid); PCT WO 97/38983 (Warner-Lambert); PCT WO 99/06378 (Warner-Lambert); PCT WO 99/06396 (Warner-Lambert); PCT WO 96/30347 (Pfizer, Inc); PCT WO 96/33978 (AstraZeneca); PCT WO96/3397 (AstraZeneca); PCT WO 96/33980 (AstraZeneca), gefitinib (IRESSA™, ZD1839, AstraZeneca), and OSI-774 (Tarceva™, OSI Pharmaceuticals/Genentech); all expressly incorporated by reference.

In another embodiment, the Ep-CAM targeting protein is administered with one or more immunomodulatory agents. Such agents may increase or decrease production of one or more cytokines, up- or down-regulate self-antigen presentation, mask MHC antigens, or promote the proliferation, differentiation, migration, or activation state of one or more types of immune cells. Immunomodulatory agents include but not limited to: non-steroidal anti-inflammatory drugs (NSAIDs) such as asprin, ibuprofed, celecoxib, diclofenac, etodolac, fenoprofen, indomethacin, ketoralac, oxaprozin, nabumentone, sulindac, tolmentin, rofecoxib, naproxen, ketoprofen, and nabumetone; steroids (eg. glucocorticoids, dexamethasone, cortisone, hydroxycortisone, methylprednisolone, prednisone, prednisolone, trimcinolone, azulfidineicosanoids such as prostaglandins, thromboxanes, and leukotrienes; as well as topical steroids such as anthralin, calcipotriene, clobetasol, and tazarotene); cytokines such as TGFb, IFNa, IFNb, IFNg, IL-2, IL-4, IL-10; cytokine, chemokine, or receptor antagonists including antibodies, soluble receptors, and receptor-Fc fusions against BAFF, B7, CCR2, CCR5, CD2, CD3, CD4, CD6, CD7, CD8, CD11, CD14, CD15, CD17, CD18, CD20, CD23, CD28, CD40, CD40L, CD44, CD45, CD52, CD64, CD80, CD86, CD147, CD152, complement factors (C5, D) CTLA4, eotaxin, Fas, ICAM, ICOS, IFNα, IFNβ, IFNγ, IFNAR, IgE, IL-1, IL-2, IL-2R, IL-4, IL-5R, IL-6, IL-8, IL-9 IL-12, IL-13, IL-13R1, IL-15, IL-18R, IL-23, integrins, LFA-1, LFA-3, MHC, selectins, TGFβ, TNFα, TNFβ, TNF-R1, T-cell receptor, including Enbrel® (etanercept), Humira® (adalimumab), and Remicade® (infliximab); heterologous anti-lymphocyte globulin, other immunomodulatory molecules such as 2-amino-6-aryl-5 substituted pyrimidines, anti-idiotypic antibodies for MHC binding peptides and MHC fragments, azathioprine, brequinar, bromocryptine, cyclophosphamide, cyclosporine A, D-penicillamine, deoxyspergualin, FK506, glutaraldehyde, gold, hydroxychloroquine, leflunomide, malononitriloamides (eg. leflunomide), methotrexate, minocycline, mizoribine, mycophenolate mofetil, rapamycin, and sulfasasazine.

In an alternate embodiment, Ep-CAM targeting protein of the present invention are administered with a cytokine. By "cytokine" as used herein is meant a generic term for proteins released by one cell population that act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (ESH), thyroid stimulating hormone (TSH), and luteinizing hormone (LH); hepatic growth factor; fibroblast growth factor; prolactin; placental lactogen; tumor necrosis factor-alpha and -beta; mulierian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSE (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines, In a preferred embodiment, cytokines or other agents that stimulate cells of the immune system are co-administered with the Ep-CAM targeting protein of the present invention. Such a mode of treatment may enhance desired effector function. For example, agents that stimulate NK cells, including but not limited to IL-2 may be co-administered. In another embodiment, agents that stimulate macrophages, including but not limited to C5a, formyl peptides such as N-formyl-methionyl-leucyl-phenylalanine (Beigier-Bompadre et. al. (2003) Scand. J. Immunol. 57: 221-8, expressly incorporated by reference), may be co-administered. Also, agents that stimulate neutrophils, including but not limited to G-CSF, GM-CSF, and the like may be administered. Furthermore, agents that promote migration of such immunostimulatory cytokines may be used. Also additional agents including but not limited to interferon gamma, IL-3 and IL-7 may promote one or more effector functions.

In an alternate embodiment, cytokines or other agents that inhibit effector cell function are co-administered with the Ep-CAM targeting protein of the present invention. Such a mode of treatment may limit unwanted effector function.

In an additional embodiment, the Ep-CAM targeting protein is administered with one or more antibiotics, including but not limited to: aminoglycoside antibiotics (eg. apramycin, arbekacin, bambermycins, butirosin, dibekacin, gentamicin, kanamycin, neomycin, netilmicin, paromomycin, ribostamycin, sisomycin, spectrinomycin), aminocyclitols (eg. sprctinomycin), amphenicol antibiotics (eg. azidamfenicol, chloramphenicol, florfrnicol, and thiamphemicol), ansamycin antibiotics (eg. rifamide and rifampin), carbapenems (eg. imipenem, meropenem, panipenem); cephalosporins (eg. cefaclor, cefadroxil, cefamandole, cefatrizine, cefazedone, cefozopran, cefpimizole, cefpiramide, cefpirome, cefprozil, cefuroxine, cefixime, cephalexin, cephradine), cephamycins (cefbuperazone, cefoxitin, cefminox, cefmetazole, and cefotetan); lincosamides (eg. clindamycin, lincomycin); macrolide (eg. azithromycin, brefeldin A, clarithromycin, erythromycin, roxithromycin, tobramycin), monobactams (eg. aztreonam, carumonam, and tigernonam); mupirocin; oxacephems (eg. flomoxef, latamoxeft and moxalactam); penicillins (eg. amdinocillin, amdinocillin pivoxil, amoxicillin, bacampicillin, bexzylpenicillinic acid, benzylpenicillin sodium, epicillin, fenbenicillin, floxacillin, penamecillin, penethamate hydriodide, penicillin o-benethamine, penicillin O, penicillin V, penicillin V benzoate, penicillin V hydrabamine, penimepicycline, and phencihicillin potassium); polypeptides (eg. bacitracin, colistin, polymixin B, teicoplanin, vancomycin); quinolones (am ifloxacin, cinoxacin, ciprofloxacin, enoxacin, enrofloxacin, feroxacin, flume-quine, gatifloxacin, gemifloxacin, grepafloxacin, lomefloxacin, moxifloxacin, nalidixic acid, norfloxacin, ofloxacin, oxotinic acid, pefloxacin, pipemidic acid, rosoxacin, rufloxacin, sparfloxacin, temafloxacin, tosufloxacin, trovafloxacin); rifampin: streptogramins (eg quinupristin, dalfopristin); sulfonamides (sulfanilamide, sulfamethoxazole); tetracyclenes (chiortetracycline, demeclocycline hydrochloride, demethylchlortetracycline, doxycycline, duramycin, minocycline, neomycin, oxytetracycline, streptomycin, tetracycline, vancomycin).

Anti-fungal agents such as amphotericin B, ciclopirox, clotrimazole, econazole, fluconazole, flucytosine, itraconazoie, ketoconazole, niconazole, nystatin, terbinafine, terconazole, and tioconazole may also be used.

Antiviral agents including protease inhibitors, reverse transcriptase inhibitors, and others, including type I interferons, viral fusion inhibitors, and neuramidase inhibitors, may also be used. Examples of antiviral agents include, but are not limited to, acyclovir, adefovir, amantadine, amprenavir, clevadine, enfuvirtide, entecavir, foscarnet, gangcyclovir, idoxuridine, indinavir, lopinavir, pleconaril, ribavirin, rimantadine, ritonavir, saquinavir, trifluridine, vidarabine, and zidovudine, may be used.

The Ep-CAM targeting proteins of the present invention may be combined with other therapeutic regimens. For example, in one embodiment, the patient to be treated with an anti-Ep-CAM antibody or fc fusion of the present invention may also receive radiation therapy. Radiation therapy can be administered according to protocols commonly employed in the art and known to the skilled artisan. Such therapy includes but is not limited to cesium, iridium, iodine, or cobalt radiation. The radiation therapy may be whole body irradiation, or may be directed locally to a specific site or tissue in or on the body, such as the lung, bladder, or prostate. Typically; radiation therapy is administered in pulses over a period of time from about 1 to 2 weeks. The radiation therapy may, however, be administered over longer periods of time. For instance, radiation therapy may be administered to patients having head and neck cancer for about 6 to about 7 weeks. Optionally, the radiation therapy may be administered as a single dose or as multiple, sequential doses. The skilled medical practitioner can determine empirically the appropriate dose or doses of radiation therapy useful herein. In accordance with another embodiment of the invention, the Ep-CAM targeting protein of the present invention and one or more other anti-cancer therapies are employed to treat cancer cells ex vivo. It is contemplated that such ex vivo treatment may be useful in bone marrow transplantation and particularly, autologous bone marrow transplantation. For instance, treatment of cells or tissue(s) containing cancer cells with Ep-CAM targeting protein and one or more other anti-cancer therapies, such as described above, can be employed to deplete or substantially deplete the cancer cells prior to transplantation in a recipient patient.

Radiation therapy may also comprise treatment with an isotopically labeled molecule, such as an antibody. Examples of radioimmunotherapeutics include but Zevalin™ (Y-90 labeled anti-CD20), LymphoCide™ (Y-90 labeled anti-CD22) and Bexxar™ (I-131 labeled anti-CD20)

It is of course contemplated that the Ep-CAM targeting proteins of the invention may employ in combination with still other therapeutic techniques such as surgery or phototherapy.

A number of the receptors that may interact with the Ep-CAM targeting proteins of the present invention are polymorphic in the human population. For a given patient or population of patients, the efficacy of the Ep-CAM targeting proteins of the present invention may be affected by the presence or absence of specific polymorphisms in proteins. For example, FcγRIIIA is polymorphic at position 158, which is commonly either V (high affinity) or F (low affinity). Patients with the V/V homozygous genotype are observed to have a better clinical response to treatment with the anti-CD20 antibody Rituxan® (rituximab), likely because these patients mount a stronger NK response (Dall'Ozzo et. al. (2004) Cancer Res. 64:4664-9, expressly incorporated by reference). Additional polymorphisms include but are not limited to FcγRIIA R131 or H131, and such polymorphisms are known to either increase or decrease Fc binding and subsequent biological activity, depending on the polymorphism. Ep-CAM targeting proteins of the present invention may bind preferentially to a particular polymorphic form of a receptor, for example FcγRIIIA 158 V, or to bind with equivalent affinity to all of the polymorphisms at a particular position in the receptor, for example both the 158V and 158F polymorphisms of FcγRIIIA. In a preferred embodiment, Ep-CAM targeting proteins of the present invention may have equivalent binding to polymorphisms may be used in an antibody to eliminate the differential efficacy seen in patients with different polymorphisms. Such a property may give greater consistency in therapeutic response and reduce non-responding patient populations. Such variant Fc with identical binding to receptor polymorphisms may have increased biological activity, such as ADCC, CDC or circulating half-life, or alternatively decreased activity, via modulation of the binding to the relevant Fc receptors. In a preferred embodiment, Ep-CAM targeting proteins of the present invention may bind with higher or lower affinity to one of the polymorphisms of a receptor, either accentuating the existing difference in binding or reversing the difference. Such a property may allow creation of therapeutics particularly tailored for efficacy with a patient population possessing such polymorphism. For example, a patient population possessing a polymorphism with a higher affinity for an inhibitory receptor such as FcγRIIB could receive a drug containing an Ep-CAM targeting protein with reduced binding to such polymorphic form of the receptor, creating a more efficacious drug.

In a preferred embodiment, patients are screened for one or more polymorphisms in order to predict the efficacy of the Ep-CAM targeting proteins of the present invention. This information may be used, for example, to select patients to include or exclude from clinical trials or, post-approval, to provide guidance to physicians and patients regarding appropriate dosages and treatment options. For example, in patients that are homozygous or heterozygous for FcγRIIIA 158F antibody drugs such as the anti-CD20 mAb, Rituximab are minimally effective (Carton 2002 Blood 99: 754-758; Weng 2003 J. Clin. Oncol. 21:3940-3947); such patients may show a much better clinical response to the antibodies of the present invention. In one embodiment, patients are selected for inclusion in clinical trials for an antibody of the present invention if their genotype indicates that they are likely to respond significantly better to an antibody of the present invention as compared to one or more currently used antibody therapeutics. In another embodiment, appropriate dosages and treatment regimens are determined using such genotype information. In another embodiment, patients are selected for inclusion in a clinical trial or for receipt of therapy post-approval based on their polymorphism genotype, where such therapy contains an Ep-CAM targeting protein engineered to be specifically efficacious for such population, or alternatively where such therapy contains an Ep-CAM targeting protein that does not show differential activity to the different forms of the polymorphism.

Included in the present invention are diagnostic tests to identify patients who are likely to show a favorable clinical response to an Ep-CAM targeting protein of the present invention, or who are likely to exhibit a significantly better response when treated with an Ep-CAM targeting protein of the present invention versus one or more currently used antibody therapeutics. Any of a number of methods for determining FcγR polymorphisms in humans known in the art may be used.

Furthermore, the present invention comprises prognostic tests performed on clinical samples such as blood and tissue samples. Such tests may assay for effector function activity, including but not limited to ADCC, CDC, phagocytosis, and opsonization, or for killing, regardless of mechanism, of cancerous or otherwise pathogenic cells. In a preferred embodiment, ADCC assays, such as those described previously, are used to predict, for a specific patient, the efficacy of a given Ep-CAM targeting protein of the present invention. Such information may be used to identify patients for inclusion or exclusion in clinical trials, or to inform decisions regarding appropriate dosages and treatment regimens. Such information may also be used to select a drug that contains a particular Ep-CAM targeting protein that shows superior activity in such assay.

EXAMPLES

Examples are provided below to illustrate the present invention. These examples are not meant to constrain the present invention to any particular application or theory of operation. For reference to immunoglobulin constant regions, positions are numbered according to the EU index as in Kabat (Kabat et al., 1991, *Sequences of Proteins of Immunological Interest*, 5th Ed., United States Public Health Service, National Institutes of Health, Bethesda; expressly incorporated by reference). Those skilled in the art of antibodies will appreciate that this convention consists of nonsequential numbering in specific regions of an immunoglobulin sequence, enabling a normalized reference to conserved positions in immunoglobulin families. Accordingly, the positions of any given immunoglobulin as defined by the EU index will not necessarily correspond to its sequential sequence.

Example 1

Anti-Ep-CAM Antibodies with Reduced Immunogenicity

FIGS. 1 and 2 provide some heavy and light chain variable region sequences of the anti-Ep-CAM antibodies used in the present study. The mouse, parent chimeric heavy and light chains are labeled H0 17-1A and L0 17-1A respectively. Due to the wide use of hybridoma technology, a substantial number of antibodies are derived from nonhuman sources. However, nonhuman proteins are often immunogenic when administered to humans, thereby greatly reducing their therapeutic utility. Immunogenicity is the result of a complex series of responses to a substance that is perceived as foreign, and may include production of neutralizing and non-neutralizing antibodies, formation of immune complexes, complement activation, mast cell activation, inflammation, hypersensitivity responses, and anaphylaxis. Several factors can contribute to protein immunogenicity, including but not limited to protein sequence, route and frequency of administration, and patient population. Immunogenicity may limit the efficacy and safety of a protein therapeutic in multiple ways. Efficacy can be reduced directly by the formation of neutralizing antibodies. Efficacy may also be reduced indirectly, as binding to either neutralizing or non-neutralizing antibodies typically leads to rapid clearance from serum. Severe side effects and even death may occur when an immune reaction is raised. Thus in a preferred embodiment, protein engineering is used to reduce the immunogenicity of the Ep-CAM targeting proteins of the present invention.

In order to reduce the potential for immunogenicity of the anti-Ep-CAM proteins of the present invention, the immunogenicity of the anti-Ep-CAM antibody 17-1A was reduced using a method described in U.S. Ser. No. 60/619,483, filed Oct. 14, 2004 and U.S. Ser. No. 11/004,590, entitled "Methods of Generating Variant Proteins with Increased Host String Content and Compositions Thereof", filed on Dec. 6, 2004. The methods reduce the potential for immunogenicity by increasing the human string content of the antibody through mutations. The heavy and light chains with reduced potential for immunogenicity are named H1, H2, H3, H4, H5, H6, H2.1, H2.2, etc and L1, L2, L3, L4, L3.1, L3.2 etc and are shown in FIGS. 1 and 2. The heavy and light chains of the original antibody, 17-1A, are referred to as H0 and L0.

Example 2

Combinations of the different heavy and light chains were expressed and the resulting antibodies, with names such as H3L3, H3/L3 or H3_L3, were purified and examined. Anti-Ep-CAM antibodies were expressed by transient transfection of vectors encoding the heavy and light chains into 293T cells grown in 10% ultra low IgG fetal bovine serum with 1 mM sodium pyruvate and 1× non-essential amino acids (Gibco®, Invitrogen Hayward Calif.). Five days after transfection, the culture media was removed and ran through a protein A column (Pierce Biotechnology Inc, Rockford Md.) FIG. 4 shows typical yields of some Ep-CAM-binding proteins. FIGS. 5 and 6 contain gels showing the heavy and light chains of some purified antibodies of the present invention. The heavy chains may be made with any type of constant domain including, in humans, IgG1, IgG2 and hybrids comprising IgG1 and IgG2 as well as mouse constant domains such as IgG1 and IgG2a, which may be referred to as mlgG1 and mlgG2a. The sequences of many of these heavy chains may be found in FIG. 3. Data demonstrating the use of the hybrid IgG1, IgG2 heavy chain may be found in FIGS. 4, 5 and 20.

Example 3

Binding Properties of Anti-Ep-CAM Humanized Antibodies

FIG. 7 shows a schematic representation of the AlphaScreen assay. Binding affinity of anti-Ep-CAM antibodies to the extracellular domain of Ep-CAM was measured using a quantitative and sensitive method, AlphaScreen™ assay. The AlphaScreen™ assay is a bead-based non-radioactive luminescent proximity assay. Laser excitation of a donor bead excites oxygen, which if sufficiently close to the acceptor bead will generate a cascade of chemiluminescent events, ultimately leading to fluorescence emission at 520-620 nm. The AlphaScreen™ assay was applied as a competition assay for screening the antibodies. Wild-type IgG1 Ep-CAM antibody was biotinylated and extracellular domain of Ep-CAM was DIGylated by standard methods for attachment to streptavidin donor beads and anti-DIG acceptor beads. In the absence of competing anti-Ep-CAM antibodies (unlabeled), wild-type antibody (biotinylated) and Ep-CAM (DIGylated) interact and produce a signal at 520-620 nm. Addition of untagged antibody competes with wild-type biotinylated anti-Ep-CAM and DIGylated-Ep-CAM interaction, reducing fluorescence quantitatively to enable determination of relative binding affinities.

FIGS. 8 to 13 show representative AlphaScreen™ data of various humanized antibodies of the present invention. These figure show competition AlphaScreen™ data in which tested antibody, in this case, competes with a reference antibody for the binding to Ep-CAM or an antibody binding protein. The binding of the humanized antibodies for the antigen, Ep-CAM, and protein A are shown on the left and right sides, respectively, of the FIG. 8. The results are also summarized in FIG. 9. Most humanized antibodies have an Ep-CAM binding affinity within 2-fold of the wild type. That is, they have between 0.5 and 2.0 fold increases in binding affinity relative to the wild type. Fold increase values greater than 1.0 demonstrate stronger binding than the wild type, 17-1A. FIGS. 10 to 13 show repeat measurements of the humanized antibodies using the AlphaScreen™ method.

FIGS. 14 to 16 show binding reactions for WT and variant anti-Ep-CAM antibodies measured with surface plasmon resonance. The kinetic constants for the binding of anti-Ep-CAM antibodies to Ep-CAM antigen were determined using surface plasmon resonance-based measurements on a BIAcore 3000 instrument (Biacore, Uppsala, Sweden). For the data in FIG. 14, the second and fourth CM5 sensor chip flow cells were coupled with recombinant human Ep-CAM/Fc (R&D Systems, Minneapolis, Minn.) using amine chemistry. Approximately 1000 and 6000 response units were respectively immobilized, The first and third flow cells were ethanolamine blocked to serve as reference flow cells. Binding experiments were performed by injecting antibodies over the Ep-CAM/Fc and reference flow cells at varying concentrations ranging from 1 nM to 1000 nM in 110 mM HEPES, pH 7.4, 150 mM NaCl, 3 mM EDTA, 0.005% Surfactant P20, filtered & degassed (HBS-EP, Biacore, Uppsala, Sweden) using KINJECT (2 minutes association, 2 minutes dissociation) at 50 μl/minute. The sensor chip was regenerated with 10 mM glycine, pH 1.5. Data transformation was prepared by subtraction of blank injections (buffer without analyte) and y-transform prior to the injection start to zero using BIAevaluation software. The responses between 12.5 and 100 nM were globally analyzed using a one to one interaction (Langmuir) binding model. The corresponding association rate constant ($k_a$), dissociation rate constant ($k_d$), maximum analyte binding capacity ($R_{max}$), bulk refractive index contribution (RI), equilibrium association constant ($K_A$), equilibrium dissociation constant ($K_D$), steady state binding level ($R_{eq}$), and observed rate constant ($k_{obs}$) derived from these fits are presented in FIG. 14, along with the chi-square ($X^2$) value which represents the closeness of fit between the fit curve and the actual data curve.

The data for the variants in FIG. 15 was collected similarly, but the resulting binding/dissociation curves were not fit to a particular binding model. The binding strength is presented as the SPR signal, the response units, after a fixed time of flowing the analyte over the surface. Stronger binding interactions yield a higher number of response units after this fixed time.

The SPR association/dissociation curves of three variants are shown in FIG. 16. Three different concentrations are shown for each variant and over-laid onto the data curves are fitted curve generated with a 1:1 binding model containing a drifting baseline. The three curves for each variant were fit simultaneously to the model yielding one dissociation constant describing the binding of the variant to Ep-CAM. For example, the variant H3.77/L3 showed a dissociation constant of 6.49e-8 $M^{-1}$ in this assay.

Example 4

ADCC of Variants

Antibody-dependent cellular cytotoxicity measurements were done to assess the interaction of the antibodies of the present invention with components of the immune system. First, the relative binding of a humanized anti-Ep-CAM and trastuzumab to two different cell lines was measured. FIG. 17 shows the binding of a humanized anti-Ep-CAM and trastuzumab to the gastric carcinoma line, KATOIII, and the breast cancer line, SkBr3. Each cell line was dissociated using Accutase wash, resuspended and seeded at 50,000 cells per well of a 96-well plate. Cells were either treated with a secondary antibody-fluor (PE) conjugate or first treated with either trastuzumab or anti-Ep-CAM followed by secondary mAb treatment. After 20 minutes of incubation on ice, the relative binding of each mAb was measured using a Guava Technologies™ flow cytometry unit. The following histograms show the binding profile and mean fluorescence of each population consisting a total of 4000 cell counts per histogram. The results show that about 3 times as much Ep-CAM is present on KATOIII cells than SkBr3 cells.

ADCC was measured using either the DELFIA® EuTDA-based cytotoxicity assay (Perkin Elmer) or LDH Cytotoxicity Detection Kit (Roche Diagnostic). Human PBMCs were purified from leukopacks using a ficoll gradient. NK cells were isolated from human PBMCs using negative selection and magnetic beads (Miltenyi Biotec). For europium-based detection, target cells were first loaded with BATDA at $1\times10^6$ cells/ml and washed 4 times. For both europium- and LDH-based detection, target cells were seeded into 96-well plates at 10,000 cells/well, and opsonized using antibodies at the indicated final concentration. Triton X100 and PBMCs alone were typically run as positive and negative controls. Effector cells were added at 25:1 PBMCs:target cells or 4:1 NK Cells target cells, and the plate was incubated at 37° C. for 4 hrs. Cells were incubated with either Eu3+ solution or LDH reaction mixture, and fluorescence was measured using the Fusion Alpha-FP. Data were normalized to maximal (triton) and minimal (PBMCs alone) lysis, and fit to a sigmoidal dose-response model.

FIGS. 18 to 24 display the results of ADCC assays of various anti-Ep-CAM antibodies. Improved, ie greater, levels of ADCC may be seen as either a shift in potency or efficacy. Improved potency of antibody is seen as a left shift of an ADCC curve compared to a reference curve. The left shift indicates that less antibody is required to achieve the same degree of cytotoxicy as the reference antibody. In addition, improved ADCC may also be evident as improved efficacy, which is seen as an upward shift in the ADCC curve compared to a reference curve. The upward shift indicates that the same amount of antibody produces a greater degree of cytotoxicity. Improvements in potency and efficacy may occur simultaneously or separately depending on the two antibodies being compared, the assay conditions (cell lines used, antibody concentrations, etc) and other factors.

Figure 20A:
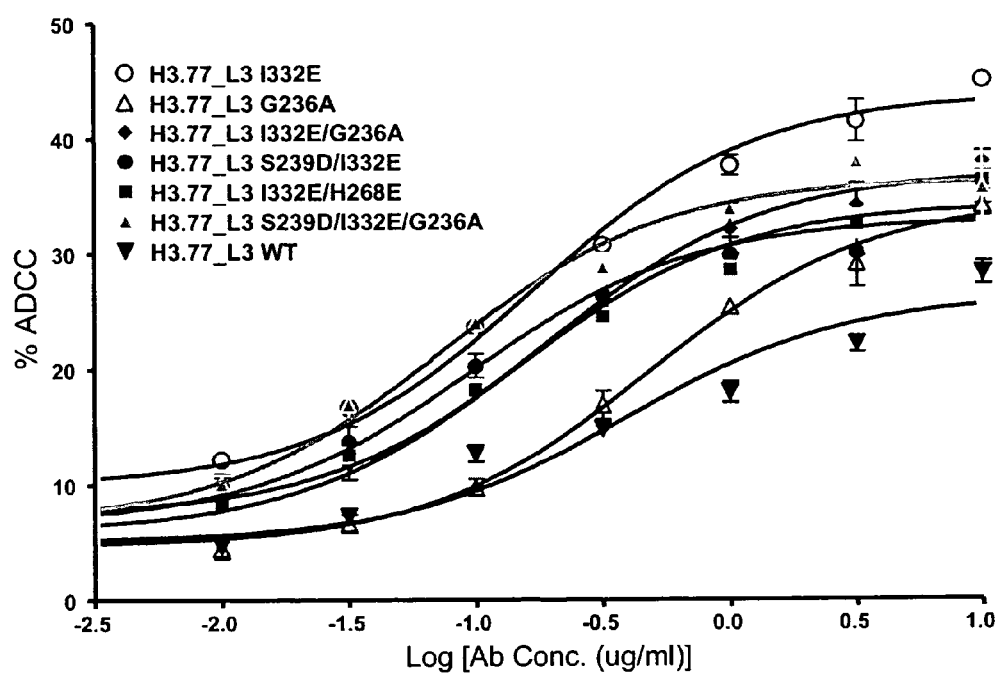

For example, in FIG. 20a the humanized anti-Ep-CAM antibody H3.77_L3 WT may be used as a reference, wild-type, antibody. In comparison to this reference, H3.77-L3 S239D/I332E shows a large increase in potency in that the midpoint of the ADCC curve has shifted to lower antibody concentrations by about 0.5 log of antibody concentration (log antibody concentration=−1.0 vs −0.5 for the reference antibody). This antibody also shows an increase in efficacy, because at log antibody concentration of 1.0, it has about 30% cytoxicity whereas the reference antibody has about 20% cytotoxicity. H3.77_L3 G236A shows increased efficacy, but very little change in potency as it shows more cytoxicity at higher antibody concentrations, but very little change in the midpoint of its ADCC curve. Also indicated in FIG. 20a is the improved potency of H3.77_L3 S239D/I332E compared to H3.77_L3 G236A with very little change in efficacy. Relative to the H3.77_L3 WT antibody, all of the other antibodies shown in FIG. 20a have improved efficacy, improved potency, or an improvement in both efficacy and potency.

Example 5

Ep-CAM-Binding Antibodies with Fc Substitutions

Ep-CAM-binding antibodies may comprise substitutions in the Fc region, or other regions, to optimize the antibody function. FIGS. 4, 5, 13, and 20 to 23 comprise data of anti-Ep-CAM antibodies comprising substitutions in the Fc domain. The substitutions S239D, I332E, G326A, L235G, G236R, A330Y, H268E affect binding to the Fcgamma receptors (See U.S. Ser. No. 11/124,620 entitled "Optimized Fc Variants"). The substitutions P257L, P257N, V308F, V308Y, V279Y, and Q311V affect binding to FcRn (See PCT WO06053301A2 entitled "Fc Variants with altered binding to FCRN"). The altered Fc receptor binding and effector function (ADCC) of many variants are shown in FIGS. 13 and 20 to 23. Many anti-Ep-CAM antibodies were found to have increased killing of LS180 and HT29 cells, particularly those that comprise the modifications S239D, I332E, G326A, L235G, G236R, A330Y, or H268E. The increased ADCC of these variants may be made in human or mouse Fc regions including human IgG1, and hybrids of two different human IgG's, as shown for example in FIG. 13.

Example 6

Effector Function—Glcoforms

The optimal anti-Ep-CAM clinical candidate may comprise an altered glycoform. An Ep-CAM binding protein was expressed in Lec13 cells and purified by the standard methods described herein, including protein A chromatography. This Lec13 expressed antibody is a glycoform variant in that it is defucosylated; it lacks the fucose residue on it N-linked carbohydrate moiety connected to Asn297. The purified protein is shown in FIG. 6 and shows the expected molecular weights of the heavy and light chains. This defucosylated anti-Ep-CAM has stronger binding to the Fc receptor, FcgammaRIIIa (Val variant), as shown in FIG. 25, lower panel. The defucosylated variant has an affinity of Kd=$2.8*10^{-8}$ compared to Kd=$2.8*10-7$ for the typically glycosylated form. The Kd measurement were made with Surface Plasmon Resonance fixing the antibody on the surface and flowing FcgammaRIIIA over the chip.

Example 7

Because of the sequence differences between the various human Fc receptors, modifications to the Fc domain of antibodies can specifically modulate their affinity for different human FcR's. The importance of the different FcR's on different effector functions has been seen through the use of FcR knockout mice (Nimmerman and Ravetch 2005 Science 310: 1510-1512). The FcR affinity differences may potentially impact activation of various immune effector cells, because different effector cells have differential expression of each receptor (Pricop et al 2001 J Immunology 166:531-537, Samuelsson et al 2001 Science 19(291):484-486, For example, neutrophil activation is influenced by the FcγRIIa/FcγRIIb ratio (Van Mirre et al. 2006 Blood 108(2):584-590).

Additionally, immune complexes and FcγRIIa binding stimulate dendritic cell maturation, but FcγRIIb activity is know to suppress their maturation (Boruchov et al. Journal of Clinical Investigation 115(10):2914-2923. Nimmerman and Ravetch, 2006 Immunity 24:19-28).

Additionally, phagocytosis by monocytes and macrophages may be initiated by antibody binding to FcγRIIa (Hunter et al. Blood 91(5):1762-1768, Tridandapani et al 2002 Journal of Biological Chemistry 277(7):5082-5089). FcγRIIb, on the other hand, may also bind the antibodies but FcγRIIb does not induce phagocytosis by monocytes and macrophages. Therefore, FcγRIIb may passively inhibit phagocytosis by binding antibody that otherwise may be available to bind to FcγRIIA as well under go its more active inhibitory functions.

Additionally, FcγRIIIa is the important Fc receptor for causing activation of NK cells, Alternatively, FcγRIIa and FcγRIIb are expressed on monocytes, macrophages, neutrophils, and dendritic cells, and some of these cell types are also known to express FcγRIIIa. It is well known in the art that activation of these cell types can depend on the relative expression and/or activation of FcγRIIa compared to FcγRIIb, and that coactivation of FcγRIIb with FcγRIIa can decrease the activation via FcγRIIa. We therefore determined the affinity of several Fc modified Ep-CAM-targeting antibodies to several human FcR's.

To determine the affinity of various Fc modified Ep-CAM-targeting antibodies for human FcR, surface plasmon resonance experiments were performed on a Biacore 3000 instrument. Antibody was immobilized on a protein A/G surface and purified forms of three human Fc receptors (FcγRI, FcγRIIIa, FcγRIIa and FcγRIIb) were added in the solution phase as analyte. Global curve-fitting of a set of sensor grams derived from a FcR concentration series was used to determine dissociation constants (Kd) between each variant and each of the FcRs included in the study. Note that the allotype of FcRIIIa used in the experiments was the 158V form, and that of FcRIIa was the 131R form.

The Kd values for a series of Fc modified Ep-CAM-targeting antibodies are shown in FIGS. 26 and 27. The affinity values show several important trends. First, variants containing the substitutions S239D, I332E and H268E all have increased affinity for FcγRIIIa relative to the wt IgG1 control. These substitutions, individually or in combinations, have "Fold KD" (FIG. 27) values greater than one. For example, H3.77_L3 S239D IgG1 has a FcγyRIIIa Fold KD value of 5.6, demonstrating that it has 5.6-fold stronger binding to FcγRIIIa than the wild type. Antibodies with these modifications also have increase affinity for the Fc receptors FcγRIIa and FcγRIIb.

Of additional interest are variants containing the G236A substitutions. All of these variants have specifically enhanced affinity for FcγRIIa. G236A results in a specific enhancement of FcγRIIa binding compared to FcγRIIb binding. Indeed, the RIIa/RIIb affinity ratio of G236A-containing variants is systematically improved, having a –log(RIIa/RIIB) value of about 1.0. This value means that the variants have about a full log, or 10-fold, increased binding for FcγRIIa compared to FcγRIIb. These variants will find utility in treatment of Ep-CAM expressing cancers, where monocytes, macrophages, neutrophils, and dendritic cells are important effector cells.

The effect of particular substitutions on specific FcR's is seen in Ep-CAM-targeting proteins comprising different Fc domains. For example, FIGS. 26 and 27 show data collected with antibodies comprising either the human IgG1 or a hybrid Fc comprising both IgG1 and IgG2 sequences. FIG. 3 shows the sequences of some Fc domains used herein.

Example 8

In alternate embodiments, other IgG allotypes may be used as Fc domains in an Ep-CAM-targeting protein. Gm polymorphism is determined by the IGH1, IGH2, and IGH3 genes, which have alleles encoding aflotypic antigenic determinants referred to as G1m, G2m, and G3m allotypes for markers of the human IgG1, IgG2 and IgG3 molecules. FIG. 28a provides some common allotypes, as is well known in the art. One or more of these allotypic mutations could be made in either the IgG1 or hybrid Ep-CAM-targeting antibodies by incorporating substitution, as illustrated in FIG. 28b.

We claim:

1. A humanized variant anti-EpCAM antibody variable domain relative to antibody 17-1A variable domain, wherein said 17-1A variable domain comprises a heavy chain, SEQ ID NO: 1, and a light chain SEQ ID NO: 105, and, wherein said variant comprises at least one modification selected from the group consisting of: a first variant heavy chain framework region, a second variant heavy chain framework region, a third variant heavy chain framework region, a first variant light chain framework region, a second variant light chain framework region, and a third variant light chain framework region, wherein said first variant heavy chain framework region consists of Q5V and R13Q relative to SEQ ID NO: 1, wherein said second variant heavy chain framework region consists of K38R, R40A and I48M relative to SEQ ID NO: 1, wherein said third variant heavy chain framework region consists of K63S, F64L, G66S, K67R, A68V, L70I and T71S relative to SEQ ID NO: 1, wherein said first variant light chain framework region consists of K9D, M11L, S12A, M13V and V15L relative to SEQ ID NO: 105, wherein said second variant light chain framework region consists of E41G and K45Q relative to SEQ ID NO: 105, and, wherein said third variant light chain framework region consists of S76N, V78L, Q79E, L83A, D85T and H87Y relative to SEQ ID NO: 105, wherein said variant anti-EpCAM antibody variable domain contains an increased human string content relative to antibody 17-1A variable domain.

2. The humanized variant anti-EpCAM antibody variable domain of claim 1, where said at least one modification comprises said first variant heavy chain framework.

3. The humanized variant anti-EpCAM antibody variable domain of claim 1, where said at least one modification comprises said second variant heavy chain framework.

4. The humanized variant anti-EpCAM antibody variable domain of claim 1, where said at least one modification comprises said third variant heavy chain framework.

5. The humanized variant anti-EpCAM antibody variable domain of claim 1, where said at least one modification comprises said first variant light chain framework.

6. The humanized variant anti-EpCAM antibody variable domain of claim 1, where said at least one modification comprises said second variant light chain framework.

7. The humanized variant anti-EpCAM antibody variable domain of claim 1, where said at least one modification comprises said third variant light chain framework.

8. The humanized variant anti-EpCAM antibody variable domain of claim 1, where said at least one modification comprises said first variant heavy chain framework and said second variant heavy chain framework and said third variant heavy chain framework.

9. The humanized variant anti-EpCAM antibody variable domain of claim 1, where said at least one modification comprises said first variant light chain framework and said second variant light chain framework and said third variant light chain framework.

10. The humanized variant anti-EpCAM antibody variable domain of claim 9, where said at least one modification further comprises said first variant heavy chain framework and said second variant heavy chain framework and said third variant heavy chain framework.

* * * * *

SEQUENCE LISTING

```
<160> NUMBER OF SEQ ID NOS: 170

<210> SEQ ID NO 1
<211> LENGTH: 116
<212> TYPE: PRT
<213> ORGANISM: Artificial
<220> FEATURE:
<223> OTHER INFORMATION: Synthetic

<400> SEQUENCE: 1

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
            20                  25                  30

Leu Ile Glu Trp Val Lys Gln Arg Pro Gly Gln Gly Leu Glu Trp Ile
        35                  40                  45

Gly Val Ile Asn Pro Gly Ser Gly Gly Thr Asn Tyr Asn Glu Lys Phe
    50                  55                  60
```

Lys Gly Lys Ala Thr Leu Thr Ala Asp Lys Ser Ser Thr Ala Tyr
65                  70                  75                  80

Met Gln Leu Ser Ser Leu Thr Ser Asp Ser Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ala
        115

<210> SEQ ID NO 2
<211> LENGTH: 116
<212> TYPE: PRT
<213> ORGANISM: Artificial
<220> FEATURE:
<223> OTHER INFORMATION: Synthetic

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 3
<211> LENGTH: 116
<212> TYPE: PRT
<213> ORGANISM: Artificial
<220> FEATURE:
<223> OTHER INFORMATION: Synthetic

<400> SEQUENCE: 3

Gln Val Gln Leu Val Gln Ser Gly His Glu Val Lys Gln Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser

```
                    115

<210> SEQ ID NO 4
<211> LENGTH: 116
<212> TYPE: PRT
<213> ORGANISM: Artificial
<220> FEATURE:
<223> OTHER INFORMATION: Synthetic

<400> SEQUENCE: 4

Gln Val Gln Leu Val Gln Ser Gly His Glu Val Lys Gln Pro Ser Gln
1               5                   10                  15

Thr Leu Ser Leu Thr Cys Ala Ile Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 5
<211> LENGTH: 116
<212> TYPE: PRT
<213> ORGANISM: Artificial
<220> FEATURE:
<223> OTHER INFORMATION: Synthetic

<400> SEQUENCE: 5

Gln Val Gln Leu Val Gln Ser Gly Ser Gly Leu Val Lys Pro Ser Gln
1               5                   10                  15

Thr Leu Ser Leu Thr Cys Ala Val Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 6
<211> LENGTH: 116
<212> TYPE: PRT
<213> ORGANISM: Artificial
<220> FEATURE:
<223> OTHER INFORMATION: Synthetic

<400> SEQUENCE: 6
```

Gln Val Gln Leu Val Gln Ser Gly Pro Gly Leu Val Lys Pro Ser Gln
1               5                   10                  15

Thr Leu Ser Leu Thr Cys Ala Ile Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
                100                 105                 110

Thr Val Ser Ser
        115

<210> SEQ ID NO 7
<211> LENGTH: 116
<212> TYPE: PRT
<213> ORGANISM: Artificial
<220> FEATURE:
<223> OTHER INFORMATION: Synthetic

<400> SEQUENCE: 7

Gln Val Gln Leu Gln Glu Ser Gly Pro Gly Leu Val Lys Pro Pro Gly
1               5                   10                  15

Thr Leu Ser Leu Thr Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
                100                 105                 110

Thr Val Ser Ser
        115

<210> SEQ ID NO 8
<211> LENGTH: 116
<212> TYPE: PRT
<213> ORGANISM: Artificial
<220> FEATURE:
<223> OTHER INFORMATION: Synthetic

<400> SEQUENCE: 8

Gln Val Thr Leu Arg Glu Ser Gly Pro Ala Leu Val Lys Pro Thr Gln
1               5                   10                  15

Thr Leu Thr Leu Thr Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu

```
                50                  55                  60
Lys Ser Arg Val Thr Ile Ser Ala Asp Lys Ser Ile Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg Asp Gly Pro Trp Phe Ala Tyr Trp Gly Gln Gly Thr Leu Val
                100                 105                 110

Thr Val Ser Ser
        115

<210> SEQ ID NO 9
<211> LENGTH: 116
<212> TYPE: PRT
<213> ORGANISM: Artificial
<220> FEATURE:
<223> OTHER INFORMATION: Synthetic

<400> SEQUENCE: 9

Gln Val Thr Leu Lys Glu Ser Gly Pro Val Leu Val Lys Pro Thr Glu
 1               5                  10                  15

Thr Leu Thr Leu Thr Cys Thr Val Ser Gly Tyr Ala Phe Thr Asn Tyr
                 20                  25                  30

Leu Ile Glu Trp Val Arg Gln Ala Pro Gly Gln Gly Leu Glu Trp Met
             35                  40                  45

Gly Val Ile Asn Pro Gly Ser Gly Gly Thr Asn Tyr Asn Glu Ser Leu
         50                  55                  60

Lys Ser Arg Val Thr Ile Ser Ala Asp Lys Ser Ile Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg Asp Gly Pro Trp Phe Ala Tyr Trp Gly Gln Gly Thr Leu Val
                100                 105                 110

Thr Val Ser Ser
        115

<210> SEQ ID NO 10
<211> LENGTH: 116
<212> TYPE: PRT
<213> ORGANISM: Artificial
<220> FEATURE:
<223> OTHER INFORMATION: Synthetic

<400> SEQUENCE: 10

Gln Val Gln Leu Val Gln Ser Gly Pro Val Leu Val Lys Pro Thr Glu
 1               5                  10                  15

Thr Leu Thr Leu Thr Cys Lys Ala Ser Gly Tyr Ala Phe Thr Asn Tyr
                 20                  25                  30

Leu Ile Glu Trp Val Arg Gln Ala Pro Gly Gln Gly Leu Glu Trp Met
             35                  40                  45

Gly Val Ile Asn Pro Gly Ser Gly Gly Thr Asn Tyr Asn Glu Ser Leu
         50                  55                  60

Lys Ser Arg Val Thr Ile Ser Ala Asp Lys Ser Ile Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg Asp Gly Pro Trp Phe Ala Tyr Trp Gly Gln Gly Thr Leu Val
                100                 105                 110
```

-continued

```
Thr Val Ser Ser
        115

<210> SEQ ID NO 11
<211> LENGTH: 116
<212> TYPE: PRT
<213> ORGANISM: Artificial
<220> FEATURE:
<223> OTHER INFORMATION: Synthetic

<400> SEQUENCE: 11

Gln Leu Gln Leu Gln Glu Ser Gly Pro Gly Leu Val Lys Pro Ser Glu
1               5                   10                  15

Thr Leu Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 12
<211> LENGTH: 116
<212> TYPE: PRT
<213> ORGANISM: Artificial
<220> FEATURE:
<223> OTHER INFORMATION: Synthetic

<400> SEQUENCE: 12

Gln Ile Thr Leu Lys Glu Ser Gly Pro Thr Leu Val Lys Pro Thr Gln
1               5                   10                  15

Thr Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 13
<211> LENGTH: 116
<212> TYPE: PRT
<213> ORGANISM: Artificial
<220> FEATURE:
<223> OTHER INFORMATION: Synthetic
```

-continued

```
<400> SEQUENCE: 13

Gln Val Gln Leu Leu Glu Ser Gly Gly Gly Leu Val Gln Pro Gly Gly
1               5                   10                  15

Ser Leu Arg Leu Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 14
<211> LENGTH: 116
<212> TYPE: PRT
<213> ORGANISM: Artificial
<220> FEATURE:
<223> OTHER INFORMATION: Synthetic

<400> SEQUENCE: 14

Gln Val Gln Leu Val Glu Ser Gly Gly Gly Leu Val Glu Pro Gly Gly
1               5                   10                  15

Ser Leu Arg Leu Ser Cys Ala Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 15
<211> LENGTH: 116
<212> TYPE: PRT
<213> ORGANISM: Artificial
<220> FEATURE:
<223> OTHER INFORMATION: Synthetic

<400> SEQUENCE: 15

Gln Val Gln Leu Val Gln Ser Gly His Glu Val Lys Gln Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45
```

```
Gly Val Ile Asn Pro Gly Ser Gly Gly Thr Asn Tyr Asn Glu Ser Leu
            50                  55                  60

Lys Ser Arg Val Thr Ile Ser Ala Asp Lys Ser Ile Ser Gln Val Val
 65                  70                  75                  80

Leu Thr Met Thr Asn Met Asp Pro Val Asp Thr Ala Val Tyr Phe Cys
                     85                  90                  95

Ala Arg Asp Gly Pro Trp Phe Ala Tyr Trp Gly Gln Gly Thr Leu Val
                100                 105                 110

Thr Val Ser Ser
            115

<210> SEQ ID NO 16
<211> LENGTH: 116
<212> TYPE: PRT
<213> ORGANISM: Artificial
<220> FEATURE:
<223> OTHER INFORMATION: Synthetic

<400> SEQUENCE: 16

Gln Val Gln Leu Val Gln Ser Gly His Glu Val Lys Gln Pro Gly Ala
 1               5                  10                  15

Ser Val Lys Val Ser Cys Lys Ala Ser Gly Tyr Ala Phe Thr Asn Tyr
                20                  25                  30

Leu Ile Glu Trp Val Arg Gln Ala Pro Gly Gln Gly Leu Glu Trp Met
             35                  40                  45

Gly Val Ile Asn Pro Gly Ser Gly Gly Thr Asn Tyr Asn Glu Ser Leu
            50                  55                  60

Lys Ser Arg Val Thr Ile Ser Ala Asp Lys Ser Ile Ser Thr Ala Tyr
 65                  70                  75                  80

Leu Thr Met Thr Asn Met Asp Pro Val Asp Thr Ala Val Tyr Phe Cys
                     85                  90                  95

Ala Arg Asp Gly Pro Trp Phe Ala Tyr Trp Gly Gln Gly Thr Leu Val
                100                 105                 110

Thr Val Ser Ser
            115

<210> SEQ ID NO 17
<211> LENGTH: 116
<212> TYPE: PRT
<213> ORGANISM: Artificial
<220> FEATURE:
<223> OTHER INFORMATION: Synthetic

<400> SEQUENCE: 17

Gln Val Gln Leu Val Gln Ser Gly His Glu Val Lys Gln Pro Gly Ala
 1               5                  10                  15

Ser Val Lys Val Ser Cys Lys Ala Ser Gly Tyr Ala Phe Thr Asn Tyr
                20                  25                  30

Leu Ile Glu Trp Val Arg Gln Ala Pro Gly Gln Gly Leu Glu Trp Met
             35                  40                  45

Gly Val Ile Asn Pro Gly Ser Gly Gly Thr Asn Tyr Asn Glu Ser Leu
            50                  55                  60

Lys Ser Arg Leu Thr Ile Thr Lys Asp Thr Ser Lys Asn Gln Val Val
 65                  70                  75                  80

Leu Thr Met Thr Asn Met Asp Ser Glu Asp Thr Ala Val Tyr Phe Cys
                     85                  90                  95

Ala Arg Asp Gly Pro Trp Phe Ala Tyr Trp Gly Gln Gly Thr Leu Val
                100                 105                 110
```

Thr Val Ser Ser
        115

<210> SEQ ID NO 18
<211> LENGTH: 116
<212> TYPE: PRT
<213> ORGANISM: Artificial
<220> FEATURE:
<223> OTHER INFORMATION: Synthetic

<400> SEQUENCE: 18

Gln Val Gln Leu Val Gln Ser Gly His Glu Val Lys Gln Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Leu Thr Ile Ser Lys Asp Thr Ser Lys Asn Gln Val Val
65                  70                  75                  80

Leu Thr Met Thr Asn Met Asp Pro Val Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 19
<211> LENGTH: 116
<212> TYPE: PRT
<213> ORGANISM: Artificial
<220> FEATURE:
<223> OTHER INFORMATION: Synthetic

<400> SEQUENCE: 19

Gln Val Gln Leu Val Gln Ser Gly His Glu Val Lys Gln Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Asn Thr Leu Tyr
65                  70                  75                  80

Leu Gln Met Asn Asn Leu Arg Ala Glu Gly Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 20
<211> LENGTH: 116
<212> TYPE: PRT
<213> ORGANISM: Artificial
<220> FEATURE:
<223> OTHER INFORMATION: Synthetic

```
<400> SEQUENCE: 20

Gln Val Gln Leu Val Gln Ser Gly His Glu Val Lys Gln Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Lys Asn Gln Phe Ser
65                  70                  75                  80

Leu Lys Leu Ser Ser Val Thr Ala Ala Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
            115

<210> SEQ ID NO 21
<211> LENGTH: 116
<212> TYPE: PRT
<213> ORGANISM: Artificial
<220> FEATURE:
<223> OTHER INFORMATION: Synthetic

<400> SEQUENCE: 21

Gln Val Gln Leu Val Gln Ser Gly His Glu Val Lys Gln Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Val Asp Arg Ser Lys Asn Gln Phe Ser
65                  70                  75                  80

Leu Lys Leu Ser Ser Val Thr Ala Ala Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
            115

<210> SEQ ID NO 22
<211> LENGTH: 115
<212> TYPE: PRT
<213> ORGANISM: Artificial
<220> FEATURE:
<223> OTHER INFORMATION: Synthetic

<400> SEQUENCE: 22

Gln Val Gln Leu Val Gln Ser Gly His Glu Val Lys Gln Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45
```

Gly Val Ile Asn Pro Gly Ser Gly Gly Thr Asn Tyr Asn Glu Ser Leu
         50                  55                  60

Lys Ser Arg Val Thr Ile Asn Pro Asp Thr Ser Lys Asn Gln Phe Ser
 65                  70                  75                  80

Leu Gln Leu Asn Ser Val Thr Pro Glu Asp Thr Ala Val Tyr Phe Cys
                 85                  90                  95

Ala Arg Asp Gly Pro Trp Phe Ala Tyr Trp Gly Gln Gly Thr Leu Val
             100                 105                 110

Thr Val Ser
        115

<210> SEQ ID NO 23
<211> LENGTH: 116
<212> TYPE: PRT
<213> ORGANISM: Artificial
<220> FEATURE:
<223> OTHER INFORMATION: Synthetic

<400> SEQUENCE: 23

Gln Val Gln Leu Val Gln Ser Gly His Glu Val Lys Gln Pro Gly Ala
 1               5                  10                  15

Ser Val Lys Val Ser Cys Lys Ala Ser Gly Tyr Ala Phe Thr Asn Tyr
                 20                  25                  30

Leu Ile Glu Trp Val Arg Gln Ala Pro Gly Gln Gly Leu Glu Trp Met
             35                  40                  45

Gly Val Ile Asn Pro Gly Ser Gly Gly Thr Asn Tyr Asn Glu Ser Leu
         50                  55                  60

Lys Ser Arg Ile Thr Ile Asn Pro Asp Thr Ser Lys Asn Gln Phe Ser
 65                  70                  75                  80

Leu Gln Leu Asn Ser Val Thr Ser Glu Asp Thr Ala Val Tyr Phe Cys
                 85                  90                  95

Ala Arg Asp Gly Pro Trp Phe Ala Tyr Trp Gly Gln Gly Thr Leu Val
             100                 105                 110

Thr Val Ser Ser
        115

<210> SEQ ID NO 24
<211> LENGTH: 116
<212> TYPE: PRT
<213> ORGANISM: Artificial
<220> FEATURE:
<223> OTHER INFORMATION: Synthetic

<400> SEQUENCE: 24

Gln Val Gln Leu Val Gln Ser Gly Pro Glu Leu Val Lys Pro Thr Glu
 1               5                  10                  15

Thr Leu Thr Leu Thr Cys Lys Ala Ser Gly Tyr Ala Phe Thr Asn Tyr
                 20                  25                  30

Leu Ile Glu Trp Val Arg Gln Ala Pro Gly Gln Gly Leu Glu Trp Met
             35                  40                  45

Gly Val Ile Asn Pro Gly Ser Gly Gly Thr Asn Tyr Asn Glu Ser Leu
         50                  55                  60

Lys Ser Arg Val Thr Ile Ser Ala Asp Lys Ser Ile Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg Asp Gly Pro Trp Phe Ala Tyr Trp Gly Gln Gly Thr Leu Val

```
                100               105                110
Thr Val Ser Ser
        115

<210> SEQ ID NO 25
<211> LENGTH: 116
<212> TYPE: PRT
<213> ORGANISM: Artificial
<220> FEATURE:
<223> OTHER INFORMATION: Synthetic

<400> SEQUENCE: 25

Gln Val Gln Leu Val Gln Ser Gly His Glu Val Lys Gln Pro Gly Ala
1               5                  10                  15

Ser Val Lys Val Ser Cys Lys Ala Ser Gly Tyr Ser Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Pro Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 26
<211> LENGTH: 116
<212> TYPE: PRT
<213> ORGANISM: Artificial
<220> FEATURE:
<223> OTHER INFORMATION: Synthetic

<400> SEQUENCE: 26

Gln Val Gln Leu Val Gln Ser Gly His Glu Val Lys Gln Pro Gly Ala
1               5                  10                  15

Ser Val Lys Val Ser Cys Lys Ala Ser Gly Tyr Ser Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 27
<211> LENGTH: 116
<212> TYPE: PRT
<213> ORGANISM: Artificial
<220> FEATURE:
```

<223> OTHER INFORMATION: Synthetic

<400> SEQUENCE: 27

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115
```

<210> SEQ ID NO 28
<211> LENGTH: 116
<212> TYPE: PRT
<213> ORGANISM: Artificial
<220> FEATURE:
<223> OTHER INFORMATION: Synthetic

<400> SEQUENCE: 28

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115
```

<210> SEQ ID NO 29
<211> LENGTH: 116
<212> TYPE: PRT
<213> ORGANISM: Artificial
<220> FEATURE:
<223> OTHER INFORMATION: Synthetic

<400> SEQUENCE: 29

```
Thr Val Gln Leu Val Glu Ser Gly Gly Gly Leu Val Gln Pro Gly Gly
1               5                   10                  15

Ser Leu Arg Leu Ser Cys Ala Ala Ser Gly Tyr Ala Phe Thr Asn Tyr
            20                  25                  30

Leu Ile Glu Trp Val Arg Gln Ala Pro Gly Gln Gly Leu Glu Trp Met
```

-continued

```
                35                  40                  45
Gly Val Ile Asn Pro Gly Ser Gly Gly Thr Asn Tyr Asn Glu Ser Leu
 50                  55                  60

Lys Ser Arg Val Thr Ile Ser Ala Asp Lys Ser Ile Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg Asp Gly Pro Trp Phe Ala Tyr Trp Gly Gln Gly Thr Leu Val
                100                 105                 110

Thr Val Ser Ser
        115

<210> SEQ ID NO 30
<211> LENGTH: 116
<212> TYPE: PRT
<213> ORGANISM: Artificial
<220> FEATURE:
<223> OTHER INFORMATION: Synthetic

<400> SEQUENCE: 30

Glu Leu Gln Leu Val Glu Ser Gly Gly Gly Leu Val Gln Pro Gly Gly
 1               5                  10                  15

Ser Leu Arg Leu Ser Cys Ala Ala Ser Gly Tyr Ala Phe Thr Asn Tyr
                20                  25                  30

Leu Ile Glu Trp Val Arg Gln Ala Pro Gly Gln Gly Leu Glu Trp Met
             35                  40                  45

Gly Val Ile Asn Pro Gly Ser Gly Gly Thr Asn Tyr Asn Glu Ser Leu
 50                  55                  60

Lys Ser Arg Val Thr Ile Ser Ala Asp Lys Ser Ile Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg Asp Gly Pro Trp Phe Ala Tyr Trp Gly Gln Gly Thr Leu Val
                100                 105                 110

Thr Val Ser Ser
        115

<210> SEQ ID NO 31
<211> LENGTH: 116
<212> TYPE: PRT
<213> ORGANISM: Artificial
<220> FEATURE:
<223> OTHER INFORMATION: Synthetic

<400> SEQUENCE: 31

Glu Val Glu Leu Val Glu Ser Gly Gly Gly Leu Val Gln Pro Gly Gly
 1               5                  10                  15

Ser Leu Arg Leu Ser Cys Ala Ala Ser Gly Tyr Ala Phe Thr Asn Tyr
                20                  25                  30

Leu Ile Glu Trp Val Arg Gln Ala Pro Gly Gln Gly Leu Glu Trp Met
             35                  40                  45

Gly Val Ile Asn Pro Gly Ser Gly Gly Thr Asn Tyr Asn Glu Ser Leu
 50                  55                  60

Lys Ser Arg Val Thr Ile Ser Ala Asp Lys Ser Ile Ser Thr Ala Tyr
 65                  70                  75                  80

Met Glu Leu Ser Ser Leu Arg Ser Glu Asp Thr Ala Val Tyr Phe Cys
                 85                  90                  95
```

```
Ala Arg Asp Gly Pro Trp Phe Ala Tyr Trp Gly Gln Gly Thr Leu Val
                100                 105                 110

Thr Val Ser Ser
        115

<210> SEQ ID NO 32
<211> LENGTH: 116
<212> TYPE: PRT
<213> ORGANISM: Artificial
<220> FEATURE:
<223> OTHER INFORMATION: Synthetic

<400> SEQUENCE: 32

Glu Val Gln Ile Val Glu Ser Gly Gly Leu Val Gln Pro Gly Gly
1               5                   10                  15

Ser Leu Arg Leu Ser Cys Ala Ala Ser Gly Tyr Ala Phe Thr Asn Tyr
                20                  25                  30

Leu Ile Glu Trp Val Arg Gln Ala Pro Gly Gln Gly Leu Glu Trp Met
            35                  40                  45

Gly Val Ile Asn Pro Gly Ser Gly Gly Thr Asn Tyr Asn Glu Ser Leu
        50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
                100                 105                 110

Thr Val Ser Ser
        115

<210> SEQ ID NO 33
<211> LENGTH: 116
<212> TYPE: PRT
<213> ORGANISM: Artificial
<220> FEATURE:
<223> OTHER INFORMATION: Synthetic

<400> SEQUENCE: 33

Glu Val Gln Leu Gln Glu Ser Gly Gly Gly Leu Val Gln Pro Gly Gly
1               5                   10                  15

Ser Leu Arg Leu Ser Cys Ala Ala Ser Gly Tyr Ala Phe Thr Asn Tyr
                20                  25                  30

Leu Ile Glu Trp Val Arg Gln Ala Pro Gly Gln Gly Leu Glu Trp Met
            35                  40                  45

Gly Val Ile Asn Pro Gly Ser Gly Gly Thr Asn Tyr Asn Glu Ser Leu
        50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
                100                 105                 110

Thr Val Ser Ser
        115

<210> SEQ ID NO 34
<211> LENGTH: 116
<212> TYPE: PRT
<213> ORGANISM: Artificial
```

```
<220> FEATURE:
<223> OTHER INFORMATION: Synthetic

<400> SEQUENCE: 34

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
            115

<210> SEQ ID NO 35
<211> LENGTH: 116
<212> TYPE: PRT
<213> ORGANISM: Artificial
<220> FEATURE:
<223> OTHER INFORMATION: Synthetic

<400> SEQUENCE: 35

Glu Val Gln Leu Val Gln Ser Gly Gly Gly Leu Val Gln Pro Gly Gly
1               5                   10                  15

Ser Leu Arg Leu Ser Cys Ala Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
            115

<210> SEQ ID NO 36
<211> LENGTH: 116
<212> TYPE: PRT
<213> ORGANISM: Artificial
<220> FEATURE:
<223> OTHER INFORMATION: Synthetic

<400> SEQUENCE: 36

Glu Val Gln Leu Val Glu Ser Gly His Gly Leu Val Gln Pro Gly Gly
1               5                   10                  15

Ser Leu Arg Leu Ser Cys Ala Ala Ser Gly Tyr Ala Phe Thr Asn Tyr
            20                  25                  30
```

```
Leu Ile Glu Trp Val Arg Gln Ala Pro Gly Gln Gly Leu Glu Trp Met
            35                  40                  45

Gly Val Ile Asn Pro Gly Ser Gly Gly Thr Asn Tyr Asn Glu Ser Leu
        50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 37
<211> LENGTH: 116
<212> TYPE: PRT
<213> ORGANISM: Artificial
<220> FEATURE:
<223> OTHER INFORMATION: Synthetic

<400> SEQUENCE: 37

Glu Val Gln Leu Val Glu Ser Gly Ala Gly Leu Val Gln Pro Gly Gly
1               5                   10                  15

Ser Leu Arg Leu Ser Cys Ala Ala Ser Gly Tyr Ala Phe Thr Asn Tyr
            20                  25                  30

Leu Ile Glu Trp Val Arg Gln Ala Pro Gly Gln Gly Leu Glu Trp Met
            35                  40                  45

Gly Val Ile Asn Pro Gly Ser Gly Gly Thr Asn Tyr Asn Glu Ser Leu
        50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 38
<211> LENGTH: 116
<212> TYPE: PRT
<213> ORGANISM: Artificial
<220> FEATURE:
<223> OTHER INFORMATION: Synthetic

<400> SEQUENCE: 38

Glu Val Gln Leu Val Glu Ser Gly Gly Glu Leu Val Gln Pro Gly Gly
1               5                   10                  15

Ser Leu Arg Leu Ser Cys Ala Ala Ser Gly Tyr Ala Phe Thr Asn Tyr
            20                  25                  30

Leu Ile Glu Trp Val Arg Gln Ala Pro Gly Gln Gly Leu Glu Trp Met
            35                  40                  45

Gly Val Ile Asn Pro Gly Ser Gly Gly Thr Asn Tyr Asn Glu Ser Leu
        50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95
```

```
Ala Arg Asp Gly Pro Trp Phe Ala Tyr Trp Gly Gln Gly Thr Leu Val
            100                 105                 110

Thr Val Ser Ser
        115

<210> SEQ ID NO 39
<211> LENGTH: 116
<212> TYPE: PRT
<213> ORGANISM: Artificial
<220> FEATURE:
<223> OTHER INFORMATION: Synthetic

<400> SEQUENCE: 39

Glu Val Gln Leu Val Glu Ser Gly Gly Gly Val Val Gln Pro Gly Gly
1               5                   10                  15

Ser Leu Arg Leu Ser Cys Ala Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 40
<211> LENGTH: 116
<212> TYPE: PRT
<213> ORGANISM: Artificial
<220> FEATURE:
<223> OTHER INFORMATION: Synthetic

<400> SEQUENCE: 40

Glu Val Gln Leu Val Glu Ser Gly Gly Gly Leu Lys Gln Pro Gly Gly
1               5                   10                  15

Ser Leu Arg Leu Ser Cys Ala Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 41
<211> LENGTH: 116
<212> TYPE: PRT
```

<213> ORGANISM: Artificial
<220> FEATURE:
<223> OTHER INFORMATION: Synthetic

<400> SEQUENCE: 41

Glu Val Gln Leu Val Glu Ser Gly Gly Gly Leu Val Lys Pro Gly Gly
1               5                   10                  15

Ser Leu Arg Leu Ser Cys Ala Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
            115

<210> SEQ ID NO 42
<211> LENGTH: 116
<212> TYPE: PRT
<213> ORGANISM: Artificial
<220> FEATURE:
<223> OTHER INFORMATION: Synthetic

<400> SEQUENCE: 42

Glu Val Gln Leu Val Glu Ser Gly Gly Gly Leu Val Arg Pro Gly Gly
1               5                   10                  15

Ser Leu Arg Leu Ser Cys Ala Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
            115

<210> SEQ ID NO 43
<211> LENGTH: 116
<212> TYPE: PRT
<213> ORGANISM: Artificial
<220> FEATURE:
<223> OTHER INFORMATION: Synthetic

<400> SEQUENCE: 43

Glu Val Gln Leu Val Glu Ser Gly Gly Gly Leu Val Gln Pro Gly Ala
1               5                   10                  15

Ser Leu Arg Leu Ser Cys Ala Ala Ser Gly Tyr Ala Phe Thr Asn Tyr
            20                  25                  30

```
Leu Ile Glu Trp Val Arg Gln Ala Pro Gly Gln Gly Leu Glu Trp Met
            35                  40                  45

Gly Val Ile Asn Pro Gly Ser Gly Gly Thr Asn Tyr Asn Glu Ser Leu
        50                  55                  60

Lys Ser Arg Val Thr Ile Ser Ala Asp Lys Ser Ile Ser Thr Ala Tyr
 65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 44
<211> LENGTH: 116
<212> TYPE: PRT
<213> ORGANISM: Artificial
<220> FEATURE:
<223> OTHER INFORMATION: Synthetic

<400> SEQUENCE: 44

Glu Val Gln Leu Val Glu Ser Gly Gly Gly Leu Val Gln Pro Gly Thr
 1               5                  10                  15

Ser Leu Arg Leu Ser Cys Ala Ala Ser Gly Tyr Ala Phe Thr Asn Tyr
                20                  25                  30

Leu Ile Glu Trp Val Arg Gln Ala Pro Gly Gln Gly Leu Glu Trp Met
            35                  40                  45

Gly Val Ile Asn Pro Gly Ser Gly Gly Thr Asn Tyr Asn Glu Ser Leu
        50                  55                  60

Lys Ser Arg Val Thr Ile Ser Ala Asp Lys Ser Ile Ser Thr Ala Tyr
 65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 45
<211> LENGTH: 116
<212> TYPE: PRT
<213> ORGANISM: Artificial
<220> FEATURE:
<223> OTHER INFORMATION: Synthetic

<400> SEQUENCE: 45

Glu Val Gln Leu Val Glu Ser Gly Gly Gly Leu Val Gln Pro Gly Arg
 1               5                  10                  15

Ser Leu Arg Leu Ser Cys Ala Ala Ser Gly Tyr Ala Phe Thr Asn Tyr
                20                  25                  30

Leu Ile Glu Trp Val Arg Gln Ala Pro Gly Gln Gly Leu Glu Trp Met
            35                  40                  45

Gly Val Ile Asn Pro Gly Ser Gly Gly Thr Asn Tyr Asn Glu Ser Leu
        50                  55                  60

Lys Ser Arg Val Thr Ile Ser Ala Asp Lys Ser Ile Ser Thr Ala Tyr
 65                  70                  75                  80

Met Glu Leu Ser Ser Leu Arg Ser Glu Asp Thr Ala Val Tyr Phe Cys
```

```
                 85                  90                  95
Ala Arg Asp Gly Pro Trp Phe Ala Tyr Trp Gly Gln Gly Thr Leu Val
            100                 105                 110

Thr Val Ser Ser
        115

<210> SEQ ID NO 46
<211> LENGTH: 116
<212> TYPE: PRT
<213> ORGANISM: Artificial
<220> FEATURE:
<223> OTHER INFORMATION: Synthetic

<400> SEQUENCE: 46

Glu Val Gln Leu Val Glu Ser Gly Gly Gly Leu Val Gln Pro Gly Gly
1               5                  10                  15

Ser Val Arg Leu Ser Cys Ala Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 47
<211> LENGTH: 116
<212> TYPE: PRT
<213> ORGANISM: Artificial
<220> FEATURE:
<223> OTHER INFORMATION: Synthetic

<400> SEQUENCE: 47

Glu Val Gln Leu Val Glu Ser Gly Gly Gly Leu Val Gln Pro Gly Gly
1               5                  10                  15

Ser Leu Lys Leu Ser Cys Ala Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 48
<211> LENGTH: 116
```

```
<212> TYPE: PRT
<213> ORGANISM: Artificial
<220> FEATURE:
<223> OTHER INFORMATION: Synthetic

<400> SEQUENCE: 48

Glu Val Gln Leu Val Glu Ser Gly Gly Gly Leu Val Gln Pro Gly Gly
1               5                   10                  15

Ser Leu Arg Val Ser Cys Ala Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 49
<211> LENGTH: 116
<212> TYPE: PRT
<213> ORGANISM: Artificial
<220> FEATURE:
<223> OTHER INFORMATION: Synthetic

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 50
<211> LENGTH: 116
<212> TYPE: PRT
<213> ORGANISM: Artificial
<220> FEATURE:
<223> OTHER INFORMATION: Synthetic

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Arg Ala Ser Gly Tyr Ala Phe Thr Asn Tyr
```

-continued

```
                    20                  25                  30
Leu Ile Glu Trp Val Arg Gln Ala Pro Gly Gln Gly Leu Glu Trp Met
            35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 51
<211> LENGTH: 116
<212> TYPE: PRT
<213> ORGANISM: Artificial
<220> FEATURE:
<223> OTHER INFORMATION: Synthetic

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Thr Ala Ser Gly Tyr Ala Phe Thr Asn Tyr
            20                  25                  30

Leu Ile Glu Trp Val Arg Gln Ala Pro Gly Gln Gly Leu Glu Trp Met
        35                      40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 52
<211> LENGTH: 116
<212> TYPE: PRT
<213> ORGANISM: Artificial
<220> FEATURE:
<223> OTHER INFORMATION: Synthetic

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Ala Phe Thr Asn Tyr
            20                  25                  30

Leu Ile Glu Trp Val Arg Gln Ala Pro Gly Gln Gly Leu Glu Trp Met
        35                      40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80
```

```
Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 53
<211> LENGTH: 116
<212> TYPE: PRT
<213> ORGANISM: Artificial
<220> FEATURE:
<223> OTHER INFORMATION: Synthetic

<400> SEQUENCE: 53

Glu Val Gln Leu Val Glu Ser Gly Gly Gly Leu Val Gln Pro Gly Gly
1               5                   10                  15

Ser Leu Arg Leu Ser Cys Ala Ala Thr Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 54
<211> LENGTH: 116
<212> TYPE: PRT
<213> ORGANISM: Artificial
<220> FEATURE:
<223> OTHER INFORMATION: Synthetic

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Ala Ser Ala Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 55
```

```
<211> LENGTH: 116
<212> TYPE: PRT
<213> ORGANISM: Artificial
<220> FEATURE:
<223> OTHER INFORMATION: Synthetic

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 56
<211> LENGTH: 116
<212> TYPE: PRT
<213> ORGANISM: Artificial
<220> FEATURE:
<223> OTHER INFORMATION: Synthetic

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 57
<211> LENGTH: 116
<212> TYPE: PRT
<213> ORGANISM: Artificial
<220> FEATURE:
<223> OTHER INFORMATION: Synthetic

<400> SEQUENCE: 57

Glu Val Gln Leu Val Glu Ser Gly Gly Gly Leu Val Gln Pro Gly Gly
1               5                   10                  15
```

Ser Leu Arg Leu Ser Cys Ala Ala Ser Gly Tyr Ala Phe Ser Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 58
<211> LENGTH: 116
<212> TYPE: PRT
<213> ORGANISM: Artificial
<220> FEATURE:
<223> OTHER INFORMATION: Synthetic

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ala Phe Thr Asp Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 59
<211> LENGTH: 116
<212> TYPE: PRT
<213> ORGANISM: Artificial
<220> FEATURE:
<223> OTHER INFORMATION: Synthetic

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ala Phe Thr Asn Tyr
            20                  25                  30

Leu Leu Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 60
<211> LENGTH: 116
<212> TYPE: PRT
<213> ORGANISM: Artificial
<220> FEATURE:
<223> OTHER INFORMATION: Synthetic

<400> SEQUENCE: 60

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ala Phe Thr Asn Tyr
            20                  25                  30

Leu Met Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 61
<211> LENGTH: 116
<212> TYPE: PRT
<213> ORGANISM: Artificial
<220> FEATURE:
<223> OTHER INFORMATION: Synthetic

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ala Phe Thr Asn Tyr
            20                  25                  30

Leu Ile Ser Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

```
<210> SEQ ID NO 62
<211> LENGTH: 116
<212> TYPE: PRT
<213> ORGANISM: Artificial
<220> FEATURE:
<223> OTHER INFORMATION: Synthetic

<400> SEQUENCE: 62

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ala Phe Thr Asn Tyr
            20                  25                  30

Leu Ile Asn Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 63
<211> LENGTH: 116
<212> TYPE: PRT
<213> ORGANISM: Artificial
<220> FEATURE:
<223> OTHER INFORMATION: Synthetic

<400> SEQUENCE: 63

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ala Phe Thr Asn Tyr
            20                  25                  30

Leu Ile Asp Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 64
<211> LENGTH: 116
<212> TYPE: PRT
<213> ORGANISM: Artificial
<220> FEATURE:
<223> OTHER INFORMATION: Synthetic

<400> SEQUENCE: 64

Glu Val Gln Leu Val Glu Ser Gly Gly Gly Leu Val Gln Pro Gly Gly
1               5                   10                  15
```

Ser Leu Arg Leu Ser Cys Ala Ala Ser Gly Tyr Ala Phe Thr Asn Tyr
            20                  25                  30

Leu Ile Tyr Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 65
<211> LENGTH: 116
<212> TYPE: PRT
<213> ORGANISM: Artificial
<220> FEATURE:
<223> OTHER INFORMATION: Synthetic

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ala Phe Thr Asn Tyr
            20                  25                  30

Leu Ile Glu Trp Ile Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 66
<211> LENGTH: 116
<212> TYPE: PRT
<213> ORGANISM: Artificial
<220> FEATURE:
<223> OTHER INFORMATION: Synthetic

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ala Phe Thr Asn Tyr
            20                  25                  30

Leu Ile Glu Trp Val Arg Gln Arg Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr

```
                65                  70                  75                  80
Met Glu Leu Ser Ser Leu Arg Ser Glu Asp Thr Ala Val Tyr Phe Cys
                    85                  90                  95

Ala Arg Asp Gly Pro Trp Phe Ala Tyr Trp Gly Gln Gly Thr Leu Val
                100                 105                 110

Thr Val Ser Ser
        115

<210> SEQ ID NO 67
<211> LENGTH: 116
<212> TYPE: PRT
<213> ORGANISM: Artificial
<220> FEATURE:
<223> OTHER INFORMATION: Synthetic

<400> SEQUENCE: 67

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ala Phe Thr Asn Tyr
                20                  25                  30

Leu Ile Glu Trp Val Arg Gln Ala Pro Gly Gln Gly Leu Glu Trp Met
            35                  40                  45

Gly Gly Ile Asn Pro Gly Ser Gly Gly Thr Asn Tyr Asn Glu Ser Leu
        50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                    85                  90                  95

Ala Arg Asp Gly Pro Trp Phe Ala Tyr Trp Gly Gln Gly Thr Leu Val
                100                 105                 110

Thr Val Ser Ser
        115

<210> SEQ ID NO 68
<211> LENGTH: 116
<212> TYPE: PRT
<213> ORGANISM: Artificial
<220> FEATURE:
<223> OTHER INFORMATION: Synthetic

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ala Phe Thr Asn Tyr
                20                  25                  30

Leu Ile Glu Trp Val Arg Gln Ala Pro Gly Gln Gly Leu Glu Trp Met
            35                  40                  45

Gly Trp Ile Asn Pro Gly Ser Gly Gly Thr Asn Tyr Asn Glu Ser Leu
        50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                    85                  90                  95

Ala Arg Asp Gly Pro Trp Phe Ala Tyr Trp Gly Gln Gly Thr Leu Val
                100                 105                 110

Thr Val Ser Ser
        115
```

```
<210> SEQ ID NO 69
<211> LENGTH: 116
<212> TYPE: PRT
<213> ORGANISM: Artificial
<220> FEATURE:
<223> OTHER INFORMATION: Synthetic

<400> SEQUENCE: 69

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Ile Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 70
<211> LENGTH: 116
<212> TYPE: PRT
<213> ORGANISM: Artificial
<220> FEATURE:
<223> OTHER INFORMATION: Synthetic

<400> SEQUENCE: 70

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Val Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 71
<211> LENGTH: 116
<212> TYPE: PRT
<213> ORGANISM: Artificial
<220> FEATURE:
<223> OTHER INFORMATION: Synthetic

<400> SEQUENCE: 71

Glu Val Gln Leu Val Glu Ser Gly Gly Gly Leu Val Gln Pro Gly Gly
```

```
                 1               5                  10                 15
Ser Leu Arg Leu Ser Cys Ala Ala Ser Gly Tyr Ala Phe Thr Asn Tyr
                20                 25                 30

Leu Ile Glu Trp Val Arg Gln Ala Pro Gly Gln Gly Leu Glu Trp Met
                35                 40                 45

Gly Val Ile Asn Pro Gly Ser Gly Ala Thr Asn Tyr Asn Glu Ser Leu
    50                 55                 60

Lys Ser Arg Val Thr Ile Ser Ala Asp Lys Ser Ile Ser Thr Ala Tyr
65                 70                 75                 80

Met Glu Leu Ser Ser Leu Arg Ser Glu Asp Thr Ala Val Tyr Phe Cys
                85                 90                 95

Ala Arg Asp Gly Pro Trp Phe Ala Tyr Trp Gly Gln Gly Thr Leu Val
                100                105                110

Thr Val Ser Ser
        115

<210> SEQ ID NO 72
<211> LENGTH: 116
<212> TYPE: PRT
<213> ORGANISM: Artificial
<220> FEATURE:
<223> OTHER INFORMATION: Synthetic

<400> SEQUENCE: 72

Glu Val Gln Leu Val Glu Ser Gly Gly Gly Leu Val Gln Pro Gly Gly
1               5                  10                 15

Ser Leu Arg Leu Ser Cys Ala Ala Ser Gly Tyr Ala Phe Thr Asn Tyr
                20                 25                 30

Leu Ile Glu Trp Val Arg Gln Ala Pro Gly Gln Gly Leu Glu Trp Met
                35                 40                 45

Gly Val Ile Asn Pro Gly Ser Gly Gly Ser Asn Tyr Asn Glu Ser Leu
    50                 55                 60

Lys Ser Arg Val Thr Ile Ser Ala Asp Lys Ser Ile Ser Thr Ala Tyr
65                 70                 75                 80

Met Glu Leu Ser Ser Leu Arg Ser Glu Asp Thr Ala Val Tyr Phe Cys
                85                 90                 95

Ala Arg Asp Gly Pro Trp Phe Ala Tyr Trp Gly Gln Gly Thr Leu Val
                100                105                110

Thr Val Ser Ser
        115

<210> SEQ ID NO 73
<211> LENGTH: 116
<212> TYPE: PRT
<213> ORGANISM: Artificial
<220> FEATURE:
<223> OTHER INFORMATION: Synthetic

<400> SEQUENCE: 73

Glu Val Gln Leu Val Glu Ser Gly Gly Gly Leu Val Gln Pro Gly Gly
1               5                  10                 15

Ser Leu Arg Leu Ser Cys Ala Ala Ser Gly Tyr Ala Phe Thr Asn Tyr
                20                 25                 30

Leu Ile Glu Trp Val Arg Gln Ala Pro Gly Gln Gly Leu Glu Trp Met
                35                 40                 45

Gly Val Ile Asn Pro Gly Ser Gly Gly Thr Tyr Tyr Asn Glu Ser Leu
    50                 55                 60
```

```
Lys Ser Arg Val Thr Ile Ser Ala Asp Lys Ser Ile Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 74
<211> LENGTH: 116
<212> TYPE: PRT
<213> ORGANISM: Artificial
<220> FEATURE:
<223> OTHER INFORMATION: Synthetic

<400> SEQUENCE: 74

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Ala Phe Thr Asn Tyr
                20                  25                  30

Leu Ile Glu Trp Val Arg Gln Ala Pro Gly Gln Gly Leu Glu Trp Met
            35                  40                  45

Gly Val Ile Asn Pro Gly Ser Gly Gly Thr Asn Tyr Asn Pro Ser Leu
        50                  55                  60

Lys Ser Arg Val Thr Ile Ser Ala Asp Lys Ser Ile Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 75
<211> LENGTH: 116
<212> TYPE: PRT
<213> ORGANISM: Artificial
<220> FEATURE:
<223> OTHER INFORMATION: Synthetic

<400> SEQUENCE: 75

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Ala Phe Thr Asn Tyr
                20                  25                  30

Leu Ile Glu Trp Val Arg Gln Ala Pro Gly Gln Gly Leu Glu Trp Met
            35                  40                  45

Gly Val Ile Asn Pro Gly Ser Gly Gly Thr Asn Tyr Asn Glu Lys Leu
        50                  55                  60

Lys Ser Arg Val Thr Ile Ser Ala Asp Lys Ser Ile Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg Asp Gly Pro Trp Phe Ala Tyr Trp Gly Gln Gly Thr Leu Val
            100                 105                 110

Thr Val Ser Ser
        115
```

<210> SEQ ID NO 76
<211> LENGTH: 116
<212> TYPE: PRT
<213> ORGANISM: Artificial
<220> FEATURE:
<223> OTHER INFORMATION: Synthetic

<400> SEQUENCE: 76

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Arg Asp Lys Ser Ile Ser Thr Ala Tyr
 65                 70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115
```

<210> SEQ ID NO 77
<211> LENGTH: 116
<212> TYPE: PRT
<213> ORGANISM: Artificial
<220> FEATURE:
<223> OTHER INFORMATION: Synthetic

<400> SEQUENCE: 77

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Lys Ser Thr Ala Tyr
 65                 70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115
```

<210> SEQ ID NO 78
<211> LENGTH: 116
<212> TYPE: PRT
<213> ORGANISM: Artificial
<220> FEATURE:
<223> OTHER INFORMATION: Synthetic

<400> SEQUENCE: 78

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Asn Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
                100                 105                 110

Thr Val Ser Ser
        115

<210> SEQ ID NO 79
<211> LENGTH: 116
<212> TYPE: PRT
<213> ORGANISM: Artificial
<220> FEATURE:
<223> OTHER INFORMATION: Synthetic

<400> SEQUENCE: 79

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Thr Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
                100                 105                 110

Thr Val Ser Ser
        115

<210> SEQ ID NO 80
<211> LENGTH: 116
<212> TYPE: PRT
<213> ORGANISM: Artificial
<220> FEATURE:
<223> OTHER INFORMATION: Synthetic

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60
```

```
Lys Ser Arg Val Thr Ile Ser Ala Asp Lys Ser Ile Ser Ser Ala Tyr
 65                  70                  75                  80

Met Glu Leu Ser Ser Leu Arg Ser Glu Asp Thr Ala Val Tyr Phe Cys
                 85                  90                  95

Ala Arg Asp Gly Pro Trp Phe Ala Tyr Trp Gly Gln Gly Thr Leu Val
            100                 105                 110

Thr Val Ser Ser
        115
```

<210> SEQ ID NO 81
<211> LENGTH: 116
<212> TYPE: PRT
<213> ORGANISM: Artificial
<220> FEATURE:
<223> OTHER INFORMATION: Synthetic

<400> SEQUENCE: 81

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Ala Phe Thr Asn Tyr
                20                  25                  30

Leu Ile Glu Trp Val Arg Gln Ala Pro Gly Gln Gly Leu Glu Trp Met
            35                  40                  45

Gly Val Ile Asn Pro Gly Ser Gly Gly Thr Asn Tyr Asn Glu Ser Leu
 50                  55                  60

Lys Ser Arg Val Thr Ile Ser Ala Asp Lys Ser Ile Ser Thr Leu Tyr
 65                  70                  75                  80

Met Glu Leu Ser Ser Leu Arg Ser Glu Asp Thr Ala Val Tyr Phe Cys
                 85                  90                  95

Ala Arg Asp Gly Pro Trp Phe Ala Tyr Trp Gly Gln Gly Thr Leu Val
            100                 105                 110

Thr Val Ser Ser
        115
```

<210> SEQ ID NO 82
<211> LENGTH: 116
<212> TYPE: PRT
<213> ORGANISM: Artificial
<220> FEATURE:
<223> OTHER INFORMATION: Synthetic

<400> SEQUENCE: 82

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Ala Phe Thr Asn Tyr
                20                  25                  30

Leu Ile Glu Trp Val Arg Gln Ala Pro Gly Gln Gly Leu Glu Trp Met
            35                  40                  45

Gly Val Ile Asn Pro Gly Ser Gly Gly Thr Asn Tyr Asn Glu Ser Leu
 50                  55                  60

Lys Ser Arg Val Thr Ile Ser Ala Asp Lys Ser Ile Ser Thr Val Tyr
 65                  70                  75                  80

Met Glu Leu Ser Ser Leu Arg Ser Glu Asp Thr Ala Val Tyr Phe Cys
                 85                  90                  95

Ala Arg Asp Gly Pro Trp Phe Ala Tyr Trp Gly Gln Gly Thr Leu Val
            100                 105                 110

Thr Val Ser Ser
```

<210> SEQ ID NO 83
<211> LENGTH: 116
<212> TYPE: PRT
<213> ORGANISM: Artificial
<220> FEATURE:
<223> OTHER INFORMATION: Synthetic

<400> SEQUENCE: 83

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Leu Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
            115
```

<210> SEQ ID NO 84
<211> LENGTH: 116
<212> TYPE: PRT
<213> ORGANISM: Artificial
<220> FEATURE:
<223> OTHER INFORMATION: Synthetic

<400> SEQUENCE: 84

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Gln Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
            115
```

<210> SEQ ID NO 85
<211> LENGTH: 116
<212> TYPE: PRT
<213> ORGANISM: Artificial
<220> FEATURE:
<223> OTHER INFORMATION: Synthetic

<400> SEQUENCE: 85

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Tyr Ala Phe Thr Asn Tyr
             20                  25                  30

Leu Ile Glu Trp Val Arg Gln Ala Pro Gly Gln Gly Leu Glu Trp Met
         35                  40                  45

Gly Val Ile Asn Pro Ser Gly Gly Thr Asn Tyr Asn Glu Ser Leu
     50                  55                  60

Lys Ser Arg Val Thr Ile Ser Ala Asp Lys Ser Ile Ser Thr Ala Tyr
 65                  70                  75                  80

Met Glu Met Ser Ser Leu Arg Ser Glu Asp Thr Ala Val Tyr Phe Cys
                 85                  90                  95

Ala Arg Asp Gly Pro Trp Phe Ala Tyr Trp Gly Gln Gly Thr Leu Val
             100                 105                 110

Thr Val Ser Ser
         115
```

<210> SEQ ID NO 86
<211> LENGTH: 116
<212> TYPE: PRT
<213> ORGANISM: Artificial
<220> FEATURE:
<223> OTHER INFORMATION: Synthetic

<400> SEQUENCE: 86

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Tyr Ala Phe Thr Asn Tyr
             20                  25                  30

Leu Ile Glu Trp Val Arg Gln Ala Pro Gly Gln Gly Leu Glu Trp Met
         35                  40                  45

Gly Val Ile Asn Pro Ser Gly Gly Thr Asn Tyr Asn Glu Ser Leu
     50                  55                  60

Lys Ser Arg Val Thr Ile Ser Ala Asp Lys Ser Ile Ser Thr Ala Tyr
 65                  70                  75                  80

Met Glu Leu Asn Ser Leu Arg Ser Glu Asp Thr Ala Val Tyr Phe Cys
                 85                  90                  95

Ala Arg Asp Gly Pro Trp Phe Ala Tyr Trp Gly Gln Gly Thr Leu Val
             100                 105                 110

Thr Val Ser Ser
         115
```

<210> SEQ ID NO 87
<211> LENGTH: 116
<212> TYPE: PRT
<213> ORGANISM: Artificial
<220> FEATURE:
<223> OTHER INFORMATION: Synthetic

<400> SEQUENCE: 87

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Tyr Ala Phe Thr Asn Tyr
             20                  25                  30

Leu Ile Glu Trp Val Arg Gln Ala Pro Gly Gln Gly Leu Glu Trp Met
         35                  40                  45

Gly Val Ile Asn Pro Ser Gly Gly Thr Asn Tyr Asn Glu Ser Leu
     50                  55                  60
```

```
            50                  55                  60
Lys Ser Arg Val Thr Ile Ser Ala Asp Lys Ser Ile Ser Thr Ala Tyr
 65                  70                  75                  80

Met Glu Leu Ser Ser Leu Arg Ala Glu Asp Thr Ala Val Tyr Phe Cys
                 85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 88
<211> LENGTH: 116
<212> TYPE: PRT
<213> ORGANISM: Artificial
<220> FEATURE:
<223> OTHER INFORMATION: Synthetic

<400> SEQUENCE: 88

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Ala Phe Thr Asn Tyr
             20                  25                  30

Leu Ile Glu Trp Val Arg Gln Ala Pro Gly Gln Gly Leu Glu Trp Met
         35                  40                  45

Gly Val Ile Asn Pro Gly Ser Gly Gly Thr Asn Tyr Asn Glu Ser Leu
     50                  55                  60

Lys Ser Arg Val Thr Ile Ser Ala Asp Lys Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 89
<211> LENGTH: 116
<212> TYPE: PRT
<213> ORGANISM: Artificial
<220> FEATURE:
<223> OTHER INFORMATION: Synthetic

<400> SEQUENCE: 89

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Ala Phe Thr Asn Tyr
             20                  25                  30

Leu Ile Glu Trp Val Arg Gln Ala Pro Gly Gln Gly Leu Glu Trp Met
         35                  40                  45

Gly Val Ile Asn Pro Gly Ser Gly Gly Thr Asn Tyr Asn Glu Ser Leu
     50                  55                  60

Lys Ser Arg Val Thr Ile Ser Ala Asp Lys Ser Ile Ser Thr Ala Tyr
 65                  70                  75                  80

Met Glu Leu Ser Ser Leu Arg Ser Glu Asp Thr Ala Val Tyr Phe Cys
                 85                  90                  95

Val Arg Asp Gly Pro Trp Phe Ala Tyr Trp Gly Gln Gly Thr Leu Val
            100                 105                 110
```

-continued

Thr Val Ser Ser
        115

<210> SEQ ID NO 90
<211> LENGTH: 116
<212> TYPE: PRT
<213> ORGANISM: Artificial
<220> FEATURE:
<223> OTHER INFORMATION: Synthetic

<400> SEQUENCE: 90

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Gly Arg Asp Gly Pro Trp Phe Ala Tyr Trp Gly Gln Gly Thr Leu Val
            100                 105                 110

Thr Val Ser Ser
        115

<210> SEQ ID NO 91
<211> LENGTH: 116
<212> TYPE: PRT
<213> ORGANISM: Artificial
<220> FEATURE:
<223> OTHER INFORMATION: Synthetic

<400> SEQUENCE: 91

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Lys Asp Gly Pro Trp Phe Ala Tyr Trp Gly Gln Gly Thr Leu Val
            100                 105                 110

Thr Val Ser Ser
        115

<210> SEQ ID NO 92
<211> LENGTH: 116
<212> TYPE: PRT
<213> ORGANISM: Artificial
<220> FEATURE:
<223> OTHER INFORMATION: Synthetic

<400> SEQUENCE: 92

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Tyr | Ala | Phe | Thr | Asn | Tyr |
|---|---|---|---|---|---|---|---|---|---|---|---|---|---|---|---|
| | | | 20 | | | | | 25 | | | | | 30 | | |

| Leu | Ile | Glu | Trp | Val | Arg | Gln | Ala | Pro | Gly | Gln | Gly | Leu | Glu | Trp | Met |
|---|---|---|---|---|---|---|---|---|---|---|---|---|---|---|---|
| | | 35 | | | | | 40 | | | | | 45 | | | |

| Gly | Val | Ile | Asn | Pro | Gly | Ser | Gly | Gly | Thr | Asn | Tyr | Asn | Glu | Ser | Leu |
|---|---|---|---|---|---|---|---|---|---|---|---|---|---|---|---|
| 50 | | | | | 55 | | | | | 60 | | | | | |

| Lys | Ser | Arg | Val | Thr | Ile | Ser | Ala | Asp | Lys | Ser | Ile | Ser | Thr | Ala | Tyr |
|---|---|---|---|---|---|---|---|---|---|---|---|---|---|---|---|
| 65 | | | | | 70 | | | | | 75 | | | | | 80 |

| Met | Glu | Leu | Ser | Ser | Leu | Arg | Ser | Glu | Asp | Thr | Ala | Val | Tyr | Phe | Cys |
|---|---|---|---|---|---|---|---|---|---|---|---|---|---|---|---|
| | | | | 85 | | | | | 90 | | | | | 95 | |

| Ala | Arg | Asp | Gly | Pro | Trp | Tyr | Ala | Tyr | Trp | Gly | Gln | Gly | Thr | Leu | Val |
|---|---|---|---|---|---|---|---|---|---|---|---|---|---|---|---|
| | | | 100 | | | | | 105 | | | | | 110 | | |

| Thr | Val | Ser | Ser |
|---|---|---|---|
| | | | 115 |

<210> SEQ ID NO 93
<211> LENGTH: 116
<212> TYPE: PRT
<213> ORGANISM: Artificial
<220> FEATURE:
<223> OTHER INFORMATION: Synthetic

<400> SEQUENCE: 93

| Glu | Val | Gln | Leu | Val | Gln | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Tyr | Ser | Phe | Thr | Asn | Tyr |
|---|---|---|---|---|---|---|---|---|---|---|---|---|---|---|---|
| | | | 20 | | | | | 25 | | | | | 30 | | |

| Leu | Ile | Glu | Trp | Val | Arg | Gln | Ala | Pro | Gly | Gln | Gly | Leu | Glu | Trp | Met |
|---|---|---|---|---|---|---|---|---|---|---|---|---|---|---|---|
| | | 35 | | | | | 40 | | | | | 45 | | | |

| Gly | Val | Ile | Asn | Pro | Gly | Ser | Gly | Gly | Thr | Asn | Tyr | Asn | Glu | Ser | Leu |
|---|---|---|---|---|---|---|---|---|---|---|---|---|---|---|---|
| 50 | | | | | 55 | | | | | 60 | | | | | |

| Lys | Ser | Arg | Val | Thr | Ile | Ser | Ala | Asp | Lys | Ser | Ile | Ser | Thr | Ala | Tyr |
|---|---|---|---|---|---|---|---|---|---|---|---|---|---|---|---|
| 65 | | | | | 70 | | | | | 75 | | | | | 80 |

| Met | Glu | Leu | Ser | Ser | Leu | Arg | Ser | Glu | Asp | Thr | Ala | Val | Tyr | Phe | Cys |
|---|---|---|---|---|---|---|---|---|---|---|---|---|---|---|---|
| | | | | 85 | | | | | 90 | | | | | 95 | |

| Ala | Arg | Asp | Gly | Pro | Trp | Phe | Ala | Tyr | Trp | Gly | Gln | Gly | Thr | Leu | Val |
|---|---|---|---|---|---|---|---|---|---|---|---|---|---|---|---|
| | | | 100 | | | | | 105 | | | | | 110 | | |

| Thr | Val | Ser | Ser |
|---|---|---|---|
| | | | 115 |

<210> SEQ ID NO 94
<211> LENGTH: 116
<212> TYPE: PRT
<213> ORGANISM: Artificial
<220> FEATURE:
<223> OTHER INFORMATION: Synthetic

<400> SEQUENCE: 94

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Tyr | Ser | Phe | Thr | Asn | Tyr |
|---|---|---|---|---|---|---|---|---|---|---|---|---|---|---|---|
| | | | 20 | | | | | 25 | | | | | 30 | | |

| Leu | Ile | Glu | Trp | Val | Arg | Gln | Ala | Pro | Gly | Gln | Gly | Leu | Glu | Trp | Met |
|---|---|---|---|---|---|---|---|---|---|---|---|---|---|---|---|
| | | 35 | | | | | 40 | | | | | 45 | | | |

Gly Ile Ile Asn Pro Gly Ser Gly Gly Thr Asn Tyr Asn Glu Ser Leu
            50                  55                  60

Lys Ser Arg Val Thr Ile Ser Ala Asp Lys Ser Ile Ser Thr Ala Tyr
 65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
                100                 105                 110

Thr Val Ser Ser
        115

<210> SEQ ID NO 95
<211> LENGTH: 116
<212> TYPE: PRT
<213> ORGANISM: Artificial
<220> FEATURE:
<223> OTHER INFORMATION: Synthetic

<400> SEQUENCE: 95

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Ser Phe Thr Asn Tyr
                20                  25                  30

Leu Ile Glu Trp Val Arg Gln Ala Pro Gly Gln Gly Leu Glu Trp Met
                35                  40                  45

Gly Ile Ile Asn Pro Gly Ser Gly Gly Thr Asn Tyr Asn Pro Ser Leu
            50                  55                  60

Lys Ser Arg Val Thr Ile Ser Ala Asp Lys Ser Ile Ser Thr Ala Tyr
 65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
                100                 105                 110

Thr Val Ser Ser
        115

<210> SEQ ID NO 96
<211> LENGTH: 116
<212> TYPE: PRT
<213> ORGANISM: Artificial
<220> FEATURE:
<223> OTHER INFORMATION: Synthetic

<400> SEQUENCE: 96

Glu Val Gln Leu Val Gln Ser Gly Gly Gly Leu Val Gln Pro Gly Gly
 1               5                  10                  15

Ser Leu Arg Leu Ser Cys Ala Ala Ser Gly Tyr Ser Phe Thr Asn Tyr
                20                  25                  30

Leu Ile Glu Trp Val Arg Gln Ala Pro Gly Gln Gly Leu Glu Trp Met
                35                  40                  45

Gly Ile Ile Asn Pro Gly Ser Gly Gly Thr Asn Tyr Asn Pro Ser Leu
            50                  55                  60

Lys Ser Arg Val Thr Ile Ser Ala Asp Lys Ser Ile Ser Thr Ala Tyr
 65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
                100                 105                 110

-continued

Thr Val Ser Ser
        115

<210> SEQ ID NO 97
<211> LENGTH: 116
<212> TYPE: PRT
<213> ORGANISM: Artificial
<220> FEATURE:
<223> OTHER INFORMATION: Synthetic

<400> SEQUENCE: 97

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Pro Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 98
<211> LENGTH: 116
<212> TYPE: PRT
<213> ORGANISM: Artificial
<220> FEATURE:
<223> OTHER INFORMATION: Synthetic

<400> SEQUENCE: 98

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Asn Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 99
<211> LENGTH: 116
<212> TYPE: PRT
<213> ORGANISM: Artificial
<220> FEATURE:
<223> OTHER INFORMATION: Synthetic -continued

```
<400> SEQUENCE: 99

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Thr Asn Tyr Asn Glu Ala Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
                100                 105                 110

Thr Val Ser Ser
            115

<210> SEQ ID NO 100
<211> LENGTH: 116
<212> TYPE: PRT
<213> ORGANISM: Artificial
<220> FEATURE:
<223> OTHER INFORMATION: Synthetic

<400> SEQUENCE: 100

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Ala Glu Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
                100                 105                 110

Thr Val Ser Ser
            115

<210> SEQ ID NO 101
<211> LENGTH: 116
<212> TYPE: PRT
<213> ORGANISM: Artificial
<220> FEATURE:
<223> OTHER INFORMATION: Synthetic

<400> SEQUENCE: 101

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Asn Tyr
            20                  25                  30

Leu Ile Glu Trp Val Arg Gln Ala Pro Gly Gln Gly Leu Glu Trp Met
        35                  40                  45
```

Gly Val Ile Asn Pro Gly Ser Gly Thr Asn Tyr Gln Glu Ser Leu
            50                  55                  60

Lys Ser Arg Val Thr Ile Ser Ala Asp Lys Ser Ile Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg Asp Gly Pro Trp Phe Ala Tyr Trp Gly Gln Gly Thr Leu Val
                100                 105                 110

Thr Val Ser Ser
        115

<210> SEQ ID NO 102
<211> LENGTH: 116
<212> TYPE: PRT
<213> ORGANISM: Artificial
<220> FEATURE:
<223> OTHER INFORMATION: Synthetic

<400> SEQUENCE: 102

Gln Val Gln Leu Val Glu Ser Gly Gly Gly Leu Val Gln Pro Gly Gly
 1               5                  10                  15

Ser Leu Arg Leu Ser Cys Ala Ala Ser Gly Tyr Ala Phe Thr Asn Tyr
                20                  25                  30

Leu Ile Glu Trp Val Arg Gln Ala Pro Gly Gln Gly Leu Glu Trp Met
            35                  40                  45

Gly Val Ile Asn Pro Gly Ser Gly Thr Asn Tyr Asn Glu Lys Phe
        50                  55                  60

Gln Gly Arg Val Thr Ile Thr Arg Asp Thr Ser Ala Ser Thr Ala Tyr
 65                  70                  75                  80

Leu Gln Ile Ser Ser Leu Lys Ala Glu Asp Thr Ala Val Tyr Phe Cys
                 85                  90                  95

Ala Arg Asp Gly Pro Trp Phe Ala Tyr Trp Gly Gln Gly Thr Leu Val
                100                 105                 110

Thr Val Ser Ser
        115

<210> SEQ ID NO 103
<211> LENGTH: 116
<212> TYPE: PRT
<213> ORGANISM: Artificial
<220> FEATURE:
<223> OTHER INFORMATION: Synthetic

<400> SEQUENCE: 103

Gln Val Gln Leu Val Glu Ser Gly Gly Gly Leu Val Gln Pro Gly Gly
 1               5                  10                  15

Ser Leu Arg Leu Ser Cys Ala Ala Ser Gly Tyr Ala Phe Thr Asn Tyr
                20                  25                  30

Leu Ile Glu Trp Val Arg Gln Ala Pro Gly Gln Gly Leu Glu Trp Met
            35                  40                  45

Gly Val Ile Asn Pro Gly Ser Gly Thr Asn Tyr Ala Glu Lys Phe
        50                  55                  60

Gln Gly Arg Val Thr Ile Thr Arg Asp Thr Ser Ala Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Arg Asp Gly Pro Trp Phe Ala Tyr Trp Gly Gln Gly Thr Leu Val 100                 105                 110

Thr Val Ser Ser
        115

<210> SEQ ID NO 104
<211> LENGTH: 116
<212> TYPE: PRT
<213> ORGANISM: Artificial
<220> FEATURE:
<223> OTHER INFORMATION: Synthetic

<400> SEQUENCE: 104

Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ala Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Glu Lys Phe
    50                  55                  60

Gln Gly Arg Val Thr Met Thr Thr Asp Thr Ser Thr Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser
        115

<210> SEQ ID NO 105
<211> LENGTH: 107
<212> TYPE: PRT
<213> ORGANISM: Artificial
<220> FEATURE:
<223> OTHER INFORMATION: Synthetic

<400> SEQUENCE: 105

Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Val Val Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Tyr Ser Tyr Pro Tyr
                85                  90                  95

Thr Phe Gly Gly Gly Thr Lys Leu Glu Ile Lys
            100                 105

<210> SEQ ID NO 106
<211> LENGTH: 107
<212> TYPE: PRT
<213> ORGANISM: Artificial
<220> FEATURE:
<223> OTHER INFORMATION: Synthetic

<400> SEQUENCE: 106

Asn Ile Val Met Thr Gln Ser Pro Ser Ser Leu Ser Ala Ser Val Gly
1               5                   10                  15

Asp Arg Val Thr Ile Thr Cys Gln Ala Ser Glu Asn Val Val Thr Tyr
                20                  25                  30

Val Ser Trp Tyr Gln Gln Lys Pro Asp Gln Ser Pro Lys Leu Leu Ile
            35                  40                  45

Tyr Gly Ala Ser Asn Arg Tyr Thr Gly Val Pro Asp Arg Phe Thr Gly
        50                  55                  60

Ser Gly Ser Ala Thr Glu Phe Thr Leu Thr Ile Ser Ser Leu Gln Ser
65                  70                  75                  80

Glu Asp Phe Ala Asp Tyr His Cys Gly Gln Gly Tyr Ser Tyr Pro Tyr
                85                  90                  95

Thr Phe Gly Gly Gly Thr Lys Leu Glu Ile Lys
            100                 105

<210> SEQ ID NO 107
<211> LENGTH: 107
<212> TYPE: PRT
<213> ORGANISM: Artificial
<220> FEATURE:
<223> OTHER INFORMATION: Synthetic

<400> SEQUENCE: 107

Asn Ile Val Met Thr Gln Ser Pro Ala Thr Leu Ser Leu Ser Pro Gly
1               5                   10                  15

Glu Arg Ala Thr Leu Ser Cys Arg Ala Ser Glu Asn Val Val Thr Tyr
                20                  25                  30

Val Ser Trp Tyr Gln Gln Lys Pro Asp Gln Ser Pro Lys Leu Leu Ile
            35                  40                  45

Tyr Gly Ala Ser Asn Arg Tyr Thr Gly Val Pro Asp Arg Phe Thr Gly
        50                  55                  60

Ser Gly Ser Ala Thr Asp Phe Thr Leu Thr Ile Ser Ser Leu Gln Ala
65                  70                  75                  80

Glu Asp Val Ala Val Tyr His Cys Gly Gln Gly Tyr Ser Tyr Pro Tyr
                85                  90                  95

Thr Phe Gly Gly Gly Thr Lys Leu Glu Ile Lys
            100                 105

<210> SEQ ID NO 108
<211> LENGTH: 107
<212> TYPE: PRT
<213> ORGANISM: Artificial
<220> FEATURE:
<223> OTHER INFORMATION: Synthetic

<400> SEQUENCE: 108

Asn Ile Val Met Thr Gln Ser Pro Asp Ser Leu Ala Val Ser Leu Gly
1               5                   10                  15

Glu Arg Ala Thr Leu Ser Cys Arg Ala Ser Glu Asn Val Val Thr Tyr
                20                  25                  30

Val Ser Trp Tyr Gln Gln Lys Pro Gly Gln Ser Pro Gln Leu Leu Ile
            35                  40                  45

Tyr Gly Ala Ser Asn Arg Tyr Thr Gly Val Pro Asp Arg Phe Thr Gly
        50                  55                  60

Ser Gly Ser Ala Thr Asp Phe Thr Leu Thr Ile Asn Ser Leu Glu Ala
65                  70                  75                  80

Glu Asp Ala Ala Thr Tyr Tyr Cys Gly Gln Gly Tyr Ser Tyr Pro Tyr

```
                            85                  90                  95

Thr Phe Gly Gly Gly Thr Lys Leu Glu Ile Lys
            100                 105

<210> SEQ ID NO 109
<211> LENGTH: 107
<212> TYPE: PRT
<213> ORGANISM: Artificial
<220> FEATURE:
<223> OTHER INFORMATION: Synthetic

<400> SEQUENCE: 109

Asn Ile Val Met Thr Gln Ser Pro Asp Ser Leu Ala Val Ser Leu Gly
1               5                   10                  15

Glu Arg Ala Thr Leu Ser Cys Arg Ala Ser Gln Asn Val Val Thr Tyr
            20                  25                  30

Val Ser Trp Tyr Gln Gln Lys Pro Gly Gln Ser Pro Gln Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Asn Ser Leu Glu Ala
65                  70                  75                  80

Glu Asp Ala Ala Thr Tyr Tyr Cys Gly Gln Gly Tyr Ser Tyr Pro Tyr
                85                  90                  95

Thr Phe Gly Gly Gly Thr Lys Leu Glu Ile Lys
            100                 105

<210> SEQ ID NO 110
<211> LENGTH: 107
<212> TYPE: PRT
<213> ORGANISM: Artificial
<220> FEATURE:
<223> OTHER INFORMATION: Synthetic

<400> SEQUENCE: 110

Asn Ile Val Met Thr Gln Ser Pro Asp Ser Leu Ala Val Ser Leu Gly
1               5                   10                  15

Glu Arg Ala Thr Leu Ser Cys Arg Ala Ser Glu Asn Val Val Thr Tyr
            20                  25                  30

Leu Ser Trp Tyr Gln Gln Lys Pro Gly Gln Ser Pro Gln Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Asn Ser Leu Glu Ala
65                  70                  75                  80

Glu Asp Ala Ala Thr Tyr Tyr Cys Gly Gln Gly Tyr Ser Tyr Pro Tyr
                85                  90                  95

Thr Phe Gly Gly Gly Thr Lys Leu Glu Ile Lys
            100                 105

<210> SEQ ID NO 111
<211> LENGTH: 107
<212> TYPE: PRT
<213> ORGANISM: Artificial
<220> FEATURE:
<223> OTHER INFORMATION: Synthetic

<400> SEQUENCE: 111

Asn Ile Val Met Thr Gln Ser Pro Asp Ser Leu Ala Val Ser Leu Gly
1               5                   10                  15
```

Glu Arg Ala Thr Leu Ser Cys Arg Ala Ser Glu Asn Val Val Thr Tyr
            20                  25                  30

Val Ser Trp Tyr Leu Gln Lys Pro Gly Gln Ser Pro Gln Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Asn Ser Leu Glu Ala
65                  70                  75                  80

Glu Asp Ala Ala Thr Tyr Tyr Cys Gly Gln Gly Tyr Ser Tyr Pro Tyr
                85                  90                  95

Thr Phe Gly Gly Gly Thr Lys Leu Glu Ile Lys
            100                 105

<210> SEQ ID NO 112
<211> LENGTH: 107
<212> TYPE: PRT
<213> ORGANISM: Artificial
<220> FEATURE:
<223> OTHER INFORMATION: Synthetic

<400> SEQUENCE: 112

Asn Ile Val Met Thr Gln Ser Pro Asp Ser Leu Ala Val Ser Leu Gly
1               5                   10                  15

Glu Arg Ala Thr Leu Ser Cys Arg Ala Ser Glu Asn Val Val Thr Tyr
            20                  25                  30

Val Ser Trp Tyr Gln Gln Lys Pro Gly Gln Pro Pro Gln Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Asn Ser Leu Glu Ala
65                  70                  75                  80

Glu Asp Ala Ala Thr Tyr Tyr Cys Gly Gln Gly Tyr Ser Tyr Pro Tyr
                85                  90                  95

Thr Phe Gly Gly Gly Thr Lys Leu Glu Ile Lys
            100                 105

<210> SEQ ID NO 113
<211> LENGTH: 107
<212> TYPE: PRT
<213> ORGANISM: Artificial
<220> FEATURE:
<223> OTHER INFORMATION: Synthetic

<400> SEQUENCE: 113

Asn Ile Val Met Thr Gln Ser Pro Asp Ser Leu Ala Val Ser Leu Gly
1               5                   10                  15

Glu Arg Ala Thr Leu Ser Cys Arg Ala Ser Glu Asn Val Val Thr Tyr
            20                  25                  30

Val Ser Trp Tyr Gln Gln Lys Pro Gly Gln Ser Pro Gln Leu Leu Ile
        35                  40                  45

Tyr Asp Ala Ser Asn Arg Tyr Thr Gly Val Pro Asp Arg Phe Thr Gly
    50                  55                  60

Ser Gly Ser Ala Thr Asp Phe Thr Leu Thr Ile Asn Ser Leu Glu Ala
65                  70                  75                  80

Glu Asp Ala Ala Thr Tyr Tyr Cys Gly Gln Gly Tyr Ser Tyr Pro Tyr
                85                  90                  95

Thr Phe Gly Gly Gly Thr Lys Leu Glu Ile Lys

<210> SEQ ID NO 114
<211> LENGTH: 107
<212> TYPE: PRT
<213> ORGANISM: Artificial
<220> FEATURE:
<223> OTHER INFORMATION: Synthetic

<400> SEQUENCE: 114

Asn Ile Val Met Thr Gln Ser Pro Asp Ser Leu Ala Val Ser Leu Gly
1               5                   10                  15

Glu Arg Ala Thr Leu Ser Cys Arg Ala Ser Glu Asn Val Val Thr Tyr
            20                  25                  30

Val Ser Trp Tyr Gln Gln Lys Pro Gly Gln Ser Pro Gln Leu Leu Ile
        35                  40                  45

Tyr Gly Ala Ser Asn Arg Tyr Thr Gly Val Pro Asp Arg Phe Ser Gly
    50                  55                  60

Ser Gly Ser Ala Thr Asp Phe Thr Leu Thr Ile Asn Ser Leu Glu Ala
65                  70                  75                  80

Glu Asp Ala Ala Thr Tyr Tyr Cys Gly Gln Gly Tyr Ser Tyr Pro Tyr
                85                  90                  95

Thr Phe Gly Gly Gly Thr Lys Leu Glu Ile Lys
            100                 105

<210> SEQ ID NO 115
<211> LENGTH: 107
<212> TYPE: PRT
<213> ORGANISM: Artificial
<220> FEATURE:
<223> OTHER INFORMATION: Synthetic

<400> SEQUENCE: 115

Asn Ile Val Met Thr Gln Ser Pro Asp Ser Leu Ala Val Ser Leu Gly
1               5                   10                  15

Glu Arg Ala Thr Leu Ser Cys Arg Ala Ser Glu Asn Val Val Thr Tyr
            20                  25                  30

Val Ser Trp Tyr Gln Gln Lys Pro Gly Gln Ser Pro Gln Leu Leu Ile
        35                  40                  45

Tyr Gly Ala Ser Asn Arg Tyr Thr Gly Val Pro Asp Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gly Gln Gly Tyr Ser Tyr Pro Tyr
                85                  90                  95

Thr Phe Gly Gly Gly Thr Lys Leu Glu Ile Lys
            100                 105

<210> SEQ ID NO 116
<211> LENGTH: 107
<212> TYPE: PRT
<213> ORGANISM: Artificial
<220> FEATURE:
<223> OTHER INFORMATION: Synthetic

<400> SEQUENCE: 116

Asn Ile Val Met Thr Gln Ser Pro Asp Ser Leu Ala Val Ser Leu Gly
1               5                   10                  15

Glu Arg Ala Thr Leu Ser Cys Arg Ala Ser Glu Asn Val Val Thr Tyr
            20                  25                  30

```
Val Ser Trp Tyr Gln Gln Lys Pro Gly Gln Ser Pro Gln Leu Leu Ile
         35                  40                  45

Tyr Gly Ala Ser Asn Arg Tyr Thr Gly Val Pro Asp Arg Phe Thr Gly
     50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys Gly Gln Gly Tyr Ser Tyr Pro Tyr
                 85                  90                  95

Thr Phe Gly Gly Gly Thr Lys Leu Glu Ile Lys
             100                 105
```

<210> SEQ ID NO 117
<211> LENGTH: 107
<212> TYPE: PRT
<213> ORGANISM: Artificial
<220> FEATURE:
<223> OTHER INFORMATION: Synthetic

<400> SEQUENCE: 117

```
Asn Ile Val Met Thr Gln Ser Pro Asp Ser Leu Ala Val Ser Leu Gly
 1               5                  10                  15

Glu Arg Ala Thr Leu Ser Cys Arg Ala Ser Glu Asn Val Val Thr Tyr
             20                  25                  30

Val Ser Trp Tyr Gln Gln Lys Pro Gly Gln Ser Pro Gln Leu Leu Ile
         35                  40                  45

Tyr Gly Ala Ser Asn Arg Tyr Thr Gly Val Pro Asp Arg Phe Thr Gly
     50                  55                  60

Ser Gly Ser Ala Thr Asp Phe Thr Leu Thr Ile Asn Ser Leu Glu Ala
 65                  70                  75                  80

Glu Asp Ala Ala Thr Tyr Tyr Cys His Gln Gly Tyr Ser Tyr Pro Tyr
                 85                  90                  95

Thr Phe Gly Gly Gly Thr Lys Leu Glu Ile Lys
             100                 105
```

<210> SEQ ID NO 118
<211> LENGTH: 107
<212> TYPE: PRT
<213> ORGANISM: Artificial
<220> FEATURE:
<223> OTHER INFORMATION: Synthetic

<400> SEQUENCE: 118

```
Asn Ile Val Met Thr Gln Ser Pro Asp Ser Leu Ala Val Ser Leu Gly
 1               5                  10                  15

Glu Arg Ala Thr Leu Ser Cys Arg Ala Ser Glu Asn Val Val Thr Tyr
             20                  25                  30

Val Ser Trp Tyr Gln Gln Lys Pro Gly Gln Ser Pro Gln Leu Leu Ile
         35                  40                  45

Tyr Gly Ala Ser Asn Arg Tyr Thr Gly Val Pro Asp Arg Phe Thr Gly
     50                  55                  60

Ser Gly Ser Ala Thr Asp Phe Thr Leu Thr Ile Asn Ser Leu Glu Ala
 65                  70                  75                  80

Glu Asp Ala Ala Thr Tyr Tyr Cys Gln Gln Gly Tyr Ser Tyr Pro Tyr
                 85                  90                  95

Thr Phe Gly Gly Gly Thr Lys Leu Glu Ile Lys
             100                 105
```

<210> SEQ ID NO 119
<211> LENGTH: 107
<212> TYPE: PRT
<213> ORGANISM: Artificial
<220> FEATURE:
<223> OTHER INFORMATION: Synthetic

<400> SEQUENCE: 119

Asn Ile Val Met Thr Gln Ser Pro Asp Ser Leu Ala Val Ser Leu Gly
1               5                   10                  15

Glu Arg Ala Thr Leu Ser Cys Arg Ala Ser Glu Asn Val Val Thr Tyr
            20                  25                  30

Val Ser Trp Tyr Gln Gln Lys Pro Gly Gln Ser Pro Gln Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Asn Ser Leu Glu Ala
65                  70                  75                  80

Glu Asp Ala Ala Thr Tyr Tyr Cys Gln Gln Tyr Tyr Ser Tyr Pro Tyr
                85                  90                  95

Thr Phe Gly Gly Gly Thr Lys Leu Glu Ile Lys
            100                 105

<210> SEQ ID NO 120
<211> LENGTH: 107
<212> TYPE: PRT
<213> ORGANISM: Artificial
<220> FEATURE:
<223> OTHER INFORMATION: Synthetic

<400> SEQUENCE: 120

Asn Ile Val Met Thr Gln Ser Pro Asp Ser Leu Ala Val Ser Leu Gly
1               5                   10                  15

Glu Arg Ala Thr Leu Ser Cys Lys Ala Ser Gln Asn Val Val Thr Tyr
            20                  25                  30

Val Ser Trp Tyr Gln Gln Lys Pro Gly Gln Ser Pro Gln Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Asn Ser Leu Glu Ala
65                  70                  75                  80

Glu Asp Ala Ala Thr Tyr Tyr Cys Gly Gln Gly Tyr Ser Tyr Pro Tyr
                85                  90                  95

Thr Phe Gly Gly Gly Thr Lys Leu Glu Ile Lys
            100                 105

<210> SEQ ID NO 121
<211> LENGTH: 107
<212> TYPE: PRT
<213> ORGANISM: Artificial
<220> FEATURE:
<223> OTHER INFORMATION: Synthetic

<400> SEQUENCE: 121

Asn Ile Val Met Thr Gln Ser Pro Asp Ser Leu Ala Val Ser Leu Gly
1               5                   10                  15

Glu Arg Ala Thr Leu Ser Cys Arg Ala Ser Glu Asn Val Val Thr Tyr
            20                  25                  30

Val Ser Trp Tyr Gln Gln Lys Pro Gly Gln Pro Pro Gln Leu Leu Ile
        35                  40                  45

```
Tyr Gly Ala Ser Asn Arg Tyr Thr Gly Val Pro Asp Arg Phe Thr Gly
    50                  55                  60
Ser Gly Ser Gly Thr Asp Phe Thr Leu Thr Ile Asn Ser Leu Glu Ala
65                  70                  75                  80
Glu Asp Ala Ala Val Tyr Tyr Cys Gly Gln Gly Tyr Ser Tyr Pro Tyr
                85                  90                  95
Thr Phe Gly Gly Gly Thr Lys Leu Glu Ile Lys
            100                 105

<210> SEQ ID NO 122
<211> LENGTH: 7
<212> TYPE: PRT
<213> ORGANISM: Artificial
<220> FEATURE:
<223> OTHER INFORMATION: Synthetic

<400> SEQUENCE: 122

Tyr Ala Phe Thr Asn Tyr Leu
1               5

<210> SEQ ID NO 123
<211> LENGTH: 7
<212> TYPE: PRT
<213> ORGANISM: Artificial
<220> FEATURE:
<223> OTHER INFORMATION: Synthetic

<400> SEQUENCE: 123

Tyr Ser Phe Thr Asn Tyr Leu
1               5

<210> SEQ ID NO 124
<211> LENGTH: 7
<212> TYPE: PRT
<213> ORGANISM: Artificial
<220> FEATURE:
<223> OTHER INFORMATION: Synthetic

<400> SEQUENCE: 124

Phe Ala Phe Thr Asn Tyr Leu
1               5

<210> SEQ ID NO 125
<211> LENGTH: 7
<212> TYPE: PRT
<213> ORGANISM: Artificial
<220> FEATURE:
<223> OTHER INFORMATION: Synthetic

<400> SEQUENCE: 125

Tyr Ala Phe Ser Asn Tyr Leu
1               5

<210> SEQ ID NO 126
<211> LENGTH: 7
<212> TYPE: PRT
<213> ORGANISM: Artificial
<220> FEATURE:
<223> OTHER INFORMATION: Synthetic

<400> SEQUENCE: 126

Tyr Ala Phe Thr Asp Tyr Leu
1               5
```

```
<210> SEQ ID NO 127
<211> LENGTH: 6
<212> TYPE: PRT
<213> ORGANISM: Artificial
<220> FEATURE:
<223> OTHER INFORMATION: Synthetic

<400> SEQUENCE: 127

Asn Pro Gly Ser Gly Gly
1               5

<210> SEQ ID NO 128
<211> LENGTH: 6
<212> TYPE: PRT
<213> ORGANISM: Artificial
<220> FEATURE:
<223> OTHER INFORMATION: Synthetic

<400> SEQUENCE: 128

Asn Pro Gly Ser Gly Ala
1               5

<210> SEQ ID NO 129
<211> LENGTH: 7
<212> TYPE: PRT
<213> ORGANISM: Artificial
<220> FEATURE:
<223> OTHER INFORMATION: Synthetic

<400> SEQUENCE: 129

Asp Gly Pro Trp Phe Ala Tyr
1               5

<210> SEQ ID NO 130
<211> LENGTH: 7
<212> TYPE: PRT
<213> ORGANISM: Artificial
<220> FEATURE:
<223> OTHER INFORMATION: Synthetic

<400> SEQUENCE: 130

Asp Gly Pro Trp Tyr Ala Tyr
1               5

<210> SEQ ID NO 131
<211> LENGTH: 6
<212> TYPE: PRT
<213> ORGANISM: Artificial
<220> FEATURE:
<223> OTHER INFORMATION: Synthetic

<400> SEQUENCE: 131

Glu Asn Val Val Thr Tyr
1               5

<210> SEQ ID NO 132
<211> LENGTH: 6
<212> TYPE: PRT
<213> ORGANISM: Artificial
<220> FEATURE:
<223> OTHER INFORMATION: Synthetic

<400> SEQUENCE: 132

Gln Asn Val Val Thr Tyr
1               5

<210> SEQ ID NO 133
```

```
<211> LENGTH: 7
<212> TYPE: PRT
<213> ORGANISM: Artificial
<220> FEATURE:
<223> OTHER INFORMATION: Synthetic

<400> SEQUENCE: 133

Gly Ala Ser Asn Arg Tyr Thr
1               5

<210> SEQ ID NO 134
<211> LENGTH: 7
<212> TYPE: PRT
<213> ORGANISM: Artificial
<220> FEATURE:
<223> OTHER INFORMATION: Synthetic

<400> SEQUENCE: 134

Asp Ala Ser Asn Arg Tyr Thr
1               5

<210> SEQ ID NO 135
<211> LENGTH: 7
<212> TYPE: PRT
<213> ORGANISM: Artificial
<220> FEATURE:
<223> OTHER INFORMATION: Synthetic

<400> SEQUENCE: 135

Gly Tyr Ser Tyr Pro Tyr Thr
1               5

<210> SEQ ID NO 136
<211> LENGTH: 7
<212> TYPE: PRT
<213> ORGANISM: Artificial
<220> FEATURE:
<223> OTHER INFORMATION: Synthetic

<400> SEQUENCE: 136

Tyr Tyr Ser Tyr Pro Tyr Thr
1               5

<210> SEQ ID NO 137
<211> LENGTH: 330
<212> TYPE: PRT
<213> ORGANISM: Homo sapiens

<400> SEQUENCE: 137

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110
```

```
Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 138
<211> LENGTH: 330
<212> TYPE: PRT
<213> ORGANISM: Homo sapiens

<400> SEQUENCE: 138

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Gln Phe Asn Trp
145                 150                 155                 160
```

```
Tyr Val Asp Gly Val Glu Val His Asn Ala Lys Thr Lys Pro Arg Glu
                165                 170                 175

Glu Gln Phe Asn Ser Thr Phe Arg Val Val Ser Val Leu Thr Val Val
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Thr Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Met Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 139
<211> LENGTH: 330
<212> TYPE: PRT
<213> ORGANISM: Homo sapiens

<400> SEQUENCE: 139

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Asp Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Gln Phe Asn Trp
145                 150                 155                 160

Tyr Val Asp Gly Val Glu Val His Asn Ala Lys Thr Lys Pro Arg Glu
                165                 170                 175

Glu Gln Phe Asn Ser Thr Phe Arg Val Val Ser Val Leu Thr Val Val
            180                 185                 190

His Gln Asp Trp Leu Asn Gly Lys Glu Tyr Lys Cys Lys Val Ser Asn
```

```
                195                 200                 205
Lys Ala Leu Pro Ala Pro Glu Glu Lys Thr Ile Ser Lys Thr Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Met Leu Asp Ser Asp Gly Ser Phe Phe
                275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 140
<211> LENGTH: 330
<212> TYPE: PRT
<213> ORGANISM: Mus musculus

<400> SEQUENCE: 140

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
                20                  25                  30

Phe Pro Glu Pro Val Thr Leu Thr Trp Asn Ser Gly Ser Leu Ser Ser
            35                  40                  45

Gly Val His Thr Phe Pro Ala Val Leu Gln Ser Asp Leu Tyr Thr Leu
        50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Met Val Thr Cys
130                 135                 140

Val Val Val Asp Val Ser Glu Asp Asp Pro Asp Val Gln Ile Ser Trp
145                 150                 155                 160

Phe Val Asn Asn Val Glu Val Leu Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Ala Leu Pro Ala Pro Ile Glu Arg Thr Ile Ser Lys Pro Lys Gly
            210                 215                 220

Ser Val Arg Ala Pro Gln Val Tyr Val Leu Pro Pro Pro Glu Glu Glu
225                 230                 235                 240
```

```
Met Thr Lys Lys Gln Val Thr Leu Thr Cys Met Val Thr Asp Phe Met
            245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
            275                 280                 285

Met Tyr Ser Lys Leu Arg Val Glu Lys Lys Asn Trp Val Glu Arg Asn
            290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
            325                 330

<210> SEQ ID NO 141
<211> LENGTH: 324
<212> TYPE: PRT
<213> ORGANISM: Mus musculus

<400> SEQUENCE: 141

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
            35                  40                  45

Gly Val His Thr Phe Pro Ala Val Leu Gln Ser Asp Leu Tyr Thr Leu
        50                  55                  60

Ser Ser Ser Val Thr Val Pro Ser Ser Thr Trp Pro Ser Gln Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
            115                 120                 125

Thr Ile Thr Leu Thr Pro Lys Val Thr Cys Val Val Val Asp Ile Ser
        130                 135                 140

Lys Asp Asp Pro Glu Val Gln Phe Ser Trp Phe Val Asp Asp Val Glu
145                 150                 155                 160

Val His Thr Ala Gln Thr Lys Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285
```

```
Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys

<210> SEQ ID NO 142
<211> LENGTH: 107
<212> TYPE: PRT
<213> ORGANISM: Artificial
<220> FEATURE:
<223> OTHER INFORMATION: Synthetic

<400> SEQUENCE: 142

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 143
<211> LENGTH: 107
<212> TYPE: PRT
<213> ORGANISM: Mus musculus

<400> SEQUENCE: 143

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 144
<211> LENGTH: 446
<212> TYPE: PRT
<213> ORGANISM: Artificial
<220> FEATURE:
<223> OTHER INFORMATION: Synthetic

<400> SEQUENCE: 144
```

-continued

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Pro Ser Leu
50                      55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
```

```
                       420                 425                 430

Asn His Tyr Thr Gln Lys Ser Leu Ser Leu Ser Pro Gly Lys
        435                 440                 445

<210> SEQ ID NO 145
<211> LENGTH: 214
<212> TYPE: PRT
<213> ORGANISM: Artificial
<220> FEATURE:
<223> OTHER INFORMATION: Synthetic

<400> SEQUENCE: 145

Asn Ile Val Met Thr Gln Ser Pro Asp Ser Leu Ala Val Ser Leu Gly
1               5                   10                  15

Glu Arg Ala Thr Leu Ser Cys Arg Ala Ser Glu Asn Val Thr Tyr
            20                  25                  30

Val Ser Trp Tyr Gln Gln Lys Pro Gly Gln Ser Pro Gln Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Asn Ser Leu Glu Ala
65                  70                  75                  80

Glu Asp Ala Ala Thr Tyr Tyr Cys Gly Gln Gly Tyr Ser Tyr Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 146
<211> LENGTH: 446
<212> TYPE: PRT
<213> ORGANISM: Artificial
<220> FEATURE:
<223> OTHER INFORMATION: Synthetic

<400> SEQUENCE: 146

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Pro Ser Leu
    50                  55                  60
```

-continued

```
Lys Ser Arg Val Thr Ile Ser Ala Asp Lys Ser Ile Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg Asp Gly Pro Trp Phe Ala Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Asp Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Ala Leu Pro Ala Pro Glu Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 147
<211> LENGTH: 214
<212> TYPE: PRT
<213> ORGANISM: Artificial
<220> FEATURE:
<223> OTHER INFORMATION: Synthetic

<400> SEQUENCE: 147

Asn Ile Val Met Thr Gln Ser Pro Asp Ser Leu Ala Val Ser Leu Gly
1               5                   10                  15

Glu Arg Ala Thr Leu Ser Cys Arg Ala Ser Glu Asn Val Val Thr Tyr
            20                  25                  30

Val Ser Trp Tyr Gln Gln Lys Pro Gly Gln Ser Pro Gln Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Asn Ser Leu Glu Ala
65                  70                  75                  80

Glu Asp Ala Ala Thr Tyr Tyr Cys Gly Gln Gly Tyr Ser Tyr Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 148
<211> LENGTH: 446
<212> TYPE: PRT
<213> ORGANISM: Artificial
<220> FEATURE:
<223> OTHER INFORMATION: Synthetic

<400> SEQUENCE: 148

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Pro Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

```
Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Asp Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Glu Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 149
<211> LENGTH: 214
<212> TYPE: PRT
<213> ORGANISM: Artificial
<220> FEATURE:
<223> OTHER INFORMATION: Synthetic

<400> SEQUENCE: 149

Asn Ile Val Met Thr Gln Ser Pro Asp Ser Leu Ala Val Ser Leu Gly
1               5                   10                  15

Glu Arg Ala Thr Leu Ser Cys Arg Ala Ser Glu Asn Val Val Thr Tyr
            20                  25                  30

Val Ser Trp Tyr Gln Gln Lys Pro Gly Gln Ser Pro Gln Leu Leu Ile
        35                  40                  45
```

```
Tyr Gly Ala Ser Asn Arg Tyr Thr Gly Val Pro Asp Arg Phe Thr Gly
         50                  55                  60

Ser Gly Ser Ala Thr Asp Phe Thr Leu Thr Ile Asn Ser Leu Glu Ala
 65                  70                  75                  80

Glu Asp Ala Ala Thr Tyr Tyr Cys Gly Gln Gly Tyr Ser Tyr Pro Tyr
                     85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 150
<211> LENGTH: 446
<212> TYPE: PRT
<213> ORGANISM: Artificial
<220> FEATURE:
<223> OTHER INFORMATION: Synthetic

<400> SEQUENCE: 150

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Ser Phe Thr Asn Tyr
                 20                  25                  30

Leu Ile Glu Trp Val Arg Gln Ala Pro Gly Gln Gly Leu Glu Trp Met
             35                  40                  45

Gly Val Ile Asn Pro Gly Ser Gly Gly Thr Asn Tyr Asn Pro Ser Leu
         50                  55                  60

Lys Ser Arg Val Thr Ile Ser Ala Asp Lys Ser Ile Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg Asp Gly Pro Trp Phe Ala Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190
```

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Glu Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Ala Leu Pro Ala Pro Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 151
<211> LENGTH: 214
<212> TYPE: PRT
<213> ORGANISM: Artificial
<220> FEATURE:
<223> OTHER INFORMATION: Synthetic

<400> SEQUENCE: 151

Asn Ile Val Met Thr Gln Ser Pro Asp Ser Leu Ala Val Ser Leu Gly
1               5                   10                  15

Glu Arg Ala Thr Leu Ser Cys Arg Ala Ser Glu Asn Val Val Thr Tyr
            20                  25                  30

Val Ser Trp Tyr Gln Gln Lys Pro Gly Gln Ser Pro Gln Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Asn Ser Leu Glu Ala
65                  70                  75                  80

Glu Asp Ala Ala Thr Tyr Tyr Cys Gly Gln Gly Tyr Ser Tyr Pro Tyr
                85                  90                  95

Thr Phe Gly Gly Gly Thr Lys Leu Glu Ile Lys Arg Thr Val Ala Ala
            100                 105                 110

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 152
<211> LENGTH: 446
<212> TYPE: PRT
<213> ORGANISM: Artificial
<220> FEATURE:
<223> OTHER INFORMATION: Synthetic

<400> SEQUENCE: 152

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Pro Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Ala Gly Pro Asp Val Phe
225                 230                 235                 240

Leu Phe Pro Pro Lys Pro Lys Asp Thr Leu Met Ile Ser Arg Thr Pro
                245                 250                 255
```

```
Glu Val Thr Cys Val Val Val Asp Val Ser His Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Phe Arg Val Val Ser Val
        290                 295                 300

Leu Thr Val Val His Gln Asp Trp Leu Asn Gly Lys Glu Tyr Lys Cys
305                 310                 315                 320

Lys Val Ser Asn Lys Ala Leu Pro Ala Pro Glu Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 153
<211> LENGTH: 214
<212> TYPE: PRT
<213> ORGANISM: Artificial
<220> FEATURE:
<223> OTHER INFORMATION: Synthetic

<400> SEQUENCE: 153

Asn Ile Val Met Thr Gln Ser Pro Asp Ser Leu Ala Val Ser Leu Gly
1               5                   10                  15

Glu Arg Ala Thr Leu Ser Cys Arg Ala Ser Glu Asn Val Val Thr Tyr
            20                  25                  30

Val Ser Trp Tyr Gln Gln Lys Pro Gly Gln Ser Pro Gln Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Asn Ser Leu Glu Ala
65                  70                  75                  80

Glu Asp Ala Ala Thr Tyr Tyr Cys Gly Gln Gly Tyr Ser Tyr Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 154
<211> LENGTH: 446
<212> TYPE: PRT
<213> ORGANISM: Artificial
<220> FEATURE:
<223> OTHER INFORMATION: Synthetic

<400> SEQUENCE: 154

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Gly Thr Asn Tyr Asn Pro Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Asp Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

```
Lys Val Ser Asn Lys Ala Leu Pro Tyr Pro Glu Lys Thr Ile Ser
            325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 155
<211> LENGTH: 214
<212> TYPE: PRT
<213> ORGANISM: Artificial
<220> FEATURE:
<223> OTHER INFORMATION: Synthetic

<400> SEQUENCE: 155

Asn Ile Val Met Thr Gln Ser Pro Asp Ser Leu Ala Val Ser Leu Gly
1               5                   10                  15

Glu Arg Ala Thr Leu Ser Cys Arg Ala Ser Glu Asn Val Val Thr Tyr
            20                  25                  30

Val Ser Trp Tyr Gln Gln Lys Pro Gly Gln Ser Pro Gln Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Asn Ser Leu Glu Ala
65                  70                  75                  80

Glu Asp Ala Ala Thr Tyr Tyr Cys Gly Gln Gly Tyr Ser Tyr Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 156
<211> LENGTH: 446
```

<212> TYPE: PRT
<213> ORGANISM: Artificial
<220> FEATURE:
<223> OTHER INFORMATION: Synthetic

<400> SEQUENCE: 156

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Asn Tyr
            20                  25                  30

Leu Ile Glu Trp Val Arg Gln Ala Pro Gly Gln Gly Leu Glu Trp Met
        35                  40                  45

Gly Val Ile Asn Pro Gly Ser Gly Thr Asn Tyr Asn Pro Ser Leu
    50                  55                  60

Lys Ser Arg Val Thr Ile Ser Ala Asp Lys Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Gly Pro Trp Phe Ala Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380
```

```
Gln Pro Glu Asn Asn Tyr Lys Thr Thr Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

```
<210> SEQ ID NO 157
<211> LENGTH: 214
<212> TYPE: PRT
<213> ORGANISM: Artificial
<220> FEATURE:
<223> OTHER INFORMATION: Synthetic

<400> SEQUENCE: 157

Asn Ile Val Met Thr Gln Ser Pro Asp Ser Leu Ala Val Ser Leu Gly
1               5                   10                  15

Glu Arg Ala Thr Leu Ser Cys Arg Ala Ser Glu Asn Val Val Thr Tyr
            20                  25                  30

Val Ser Trp Tyr Gln Gln Lys Pro Gly Gln Ser Pro Gln Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Asn Ser Leu Glu Ala
65                  70                  75                  80

Glu Asp Ala Ala Thr Tyr Tyr Cys Gly Gln Gly Tyr Ser Tyr Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 158
<211> LENGTH: 446
<212> TYPE: PRT
<213> ORGANISM: Artificial
<220> FEATURE:
<223> OTHER INFORMATION: Synthetic

<400> SEQUENCE: 158

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Asn Tyr
            20                  25                  30
```

```
Leu Ile Glu Trp Val Arg Gln Ala Pro Gly Gln Gly Leu Glu Trp Met
        35                  40                  45
Gly Val Ile Asn Pro Gly Ser Gly Gly Thr Asn Tyr Asn Pro Ser Leu
    50                  55                  60
Lys Ser Arg Val Thr Ile Ser Ala Asp Lys Ser Ile Ser Thr Ala Tyr
65                  70                  75                  80
Met Glu Leu Ser Ser Leu Arg Ser Glu Asp Thr Ala Val Tyr Phe Cys
                85                  90                  95
Ala Arg Asp Gly Pro Trp Phe Ala Tyr Trp Gly Gln Gly Thr Leu Val
            100                 105                 110
Thr Val Ser Ser Ala Ser Thr Lys Gly Pro Ser Val Phe Pro Leu Ala
        115                 120                 125
Pro Ser Ser Lys Ser Thr Ser Gly Gly Thr Ala Ala Leu Gly Cys Leu
    130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
        195                 200                 205
Lys Val Asp Lys Lys Val Glu Pro Lys Ser Cys Asp Lys Thr His Thr
    210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
        275                 280                 285
Lys Pro Arg Glu Glu Gln Tyr Asn Ser Thr Tyr Arg Val Val Ser Val
    290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Glu Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Glu Glu Met Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
        435                 440                 445
```

```
<210> SEQ ID NO 159
<211> LENGTH: 214
<212> TYPE: PRT
<213> ORGANISM: Artificial
<220> FEATURE:
<223> OTHER INFORMATION: Synthetic

<400> SEQUENCE: 159

Asn Ile Val Met Thr Gln Ser Pro Asp Ser Leu Ala Val Ser Leu Gly
1               5                   10                  15

Glu Arg Ala Thr Leu Ser Cys Arg Ala Ser Glu Asn Val Val Thr Tyr
            20                  25                  30

Val Ser Trp Tyr Gln Gln Lys Pro Gly Gln Ser Pro Gln Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Asn Ser Leu Glu Ala
65                  70                  75                  80

Glu Asp Ala Ala Thr Tyr Tyr Cys Gly Gln Gly Tyr Ser Tyr Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 160
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be Phenylalanine or Tyrosine

<400> SEQUENCE: 160

Asp Gly Pro Trp Xaa Ala Tyr
1               5

<210> SEQ ID NO 161
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
```

```
<223> OTHER INFORMATION: Xaa can be Glycine or Tyrosine

<400> SEQUENCE: 161

Xaa Tyr Ser Tyr Pro Tyr Thr
1               5

<210> SEQ ID NO 162
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be Tyrosine or Phenylalanine
<220> FEATURE:
<221> NAME/KEY: misc_feature
<222> LOCATION: (2)..(2)
<223> OTHER INFORMATION: Xaa can be Alanine or Serine
<220> FEATURE:
<221> NAME/KEY: misc_feature
<222> LOCATION: (4)..(4)
<223> OTHER INFORMATION: Xaa can be Threonine or Serine
<220> FEATURE:
<221> NAME/KEY: misc_feature
<222> LOCATION: (5)..(5)
<223> OTHER INFORMATION: Xaa can be Asparagine or Aspartic Acid

<400> SEQUENCE: 162

Xaa Xaa Phe Xaa Xaa Tyr Leu
1               5

<210> SEQ ID NO 163
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be Glycine or Alanine

<400> SEQUENCE: 163

Asn Pro Gly Ser Gly Xaa
1               5

<210> SEQ ID NO 164
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be Glutamic Acid or Glutamine

<400> SEQUENCE: 164

Xaa Asn Val Val Thr Tyr
1               5

<210> SEQ ID NO 165
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: misc_feature
```

```
<222> LOCATION: (1)..(1)
<223> OTHER INFORMATION: Xaa can be Glycine or Aspartic Acid

<400> SEQUENCE: 165

Xaa Ala Ser Asn Arg Tyr Thr
1               5

<210> SEQ ID NO 166
<211> LENGTH: 5
<212> TYPE: PRT
<213> ORGANISM: Artificial
<220> FEATURE:
<223> OTHER INFORMATION: Synthetic

<400> SEQUENCE: 166

Thr Leu Met Ile Ser
1               5

<210> SEQ ID NO 167
<211> LENGTH: 7
<212> TYPE: PRT
<213> ORGANISM: Artificial
<220> FEATURE:
<223> OTHER INFORMATION: Synthetic

<400> SEQUENCE: 167

Leu Thr Val Leu His Gln Asp
1               5

<210> SEQ ID NO 168
<211> LENGTH: 5
<212> TYPE: PRT
<213> ORGANISM: Artificial
<220> FEATURE:
<223> OTHER INFORMATION: Synthetic

<400> SEQUENCE: 168

Gly Ser Gly Gly Ser
1               5

<210> SEQ ID NO 169
<211> LENGTH: 5
<212> TYPE: PRT
<213> ORGANISM: Artificial
<220> FEATURE:
<223> OTHER INFORMATION: Synthetic

<400> SEQUENCE: 169

Gly Gly Gly Gly Ser
1               5

<210> SEQ ID NO 170
<211> LENGTH: 4
<212> TYPE: PRT
<213> ORGANISM: Artificial
<220> FEATURE:
<223> OTHER INFORMATION: Synthetic

<400> SEQUENCE: 170

Gly Gly Gly Ser
1
```